US007157473B2

(12) United States Patent
Singh et al.

(10) Patent No.: US 7,157,473 B2
(45) Date of Patent: Jan. 2, 2007

(54) PYRIDYL SUBSTITUTED HETEROCYCLES USEFUL FOR TREATING OR PREVENTING HCV INFECTION

(75) Inventors: Rajinder Singh, Belmont, CA (US); Dane Goff, Redwood City, CA (US); John Partridge, Chapel Hill, NC (US); Henry H. Lu, Foster City, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 371 days.

(21) Appl. No.: 10/646,348

(22) Filed: Aug. 22, 2003

(65) Prior Publication Data

US 2004/0127497 A1 Jul. 1, 2004

Related U.S. Application Data

(60) Provisional application No. 60/471,373, filed on May 15, 2003, provisional application No. 60/417,837, filed on Oct. 11, 2002, provisional application No. 60/405,467, filed on Aug. 23, 2002.

(51) Int. Cl.
*C07D 213/02* (2006.01)
*A61K 31/44* (2006.01)

(52) U.S. Cl. ...................... 514/332; 514/333; 514/340; 514/342; 546/255; 546/256; 546/268.1; 546/269.7

(58) Field of Classification Search ................ 546/255, 546/256, 268.1, 269.7; 514/332, 333, 340, 514/342

See application file for complete search history.

(56) References Cited

U.S. PATENT DOCUMENTS

| | | | |
|---|---|---|---|
| 2,852,503 | A | 9/1958 | Edward et al. |
| 3,257,203 | A | 6/1966 | Klupfel et al. |
| 3,335,149 | A | 8/1967 | Preston |
| 3,910,942 | A | 10/1975 | Narayanan et al. |
| 3,964,896 | A | 6/1976 | Neidermyer et al. |
| 4,752,324 | A | 6/1988 | Thomas et al. |
| 5,151,441 | A | 9/1992 | Mueller et al. |
| 5,256,666 | A | 10/1993 | Mueller et al. |
| 5,463,071 | A | 10/1995 | Himmelsbach et al. |
| 5,814,627 | A | 9/1998 | Schwab et al. |
| 6,355,669 | B1 | 3/2002 | Yamauchi et al. |
| 2002/0035156 | A1 | 3/2002 | Roniker et al. |
| 2002/0049213 | A1 | 4/2002 | Weidner-Wells et al. |

FOREIGN PATENT DOCUMENTS

| | | | |
|---|---|---|---|
| CH | 559 195 | | 2/1975 |
| DE | 21 37 719 | | 2/1973 |
| DE | 27 21 955 | | 11/1978 |
| DE | 100 32 874 | | 1/2002 |
| DE | 101 48 598 | | 10/2002 |
| EP | 563686 | A1 | 3/1993 |
| EP | 0 776 894 | | 6/1997 |
| EP | 92/7992 | A1 | 7/1999 |
| EP | 1 180 518 | | 2/2002 |
| EP | 1 348 706 | | 10/2003 |
| FR | 1 459 375 | | 4/1966 |
| JP | 04124178 | A | 4/1992 |
| WO | WO 93/17671 | | 9/1993 |
| WO | WO 94/17059 | | 6/1994 |
| WO | WO 95/24397 | | 9/1995 |
| WO | WO 98/17652 | | 4/1998 |
| WO | WO 98/47509 | | 10/1998 |
| WO | WO 99/04390 | | 1/1999 |
| WO | WO 99/20309 | | 4/1999 |
| WO | WO 02/20436 | A2 | 3/2000 |
| WO | WO 00/40242 | | 7/2000 |
| WO | WO 00/45799 | | 8/2000 |
| WO | WO 00/78726 | A1 | 12/2000 |
| WO | WO 01/74811 | | 10/2001 |
| WO | WO 01/78648 | | 10/2001 |
| WO | WO 02/46186 | | 6/2002 |
| WO | WO 02/055025 | | 7/2002 |
| WO | WO 03/029210 | | 4/2003 |
| WO | WO 03/040112 | | 5/2003 |
| WO | WO 04/018463 | | 3/2004 |
| WO | WO 04/103366 | | 12/2004 |

OTHER PUBLICATIONS

Roth et al., "Zur Kondensation von Chalkonoxyden mit Hydroxylamin", *Arch. Pharm.*, vol. 94, pp. 769-774, 1961.

Samula, "Oksymowanic Azachalkonow", *Roczniki Chemll*, Ann. Soc. Chim. Polonorum, vol. 45, pp. 2063, 1971.

Samula, "Cyclization of Azachalcones and β-Hydroxyketones Oximes", *Roczniki Chemll*, Ann. soc. Chim, Polonorum, vol. 48, pp. 959-964, 1974.

Howe, et al., "Nitrile Oxide Cycloaddition Routes to 2-(Isoxazoly)-benzoates and 2-(1,2,4-Oxadiazol-3-yl)benzoates", *Heterocycl. Chem.*, vol. 19, No. 4, pp. 721-726, 1982.

Belgodere et al., "Studies on Isomeric Pyridylisoxazoles", *Heterocycles*, vol. 20, No. 3, pp. 501-504, 1983.

(Continued)

*Primary Examiner*—Zinna N. Davis

(74) *Attorney, Agent, or Firm*—McDonnell Boehnen Hulbert & Berghoff LLP

(57) ABSTRACT

The present invention relates to pyridyl substituted heterocycles and hydro isomers thereof and pharmaceutical compositions thereof that inhibit replication and/or proliferation of HCV virus. The present invention also relates to the use of the pyridyl heterocycles and hydro isomers thereof and/or pharmaceutical compositions comprising the compounds to treat or prevent HCV infections.

57 Claims, 84 Drawing Sheets

OTHER PUBLICATIONS

Figure 1A:
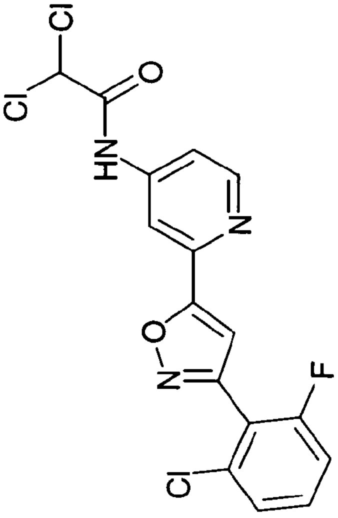
Figure 1A:
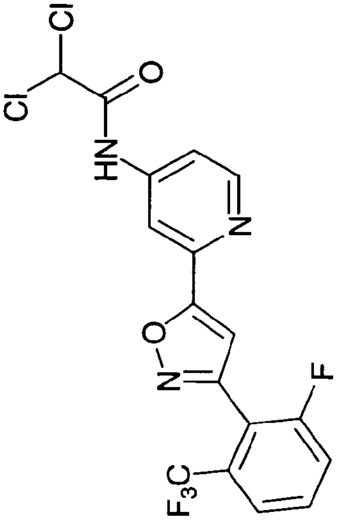
Figure 1A:
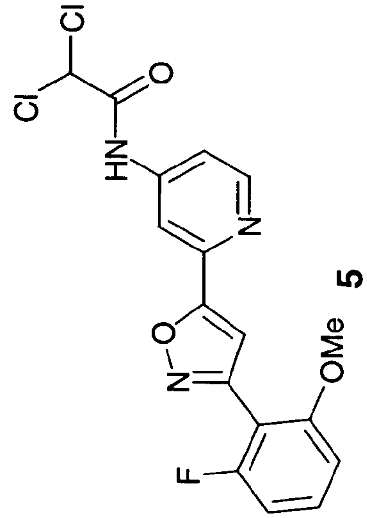
Figure 1A:
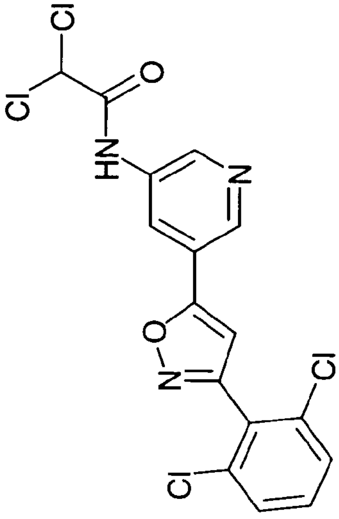
Figure 1A:
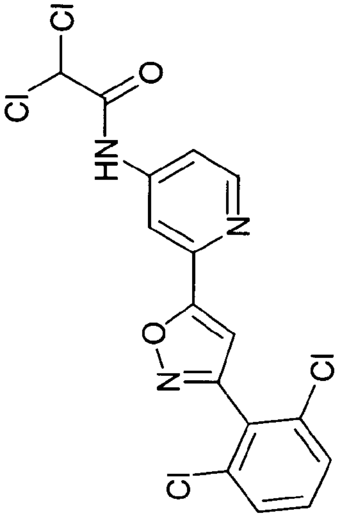
Figure 1A:
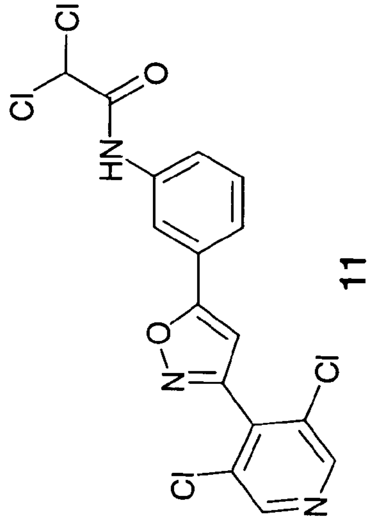
Figure 1B:
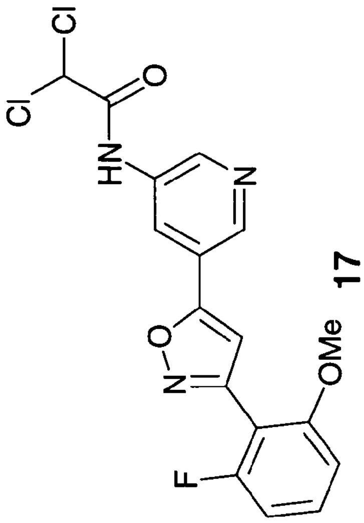
Figure 1B:
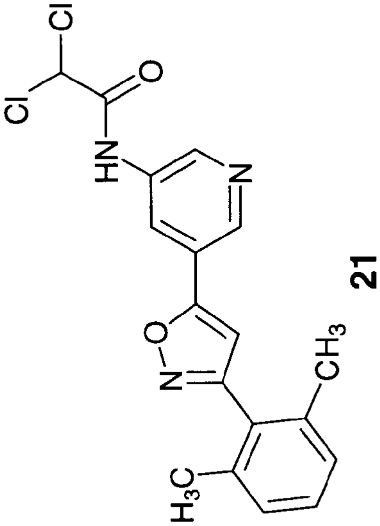
Figure 1B:
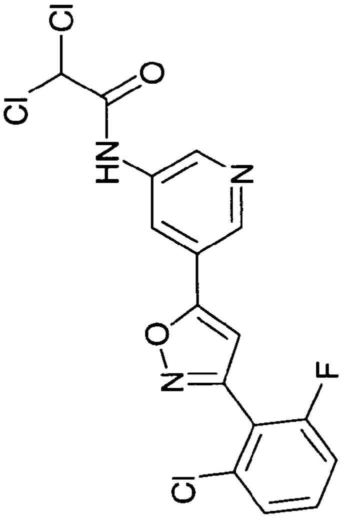
Figure 1B:
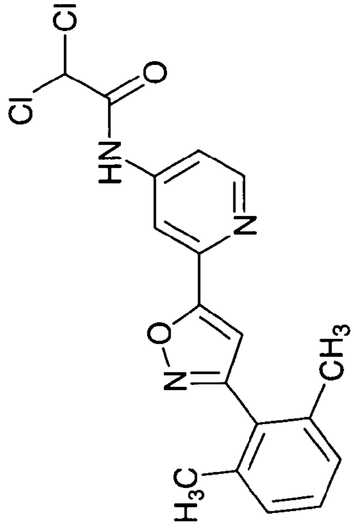
Figure 1C:
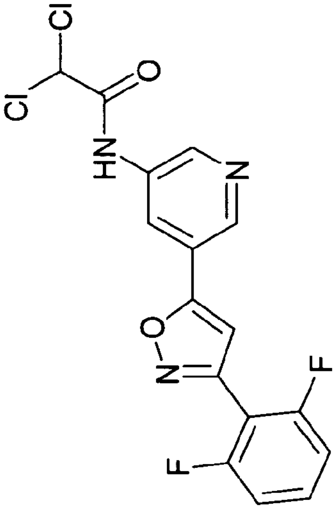
Figure 1C:
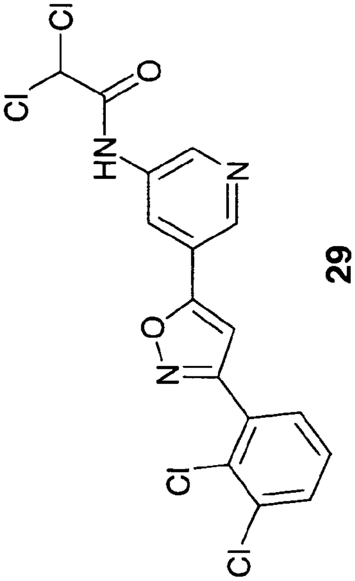
Figure 1C:
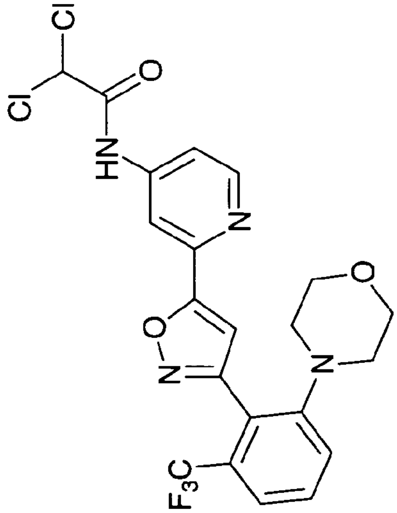
Figure 1C:
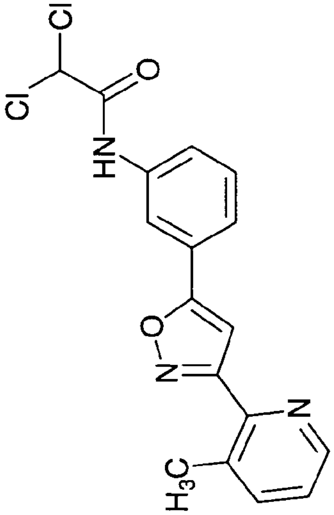
Figure 1C:
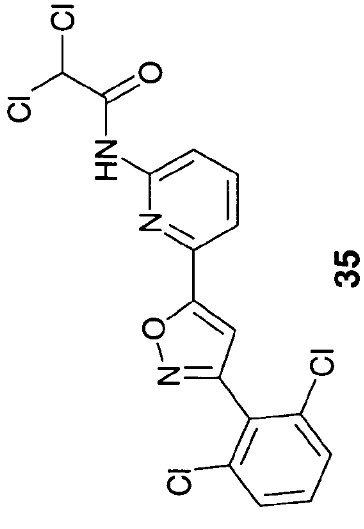
Figure 1D:
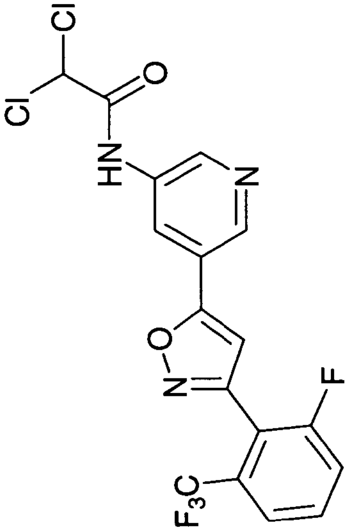
Figure 1D:
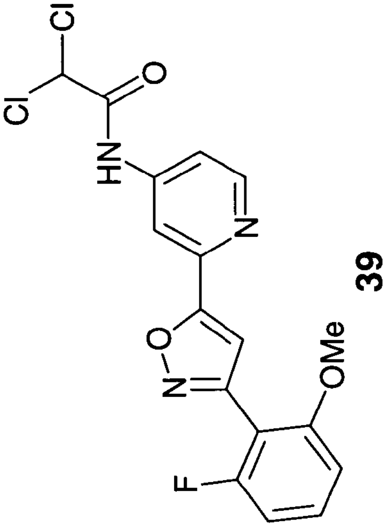
Figure 1D:
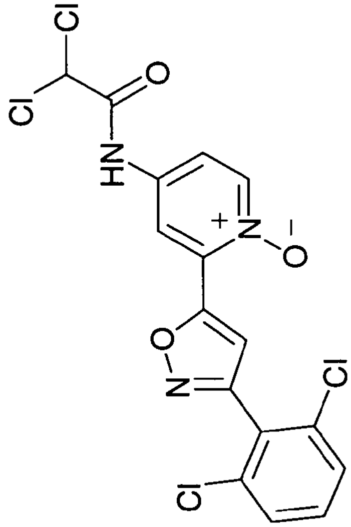
Figure 1D:
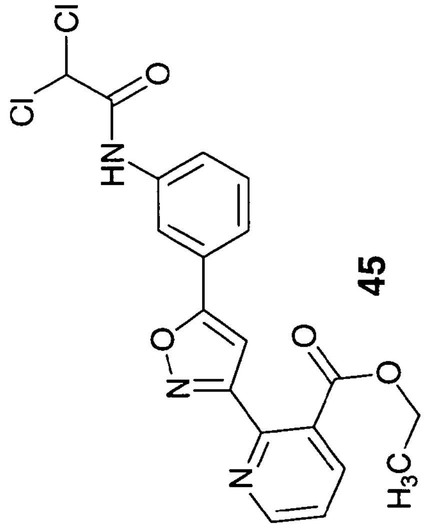
Figure 1D:
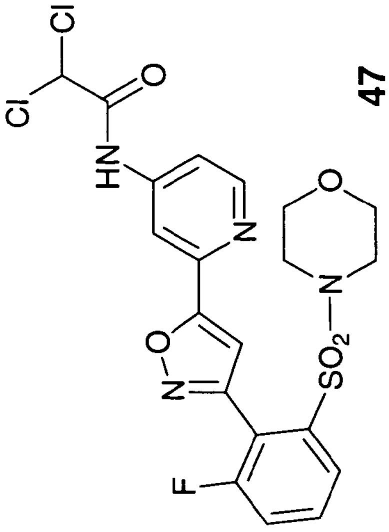
Figure 1E:
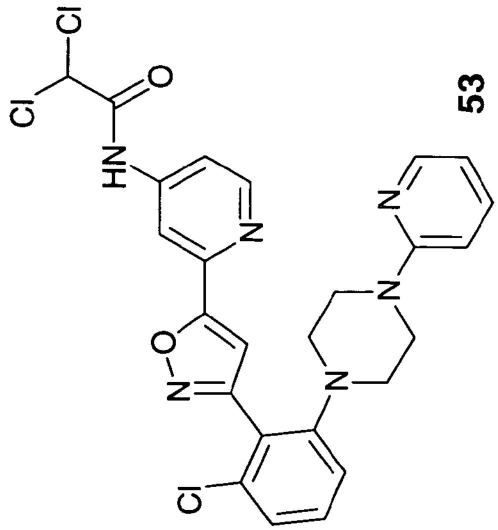
Figure 1E:
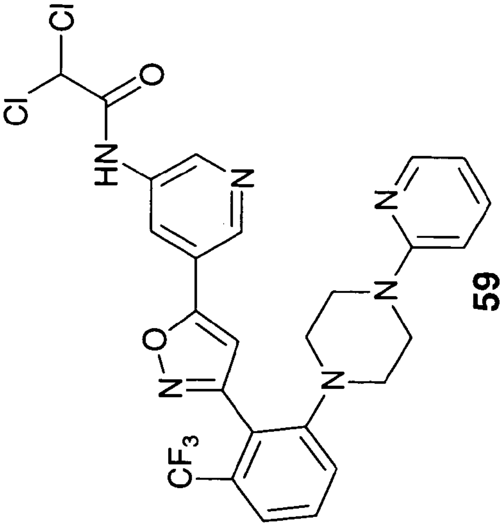
Figure 1E:
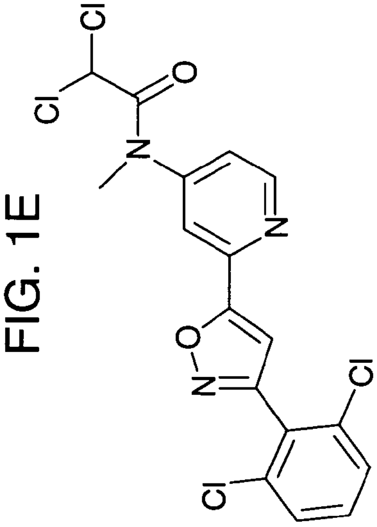
Figure 1E:
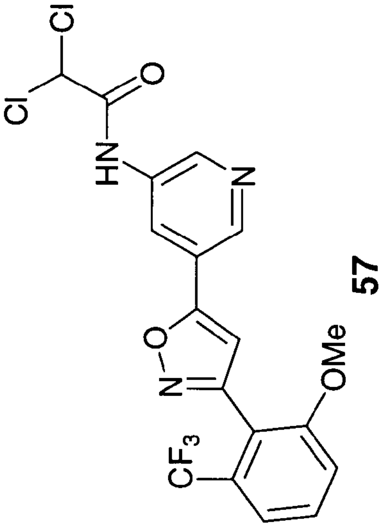
Figure 1E:
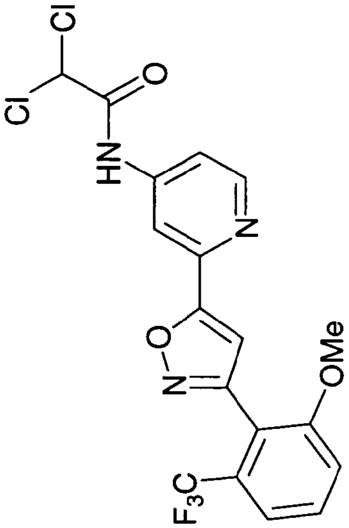
Figure 1F:
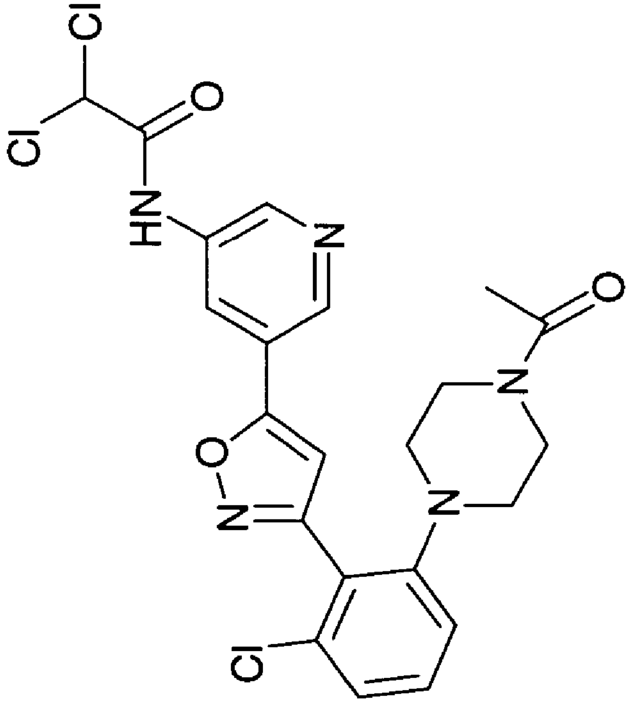
Figure 1F:
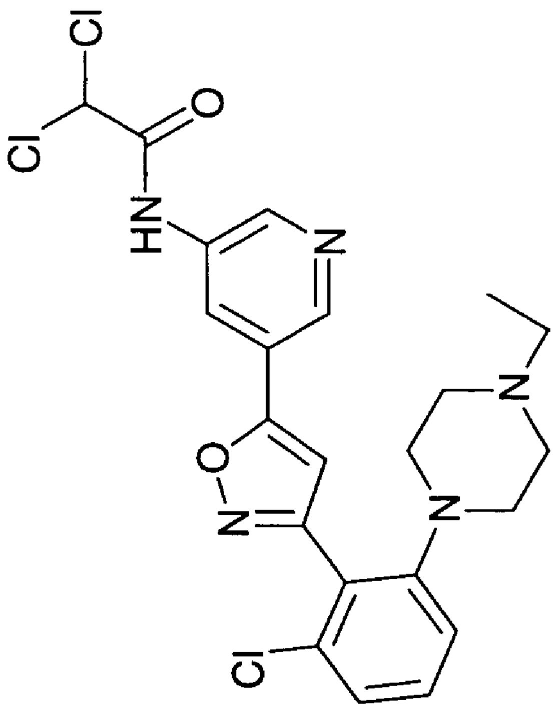

Batori et al., "Photoinduced Ring Transformation of Pyrido[1,2-b]pyridazinium-4-olate", *Tetrehedron*, vol. 50, No. 16, pp. 4699-4708, 1994.

Kanbara et al., "Preparation of Soluble and Fluorescent Poly(arylene)s by 1,3-Dipolar Polycycloaddition and Properties of the Polymers", *Polymer Bulletin*, vol. 36, pp. 673-679, 1996.

Ku et al., "Use of Iodoacetylene as a Dipolarphile in the Synthesis of 5-Iodoisoxazole Derivatives", *Organic Letters*, vol. 3, No. 26, pp. 4185-4187, 2001.

Maybridge, plc, Trevillett, Tintagel, Catalogue No. RF01972, Cornwall PL34 OHW, England.

Maybridge, plc, Trevillett, Tintagel, Catalog No. RF01996, Cornwall PL34 OHW, England.

Gatta et al, "Synthesis of [1,2,4]Triazoloquinazoline and [1,2,4]Triazolo-1,4-benzodiazepine derivatives", *J. Heterocyclic. Chem.*, vol. 30, pp. 11-16, 1993.

International Search Report.

Gatta et al. Synthesis of [1,2,4] Triazoloquinazoline and [1,2,4] Triazolo- 1,4-benzodiazepine derivatives. Journal of Heterocyclic Chemistry. (1993), vol. 30, pp. 11-16.

Database Chemcats Online! 1999m XP-002310049, Databased accession No. RN 247059-16-1.

Maybridge Hts, Order No. BTB 09742; RN 247059-16-1 Maybridge PLC, Trevillett, Tintagel, Cornwall, PL340HW, UK, Jan. 8, 2004 XP002297442.

STN File CA, Abstract 135:46129 & V.M. Barot et al, Asian Journal of Chemistry (2001), 13(1), pp. 341-343.

STN File CA, Abstract 132:265141 & S.V. Damle et al, Indian Journal of Heterocyclic Chemistry (1999), 9(2), pp. 81-86.

STN File CA, Abstract 132:180505 & V.R. Naik et al, Asian Journal of Chemistry (2000), 12(1), pp. 305-307.

STN File CA, Abstract 129:216539 & S.M. Naik et al, Oriental Journal of Chemistry (1998), 14(1), pp. 167-168.

STN File CA, Abstract 126:74789 & M. Shah et al, Indian Journal of Chemistry, Section B: Organic Chemistry Including Medicinal Chemistry (1996), 35B(12), pp. 1282-1286.

STN File CA, Abstract 122:81186 & S.R. Modi et al, Oriental Journal of Chemistry (1994), 10(1), pp. 85-86.

STN File CA, Abstract 118:191597 & T. Bandiera et al, Journal of Heterocyclic Chemistry (1992), 29(6), pp. 1423-1428.

1

3

5

7

9

11

17

21

13

19

27

29

31

33

35

37

39

43

45

47

53

59

51

57

49

61

63

201 203 205 207 209 211

213 + 215 → 217 → 219 → 221 → 9

201 223 225 227 229 207 231 209 211

213 233 235 237 239 219 241 221 9

245

247

249

211

251

253

255

9

230 232 234 236 238 240 255

252

254

256

258

260

262

245

257

259

211

251

261

263

9

265

267

269

271

273

275

277

279

281

283

285

287

289

291

293

295

297

299

301

+
-or-

Para C-ring phenyl isomer - isoxazole series

Method H

Reverse meta-isoxazole

Reverse 2-isoxazoline reverse 2-isoxazoline

2-Isoxazoline

4-Isoxazoline

Reverse 4-Isoxazoline

Reverse 4-isoxazoline

3-Isoxazoline

Reverse 3-isoxazoline

Isoxazolidines

Reverse isoxazolidines four diastereomeric reverse isoxazolidines 1,2-pyrazolidines Representative Reference:

Bull. Chem. Soc. (Japan), 1989, 62, 3944-3949.

4,5-dihydro-oxadiazoles

Representative Reference:
J.Chem.Research, Synopses, 1995, 88-89.

Reverse 4,5-dihydro-oxadiazoles

Representative Reference:

J.Chem.Research, Synopses, 1995, 88-89.

2-pyrazolines 5R- and 5S- enantiomers

Representative Reference:

Oriental J.Chem, 2001,17, 513-514.

reverse 2-pyrazolines 5R- and 5S- enantiomers

Representative Reference:

Oriental J.Chem. 2001,17, 513-514.

3-pyrazolines

Representative Reference:
<u>Synth. Commun.</u> 1989, 19, 2799-2807.

Reverse 3-pyrazolines 5R- and 5S- enantiomers

Representative Reference:

Synth. Commun., 1989,19, 2799-2807.

Isothiazole

Representative Reference:
Tetrahedron, 1992,48, 8127-8142.

Reverse Isothiazole

Representative Reference:

Tetrahedron, 1992, 48, 8127-8142.

2-Isothiazoline

Representative Reference:

Asian J.Chem., 2000,12, 1358-1360.

Reverse 2-Isothiazoline 5R- and 5S-enantiomers

Representative Reference:

Asian J.Chem., 2000,12, 1358-1360.

4,5-Dihydro-1,3,4-thiadiazole

Representative Reference:

Sovrem. Aspekty Terorii i Prakt. Farmatsii. L., 1988, 90-96.

Reverse 4,5-Dihydro-1,3,4-thiadiazole

Representative Reference:

Sovrem. Aspekty Terorii i Prakt. Farmatsii. L., 1988, 90-96.

2-Thiazoline 5R- and 5S-enantiomers

Representative References:

Collection of Czechoslovak Chemical Communications, 1978, 43(7), 1917-1923
J. Org. Chem., 1997, 62, 1106-1111.

Reverse 2-Thiazoline

Representative References:

Collection of Czechoslovak Chemical Communications, 1978, 43(7), 1917-1923
J. Org. Chem., 1997, 62, 1106-1111.

Thiazolidines cis- trans- racemates
2R,4R-, 2S, 4S-, 2R,4S- and 2S, 4R-
diastereoisomers Representative Reference:

See March's Advanced Organic Chemistry 5th Ed John Wiley & Sons, Inc. 2001, Topics related to catalytic hydrogenation.

Reverse Thiazolidines cis- trans- racemates
2R,4R-, 2S, 4S-, 2R,4S- and2S, 4R-
diastereoisomers Representative Reference:

See March's Advanced Organic Chemistry 5th Ed John Wiley & Sons, Inc. 2001, Topics related to catalytic hydrogenation.

Oxazole

Representative Reference:
Varma, R.S et al J. of Heterocyclic Chem., 1998, 35(6), 1533-1534

Reverse Oxazole

Representative Reference:

Varma, R.S et al J. of Heterocyclic Chem., 1998, 35(6), 1533-1534

2-Oxazoline 4R- and 4S- enantiomers

Representative Reference:

Li, Q et al Bioorg&Med. Chem.Lett., 2002, 12(3), 465-469.

Reverse 2-Oxazoline 5R- and 5S- enantiomers

Representative Reference:

<u>Li, Q et al Bioorg&Med. Chem.Lett.</u>,
2002, 12(3), 465-469.

3-Oxazoline 2R- and 2S- enantiomers

Representative Reference:

Paul, H et al, Chem. Ber., 1965, 98, 1450
Huisgen, R et al, Angew. Chem., 1962, 74, 31.

Reverse 3-Oxazoline 2R- and 2S- enantiomers

Representative Reference:

Paul, H et al, Chem. Ber., 1965, 98, 1450
Huisgen, R et al, Angew. Chem., 1962, 74, 31.

4-Oxazoline 2R- and 2S- enantiomers

Representative Reference:

Minakata, S et al., Tet Lett., 2001, 42(51), 9019-9022.
Stamm, H et al., Chem. Ber., 1990, 123 (11), 2227-2230.

Reverse 4-Oxazoline 2R- and 2S- enantiomers

Representative Reference:

Minakata, S et al., Tet Lett., 2001, 42(51), 9019-9022.
Stamm, H et al., Chem. Ber., 1990, 123 (11), 2227-2230.

OXAZOLIDINES cis- and trans- racemates
2R,5R-, 2S,5S-, 2R,5S- and 2S,5R
diastereoisomers Representative Reference:

Schoenenberger, H et al., Archiv der Pharmazie
1975, 308(9), 717-719.

Reverse Oxazolidines

Representative Reference:

Schoenenberger, H et al., Archiv der Pharmazie
1975, 308(9), 717-719.

cis- and trans- racemates
2R,5R-, 2S,5S-, 2R,5S- and 2S,5R
diastereoisomers

Imidazole

Representative Reference:
Zhang, P-F et al., Synthesis 2001, 14, 2075-2077.

Reverse Imidazole

Representative Reference:

Zhang, P-F et al., Synthesis 2001, 14, 2075-2077.

2-Imidazoline 4R- and 4S- enantiomers

Representative Reference:

Molina, P et al.,Synlett., 1995, 10, 1031-1032.

Reverse 2-Imidazoline 4R- and 4S- enantiomers

Representative Reference:

Molina, P et al., Synlett., 1995, 10, 1031-1032.

3-Imidazolines

Representative References:

Iyoda, M et al., Chem. Lett., 1995, 12, 1133-1134.
Katzenellenbogen, J.A et al., Tet. Lett., 1997, 38(25), 4359-4362.

cis- and trans- racemates
2R,5R-, 2S,5S-, 2R,5S- and 2S,5R
diastereoisomers

Reverse 3-Imidazolines

Representative References:

Iyoda, M et al., Chem. Lett.,1995, 12, 1133-1134.
Katzenellenbogen, J.A et al., Tet. Lett., 1997, 38(25), 4359-4362.

cis- and trans- racemates
2R,5R-, 2S,5S-, 2R,5S- and 2S,5R
diastereoisomers

Imidazolidines cis- and trans- racemates
2R,4R-, 2S,4S-, 2R,4S- and 2S,4R
diastereoisomers Representative References:

Achiwa, K et al Chem. Lett., 1981, 1213.

Reverse Imidazolidines

Representative References:

Achiwa, K et al Chem. Lett., 1981, 1213.

cis- and trans- racemates
2R,4R-, 2S,4S-, 2R,4S- and 2S,4R
diastereoisomers

Thiazole

Representative References:

Lhotak, P et al Collect Czech Chem., 1993, 58 (11), 2720-2728.

Reverse thiazole

Representative References:

Lhotak,P et al Collect Czech Chem., 1993, 58 (11), 2720-2728.

PYRIDYL SUBSTITUTED HETEROCYCLES USEFUL FOR TREATING OR PREVENTING HCV INFECTION

1. FIELD OF INVENTION

This application claims benefit under 35 U.S.C. § 119(e) to application Ser. No. 60/405,467, filed Aug. 23, 2002, application Ser. No. 60/417,837, filed Oct. 11, 2002 and application Ser. No. 60/471,373, filed May 15, 2003, the contents of which are incorporated herein by reference.

2. FIELD OF INVENTION

The present invention relates to pyridyl substituted heterocycles and compositions thereof useful for treating or preventing Hepatitis C virus (HCV) infections. In particular, the present invention relates to pyridyl substituted heterocycles and corresponding hydro isomers, compositions thereof and the use of such compounds and compositions to inhibit HCV replication and/or proliferation as a therapeutic approach towards the treatment and/or prevention of HCV infections in humans and animals.

3. BACKGROUND OF THE INVENTION

Hepatitis C virus (HCV) infection is a global human health problem with approximately 150,000 new reported cases each year in the United States alone. HCV is a single stranded RNA virus, which is the etiological agent identified in most cases of non-A, non-B post-transfusion and post-transplant hepatitis and is a common cause of acute sporadic hepatitis (Choo et al., *Science* 244:359, 1989; Kuo et al., *Science* 244:362, 1989; and Alter et al., in *Current Perspective in Hepatology*, p. 83, 1989). It is estimated that more than 50% of patients infected with HCV become chronically infected and 20% of those develop cirrhosis of the liver within 20 years (Davis et al., *New Engl. J. Med.* 321:1501, 1989; Alter et al., in *Current Perspective in Hepatology*, p. 83, 1989; Alter et al., *New Engl. J. Med.* 327:1899, 1992; and Dienstag *Gastroenterology* 85:430, 1983). Moreover, the only therapy available for treatment of HCV infection is interferon-α (INTRON® A, PEG-INTRON®A, Schering-Plough; ROFERON-A®, Roche). Most patients are unresponsive, however, and among the responders, there is a high recurrence rate within 6–12 months after cessation of treatment (Liang et al., *J. Med. Virol.* 40:69, 1993). Ribavirin, a guanosine analog with broad spectrum activity against many RNA and DNA viruses, has been shown in clinical trials to be effective against chronic HCV infection when used in combination with interferon-α (see, e.g., Poynard et al., *Lancet* 352:1426–1432, 1998; Reichard et al., *Lancet* 351:83–87, 1998), and this combination therapy has been recently approved (REBETRON, Schering-Plough). However, the response rate is still well below 50%. Therefore, additional compounds for treatment and prevention of HCV infection are needed.

4. SUMMARY OF THE INVENTION

In one aspect, the present invention provides pyridyl substituted heterocycles which are potent inhibitors of Hepatitis C virus ("HCV") replication and/or proliferation. In one embodiment, the compounds are pyridyl substituted heterocycles and B-ring hydro isomers thereof according to structural formula (I), having the following "core" and numbering convention:

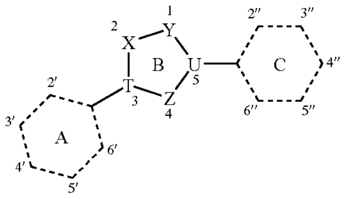

where the B ring is an aromatic or nonaromatic ring that includes from one to four heteroatoms. X, Y, Z are each, independently of one another selected from C, CH, N, $NR^{16}$, $NR^{18}$, S or O and U and T are each, independently of one another, selected from C, CH or N, provided that X and Y are not both O. One of rings "A" or "C" is a pyridyl ring and the other is a phenyl ring or a pyridyl ring. When "A" and/or "C" is a pyridyl, the ring may be attached to the illustrated "B" ring via any available carbon atom. Thus, the "A" and/or "C" rings may be pyrid-2-yl, pyrid-3-yl or pyrid-4-yl rings.

The "A" ring includes a substituent positioned ortho to the point of attachment (2'- or 6'-position) and may optionally include from 1 to 4 additional substituents. The nature of the substituents can vary broadly. Typical substituent groups useful for substituting the "A" ring include halo, fluoro, chloro, alkyl, alkylthio, alkoxy, alkoxycarbonyl, arylalkyloxycarbonyl, aryloxycarbonyl, cycloheteroalkyl, carbamoyl, haloalkyl, dialkylamino or sulfamoyl groups and substituted versions thereof. In one embodiment, the "A" ring is disubstituted at the 2'- and 6'-positions and unsubstituted at all other positions.

The "C" ring is substituted at the meta (3" or 5") position with a substituent of the formula $—NR^{11}C(O)R^{12}$, where $R^{11}$ is hydrogen, alkyl or methyl and $R^{12}$ is substituted alkyl, haloalkyl, dihalomethyl, dichloromethyl, cycloheteroalkyl or substituted cycloheteroalkyl. In one embodiment, $R^{12}$ is a haloalkyl or a dichloromethyl group. The "C" ring may also be optionally substituted at one or more of the 2"-, 4"-, 5"- and/or 6"-positions with the same or different halo groups.

As will be recognized by skilled artisans, the actual electron distribution or double bonding pattern of the "B" ring will depend upon the identities of substituents X, Y, Z, T and/or U. As illustrated, structural formula (I) is specifically intended to include at least the following six structures:

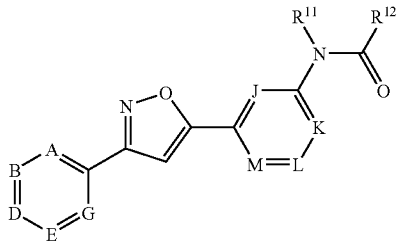
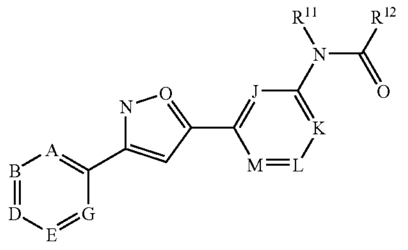
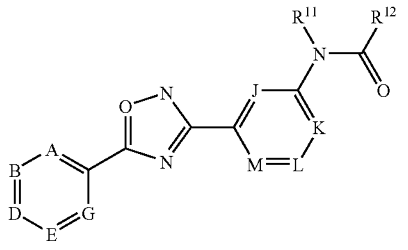
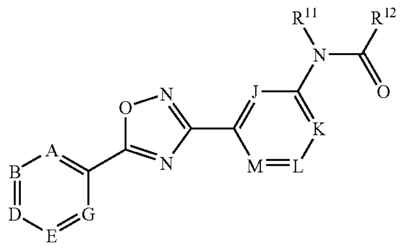
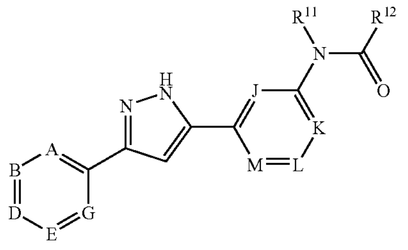
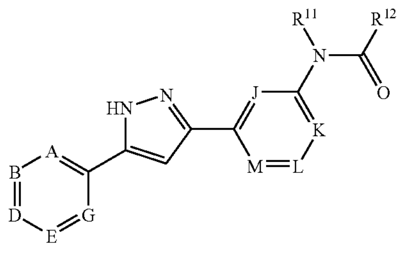
-continued
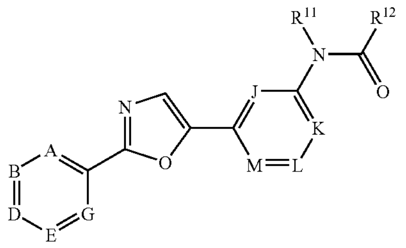
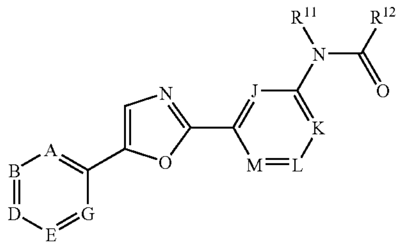
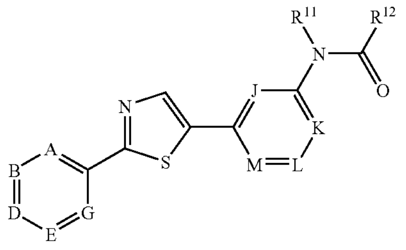
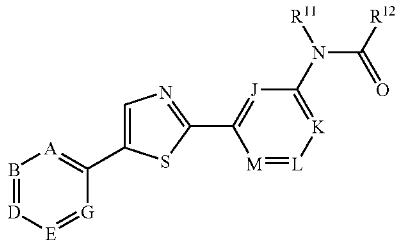
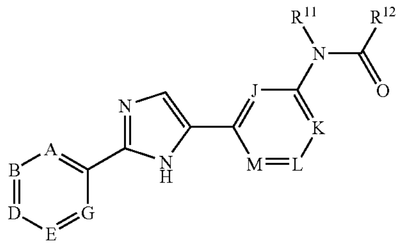
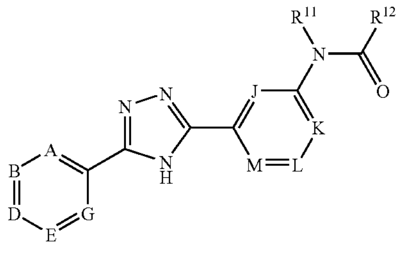

-continued
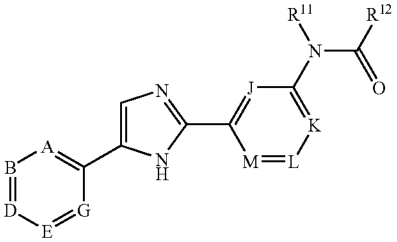
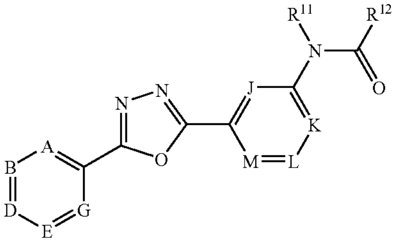
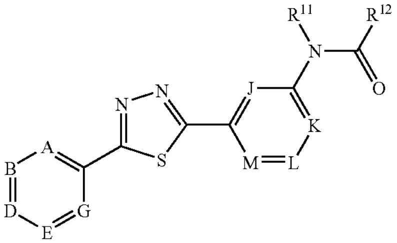
wherein A, B, D, E, G, J, K, L, M, $R^{11}$ and $R^{12}$ are defined infra.
As illustrated, structural formula (I) is specifically intended to include, for example, at least the following B-ring hydro isomers:
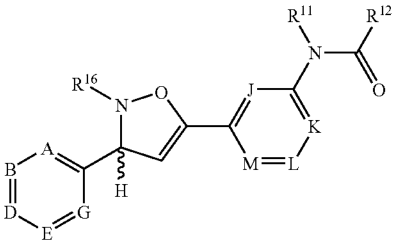
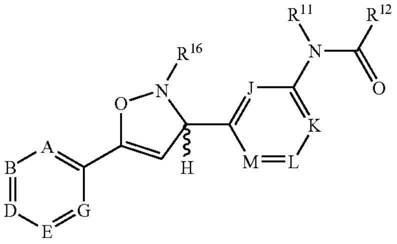
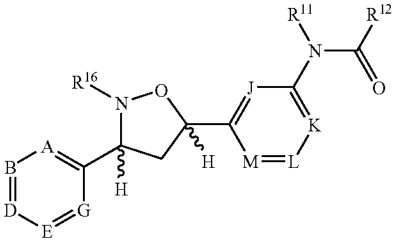
-continued
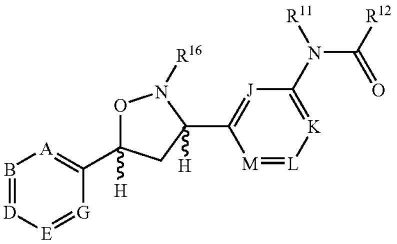
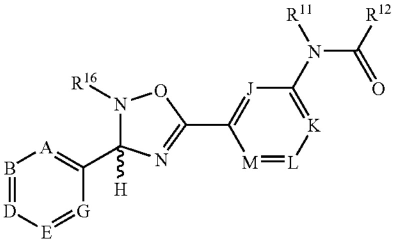
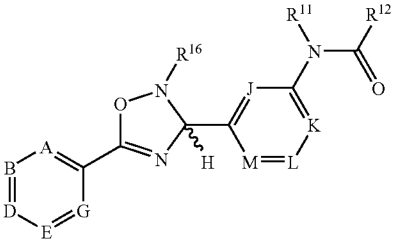
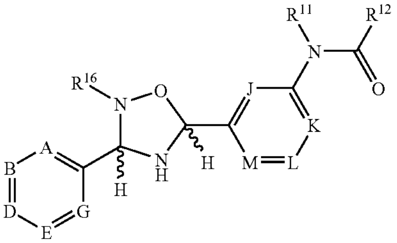
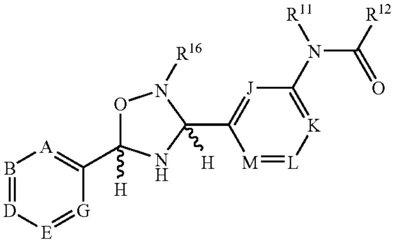
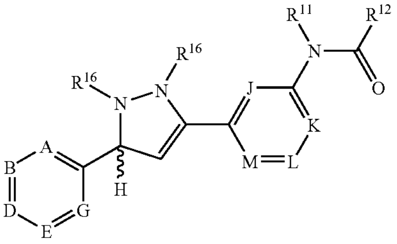

-continued

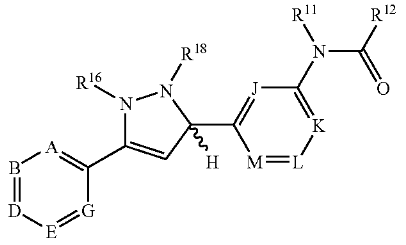

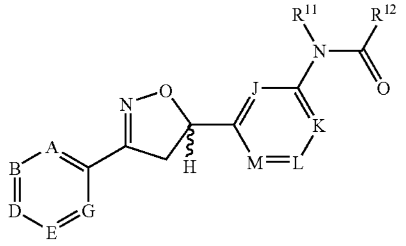

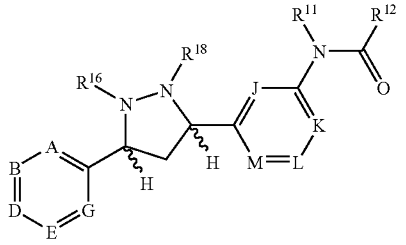

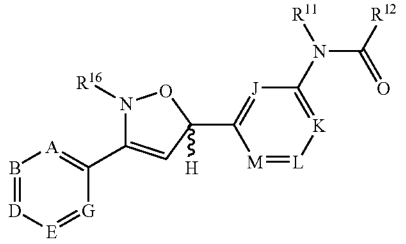

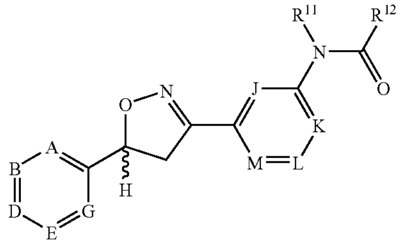

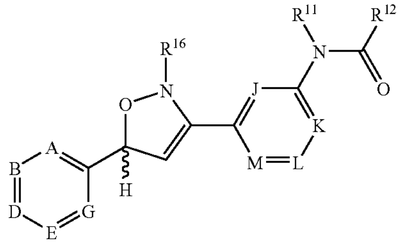

wherein A, B, D, E, G, J, K, L, M, $R^{11}$, $R^{12}$, $R^{16}$ and $R^{18}$ are defined infra.

In another aspect, the present invention provides compositions comprising the compounds of the invention. The compositions generally comprise a pyridyl substituted heterocycle or a hydro isomer (as discussed throughout the specification) of the invention or a salt, hydrate, solvate or N-oxide thereof and a suitable excipient, carrier or diluent. The composition may be formulated for veterinary uses or for use in humans.

The compounds of the invention are potent inhibitors of HCV replication and/or proliferation. Accordingly, in still another aspect, the present invention provides methods of inhibiting HCV replication and/or proliferation, comprising contacting a Hepatitis C virion with an amount of a compound or composition of the invention effective to inhibit HCV replication and/or proliferation. The methods may be practiced in vitro or in vivo, and may be used as a therapeutic approach towards the treatment and/or prevention of HCV infections.

In a final aspect, the present invention provides methods of treating and/or preventing HCV infections. The methods generally involve administering to a subject that has an HCV infection or that is at risk of developing an HCV infection an amount of a compound or composition of the invention effective to treat or prevent the HCV infection. The method may be practiced in animals in veterinary contexts or in humans.

5. BRIEF DESCRIPTION OF THE FIGS

FIG. 1 provides exemplary compounds of the invention; and

Figure 63:
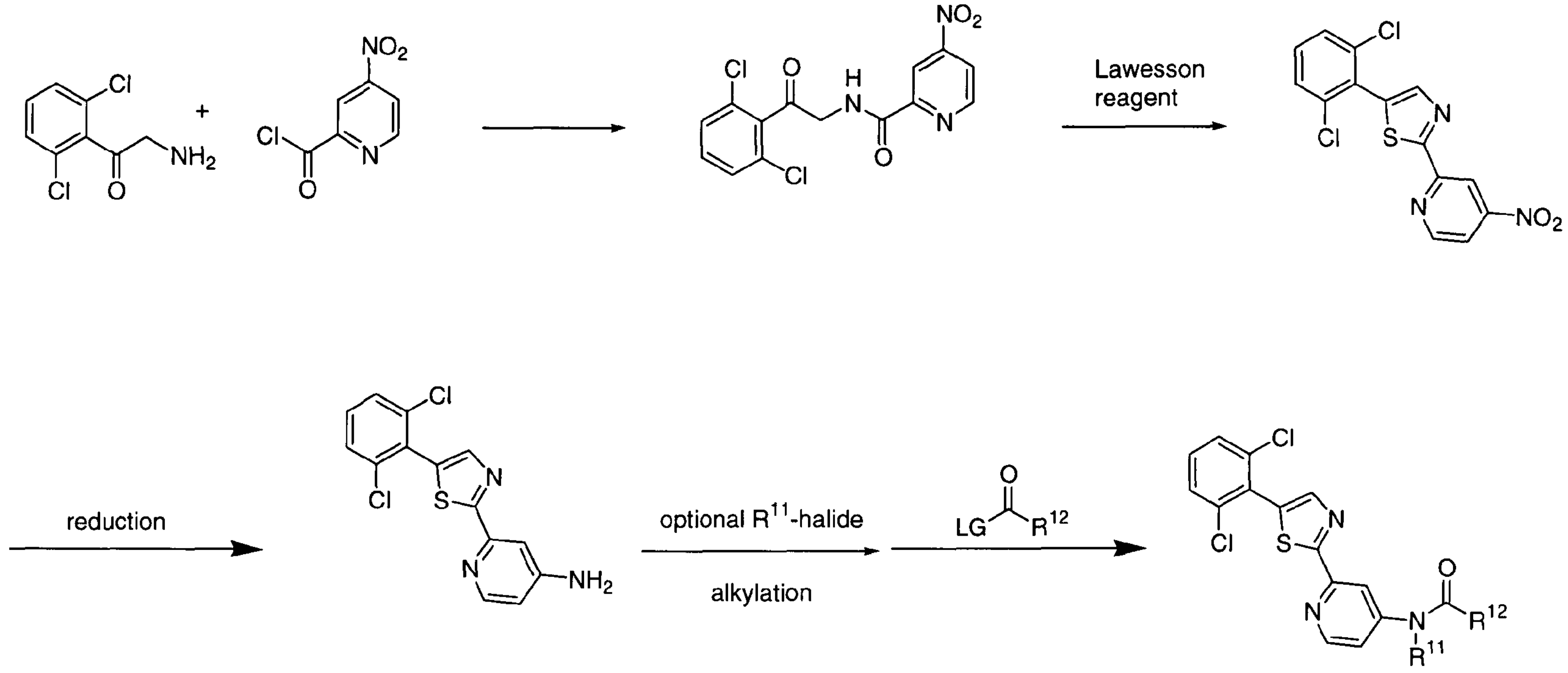

FIGS. 2–63 provide exemplary synthetic schemes for synthesizing the compounds of the invention.

6. DETAILED DESCRIPTION OF THE PREFERRED EMBODIMENTS

6.1 Definitions

As used herein, the following terms are intended to have the following meanings:

"Alkyl," by itself or as part of another substituent, refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. Preferably, an alkyl group comprises from 1 to 15 atoms ($C_1$–$C_{15}$ alkyl), more preferably from 1 to 10 carbon atoms ($C_1$–$C_{10}$ alkyl) and even more preferably from 1 to 6 carbon atoms ($C_1$–$C_6$ alkyl or lower alkyl).

"Alkanyl," by itself or as part of another substituent, refers to a saturated branched, straight-chain or cyclic alkyl radical derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl," by itself or as part of another substituent, refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl buta-1,3-dien-2-yl, cyclobut-1-en-1-yl, cyclobut-1-en-3-yl, cyclobuta-1,3-dien-1-yl, etc.; and the like.

"Alkynyl," by itself or as part of another substituent refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Alkoxy," by itself or as part of another substituent, refers to a radical of the formula —$OR^{30}$, where $R^{30}$ is an alkyl or cycloalkyl group as defined herein. Representative examples alkoxy groups include, but are not limited to, methoxy, ethoxy, propoxy, isopropoxy, butoxy, tert-butoxy, cyclopropyloxy, cyclopentyloxy, cyclohexyloxy and the like.

"Alkoxycarbonyl," by itself or as part of another substituent, refers to a radical of the formula —C(O)-alkoxy, where alkoxy is as defined herein.

"Alkylthio," by itself or as part of another substituent, refers to a radical of the formula —$SR^{31}$, where $R^{31}$ is an alkyl or cycloalkyl group as defined herein. Representative examples include, but are not limited to, methylthio, ethylthio, propylthio, isopropylthio, butylthio tert-butylthio, cyclopropylthio, cyclopentylthio, cyclohexylthio, and the like.

"Aryl," by itself or as part of another substituent, refers to a monovalent aromatic hydrocarbon group derived by the removal of one hydrogen atom from a single carbon atom of a parent aromatic ring system, as defined herein. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. Preferably, an aryl group comprises from 6 to 20 carbon atoms ($C_6$–$C_{20}$ aryl), more preferably from 6 to 15 carbon atoms ($C_6$–$C_{15}$ aryl) and even more preferably from 6 to 10 carbon atoms ($C_6$–$C_{10}$ aryl).

"Arylalkyl," by itself or as part of another substituent, refers to an acyclic alkyl group in which one of the hydrogen atoms bonded to a carbon atom, typically a terminal or $sp^3$ carbon atom, is replaced with an aryl group as, as defined herein. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. Preferably, an arylalkyl group is ($C_6$–$C_{30}$) arylalkyl, e.g., the alkanyl, alkenyl or alkynyl moiety of the arylalkyl group is ($C_1$–$C_{10}$) alkyl and the aryl moiety is ($C_6$–$C_{20}$) aryl, more preferably, an arylalkyl group is ($C_6$–$C_{20}$) arylalkyl, e.g., the alkanyl, alkenyl or alkynyl moiety of the arylalkyl group is ($C_1$–$C_8$) alkyl and the aryl moiety is ($C_6$–$C_{12}$) aryl, and even more preferably, an arylalkyl group is ($C_6$–$C_{15}$) arylalkyl, e.g., the alkanyl, alkenyl or alkynyl moiety of the arylalkyl group is ($C_1$–$C_5$) alkyl and the aryl moiety is ($C_6$–$C_{10}$) aryl.

"Aryloxy," by itself or as part of another substituent, refers to a radical of the formula —O-aryl, where aryl is as defined herein.

"Arylalkyloxy, by itself or as part of another substituent, refers to a radical of the formula —O-arylalkyl, where arylalkyl is as defined herein.

"Aryloxycarbonyl," by itself or as part of another substituent, refers to a radical of the formula —C(O)—O-aryl, where aryl is as defined herein.

"Carbamoyl," by itself or as part of another substituent, refers to a radical of the formula —$C(O)NR^{32}R^{33}$, where $R^{32}$ and $R^{33}$ are each, independently of one another, selected from the group consisting of hydrogen, alkyl and cycloalkyl as defined herein, or alternatively, $R^{32}$ and $R^{33}$, taken together with the nitrogen atom to which they are bonded, form a cycloheteroalkyl ring as defined herein.

"Compounds of the invention" refers to compounds encompassed by the various descriptions and generic formulae disclosed herein. The compounds of the invention may be identified by either their chemical structure and/or chemical name. When the chemical structure and chemical name conflict, the chemical structure is determinative of the identity of the compound. The compounds of the invention may contain one or more chiral centers and/or double bonds and therefore, may exist as stereoisomers, such as double-bond isomers (i.e., geometric isomers), rotamers, enantiomers or diastereomers. Accordingly, when stereochemistry at chiral centers is not specified, the chemical structures depicted herein encompass all possible configurations at those chiral centers including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds of the invention may also exist in several tautomeric forms including the enol form, the keto form and mixtures thereof. Accordingly, the chemical structures depicted herein encompass all possible tautomeric forms of the illustrated compounds. The compounds of the invention may also include isotopically labeled compounds where one or more atoms have an atomic mass different from the atomic mass conventionally found in nature. Examples of isotopes that may be incorporated into the compounds of the invention include, but are not limited to, $^2H$, $^3H$, $^{13}C$, $^{14}C$, $^{15}N$, $^{18}O$, $^{17}O$, $^{31}P$, $^{32}P$, $^{35}S$, $^{18}F$ and $^{36}Cl$. Compounds of the invention may exist in unsolvated forms as well as solvated forms, including hydrated forms and as N-oxides. In general, the hydrated, solvated and N-oxide forms are within the scope of the present invention. Certain compounds of the present invention may exist in multiple crystalline or amorphous forms. In general, all physical forms are equivalent for the uses contemplated by the present invention and are intended to be within the scope of the present invention.

"Cycloalkyl," by itself or as part of another substituent, refers to a saturated or unsaturated cyclic alkyl radical, as defined herein. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane, and the like. Preferably, the cycloalkyl group comprises from 3 to 10 ring atoms ($C_3$–$C_{10}$ cycloalkyl) and more preferably from 3 to 7 ring atoms ($C_3$–$C_7$ cycloalkyl).

"Cycloheteroalkyl" by itself or as part of another substituent, refers to a saturated or unsaturated cyclic alkyl radical in which one or more carbon atoms (and optionally any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, azirines, thiiranes, imidazolidine, morpholine, piperazine, piperidine, pyrazolidine, pyrrolidone, quinuclidine, and the like. Preferably, the cycloheteroalkyl group comprises from 3 to 10 ring atoms (3–10 membered cycloheteroalkyl) and more preferably from 3 to 7 ring atoms (3–7 membered cycloheteroalkyl).

"Dialkylamino," by itself or as part of another substituent, refers to a radical of the formula —$NR^{34}R^{35}$, where $R^{34}$ and $R^{35}$ are each, independently of one another, selected from the group consisting of alkyl and cycloalkyl, as defined herein. Representative examples of dialkylamino groups include, but are not limited to, dimethylamino, methylethylamino, di-(1-methylethyl)amino, (cyclohexyl)(methyl) amino, (cyclohexyl)(ethyl)amino, (cyclohexyl)(propyl) amino and the like.

"Halogen" or "Halo," by themselves or as part of another substituent refer to a fluoro, chloro, bromo and/or iodo radical.

"Haloalkyl," by itself or as part of another substituent, refers to an alkyl group as defined herein in which one or more of the hydrogen atoms is replaced with a halo group. The term "haloalkyl" is specifically meant to include monohaloalkyls, dihaloalkyls, trihaloalkyls, etc. up to perhaloalkyls. The halo groups substituting a haloalkyl group can be the same, or they can be different. For example, the expression "($C_1$–$C_2$) haloalkyl" includes 1-fluoromethyl, 1,1-fluoro-2-chloriethyl difluoromethyl, trifluoromethyl, 1-fluoroethyl, 1,1-difluoroethyl, 1,2-difluoroethyl, 1,1,1-trifluoroethyl, perfluoroethyl, etc.

"Heteroaryl," by itself or as part of another substituent, refers to a monovalent heteroaromatic radical derived by the removal of one hydrogen atom from a single atom of a parent heteroaromatic ring systems, as defined herein. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group comprises from 5 to 20 ring atoms (5–20 membered heteroaryl), more preferably from 5 to 10 ring atoms (5–10 membered heteroaryl). Preferred heteroaryl groups are those derived from thiophene, pyrrole, benzothiophene, benzofuran, indole, pyridine, quinoline, imidazole, oxazole and pyrazine.

"Heterocycle" refers to those compounds encompassed by the invention defined by the "B-ring" as depicted herein. Such compounds can be aromatic or nonaromatic (hydro isomers). The B-ring has the general formula:

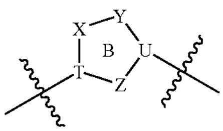

that includes from one to four heteroatoms, wherein X, Y, Z are each, independently of one another, C, CH, N, $NR^{16}$, $NR^{18}$, S or O; and U and T are each, independently of one another, C, CH or N. $R^{16}$ and $R^{18}$ are each, independently of one another, selected from the group consisting of hydrogen, lower alkyl, substituted lower alkyl, lower heteroalkyl, substituted lower heteroalkyl, cycloalkyl, substituted cycloalkyl, cycloheteroalkyl, substituted cycloheteroalkyl, lower haloalkyl, monohalomethyl, dihalomethyl, trihalomethyl, trifluoromethyl, lower alkylthio, substituted lower alkylthio, lower alkoxy, substituted lower alkoxy, methoxy, substituted methoxy, lower heteroalkoxy, substituted lower heteroalkoxy, cycloalkoxy, substituted cycloalkoxy, cycloheteroalkoxy, substituted cycloheteroalkoxy, lower haloalkoxy, monohalomethoxy, dihalomethoxy, trihalomethoxy, trifluoromethoxy, lower di- or monoalkylamino, substituted lower di- or monoalkylamino, aryl, substituted aryl, aryloxy, substituted aryloxy, phenoxy, substituted phenoxy, arylalkyl, substituted arylalkyl, arylalkyloxy, substituted arylalkyloxy, benzyl, benzyloxy, heteroaryl, substituted heteroaryl, heteroaryloxy, substituted heteroaryloxy, heteroarylalkyl, substituted heteroarylalkyl, heteroarylalkyloxy, substituted heteroarylalkyloxy, carboxyl, lower alkoxycarbonyl, substituted lower alkoxycarbonyl, aryloxycarbonyl, substituted aryloxycarbonyl, arylalkyloxycarbonyl, substituted arylalkyloxycarbonyl, carbamate, substituted carbamate, carbamoyl, substituted carbamoyl, sulfamoyl, substituted sulfamoyl and a group of the formula -L-$R^{17}$, where "L" is a linker and $R^{17}$ is cycloalkyl, substituted cycloalkyl, cycloheteroalkyl or substituted cycloheteroalkyl. The linker may be any group of atoms suitable for attaching the $R^{17}$ moiety to the nitrogen atom. Suitable linkers include, but are not limited to, moieties selected from the group consisting of —$(CH_2)_{1-6}$—, S, —C(O)—, —$SO_2$—, —NH—, —C(O)—$SO_2$NH— and combinations thereof.

Suitable heterocycles include, for example, isoxazoles, pyrazoles, oxadiazoles, oxazoles, thiazoles, imidazoles, triazoles, thiadiazoles and hydro isomers thereof. Suitable hydro isomers of the afore-mentioned heterocyclic compounds include, for example, dihydro isomers as well as tetrahydro isomers. Such hydro isomers include, for example, 2-isoxazoline, 3-isoxazoline, 4-isoxazolines, isoxazolidines, 1,2-pyrazolines, 1,2-pyrazolidines, (3H)-dihydro-1,2,4-oxadiazoles, (5H)-dihydro-1,2,4-oxadiazoles, oxazolines, oxazolidines, (3H)-dihydrothiazoles, (5H)-dihydrothiazoles, thiazolidines (tetrahydrothiazoles), (3H)-dihydrotriazoles, (5H)-dihydrotriazoles, triazolidines(tetrahydrotriazoles), dihydro-oxadiazoles, tetrahydro-oxadiazoles, (3H)-dihydro-1,2,4-thiadiazoles, (5H)-dihydro-1,2,4-thiadiazoles, 1,2,4-thiadiazolidines (tetrahydrothiadiazoles), (3H)-dihydroimidazoles, (5H)-dihydroimidazoles and tetrahydroimidazoles.

"Parent Aromatic Ring System" refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Parent Heteroaromatic Ring System" refers to a parent aromatic ring system in which one or more carbon atoms (and optionally any associated hydrogen atoms) are each independently replaced with the same or different heteroatom. Typical heteroatoms to replace the carbon atoms include, but are not limited to, N, P, O, S, Si, etc. Specifically included within the definition of "parent heteroaromatic ring system" are fused ring systems in which one or more of the rings are aromatic and one or more of the rings are saturated or unsaturated, such as, for example, arsindole, benzodioxan, benzofuran, chromane, chromene, indole, indoline, xanthene, etc. Typical parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene and the like.

"Pharmaceutically acceptable salt" refers to a salt of a compound of the invention which is made with counterions understood in the art to be generally acceptable for pharmaceutical uses and which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine, morpholine, piperidine, dimethylamine, diethylamine and the like. Also included are salts of amino acids such as arginates and the like, and salts of organic acids like glucurmic or galactunoric acids and the like (see, e.g., Berge et al., 1977, *J. Pharm. Sci.* 66:1–19).

"Pharmaceutically acceptable vehicle" refers to a diluent, adjuvant, excipient or carrier with which a compound of the invention is administered.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry,* 3$^{rd}$ Ed., 1999, John Wiley & Sons, NY and Harrison et al., *Compendium of Synthetic Organic Methods*, Vols. 1–8, 1971–1996, John Wiley & Sons, NY. Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxylprotecting groups include, but are not limited to, those where the hydroxyl group is either acylated (e.g., methyl and ethyl esters, acetate or propionate groups or glycol esters) or alkylated such as benzyl and trityl ethers, as well as alkyl ethers, tetrahydropyranyl ethers, trialkylsilyl ethers (e.g., TMS or TIPPS groups) and allyl ethers.

"Prodrug" refers to a derivative of an active compound (drug) that undergoes a transformation under the conditions of use, such as within the body, to release an active drug. Prodrugs are frequently, but not necessarily, pharmacologically inactive until converted into the active drug. Prodrugs are typically obtained by masking a functional group in the drug believed to be in part required for activity with a progroup (defined below) to form a promoiety which undergoes a transformation, such as cleavage, under the specified conditions of use to release the functional group, and hence the active drug. The cleavage of the promoiety may proceed spontaneously, such as by way of a hydrolysis reaction, or it may be catalyzed or induced by another agent, such as by an enzyme, by light, by acid, or by a change of or exposure to a physical or environmental parameter, such as a change of temperature. The agent may be endogenous to the conditions of use, such as an enzyme present in the cells to which the prodrug is administered or the acidic conditions of the stomach, or it may be supplied exogenously. In a specific embodiment, the term prodrug includes hydro isomers of the compounds of the invention. Such hydro isomers encompassed by the invention can be oxidized under physiological conditions to the corresponding aromatic ring system.

A wide variety of progroups, as well as the resultant promoieties, suitable for masking functional groups in active compounds to yield prodrugs are well-known in the art. For example, a hydroxyl functional group may be masked as a sulfonate, ester or carbonate promoiety, which may be hydrolyzed in vitro to provide the hydroxyl group. An amino functional group may be masked as an amide, imine, phosphinyl, phosphonyl, phosphoryl or sulfenyl promoiety, which may be hydrolyzed in vivo to provide the amino group. A carboxyl group may be masked as an ester (including silyl esters and thioesters), amide or hydrazide promoiety, which may be hydrolyzed in vivo to provide the carboxyl group. Other specific examples of suitable progroups and their respective promoieties will be apparent to those of skill in the art.

"Progroup" refers to a type of protecting group that, when used to mask a functional group within an active drug to form a promoiety, converts the drug into a prodrug. Progroups are typically attached to the functional group of the drug via bonds that are cleavable under specified conditions of use. Thus, a progroup is that portion of a promoiety that cleaves to release the functional group under the specified conditions of use. As a specific example, an amide promoiety of the formula —NH—C(O)$CH_3$ comprises the progroup —C(O)$CH_3$.

"Silyl ether" refers to a type of protecting group that, when used to mask a hydroxyl group within an active drug to form a promoiety, converts the drug into a prodrug. Silyl ethers are known in the art and refer to a removable group which will prevent a hydroxy group from participating in a reaction performed on the molecule. Such groups are discussed by T. W. Greene in chapters 2 and 7 of Protective Groups in Organic Synthesis, John Wiley and Sons, New York, 1981, and by J. W. Barton in chapter 2 of Protective Groups in Organic Chemistry, J. F. W. McOmie, ed., Plenum Press, New York, 1973, which are incorporated herein by reference in their entirety. Silyl ethers include, for example, trimethylsilyl, triethylsilyl, t-butyl dimethyl silyl and methyl-diisopropylsilyl groups.

"Substituted," when used to modify a specified group or radical, means that one or more hydrogen atoms of the specified group or radical are each, independently of one another, replaced with the same or different substituent(s). Typical substituents include, but are not limited to, -M, —$R^{40}$, —$O^-$, =O, —$OR^{40}$, —$SR^{40}$, —$S^-$, =S, —$NR^{40}R^{40}$, —$CM_3$, —$CF_3$, —CN, —OCN, —SCN, —NO, —$NO_2$, =$N_2$, —$N_3$, —$S(O)_2O^-$, —$S(O)_2OH$, —$S(O)_2{}^{40}$, —$OS(O_2)O^-$, —$OS(O)_2R^{40}$, —$P(O)(O^-)_2$, —$P(O)(OR^{40})(O—)$, —$OP(O)(OR^{40})(OR^{41})$, —$C(O)R^{40}$, —$C(S)R^{40}$, —$C(O)OR^{40}$, —$C(O)NR^{40}R^{41}$, —$C(O)O^-$, —$C(S)OR^{40}$, —$NR^{42}C(O)NR^{40}R^{41}$, —$NR^{42}C(S)NR^{40}R^{41}$, —$NR^{42}C(NR^{43})NR^{40}R^{41}$ and —$C(NR^{42})NR^{40}R^{41}$ where each M is independently a halogen; $R^{40}$, $R^{41}$, $R^{42}$, $R^{43}$ and $R^{44}$ are each, independently of one another, selected from the group consisting of hydrogen, alkyl, substituted alkyl, alkoxy, substituted alkoxy, cycloalkyl, substituted cycloalkyl, cycloheteroalkyl, substituted cycloheteroalkyl, —$NR^{45}R^{46}$, —$C(O)R^{45}$ and —$S(O)_2R^{45}$, or alternatively, $R^{40}$ and $R^{41}$ and/or $R^{45}$ and $R^{46}$, taken together with the respective nitrogen atoms to which they are bonded, form a cycloheteroalkyl or substituted cycloheteroalkyl ring as defined herein.

"Sulfamoyl," by itself or as part of another substituent, refers to a radical of the formula —$S(O)_2NR^{36}R^{37}$, where $R^{36}$ and $R^{37}$ are each, independently of one another, hydrogen, alkyl or cycloalkyl as defined herein, or alternatively, $R^{36}$ and $R^{37}$, taken together with the nitrogen atom to which they are bonded, form a cycloheteroalkyl or substituted cycloheteroalkyl ring as defined herein.

7. The Compounds

In one embodiment, the compounds of the invention are pyridyl-substituted heterocycles and B-ring hydro isomers according to structural formula (I):

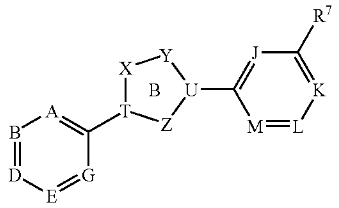

(I)

or pharmaceutically acceptable salts, hydrates, solvates or N-oxides thereof, wherein:

the B ring is an aromatic or nonaromatic ring that includes from one to four heteroatoms, wherein X, Y, Z are each, independently of one another selected from C, CH, N, $NR^{16}$, $NR^{18}$, S or O, provided that X and Y are not both O;

U and T are each, independently of one another, selected from C, CH or N;

Z is N or —CH—;

A is N or —$CR^2$—;

B is N or —$CR^3$—;

D is N or —$CR^4$—;

E is N or —$CR^5$—;

G is N or —$CR^6$—;

J is N or —$CR^{14}$—;

K is N or —$CR^8$—;

L is N or —$CR^9$—;

M is N or —$CR^{10}$—;

$R^2$ and $R^6$ are each, independently of one another, selected from the group consisting of hydrogen, halo, fluoro, chloro, alkyl, methyl, substituted alkyl, alkylthio, substituted alkylthio, alkoxy, methoxy, i-propoxy, substituted alkoxy, alkoxycarbonyl, substituted alkoxycarbonyl, arylalkyloxycarbonyl, substituted arylalkyloxycarbonyl, aryloxycarbonyl, substituted aryloxycarbonyl, cycloheteroalkyl, substituted cycloheteroalkyl, carbamoyl, substituted carbamoyl, haloalkyl, triflouromethyl, sulfamoyl, substituted sulfamoyl and silyl ether, provided that one of $R^2$ and $R^6$ is other than hydrogen;

$R^3$ and $R^5$ are each, independently of one another, selected from the group consisting of hydrogen, halo, chloro, alkyl, substituted alkyl, alkylthio, substituted alkylthio, alkoxy, substituted alkoxy, alkoxycarbonyl, substituted alkoxycarbonyl, arylalkyloxycarbonyl, substituted arylalkyloxycarbonyl, aryloxycarbonyl, substituted aryloxycarbonyl, cycloheteroalkyl, substituted cycloheteroalkyl, carbamoyl, substituted carbamoyl, haloalkyl, sulfamoyl and substituted sulfamoyl;

$R^4$ is selected from the group consisting of hydrogen, halo, alkyl, substituted alkyl, alkylthio, substituted alkylthio, carbamoyl, substituted carbamoyl, alkoxy, substituted alkoxy, alkoxycarbonyl, substituted alkoxycarbonyl, arylalkyloxycarbonyl, substituted arylalkyloxycarbonyl, aryloxycarbonyl, substituted aryloxycarbonyl, dialkylamino, substituted dialkylamino, haloalkyl, sulfamoyl and substituted sulfamoyl;

$R^7$ is —$NR^{11}C(O)R^{12}$;

$R^8$, $R^9$, $R^{10}$ and $R^{14}$ are each, independently of one another, selected from the group consisting of hydrogen, halo and fluoro;

$R^{11}$ is hydrogen, alkyl or methyl; and $R^{12}$ is substituted alkyl, haloalkyl, halomethyl, dihalomethyl, dichloromethyl, cycloheteroalkyl or substituted cycloheteroalkyl;

$R^{16}$ and $R^{18}$ are each, independently of one another, selected from the group consisting of hydrogen, lower alkyl, substituted lower alkyl, lower heteroalkyl, substituted lower heteroalkyl, cycloalkyl, substituted cycloalkyl, cycloheteroalkyl, substituted cycloheteroalkyl, lower haloalkyl, monohalomethyl, dihalomethyl, trihalomethyl, trifluoromethyl, lower alkylthio, substituted lower alkylthio, lower alkoxy, substituted lower alkoxy, methoxy, substituted methoxy, lower heteroalkoxy, substituted lower heteroalkoxy, cycloalkoxy, substituted cycloalkoxy, cycloheteroalkoxy, substituted cycloheteroalkoxy, lower haloalkoxy, monohalomethoxy, dihalomethoxy, trihalomethoxy, trifluoromethoxy, lower di- or monoalkylamino, substituted lower di- or monoalkylamino, aryl, substituted aryl, aryloxy, substituted aryloxy, phenoxy, substituted phenoxy, arylalkyl, substituted arylalkyl, arylalkyloxy, substituted arylalkyloxy, benzyl, benzyloxy, heteroaryl, substituted heteroaryl, heteroaryloxy, substituted heteroaryloxy, heteroarylalkyl, substituted heteroarylalkyl, heteroarylalkyloxy, substituted heteroarylalkyloxy, carboxyl, lower alkoxycarbonyl, substituted lower alkoxycarbonyl, aryloxycarbonyl, substituted aryloxycarbonyl, arylalkyloxycarbonyl, substituted arylalkyloxycarbonyl, carbamate, substituted carbamate, carbamoyl, substituted carbamoyl, sulfamoyl, substituted sulfamoyl and a group of the formula -L-$R^{17}$, where "L" is a linker and $R^{17}$ is cycloalkyl, substituted cycloalkyl, cycloheteroalkyl or substituted cycloheteroalkyl.

with the provisos that:

(i) at least one of A, B, D, E, G, J, K, L or M is N;

(ii) no more than one of A, B, D, E or G is N; and (iii) no more than one of J, K, L or M is N.

In another embodiment, the compounds of the invention are pyridyl-substituted thiazoles and B-ring hydro isomers according to structural formula (II):

(II)

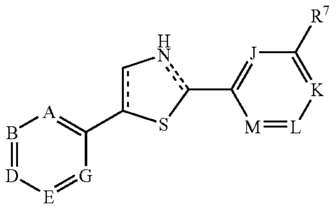

or pharmaceutically acceptable salts, hydrates, solvates or N-oxides thereof, wherein A, B, D, E, G, J, K, L, M and $R^7$ are as previously defined for structural formula (I) and subject to the same provisos and—represents either an aromatic or nonaromatic (hydro isomer) heterocyclic ring.

In one embodiment of the compounds of structural formula (I), Z is —CH— such that the compounds are isoxazoles or pyrazoles. In another embodiment of the compounds of structural formula (I), Z is N such that the compounds are oxadiazoles or azoles. In another embodiment, the compounds of structural formula (I) are isoxazoles. In a specific embodiment of isoxazoles, X is N and Y is O. In still another embodiment, the compounds of structural formula (I) are oxadiazoles.

In one embodiment of the compounds of structural formulae (I) and (II), A, B, D, E or G is N and one of J, K, L or M is N. In another embodiment, one of A, B, D, E or G is N and none of J, K, L or M is N. In still another embodiment, none of A, B, D, E or G is N and one of J, K, L or M is N. Preferably, in any of the previously-described embodiments of compounds formula (I) and/or (II), $R^7$ is —$NR^{11}C(O)R^{12}$, wherein $R^{11}$ is hydrogen or methyl and $R^{12}$ is —$CHCl_2$.

In another embodiment of the compounds of structural formulae (I) and (II), A is —$CR^2$—, G is —$CR^6$—, and $R^7$ is —$NR^{11}C(O)R^{12}$, where $R^{11}$ is hydrogen or methyl and $R^{12}$ is —$CHCl_2$. In a more specific embodiment, B is —$CR^3$—, D is N, E is —$CR^5$—, J is —$CR^{14}$—, K is —$CR^8$—, L is —$CR^9$—, M is —$CR^{10}$—, and $R^3$, $R^5$, $R^9$, $R^{10}$ and $R^{14}$ are each hydrogen. In another more specific embodiment, B is —$CR^3$—, D is —$CR^4$—, E is —$CR^5$—, J is —$CR^{14}$—, K is —$CR^8$—, L is —$CR^9$—, M is N and $R^3$, $R^4$, $R^5$, $R^8$, $R^9$ and $R^{14}$ are each hydrogen. In still another more specific embodiment, B is —$CR^3$—, D is —$CR^4$—, E is —$CR^5$—, J is —$CR^{14}$—, K is —$CR^8$—, L is N, M is —$CR^{10}$— and $R^3$, $R^4$, $R^5$, $R^8$, $R^{10}$ and $R^{14}$ are each hydrogen. Preferably, in the above embodiment, $R^2$ and $R^6$ are each, independently of one another, selected from the group consisting of chloro, fluoro, methyl, triflouromethyl, thiomethyl, methoxy, i-propoxy, N-morpholino and N-morpholinosulfamoyl. More preferably, $R^2$ and $R^6$ are each, independently of one another, selected from the group consisting of chloro, fluoro, methyl, triflouromethyl, methoxy and i-propoxy. In another embodiment, $R^2$ and $R^6$ are each the same or different halo. Preferably, in the above embodiments, X is N, Y is O and Z is —CH—.

In still another embodiment of the compounds of structural formulae (I) and (II), A is —$CR^2$—, G is —$CR^6$— and $R^7$ is —$NR^{11}C(O)R^{12}$, where $R^{11}$ is hydrogen or methyl and $R^{12}$ is —$CH_2I$. Preferably, $R^2$ and $R^6$ are each, independently of one another, selected from the group consisting of chloro, fluoro, methyl, triflouromethyl, thiomethyl, methoxy, i-propoxy, N-morpholino and N-morpholinosulfamoyl. More preferably, $R^2$ and $R^6$ are each, independently of one another, selected from the group consisting of chloro, fluoro, methyl, triflouromethyl, methoxy and i-propoxy. In another embodiment, $R^2$ and $R^6$ are each the same or different halo. Preferably, in the above embodiments, X is N, Y is O and Z is —CH—.

In still another embodiment of the compounds of structural formulae (I) and (II), A is —$CR^2$—, B is —$CR^3$—, $R^7$ is —$NR^{11}C(O)R^{12}$, where $R^{11}$ is hydrogen or methyl and $R^{12}$ is —$CHCl_2$. In a more specific embodiment, D is —$CR^4$—, G is —$CR^6$—, E is —$CR^5$—, J is —$CR^{14}$—, K is —$CR^8$—, L is —$CR^9$—, M is N and $R^4$, $R^5$, $R^6$, $R^8$, $R^9$ and $R^{14}$ are each hydrogen. In another more specific embodiment, D is —$CR^4$—, G is —$CR^6$—, E is —$CR^5$—, J is —$CR^{14}$—, K is —$CR^8$—, L is N, M is —$CR^{10}$— and $R^4$, $R^5$, $R^6$, $R^8$, $R^{10}$ and $R^{14}$ are each hydrogen. Preferably, $R^2$ and $R^6$ are each, independently of one another, selected from the group consisting of chloro, fluoro, methyl, triflouromethyl, thiomethyl, methoxy, i-propoxy, N-morpholino and N-morpholinosulfamoyl. More preferably, $R^2$ and $R^6$ are each, independently of one another, selected from the group consisting of one another chloro, fluoro, methyl, triflouromethyl, methoxy and i-propoxy. In another embodiment, $R^2$ and $R^6$ are each the same or different halo. Preferably, in the above embodiments, X is N, Y is O and Z is —CH—.

In still another embodiment of the compounds of structural formulae (I) and (II), A is —$CR^2$—, G is —$CR^6$— and $R^2$ and $R^6$ are each identical, provided that they are not hydrogen. In another embodiment, A is —$CR^2$—, B is —$CR^3$— and $R^2$ and $R^3$ are each identical, provided that they are not hydrogen. In still another embodiment, B is —$CR^3$—, E is —$CR^5$— and $R^3$ and $R^5$ are each identical, provided that they are not hydrogen. In still another embodiment, B is —$CR^3$—, D is —$CR^4$—, E is —$CR^5$—, J is —$CR^{14}$—, K is —$CR^8$— and $R^3$, $R^4$, $R^5$, $R^8$ and $R^{14}$ are each hydrogen. In still another embodiment, -D is —$CR^4$—, E is —$CR^5$—, G is $CR^6$, J is —$CR^{14}$—, K is —$CR^8$— and $R^4$, $R^5$, $R^6$, $R^8$ and $R^{14}$ are each hydrogen.

In further embodiments, the compounds of structural formula (I) and B ring hydro isomers thereof include a C ring that is a pyrid-3-yl.

In still further embodiments, the compounds of structural formula (I) and B ring hydro isomers thereof include a C ring that is a pyrid-4-yl.

In still other embodiments, the compounds of structural formula (I) are isoxazole compounds according to structural formulae (Ia), (Ib), (Ic), (Id) or (Ie):

(Ia)

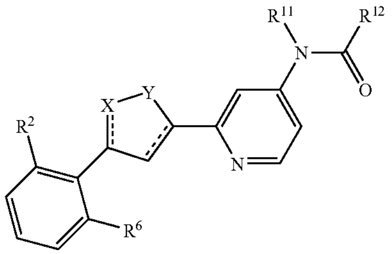

(Ib)

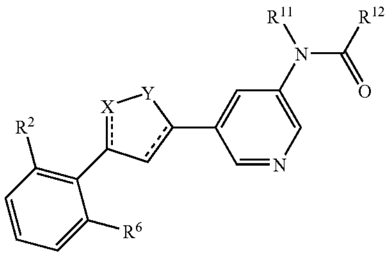

(Ic)

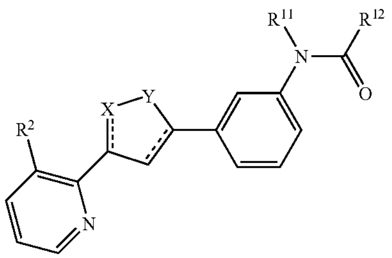

(Id)

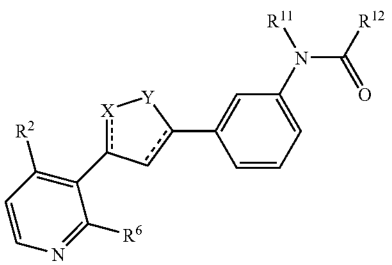

-continued (Ie)

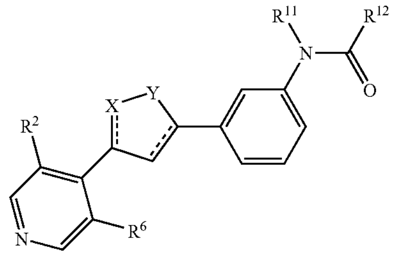

or pharmaceutically acceptable salts, hydrates or solvates thereof, wherein X, Y, $R^2$, $R^6$, $R^{11}$ and $R^{12}$ are as previously defined for structural formula (I) and—represents either an unsaturated bond (an aromatic heterocycle) or a saturated bond (a non aromatic heterocycle, e.g., a hydro isomer) of the B ring.

In one embodiment, the compounds of structural formulae (Ia), (Ib), (Ic), (Id) and (Ie) have, independently of one another, one or more features selected from the group consisting of:

X is O and Y is N;

X is N and Y is O;

$R^{11}$ is hydrogen;

$R^{12}$ is dichloromethyl;

$R^2$ and $R^6$ are each, independently of one another, selected from the group consisting of methyl, halo, fluoro, chloro, trifluoromethyl and methoxy; and $R^2$ and $R^6$ are each, independently of one another, selected from the group consisting of halo, fluoro and chloro.

In another aspect of the invention, X is N, Y is O, Z is CH, T and U are C (isoxazole ring), A is —$CR^2$—, G is —$CR^6$—.

In still another aspect of the invention, X is N, Y is O, Z is CH, T and U are C (isoxazole ring), A is —$CR^2$—, G is —$CR^6$—, wherein $R^6$ is piperazine or a substituted piperazine. Suitable substituted piperazine include, for example,

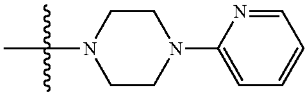,

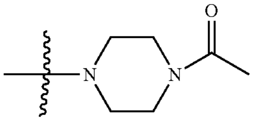, 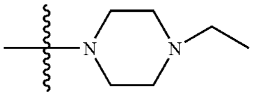,

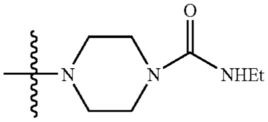 and 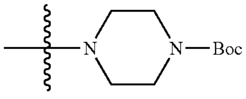

In still yet another aspect of the invention, X is N, Y is O, Z is $CH_2$, T and U are C (isoxazole ring), A is —$CR^2$—, G is —C—O—$R^6$—, such that $R^6$ is forms an ester, ether or silyl ether. Suitable $R^6$ groups that form esters, ethers or silyl ethers include, for example, alkyl, methyl, substituted alkyl, alkylthio, substituted alkylthio, alkoxy, methoxy, i-propoxy, substituted alkoxy, alkoxycarbonyl, substituted alkoxycarbonyl, arylalkyloxycarbonyl, substituted arylalkyloxycarbonyl, aryloxycarbonyl, substituted aryloxycarbonyl, cycloheteroalkyl, substituted cycloheteroalkyl, carbamoyl, substituted carbamoyl, haloalkyl, trifluoromethyl and silyl ethers.

Exemplary compounds of the invention are provided in FIG. 1 and Table 1.

Those of skill in the art will appreciate that the compounds of the invention described herein may include functional groups that can be masked with progroups to create prodrugs. Such prodrugs are usually, but need not be, pharmacologically inactive until converted into their active drug form. In the prodrugs of the invention, any available functional moiety may be masked with a progroup to yield a prodrug. Myriad progroups suitable for masking such functional groups to yield promoieties that are cleavable under the desired conditions of use are known in the art.

7.1 Methods of Synthesis

The compounds of the invention may be obtained via synthetic methods illustrated in FIGS. 2–7. It should be understood that in FIGS. 2–7, A, B, D, E, G, J, K, L, M and $R^7$ are as previously defined for structural formula (I) and subject to the same provisos.

Starting materials useful for preparing compounds of the invention and intermediates thereof are commercially available or can be prepared by well-known synthetic methods (see, e.g., Harrison et al., "Compendium of Synthetic Organic Methods", Vols. 1–8, John Wiley and Sons, 1971–1996; "Beilstein Handbook of Organic Chemistry," Beilstein Institute of Organic Chemistry, Frankfurt, Germany; Feiser et al., "Reagents for Organic Synthesis," Volumes 1–17, Wiley Interscience; Trost et al., "Comprehensive Organic Synthesis," Pergamon Press, 1991; "Theilheimer's Synthetic Methods of Organic Chemistry," Volumes 1–45, Karger, 1991; March, "Advanced Organic Chemistry," Wiley Interscience, 1991; Larock "Comprehensive Organic Transformations," VCH Publishers, 1989; Paquette, "Encyclopedia of Reagents for Organic Synthesis," John Wiley & Sons, 1995). Other methods for synthesizing the compounds described herein and/or starting materials are either described in the art or will be readily apparent to the skilled artisan. Alternatives to the reagents and/or protecting groups illustrated in FIGS. 2–7 may be found in the references provided above and in other compendiums well known to the skilled artisan. Guidance for selecting suitable protecting groups can be found, for example, in Greene & Wuts, "Protective Groups in Organic Synthesis," Wiley Interscience, 1999. Accordingly, the synthetic methods and strategy presented herein are illustrative rather than comprehensive.

Figure 2A:
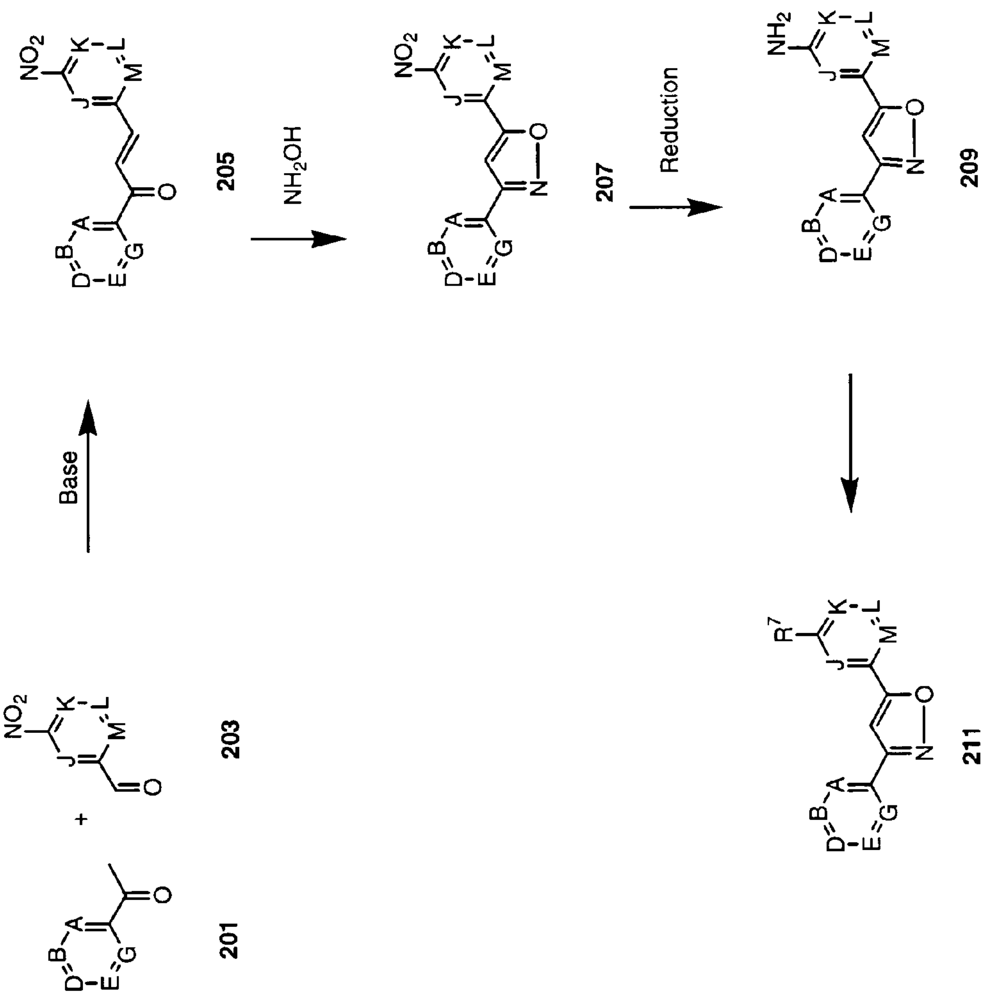
Figure 2B:
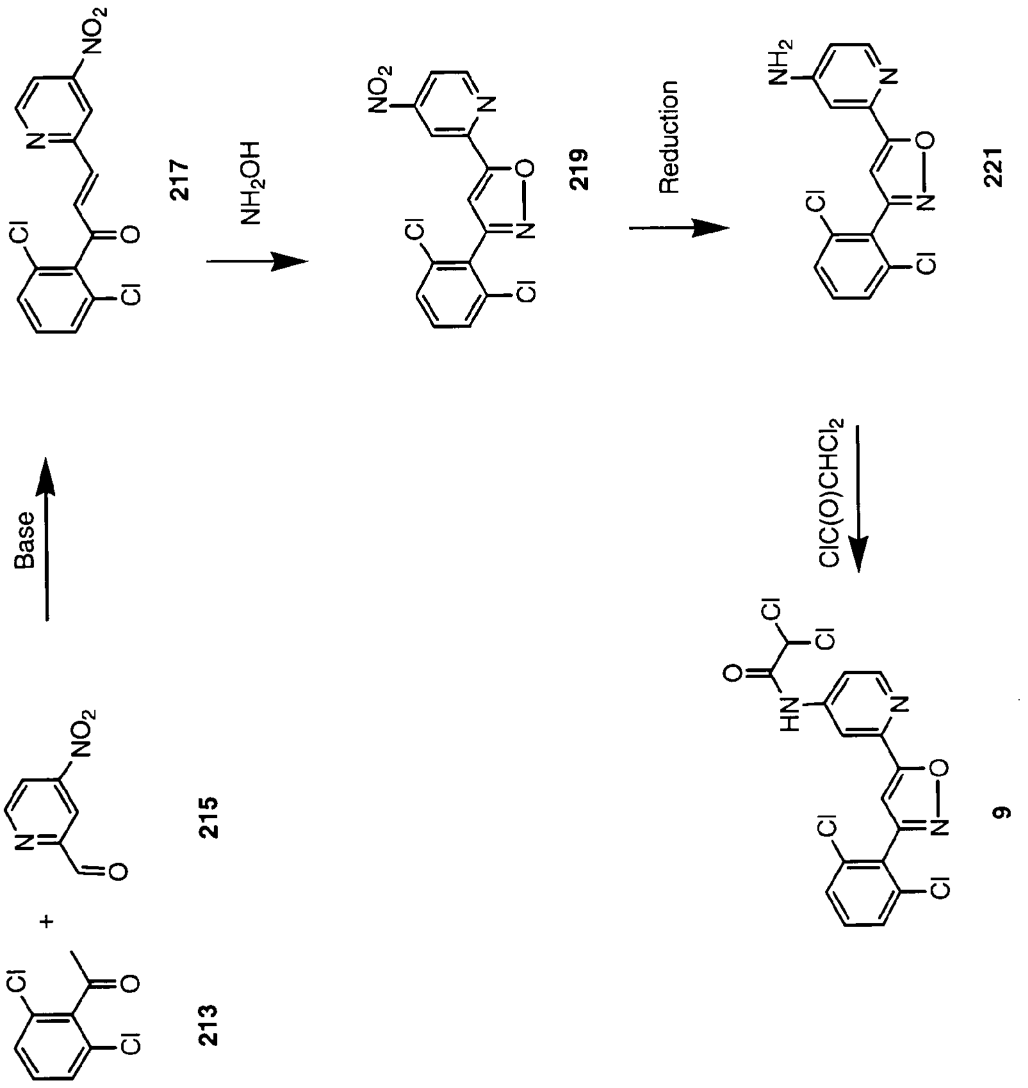

One method for synthesizing substituted isoxazoles according to structural formula (I) (when Z is —CH—) is provided in FIG. 2A. Referring to FIG. 2A, aldol condensation of methyl ketone 201 with benzaldehyde 203 under basic conditions, followed by in situ dehydration, provides α-β unsaturated enone 205, which may be readily converted to isoxazole 207 by treatment with hydroxylamine. Reduction of 207 yields the amino isoxazole 209, which may be transformed by a wide variety of methods well known to the skilled artisan to final product 211. A specific example of the synthetic method of FIG. 2A is illustrated for the preparation of isoxazole 9 in FIG. 2B.

Figure 3A:
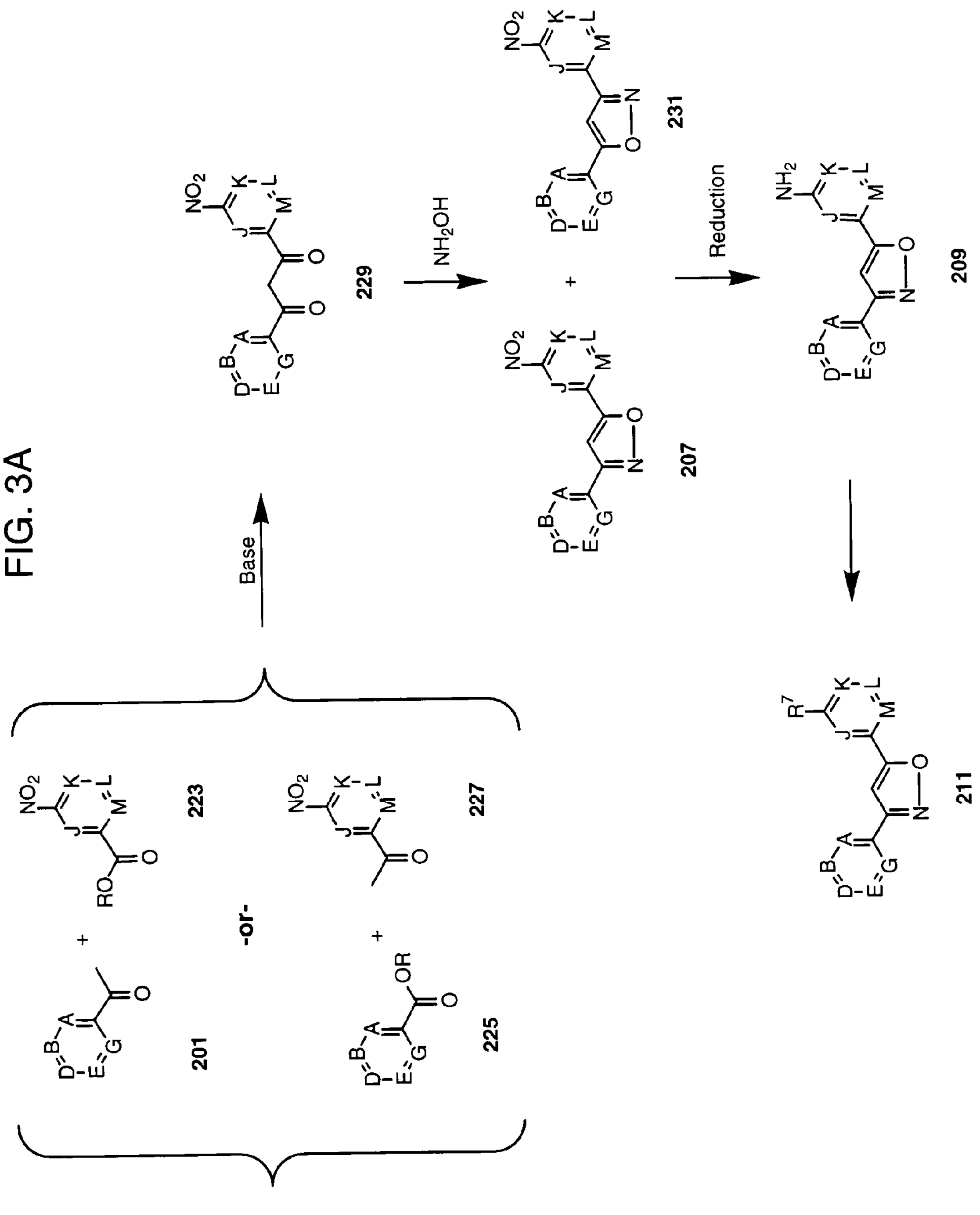
Figure 3B:
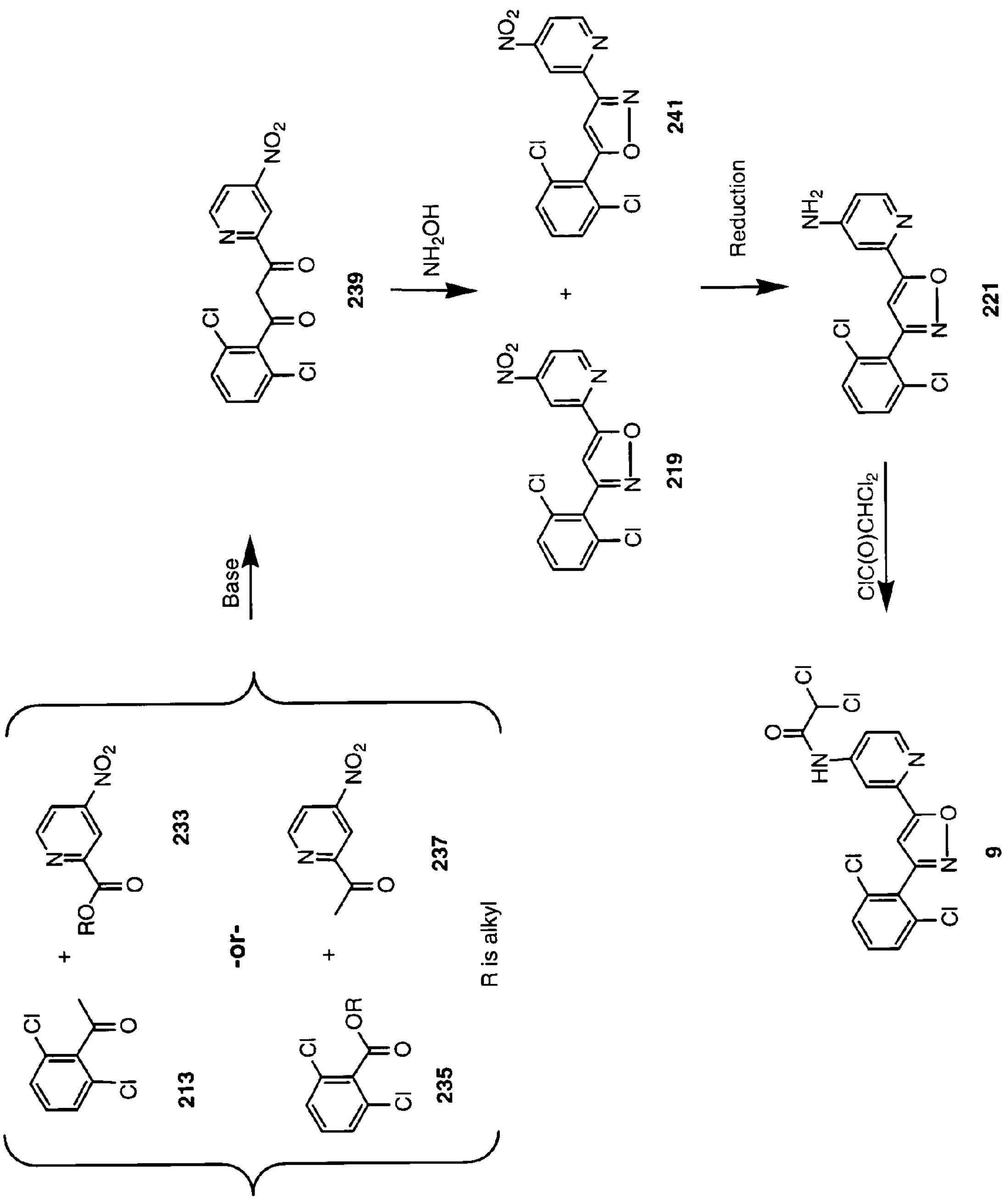

Another method for synthesizing substituted isoxazoles of structural formula (I) (when Z is —CH—) is provided in FIG. 3A. Claisen condensation of methyl ketone 201 with ester 223 under basic conditions provides 1,3 diketone 229, which may be converted to a mixture of isoxazoles 207 and 231 by treatment with hydroxylamine. As before, reduction of 207 yields the amino isoxazole 209, which may be transformed to the isoxazole 211 by well known synthetic methods. It should be noted that isoxazole 231 may be converted to the corresponding regioisomer of isoxazole 211 by the same synthetic pathway. A specific example of the synthetic method of FIG. 3A is illustrated for the preparation of isoxazole 9 in FIG. 3B.

In alternative embodiment of the pathway illustrated in FIG. 3A, ester 225 is condensed with methyl ketone 227 to provide 1,3 diketone 229, which is then carried through the remainder of the synthetic pathway as previously described.

Figure 4A:
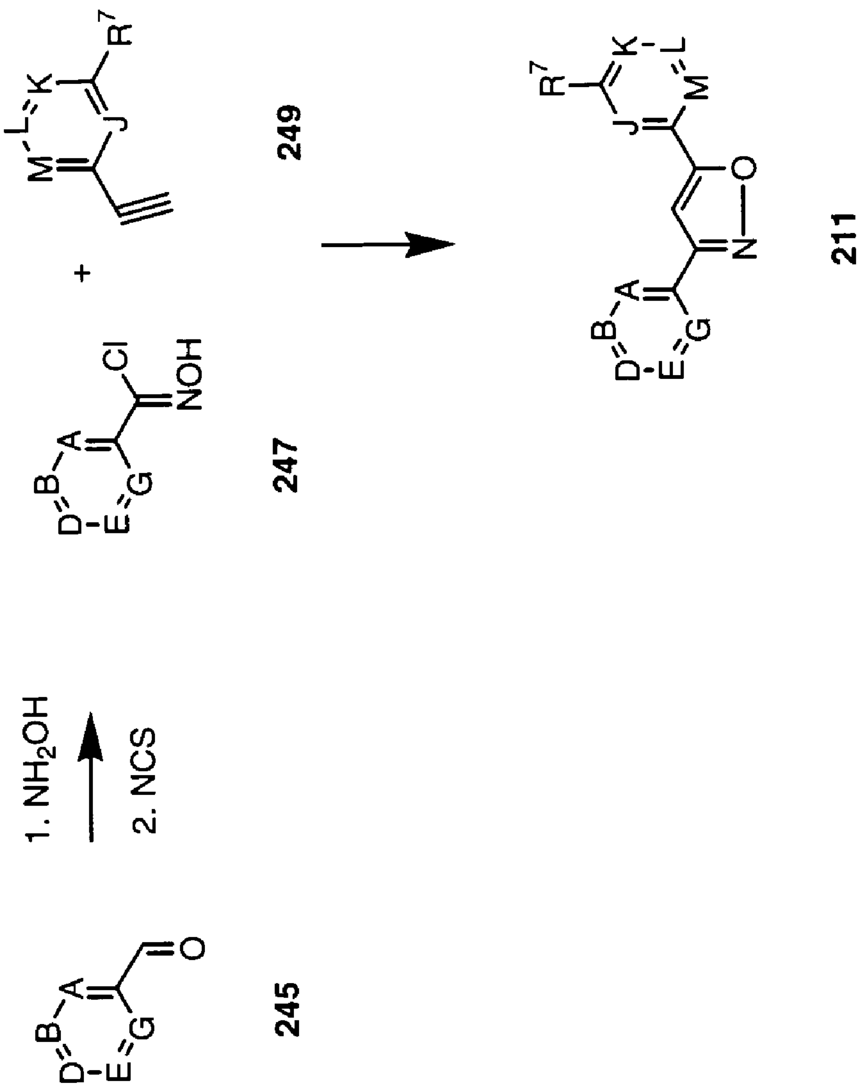

Still another method for synthesizing substituted isoxazoles of structural formula (I) (when Z is —CH—) is provided in FIG. 4A. Nucleophilic addition of hydroxylamine to benzaldehyde 245 provides an intermediate oxime, which may be converted by treatment with N-chlorosuccinimide (NCS) to the α-chlorooxime 247. Dehydrohalogenation of α-chlorooxime 247 provides a transient ylide, which undergoes 1,3 dipolar cycloaddition with acetylene 249 to provide desired isoxazole 211. Acetylene 249 may be readily prepared from commercially available precursors by well known synthetic methods.

Figure 4B:
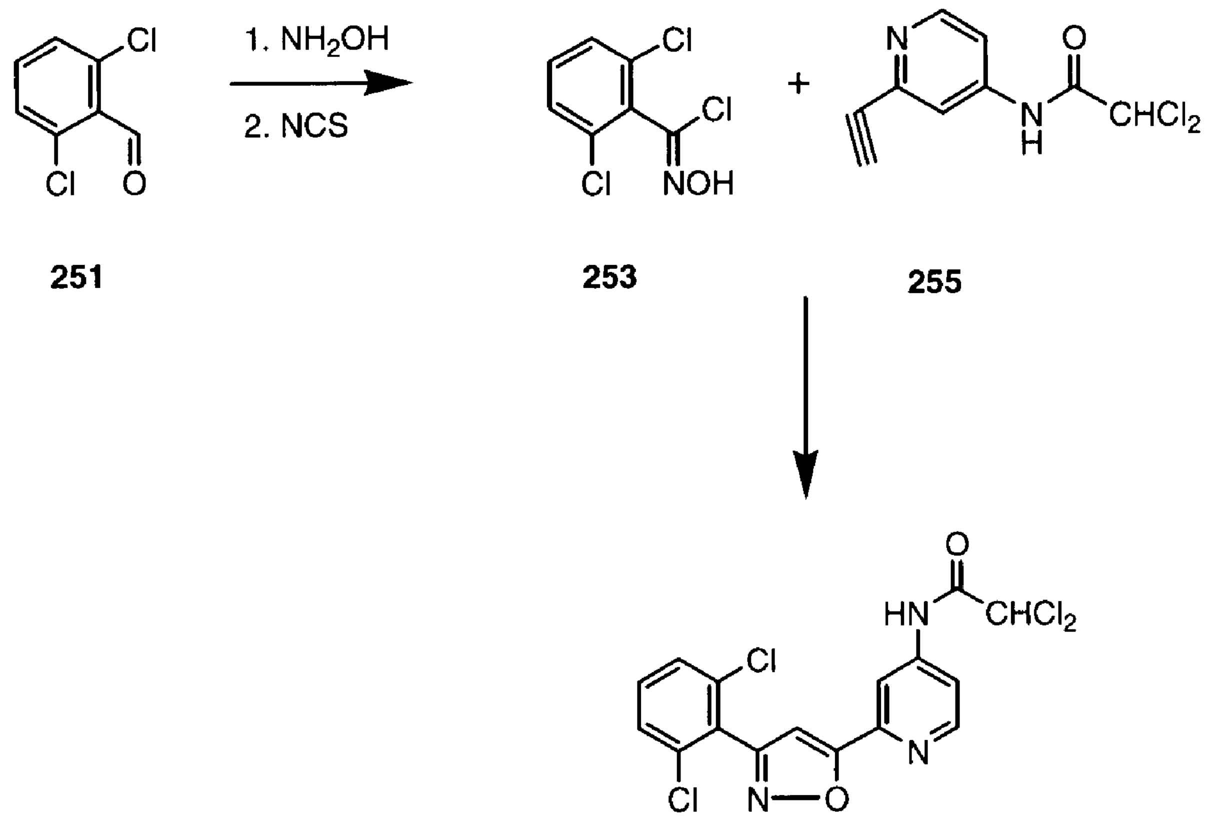
Figure 4C:
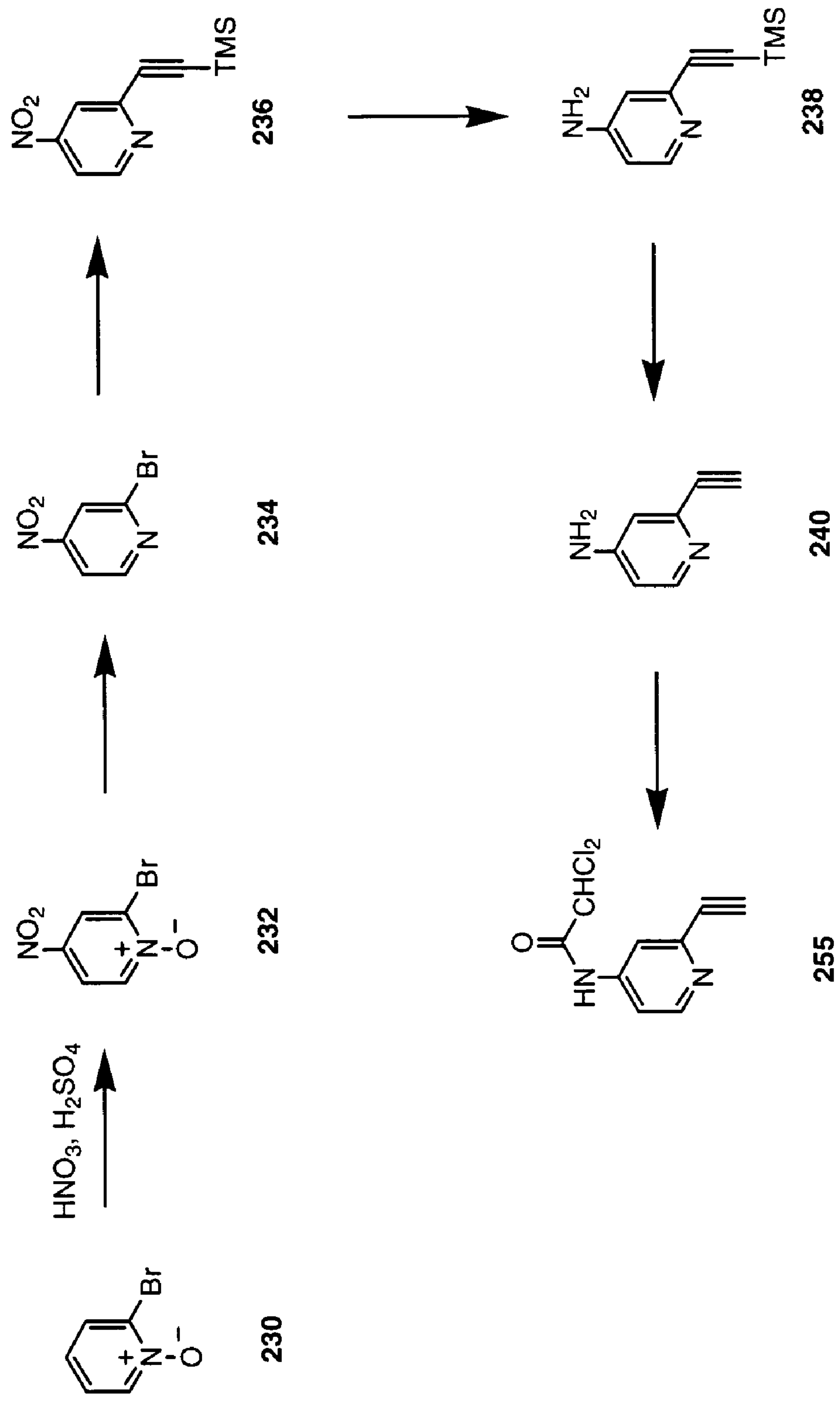
Figure 4D:
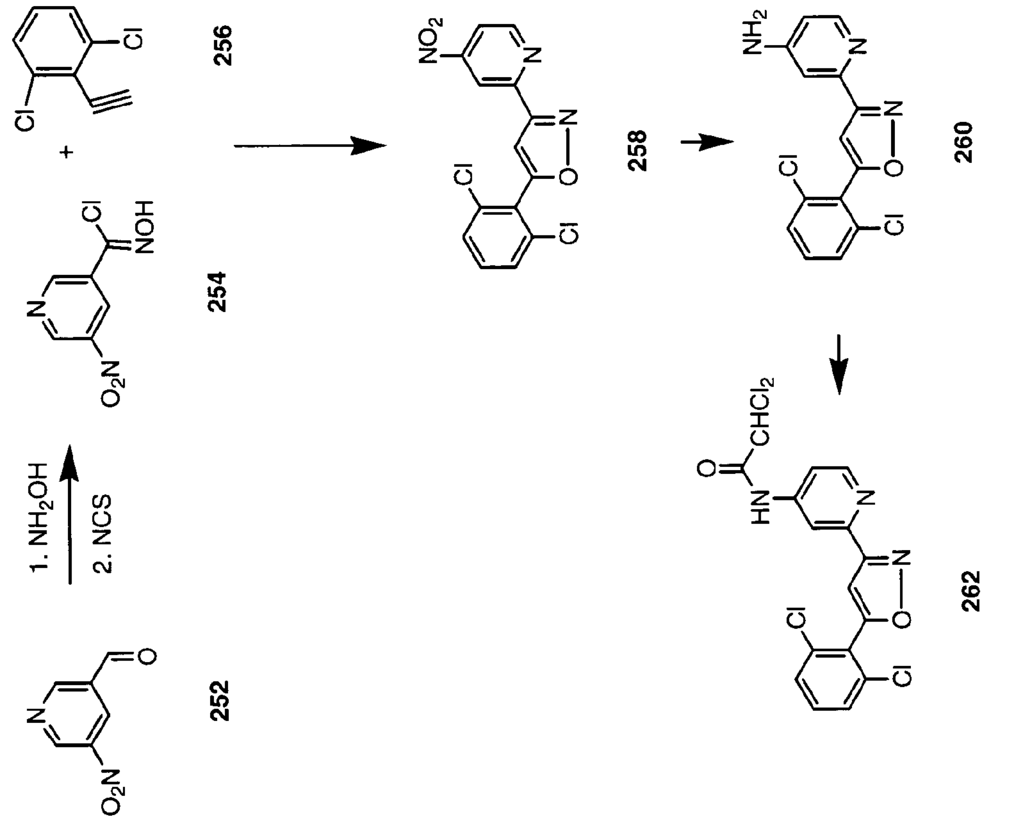

A specific example of the synthetic method of FIG. 4A is illustrated for the preparation of isoxazole 9 in FIG. 4B. FIG. 4C illustrates the preparation of acetylene 255 of FIG. 4B. Analogous methods may be used to prepare other pyridyl acetylene compounds.

Figure 5A:
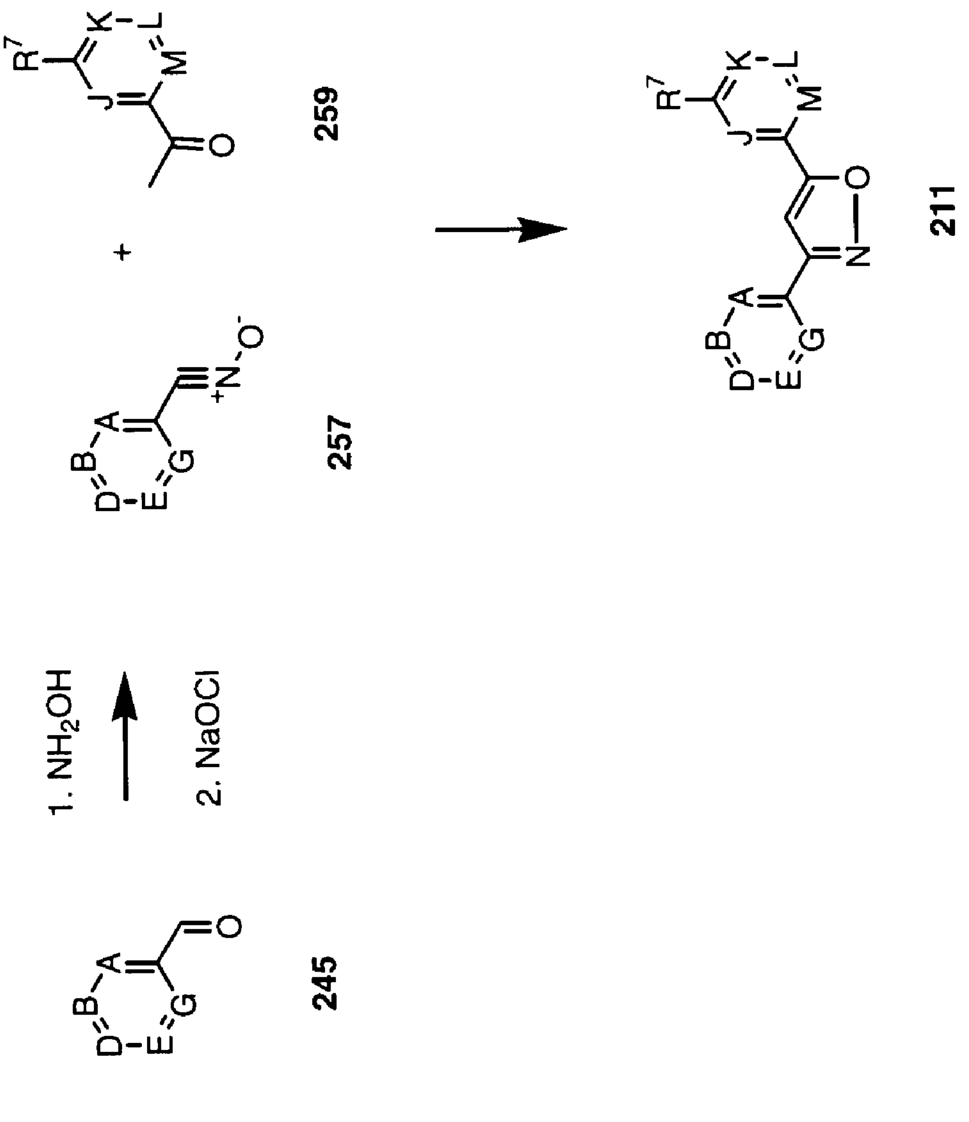
Figure 5B:
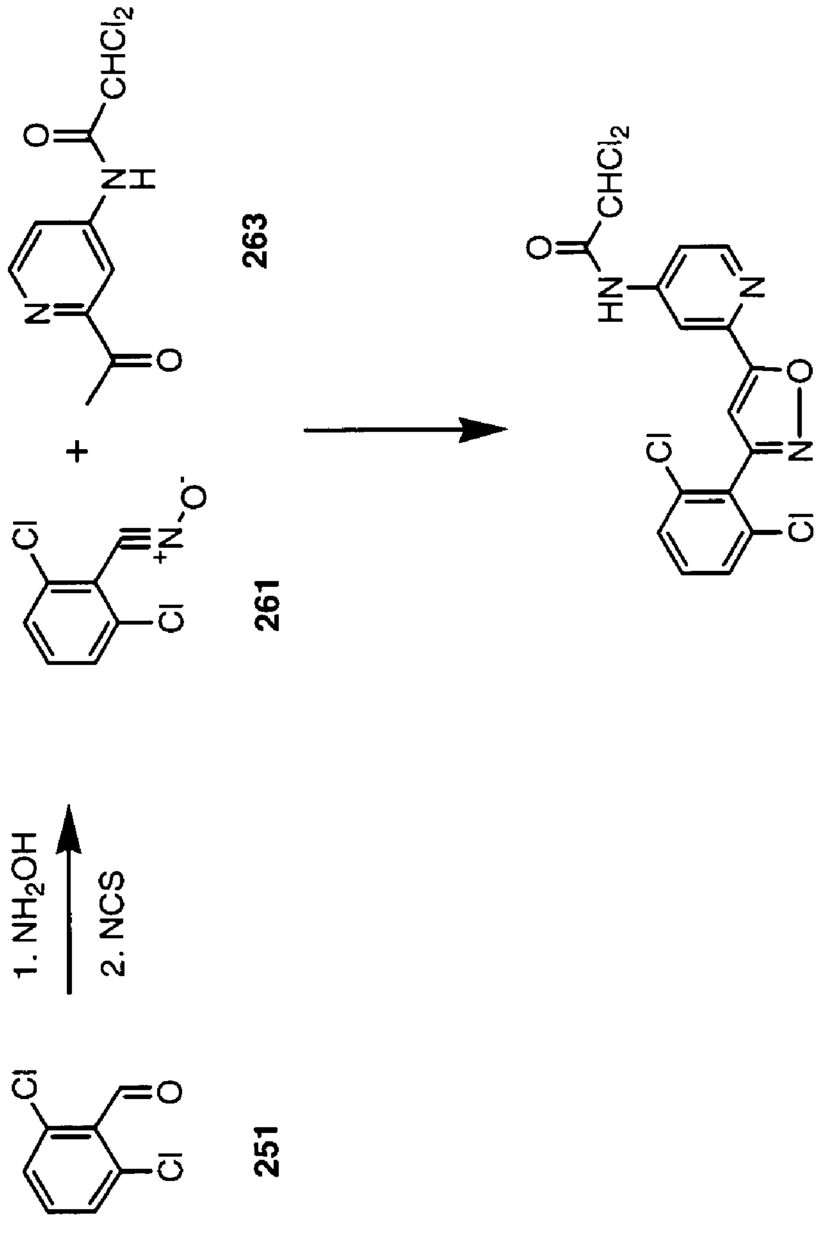

Still another method for synthesizing substituted isoxazoles of structural formula (I) (when Z is —CH—) is provided in FIG. 5A. Nucleophilic addition of hydroxylamine to benzaldehyde 245 provides an intermediate oxime, which may be directly converted to ylide 257 with NaOCl. 1,3 Dipolar cycloaddition of ylide 257 to methyl ketone 259 provides desired isoxazole 211. Methyl ketone 259 may be readily prepared from commercially available precursors by well known synthetic methods. A specific example of the synthetic method of FIG. 5A is illustrated for the preparation of isoxazole 9 in FIG. 5B.

The methods described in FIGS. 2–5 above may be readily adapted for the synthesis of pyrazoles by substituting hydrazine for hydroxylamine in the reaction sequence. Further, those of skill in the art will appreciate that isoxazole regioisomers of those depicted in the above FIGS. 2–5 may be synthesized by merely interchanging the reactive functionalities of the two different aromatic rings. An example of this approach is depicted in FIG. 4D for "reverse" isoxazole 262. As can be seen in FIG. 4D, interchanging the chlorooxime and alkyne functionalities of the two different aromatic rings (i.e., rings A and C) provides the regioisomeric isoxazole 262 (compare 253 and 255 with 254 and 256). Further, certain synthetic schemes may provide both isoxazole regioisomers (e.g., FIGS. 3A and 3B) directly, which may be isolated from one another using standard techniques.

Figure 6A:
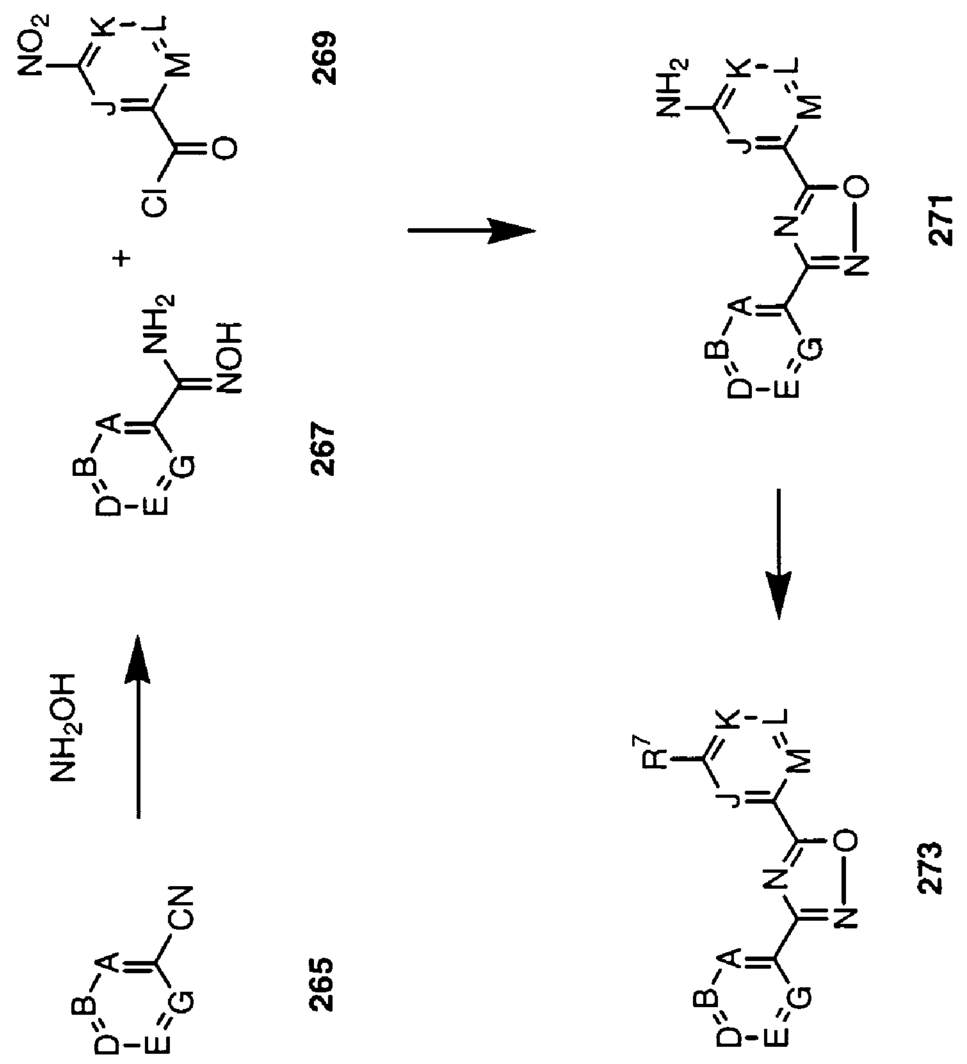
Figure 6B:
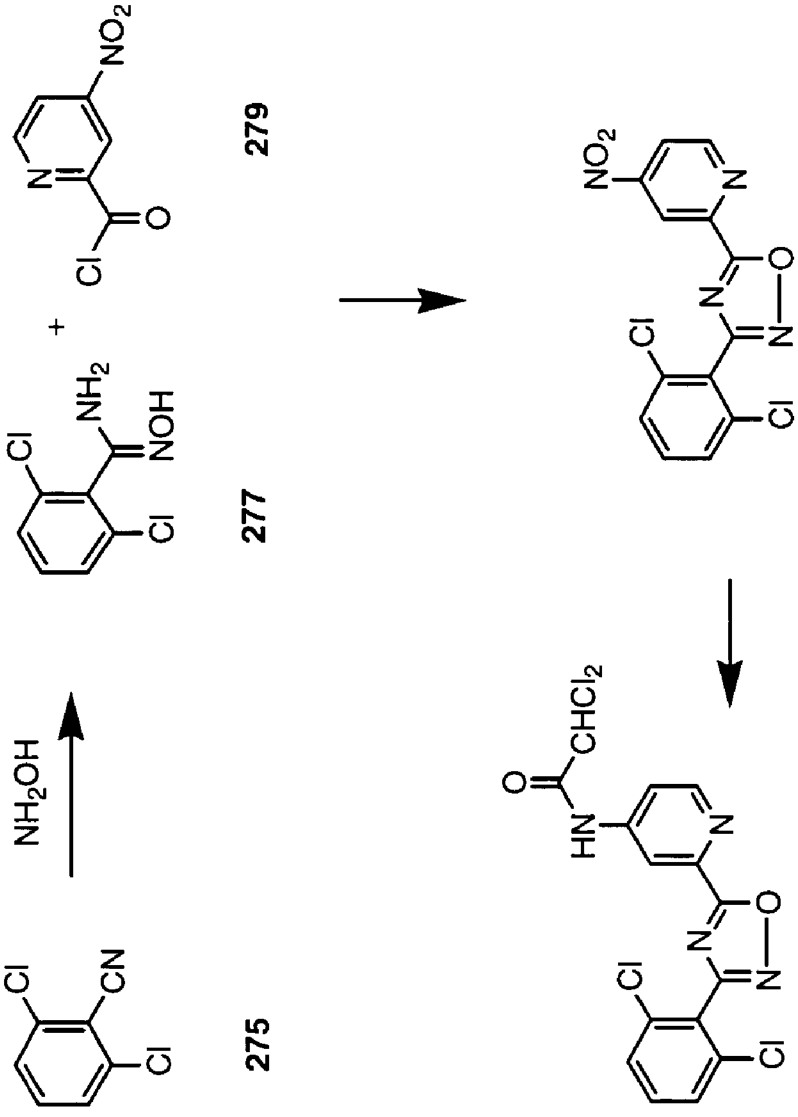

One method for synthesizing substituted oxadiazoles of structural formula (I) (when Z is —N—) is provided in FIG. 6A. Referring to FIG. 6A, nucleophilic addition of hydroxylamine to phenyl cyanide 265 yields the α-amino oxime 267, which may be condensed with acyl chloride 269 to provide oxadiazole 271 after dehydrative cyclization and reduction. Amino oxadiazole 271 may be transformed by a wide variety of methods well known to the skilled artisan to final product 273. A specific example of the synthetic method of FIG. 6A is illustrated for the preparation of oxadiazole 283 in FIG. 6B.

Figure 7A:
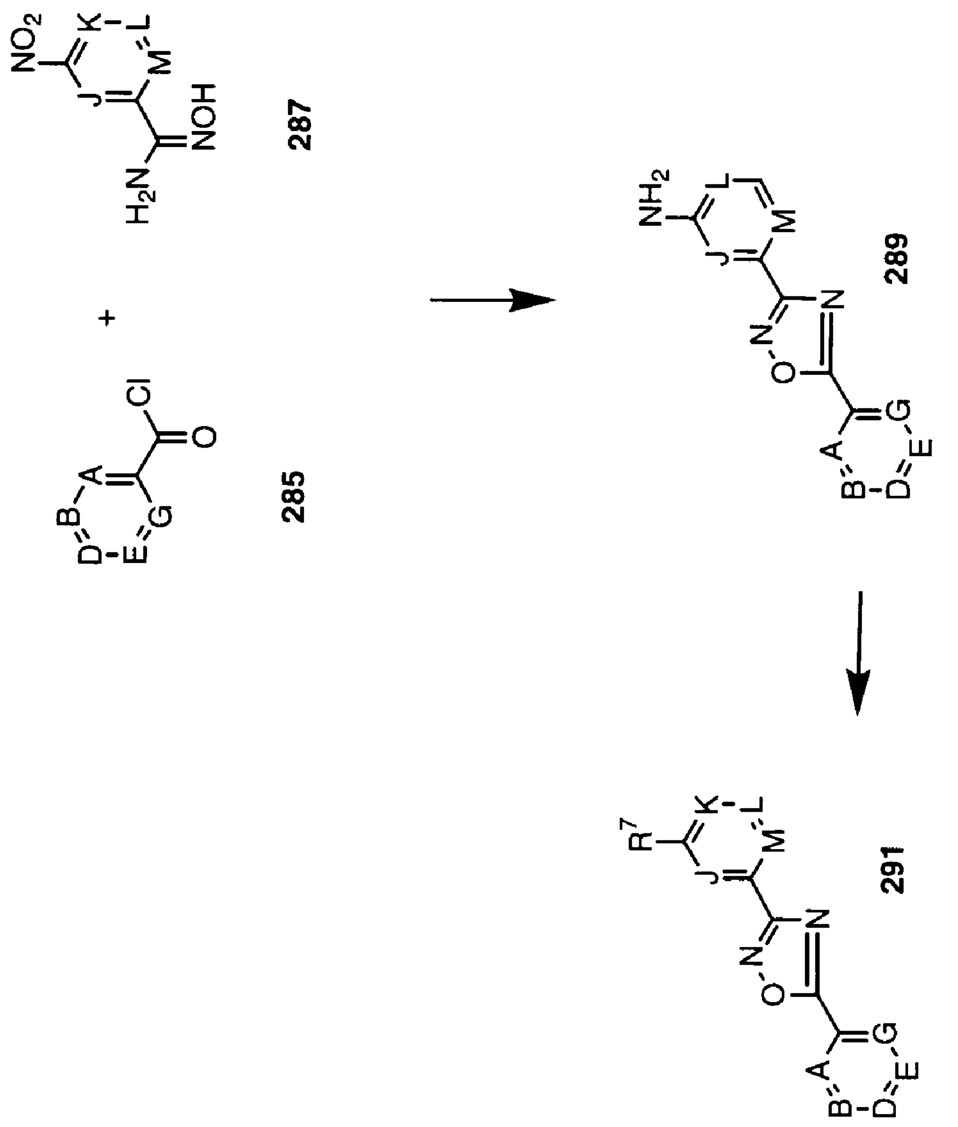
Figure 7B:
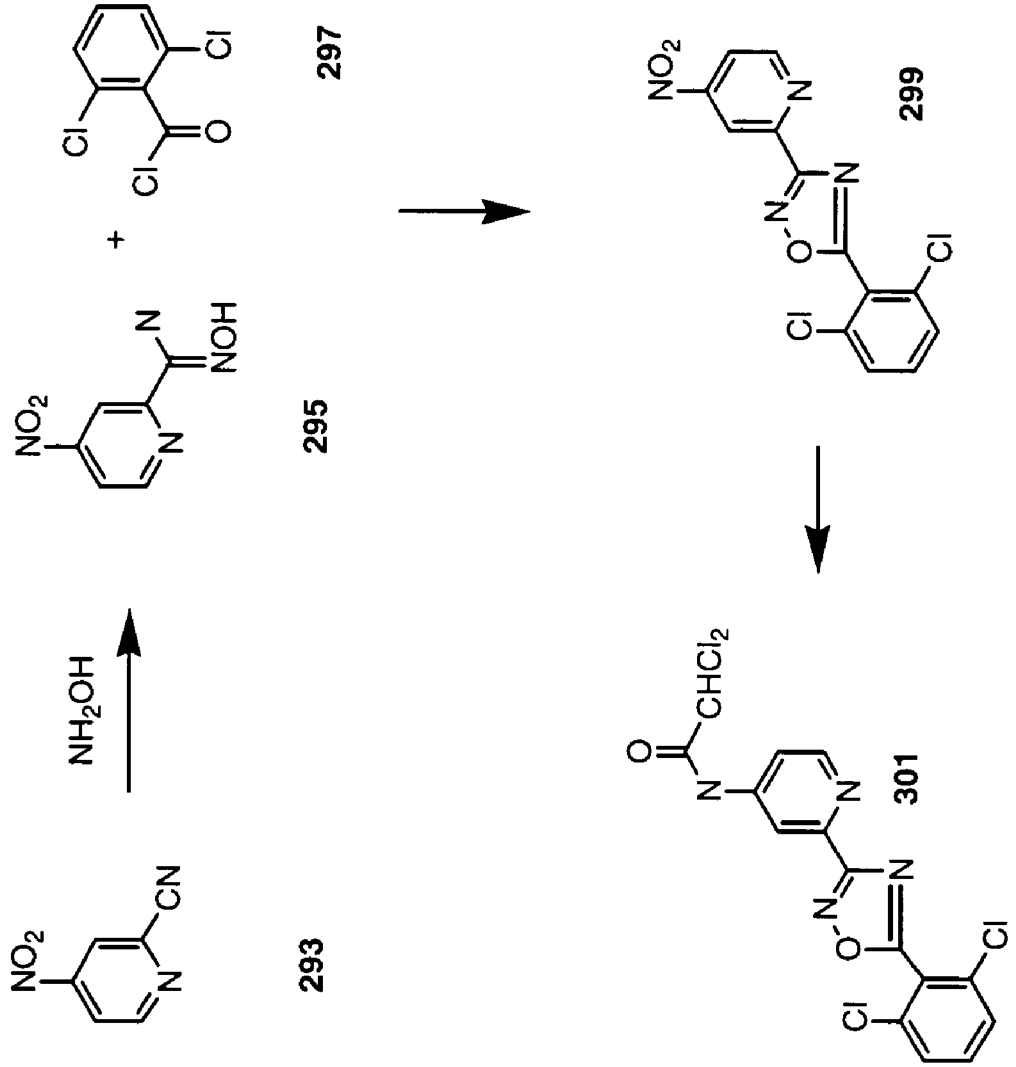

Another method for synthesizing substituted oxadiazoles of structural formula (I) (when Z is —N—), which are regioisomers of those prepared above is provided in FIG. 7A. Referring to FIG. 7A, α-amino oxime 287, (prepared by condensation of hydroxylamine with a phenyl cyanide), may be condensed with acyl chloride 285 to provide oxadiazole 289 after dehydrative cyclization and reduction. Amino oxadiazole 289 may be transformed by a wide variety of methods well known to the skilled artisan to final product 291. A specific example of the synthetic method of FIG. 7A is illustrated for the preparation of oxadiazole 301 in FIG. 7B.

It should be note that the methods described in FIGS. 6 and 7 above may be readily adapted for the synthesis of triazoles by substituting hydrazine for hydroxylamine in the depicted reaction sequences. Thiazoles of structural formula (II) may be prepared by routine adaptation of FIGS. 2–7, or by other well-known techniques.

7.2 Assays For Modulation Of HCV

The compounds of the invention are potent inhibitors of HCV replication and/or proliferation. The activity of the compounds of the invention can be confirmed in in vitro assays suitable for measuring inhibition of viral or retroviral replication or proliferation. Such assays are well-known in the art. A specific example of a replicon assay suitable for confirming the activity of specific compounds is provided in the Examples section. Alternatively, the activity of the compounds can be confirmed using quantitative Western blot assays utilizing labeled antibodies specific for HCV proteins. Another assay that can be used to confirm the anti-HCV properties of the various compounds of the invention is described in Fournier et al., 1998; J. Gen. Virol. 79(10):2367–2374, the disclosure of which is incorporated by reference. According to this method, hepatocytes can be tested in the process and absence of a specified test compound and the $IC_{50}$ of the compound determined.

Generally, active compounds are those which exhibit an $IC_{50}$ (e.g., concentration of compound that yields a 50% reduction in replication or a 50% reduction in the amount of measured HCV protein) in the particular assay in the range of about 1 mM or less. Compounds which exhibit an $IC_{50}$, for example, in the range of about 100 μM, 10 μM, 1 μM, 100 nM, 10 nM, 1 nM, or even lower, are particularly useful for as therapeutics or prophylactics to treat or prevent HCV infections. Alternatively, active compounds are those which exhibit an $LD_{50}$ (i.e., concentration of compound that kills 50% of the virus) in the range of about 1 mM or less. Compounds which exhibit a lower $LD_{50}$, for example, in the range of about 100 μM, 10 μM, 1 μM, 100 nM, 10 nM, 1 nM, or even lower, are particularly useful for as therapeutics or prophylactics to treat or prevent HCV infections.

7.3 Uses and Administration

Owing to their ability to inhibit HCV replication, and/or proliferation, the compounds of the invention and/or compositions thereof can be used in a variety of contexts. For example, the compounds of the invention can be used as controls in in vitro assays to identify additional more or less potent anti HCV compounds. As another example, the compounds of the invention and/or compositions thereof can be used as preservatives or disinfectants in clinical settings to prevent medical instruments and supplies from becoming infected with HCV virus. When used in this context, the compound of the invention and/or composition thereof may be applied to the instrument to be disinfected at a concentration that is a multiple, for example 1×, 2×, 3×, 4×, 5× or even higher, of the measured $IC_{50}$ for the compound.

The compounds of the invention and/or compositions thereof find particular use in the treatment and/or prevention of HCV infections in animals and humans. When used in this context, the compounds may be administered per se, but are typically formulated and administered in the form of a pharmaceutical composition. The exact composition needed will depend upon, among other things, the method of administration and will apparent to those of skill in the art. A wide variety of suitable pharmaceutical compositions are described, for example, in *Remington's Pharmaceutical Sciences,* $17^{th}$ ed., 1989.

Formulations suitable for oral administration can consist of (a) liquid solutions, such as an effective amount of the active compound suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compound of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Suitable formulations for rectal administration include, for example, suppositories, which consist of the packaged nucleic acid with a suppository base. Suitable suppository bases include natural or synthetic triglycerides or paraffin hydrocarbons. In addition, it is also possible to use gelatin rectal capsules which consist of a combination of the compound of choice with a base, including, for example, liquid triglycerides, polyethylene glycols, and paraffin hydrocarbons.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration, oral administration, and intravenous administration are the preferred methods of administration. The formulations of compounds can be presented in unit-dose or multi-dose sealed containers, such as ampules and vials. Injection solutions and suspensions can be prepared from sterile powders, granules, and tablets of the kind previously described.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents.

In therapeutic use for the treatment of HCV infection, the compounds utilized in the pharmaceutical method of the invention are administered to patients diagnosed with HCV infection at dosage levels suitable to achieve therapeutic benefit. By therapeutic benefit is meant that the administration of compound leads to a beneficial effect in the patient over time. For example, therapeutic benefit is achieved when the HCV titer or load in the patient is either reduced or stops increasing. Therapeutic benefit is also achieved if the administration of compound slows or halts altogether the onset of the organ damage or other adverse symptoms that typically accompany HCV infections, regardless of the HCV titer or load in the patient.

The compounds of the invention and/or compositions thereof may also be administered prophylactically in patients that are at risk of developing HCV infection, or who have been exposed to HCV, to prevent the development of HCV infection. For example, the compounds of the invention and/or compositions thereof may be administered to hospital workers accidentally stuck with needles while working with HCV patients to lower the risk of, or avoid altogether, developing an HCV infection.

Initial dosages suitable for administration to humans may be determined from in vitro assays or animal models. For example, an initial dosage may be formulated to achieve a serum concentration that includes the $IC_{50}$ of the particular compound being administered, as measured in an in vitro assay. Alternatively, an initial dosage for humans may be based upon dosages found to be effective in animal models of HCV infection, as is well-known in the art. Exemplary suitable model systems are described in Muchmore, 2001, Immumol. Rev. 183:86–93 and Lanford & Bigger, 2002, Virology 293(i): 1–9 and the references cited therein, the disclosure of which are incorporated herein by reference. As one example, the initial dosage may be in the range of about 0.001 mg/kg to about 1000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can also be used. The dosages, however, may be varied depending upon the requirements of the patient, the severity of the condition being treated, and the compound being employed. The size of the dose also will be determined by the existence, nature, and extent of any adverse side-effects that accompany the administration of a particular compound in a particular patient. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired.

7.4 Combination Therapy

In certain embodiments of the present invention, the compounds of the invention and/or compositions thereof can be used in combination therapy with at least one other therapeutic agent. A compound of the invention and/or composition thereof and the therapeutic agent can act additively or, more preferably, synergistically. In a preferred embodiment, a compound of the invention and/or a composition thereof is administered concurrently with the administration of another therapeutic agent. In another embodiment, a compound of the invention and/or composition thereof is administered prior or subsequent to administration of another therapeutic agent.

In one embodiment, the compounds of the invention and/or compositions thereof can be used in combination therapy with other antiviral agents. In an embodiment, the compounds of the invention and/or compositions thereof can be used in combination therapy with interferon-α. In another embodiment, the compounds of the invention and/or compositions thereof can be used in combination therapy with ribavarin. In another embodiment, the compounds of the invention and/or compositions thereof can be used in combination therapy with ribavarin and interferon-α.

8. EXAMPLES

The following example is provided by way of illustration only and not by way of limitation. Those of skill in the art will readily recognize a variety of noncritical parameters that could be changed or modified to yield essentially similar results.

8.1 Exemplary Compounds of the Invention Which Inhibit HCV Translation or Replication The inhibitory activity of certain exemplary compounds of the invention was confirmed using an HCV replicon assay. The HCV replicon can include such features as the HCV IRES, the HCV 3' untranslated region, selected HCV genes encoding HCV polypeptides, selectable markers, and a reporter gene such as luciferase, GFP, etc. In the assay, actively dividing 5-2Luc replicon-comprising cells were seeded at a density of between about 5,000 and 7,500 cells/well onto 96 well plates (about 90 μl of cells per well) and incubated at 37° C. and 5% $CO_2$ for 24 hours. Then, the test compound (in a volume of about 10 μl) was added at various concentrations to each well and the cells were incubated for an additional 24 hours before luciferase assay. The cells were harvested, and HCV replication or translation was monitored via a reporter assay, e.g., a luciferase reporter assay. The media was aspirated from each cell and Bright-Glo (Pharmacia, Peapack, N.J.) luciferase assay reagents were added to each well according to the manufacturer's instructions. In this assay, the amount of test compound that yielded a 50% reduction in luciferase emission ($IC_{50}$) was determined.

Certain exemplary compounds of the invention were also tested for their ability to inhibit HCV replication using a quantitative Western blot analysis with antibodies specific for certain HCV proteins. In this assay, the amount of test compound that yielded a 50% reduction in the amount of the specified HCV protein as compared to a control sample ($IC_{50}$) was determined.

The results of the Replicon and Western blot assays are provided in TABLE 1, below. The structures of the indicated compounds are provided in FIG. 1. In TABLE 1, a value of "+" indicates an $IC_{50}$ of 10 μM or less in the specified assay; a value of "–" indicates an $IC_{50}$ of greater than 10 μM in the specified assay. A number of compounds exhibited $IC_{50}$s in the Replicon assay in the nanomolar range.

TABLE 1

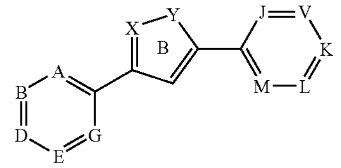

$R^7$ is $NR^{11}C(O)R^{12}$

| Compound | Replicon/Western | X | Y | A | B | D | E | G | J | V | K | L | M | $R^{11}$ | $R^{12}$ |
|---|---|---|---|---|---|---|---|---|---|---|---|---|---|---|---|
| 1 R909850 | + | N | O | CCl | CH | CH | CH | CF | CH | $CR^7$ | CH | CH | N | H | $CHCl_2$ |
| 3 R909794 | +/+ | N | O | $CCF_3$ | CH | CH | CH | CF | CH | $CR^7$ | CH | CH | N | H | $CHCl_2$ |
| 5 R911427 | −/+ | N | O | CF | CH | CH | CH | COMe | CH | $CR^7$ | CH | CH | N | H | $CHCl_2$ |
| 7 R911418 | +/+ | N | O | CCl | CH | CH | CH | CCl | CH | $CR^7$ | CH | N | CH | H | $CHCl_2$ |
| 9 R909921 | +/+ | N | O | CCl | CH | CH | CH | CCl | CH | $CR^7$ | CH | CH | N | H | $CHCl_2$ |
| 11 R909833 | −/+ | N | O | CCl | CH | N | CH | CCl | CH | $CR^7$ | CH | CH | CH | H | $CHCl_2$ |
| 13 R909845 | +/+ | N | O | CCl | CH | CH | CH | CF | CH | $CR^7$ | CH | N | CH | H | $CHCl_2$ |
| 17 R911424 | +/+ | N | O | CF | CH | CH | CH | COMe | CH | $CR^7$ | CH | N | CH | H | $CHCl_2$ |
| 19 R909851 | + | N | O | $CCH_3$ | CH | CH | CH | $CCH_3$ | CH | $CR^7$ | CH | CH | N | H | $CHCl_2$ |
| 21 R909846 | +/− | N | O | $CCH_3$ | CH | CH | CH | $CCH_3$ | CH | $CR^7$ | CH | N | CH | H | $CHCl_2$ |
| 27 R911422 | +/+ | N | O | CF | CH | CH | CH | CF | CH | $CR^7$ | CH | N | CH | H | $CHCl_2$ |
| 29 R911423 | + | N | O | CCl | CCl | CH | CH | CH | CH | $CR^7$ | CH | N | CH | H | $CHCl_2$ |
| 31 R909864 | + | N | O | $CCF_3$ | CH | CH | CH | 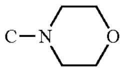 | CH | $CR^7$ | CH | CH | N | H | $CHCl_2$ |
| 33 R904855 | + | N | O | $CCH_3$ | CH | CH | CH | N | CH | $CR^7$ | CH | CH | CH | H | $CHCl_2$ |
| 35 R904800 | − | N | O | CCl | CH | CH | CH | CCl | N | $CR^7$ | CH | CH | CH | H | $CHCl_2$ |
| 37 R909793 | − | N | O | $CCF_3$ | CH | CH | CH | CF | CH | $CR^7$ | CH | N | CH | H | $CHCl_2$ |
| 39 R911427 | − | N | O | CF | CH | CH | CH | COMe | CH | $CR^7$ | CH | CH | N | H | $CHCl_2$ |
| 43 R909873 | − | N | O | CCl | CH | CH | CH | CCl | CH | $CR^7$ | CH | CH | $N^+—O^-$ | H | $CHCl_2$ |
| 45 R909878 | − | N | O | N | CH | CH | CH | CCOOEt | CH | $CR^7$ | CH | CH | CH | H | $CHCl_2$ |
| 47 R909884 | + | N | O | CF | CH | CH | CH | 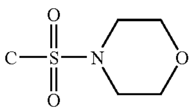 | CH | $CR^7$ | CH | CH | N | H | $CHCl_2$ |
| 49 R905952 | +/+ | N | O | $CCF_3$ | CH | CH | CH | COMe | CH | $CR^7$ | CH | CH | N | H | $CHCl_2$ |
| 51 R909909 | + | N | O | CCl | CH | CH | CH | CCl | CH | $CR^7$ | CH | CH | N | Me | $CHCl_2$ |
| 53 R905954 | +/+ | N | O | CCl | CH | CH | CH | 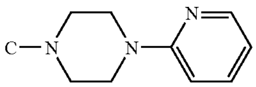 | CH | $CR^7$ | CH | CH | N | H | $CHCl_2$ |
| 57 R905948 | +/+ | N | O | $CCF_3$ | CH | CH | CH | COMe | CH | $CR^7$ | CH | N | CH | H | $CHCl_2$ |

TABLE 1-continued

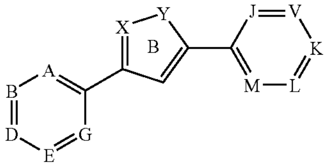

$R^7$ is $NR^{11}C(O)R^{12}$

| Compound | Replicon/Western | X | Y | A | B | D | E | G | J | V | K | L | M | $R^{11}$ | $R^{12}$ |
|---|---|---|---|---|---|---|---|---|---|---|---|---|---|---|---|
| 59 | | N | O | $CCF_3$ | CH | CH | CH | 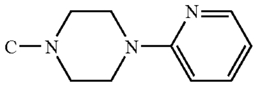 | CH | $CR^7$ | CH | N | CH | H | $CHCl_2$ |
| 61 R905961 | + | N | O | CCl | CH | CH | CH | 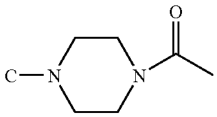 | CH | $CR^7$ | CH | N | CH | H | $CHCl_2$ |
| 63 R905962 | + | N | O | CCl | CH | CH | CH | 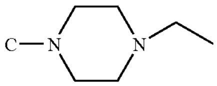 | CH | $CR^7$ | CH | N | CH | H | $CHCl_2$ |
| 65 R904857 | — | N | O | CCl | CH | CH | CH | CCl | CH | CH | $CR^7$ | N | CH | H | $CHCl_2$ |
| 67 R905451 | + | N | O | $CCF_3$ | CH | CH | CH | CH | CH | $CR^7$ | CH | N | CH | H | $CHCl_2$ |
| 69 R905949 | + | N | O | CCl | CH | CH | CH | 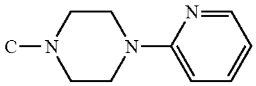 | CH | $CR^7$ | CH | N | CH | H | $CHCl_2$ |
| 71 R905965 | + | N | O | CCl | CH | CH | CH | 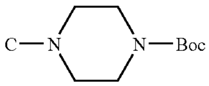 | CH | $CR^7$ | CH | N | CH | H | $CHCl_2$ |
| 73 R905966 | + | N | O | CCl | CH | CH | CH | 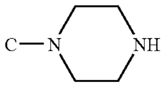 | CH | $CR^7$ | CH | N | CH | H | $CHCl_2$ |
| 75 R905967 | + | N | O | CCl | CH | CH | CH | $COSi(Me)_2$-tBu | CH | $CR^7$ | CH | N | CH | H | $CHCl_2$ |
| 77 R905968 | + | N | O | CCl | CH | CH | CH | COH | CH | $CR^7$ | CH | N | CH | H | $CHCl_2$ |
| 79 R905969 | + | N | O | CCl | CH | CH | CH | CO(CO)NHEt | CH | $CR^7$ | CH | N | CH | H | $CHCl_2$ |
| 81 R905970 | + | N | O | CCl | CH | CH | CH | 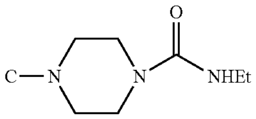 | CH | $CR^7$ | CH | N | CH | H | $CHCl_2$ |
| 83 R905971 | + | N | O | CCl | CH | CH | CH | $COSi(Me)_2$-tBu | CH | $CR^7$ | CH | CH | N | H | $CHCl_2$ |
| 85 R905973 | + | N | O | CCl | CH | CH | CH | $CO(CO)NHCH_2CH_2CH_3$ | CH | $CR^7$ | CH | CH | N | H | $CHCl_2$ |
| 87 R905982 | + | N | O | CCl | CH | CH | CH | $COCH_2OCH_3$ | CH | $CR^7$ | CH | CH | N | H | $CHCl_2$ |
| 89 R905983 | + | N | O | CCl | CH | CH | CH | COH | CH | $CR^7$ | CH | CH | N | H | $CHCl_2$ |
| 91 R905984 | + | N | O | CCl | CH | CH | N | $CN(CH_3)_2$ | CH | $CR^7$ | CH | CH | CH | H | $CHCl_2$ |
| 93 R905985 | + | N | O | CCl | CH | CH | N | CCl | CH | $CR^7$ | CH | CH | CH | H | $CHCl_2$ |

TABLE 1-continued

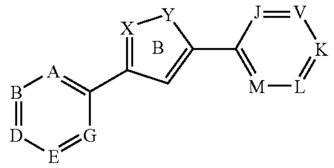

$R^7$ is $NR^{11}C(O)R^{12}$

| Compound | Replicon/ Western | X | Y | A | B | D | E | G | J | V | K | L | M | $R^{11}$ | $R^{12}$ |
|---|---|---|---|---|---|---|---|---|---|---|---|---|---|---|---|
| 95 R905987 | | N | O | 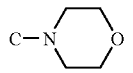 | CH | CH | N | CCl | CH | $CR^7$ | CH | CH | CH | H | $CHCl_2$ |
| 97 R909874 | – | N | O | CH | CH | CH | CBr | N | CH | $CR^7$ | CH | CH | CH | H | $CHCl_2$ |

A counter screen was used to identify non-specific inhibitors of the reporter gene. In the counter screen, a cell line carrying a construct such as a CMV-driven luciferase gene was used to identify compounds that inhibit the reporter gene, and not HCV. $IC_{50}$ values were greater than 10 μM in the counter screen luciferase inhibition assay for many of the compounds. Standard cell proliferation assays were used to determine cytotoxicity of the compounds of the invention. The measured $LD_{50}$s for many of the compounds were greater 10 μM, which confirmed that the results reflected reduced viral production not cell death.

A TaqMan RT-PCR assay (Roche Molecular Systems, Pleasanton, Calif.) was used to analyze HCV RNA copy numbers, which confirmed that the viral genome of HCV is not being replicated. Actively dividing 9-13 replicon cells were seeded at the density of $3\times10^4$ cells/well in a volume of 1 ml/well into 24-well plates. The cells were then incubated at 37° C. and 5% $CO_2$ for 24 hours. Various concentrations of compounds (in a volume of 10 ul) were added into each well 24 hours after seeding the cells. The cells were incubated with the compounds for another 24 hours, media was removed by aspiration and RNA samples prepared from each well. TaqMan one step RT-PCR was performed using the freshly prepared RNA samples according to the manufacturer's manual. The ratio of HCV RNA to cellular GAPDH RNA was used as in indication of specificity of HCV inhibition and to confirm that the viral genome was not replicated.

8.2 The Compounds are Non-Toxic in Cellular and Animal Models 8.2.1 Cytotoxicity Compounds 1, 3, 7, 9, 11, 13, 17, 19, 21, 27, 29, 31, 33, 35, 37, 39, 47, 49, 51, 57 and 69 were tested in a cytotoxicity assay with liver cells including an HCV replicon (5-2 Luc cells, 9-13 cells or Huh-7 cells). In the assay, cells were seeded onto 96-well plates (approx. 7500 cells/well in a volume of 90 μl) and grown for 24 hr at 37° C. On day 2, various concentrations of test compound (in a volume of 10 μl) were added to the wells and the cells were grown for an additional 48 hr at 37° C. On day 4, an ATP-dependent R-Luciferase assay (Cell Titer Glo assay) was performed to determine the number of viable cells. With the exception of compounds 13, 19 and 57, all compounds tested exhibited an $IC_{50}$ of greater than or equal to 10 μM, confirming that the compounds are non-toxic. Of the remaining compounds, all but compound 13, which exhibited an $IC_{50}$ of 3 μM, had $IC_{50}$s greater than 5 μM, demonstrating that these compounds are well-tolerated, as well.

8.3 Synthesis of Compounds 8.3.1 Compounds 3 (R909794) and 9 (R909921)

Step A

Referring to FIG. 4C, compound 230 (25g, 98.1 mmol) was added to 96% $H_2SO_4$ (50 mL) at 0° C. followed by 96% $HNO_3$ (17.5 mL) and the resultant mixture was heated at 130° C. for 3 hours. The reaction mixture was cooled, then poured into ice, sodium carbonate was added to cause precipitate formation (pH>7). The product was collected by filtration, washed with water and dried to yield a yellow solid 232 (17.0g, 79%).

Step B

To compound 232 (17 g, 78 mmol) in $CHCl_3$ (200 mL) was added $PBr_3$ (7.4 ml) and the subsequent mixture was refluxed for 1 hour or until completion of reaction as shown by thin layer chromatography. The reaction was cooled, the majority of the solvent removed under reduced pressure and the residue poured onto ice to produce a yellow solid. The product was collected by filtration to produce 234 (14.5 g, 92%).

Step C

To a mixture of 234 (6 g, 0.029 mol), $PdCl_2(Ph_3)_2$(620 mg, 3 mol %), CuI (338 mg, 6 mol %) under an atmosphere of nitrogen was added diisopropylethylamine (100 mL). The resulting mixture was stirred at ambient temperature for several minutes before the introduction of TMS acetylene (6.3 ml, 1.5 equiv). The contents were then heated at 60° C. for 24 hours. The solvent was removed under reduced pressure and the crude material filtered through silica gel column (hexanes:EtOAc 10:1) to give 236 as a yellow solid, 4.9 gm (76%).

Step D

A mixture of compound 236 (1.4 g), Fe powder (3.55 g, 10 equiv.), concentrated HCl (1 mL) and methanol (100 mL) was refluxed for 3 hours. After cooling, the reaction mixture was filtered, the solution concentrated, the residue diluted with $NaHCO_3$ and extracted with EtOAc (several times). The combined EtOAc extracts were dried, filtered, and concentrated to give the crude product (1.0 g) as a mixture of 238 and desilyated product 240. The oily mixture was dissolved in methanol (100 ml) and treated with $K_2CO_3$ (approx. 2 equiv.). After stirring at room temperature for 1 hour the reaction was concentrated in vacuo. The residue was dissolved in EtOAc, washed with water, dried, filtered and concentrated in vacuo. The product 240 (513 mg) was obtained as a dark purple oil.

Step E

Compound 240 (513 mg) was dissolved in dry dichloromethane (50 mL) and $Et_3N$ (0.786 ml, 1.3 equiv.) was added under nitrogen. The mixture was cooled in an ice bath and a solution of dichloroacetyl chloride (0.483 mL, 1.1 equiv.) in dry dichloromethane (5 mL) was added dropwise. The reaction was allowed to warm to room temperature over 6 hours and then diluted with EtOAc, washed with a saturated solution of sodium bicarbonate, dried, filtered and concentrated in vacuo. The crude material was passed through a plug of silica gel, eluted with 1:1 hexanes/EtOAc. The fractions were concentrated to produce a purple oil that solidified under high vacuum to yield compound 255 (658 mg).

Step F

The chlorooxime of 2-fluoro-6 triflouromethyl benzaldehyde (645 mg, 1.1 equiv.) and compound 255 (658 mg) were dissolved in dry THF (30 ml) and $Et_3N$ (0.521 ml, 1.3 equiv.) was added. The mixture was stirred at room temperature for 1 hour and then refluxed for 5 hours until completion of reaction. The solvent was removed under vacuum, the residue dissolved in EtOAc, washed with water, washed with saturated sodium chloride, dried, filtered and concentrated. The crude material was purified by chromatography (3:2 hexanes:EtOAc) to produce compound 3 (800 mg). Compound 9 was prepared in an analogous fashion from the chlorooxime of 2,6-dichlorobenzaldehyde and 255.

8.3.2 Synthesis of Compound 49 (R905952)

Preparation of 3-(2-methoxy-6-trifluoromethylphenyl)-5-(4-aminopyridyl) isoxazole To a solution of N-hydroxy-(2-methoxy-6-trifluoromethylbenzene)carboximidoyl chloride (1 g, 3.94 mmol) and 4-amino-2-ethynylpyridine (310 mg, 2.63 mmol) in THF was added triethylamine (550 mL, 3.94 mmol). The reaction mixture was stirred at room temperature for one hour and then refluxed for three hours. The mixture was cooled to room temperature, ethyl acetate and water were added. The organic layer was separated, dried over sodium sulfate, filtered and concentrated in vacuo to yield the crude product. The final product 3-(2-methoxy-6-trifluoromethylphenyl)-5-(4-aminopyridyl) isoxazole (609 mg) was obtained by purification with flash chromatography with hexanes:ethyl acetate (4:1).

MW=335.28 confirmed by LC-MS, $t_r$=8.38 min. (Method Y) $M^+$=335.28 NMR (300 MHz, CDCl3): 8.24 (m, 1H), 7.48 (m, 1H), 7.4 (m, 1H), 7.26 (m, 1H), 7.2 (m, 1H), 7.0 (s, 1H), 6.6 (m, 1H), 4.8 (bs, 2H), 3.8 (s, 3H).

Preparation of 2,2-Dichloro-N-[2-[3-(2-methoxy-6-trifluoromethylphenyl)-5-isoxazolyl]-(4-pyridyl) Acetamide A mixture of 3-(2-methoxy-6-trifluoromethylphenyl)-5-(4-aminopyridyl) isoxazole (609 mg, 1.82 mmol) and triethylamine (1.8 mL, 12.9 mmol) in dichloromethane was cooled in a ice bath. A solution of dichloroacetyl chloride (1.3 mL, 12.9 mmol) in dichloromethane was added dropwise. After stirring for one more hour, water and ethyl acetate were added. The organic layer was separated, washed with saturated sodium hydrogen carbonate, dried over sodium sulfate, filtered and concentrated in vacuo. The final product 2,2-dichloro-N-[2-[3-(2-methoxy-6-trifluoromethylphenyl)-5-isoxazolyl]-(4-pyridyl) acetamide (300 mg) was obtained by flash chromatography with hexanes: ethyl acetate (4:1).

MW=446.21 confirmed by LC-MS, $t_r$=9.84 min. (Method Y) $MH^+$=447.21. NMR (300 MHz, CDCl3): 9.84 (s, 1H), 8.63 (m, 1H), 7.9 (m, 1H), 7.62 (m, 1H), 7.41 (m, 1H), 7.22 (m, 1H), 5.64 (s, 1H), 3.8 (s, 3H).

(Replicon activity ++)

8.3.3 Synthesis of Compound 57 (R905948)

Preparation of 3-(2,2-dichloroacetamido)-5-ethynylpyridine

A mixture of 3-amino-5-ethynylpyridine (20.73 g, 23.1 mmol) and triethylamine (3.54 mL, 25.42 mmol) in dichloromethane was cooled in an ice bath. A solution of dichloroacetyl chloride (2.57 mL, 25.42 mmol) in dichloromethane was added dropwise. After stirring for one more hour, water and ethyl acetate were added. The organic layer was separated, washed with saturated sodium hydrogen carbonate, dried over sodium sulfate, filtered and concentrated in vacuo to yield 3-(2,2-dichloroacetamido)-5-ethynylpyridine (3.5 g).

MW=229.31 confirmed by LC-MS, $t_r$=9.76 min. (Method Y) $MH^+$=230.3. NMR (300 MHz, CDCl3): 8.7 (s, 1H), 8.52 (s, 1H), 8.2 (m, 2H), 6.08 (s, 1H), 3.21 (s, 1H).

Preparation of 2,2-Dichloro-N-[3-[3-(2-methoxy-6-trifluoromethylphenyl)-5-isoxazolyl]-(5-pyridyl) Acetamide To a solution of N-hydroxy-(2-methoxy-6-trifluoromethylbenzene)carboximidoyl chloride (111 mg, 0.44 mmol) and 3-(2,2-dichloroacetamido)-5-ethynylpyridine (100 mg, 0.44 mmol) in THF was added triethylamine (0.91 mL, 0.65 mmol). The reaction mixture was stirred at room temperature for one hour and then refluxed for three hours. The mixture was cooled to room temperature, ethyl acetate and water were added. The organic layer was separated, dried over sodium sulfate, filtered and concentrated in vacuo to yield the crude product. The final product 2,2-dichloro-N-[3-[3-(2-methoxy-6-trifluoromethylphenyl)-5-isoxazolyl]-(5-pyridyl) acetamide (103 mg) was obtained by purification with flash chromatography with hexanes:ethyl acetate (4:1).

MW=446.31 confirmed by LC-MS, $t_r$=13.45 min. (Method Y) $MH^+$=447.31. NMR (300 MHz, CDCl3): 9.4 (bs, 1H), 9.0 (s, 1H), 8.9 (s, 2H), 7.58 (m, 1H), 7.4 (m, 1H), 7.24 (m, 1H), 6.8 (s, 1H), 6.2 (s, 1H), 3.8 (s, 3H).

(Replicon activity ++)

8.3.4 General Syntheses of Compounds of the Invention

Additionally, compounds of the invention can be prepared by methods outlined in FIGS. 8 through 63. One skilled in the art can readily prepare compounds within the scope of the invention based upon the guidance provided herein, as well as in FIGS. 1 through 63, the references cited within the figures, and further in view of the experimental procedures provided in U.S. Provisional application 60/467,650, filed May 2, 2003, the teachings of which are incorporated herein by reference. For example, see Sections 5.3 and 6.1 et seq. for general synthesis of non nitrogen containing "C" ring isomers. Pyrid-2-yl, pyrid-3-yl or pyrid-4-yl can be utilized in the "C" ring as a replacement to the nonheteroaromatic rings depicted therein. Furthermore, it should be understood that throughout FIGS. 1 through 63, "C" ring positional isomers are utilized for convenience. It should be understood that the pyridyl ring can be either a pyrid-2-yl, pyrid-3-yl or pyrid-4-yl. Additionally, it should be noted that many of the preparations reference the "A" ring as being 2,6-dichlorophenyl. This is illustrative and is not intended to be limiting in any way.

Starting materials useful for preparing compounds of the invention and intermediates thereof are commercially available or can be prepared by well-known synthetic methods (see, e.g., Harrison et al., "Compendium of Synthetic Organic Methods", Vols. 1–8 (John Wiley and Sons, 1971–1996); "Beilstein Handbook of Organic Chemistry," Beilstein Institute of Organic Chemistry, Frankfurt, Germany; Feiser et al., "Reagents for Organic Synthesis," Volumes 1–21, Wiley Interscience; Trost et al., "Comprehensive Organic Synthesis," Pergamon Press, 1991; "Theilheimer's Synthetic Methods of Organic Chemistry," Volumes 1–45, Karger, 1991; March, "Advanced Organic Chemistry," Wiley Interscience, 1991; Larock "Comprehensive Organic Transformations," VCH Publishers, 1989; Paquette, "Encyclopedia of Reagents for Organic Synthesis," 3d Edition, John Wiley & Sons, 1995). Other methods for synthesis of the compounds described herein and/or starting materials are either described in the art or will be readily apparent to the skilled artisan. Alternatives to the reagents and/or protecting groups illustrated in FIGS. 1 through 63 may be found in the references provided above and in other compendiums well known to the skilled artisan. Guidance for selecting suitable protecting groups can be found, for example, in Greene & Wuts, "Protective Groups in Organic Synthesis," Wiley Interscience, 1999. Accordingly, the synthetic methods and strategy presented herein are illustrative rather than comprehensive.

In particular, methods for synthesizing substituted diphenyl isoxazoles according to structural formula (I) (when Z is —CH—) is provided in FIGS. 2A through 7*b* and 12C through 12E.

FIGS. 4C, 4D and 15 through 18, which describe the preparation of acetylene compounds, are discussed in the Examples section.

It should be understood that in FIGS. 1 through 63 and throughout much of the specification, "C" ring meta isomers are shown by example only. The methodology to prepare "C" ring ortho, meta, or para positional isomers can be selected by the skilled artisan. Therefore, when "C" ring meta isomers are noted, similar synthetic methodology can be applied to prepare ortho or para "C" ring isomers. The meta isomer was chosen throughout FIGS. 1 through 63 for convenience and consistency to demonstrate the ability to prepare the compounds of interest.

In FIGS. 1 through 63, substituents $R^2$, $R^3$, $R^4$, $R^5$, $R^6$, $R^8$, $R^9$, $R^{10}$ and $R^{14}$ may include reactive functional groups that require protection during synthesis. Selection of suitable protecting groups will depend on the identity of the functional group and the synthesis method employed, and will be apparent to those of skill in the art. Guidance for selecting suitable protecting groups can be found in Greene & Wuts, supra, and the various other references cited therein.

Further guidance for carrying out 1,3-dipolar cycloaddition reactions, also named 1,3-dipolar additions, [3+2]cyclizations or [3+2]cycloadditions, can be found in "Cycloaddition Reactions in Organic Synthesis", (Kobayashi, S. and Jorgensen, K. A., Editors), 2002, Wiley-VCH Publishers, pp. 1–332 pages (specifically, Chapters 6 and 7 on [3+2]cycloadditions and 1,3-dipolar additions, pp. 211–248 and 249–300); "1,3-Dipolar Cycloaddition", *Chemistry of Heterocyclic Compounds*, Vol. 59, (Padwa, A. and Pearson, W., Editors), 2002, John Wiley, New York, pp. 1–940; "Nitrile Oxides, Nitrones, Nitronates in Organic Synthesis: Novel Strategies in Synthesis", Torssel, K. B. G., 1988, VCH Publishers, New York, pp. 1–332; Barnes & Spriggs, 1945, *J. Am. Chem Soc.* 67:134; Anjaneyulu et al., 1995, *Indian J. Chem., Sect.* 5 34(11):933–938); and T. L. Gilchrist, Pitman Publishing Ltd, 1985 ISBNO-273-02237-7; Strategies for Organic Drug Synthesis and Design, Lednicer, D., John Wiley and Sons, 1998.

Further guidance for synthesizing isoxazoles and hydro isomers thereof may be found in M. Sutharchanadevi, R. Murugan in *Comprehensive Heterocyclic Chemistry II*, A. R. Katritzky, C. W. Rees, E. F. V. Scriven, Eds.; Pergamon Press, Oxford, Vol. 3, p. 221; R. Grünager, P, Vita-Finzi in *Heterocyclic Compounds*, Vol. 49, *Isoxazoles, Part one*, John Wiley and Sons, New York, 1991; K. B. G. Torssell, *Nitrile Oxides, Nitrones, and Nitronates in Organic Synthesis*, VCH Publishers, New York, 1988; Y-Y. Ku, T. Grieme, P. Sharma, Y.-M. Pu, P. Raje, H. Morton, S. King *Organic Letters*, 2001, 3, 4185; V. G. Desai, S. G. Tilve *Synth. Comm.*, 1999, 29, 3017; X. Wei, J. Fang, Y. Hu, H. Hu *Synthesis*, 1992, 1205; C. Kashima, N. Yoshihara, S. Shirai *Heterocycles*, 1981, 16, 145; A. S. R. Anjaneyulu, G. S. Rani, K. G. Annapurna, U. V. Mallavadhani, Y. L. N. Murthy *Indian J. Chem. Sect B*, 1995, 34, 933; R. P. Barnes, A. S. Spriggs, *J. Am. Chem. Soc.*, 1945, 67, 134; A. Alberola, L. Calvo, A. G. Ortega, M. L. Sábada, M. C. Sañudo, S. G. Granda, E. G. Rodriguez *Heterocycles*, 1999, 51, 2675; X. Wang, J. Tan, K. Grozinger *Tetrahedron Lett.* 2000, 41, 4713; A. R. Katritzky, M. Wang, S. Zhang, M. V. Voronkov *J. Org. Chem.*, 2001, 66, 6787; J. Bohrisch, M. Pätzel, C. Mügge, J. Liebscher *Synthesis*, 1991, 1153; SHANKAR, B. B.; Yang, D. Y.; Girton, S.; Ganguly, A. K.; Tetrahedron Lett (TELEAY) 1998, 39 (17), 2447–2448. CHENG, W. C.; Wong, M.; Olmstead, M. M.; Kurth, M. J.; Org Lett (ORLEF7) 2002, 4 (5), 741–744. KHAN, M. S. Y.; Bawa, S.; Indian J. Chem, Sect B: Org Chem Incl Med Chem (USBDB) 2001, 40 (12), 1207–1214. SIMONI, D.; et al; J Med Chem (JMCMAR) 2001, 44 (14) 2308–2318. NUGIEL, D. A.; Tetrahedron Lett (TELEAY) 2001, 42 (21), 3545–3547. ARAI, N.; Iwakoshi, M.; Tanabe, K.; Narasaka, K.; Bull Chem Soc Jpn (BCSJA8) 1999, 72 (10), 2277–2285. SAGINOVA, L. G.; Grigorev, E. V.; Chem Heterocyd Compd (N Y) (CHCCAL) 1999, 35 (2), 244–247. MURI, D.; Bode, J. W.; Carreira, E. M.; Org Lett (ORLEF7) 2000, 2 (4), 539–541. KANEMASA, S.; Matsuda, H.; Kamimura, A.; Kakinami, T.; Tetrahedron (TETRAB) 2000, 56 (8), 1057–1064. MOCHALOV, S. S.; Kuzmin, Y. I.; Fedotov, A. N.; Trofmova, E. V.; Gazzaeva, R. A.; Shabarov, Y. S.; Zefirov, N. S.; Zh Org Khim (ZORKAE) 1998, 34 (9), 1379–1387. DAVIES, C. D.; Marsden, S. P.; Stokes, E. S. E.; Tetrahedron Lett (TELEAY) 1998, 39 (46) 8513–8516. KANEMASA, S.; Matsuda, H.; Kamimura, A.; Kakinami, T.; Tetrahedron (TETRAB) 2000, 56 (8), 1057–1064. WEIDNER WELLS, M. A.; Fraga Spano, S. A.; Turchi, I. J.; J Org Chem (JOCEAH) 1998, 63 (18), 6319–6328. PADMAVATHI, V.; BhaskarReddy, A. V.; Sumathi, R. P.; Padmaja, A.; Bhaskar Reddy, D.; Indian J Chem, Sect B: Org Chem Incl Med Chem (1JSBDB) 1998, 37 (12), 1286–1289. WILLIAMS, A. R.; Angel, A. J.; French, K. L.; Hurst, D. R.; Beckman, D. D.; Beam, C. F.; Synth Commun (SYNCAV) 1999, 29 (11), 1977–1988. CARAMELLA, P.; Reami, D.; Falzoni, M.; Quadrelli, P.; Tetrahedron (TETRAB) 1999, 55 (22), 7027–7044. KIDWAJ, M.; Misra, P.; Synth Commun (SYNCAV) 1999, 29 (18), 3237–3250. SYASSI, B.; El Bakkali, B.; Benabdellah, G. A.; Hassikou, A.; Dinia, M. N.; Rivere, M.; Bougrin, K.; Soufiaoui, M.; Tetrahedron Lett (TELEAY) 1999, 40 (40), 7205–7209. SYASSI, B.; Bougrin, K.; Soufiaoui, M.; Tetrahedron Lett (TELEAY) 1997, 38 (51), 8855–8858. LI, P.; Gi, H. J.; Sun, L.; Zhao, K.; J Org Chem (JOCEAH) 1998, 63 (2), 366–369. BOUGRIN, K.; Lamri, M.; Soufiaoui, M.; Tetrahedron Lett (TELEAY) 1998, 39 (25), 4455–4458. SRIVASTAVA, Y. K.; Sukhwai, S.; Ashawa, A.; Verma, B. L.; J Indian Chem Soc (JICSAH) 1997, 74 (7) 573–574. CORSARO, A.; Buemi, G.; Chiacchio, U.; Pistara, V.; Rescifina, A.; Heterocycles (HTCYAM)

1998, 48 (5) 905–918. CORSARO, A.; Librando, V.; Chiacchio, U.; Pistara, V.; Rescifna, A.; Tetrahedron (TETRAB) 1998, 54 (31), 9187–9194. CORSARO, A.; Librando, V.; Chiacchio, U.; Pistara, V.; Tetrahedron (TETRAB) 1996, 52 (40), 13027–13034. BELENKII, L. I.; Gromova, G.; Lichitshii, B. V.; Krayushkin, M. M.; Izv Akad Nauk, Ser Khim (IASKEA) 1997, (1), 106–109. KASHIMA, C.; Takahashi, K.; Fukuchi, I.; Fukusaka, K.; Heterocycles (HTCYAM) 1997, 44 (1) 289–304. BASEL, Y.; Hassner, A.; Synthesis (SYNTBF) 1997, (3), 309–312. BANNIKOV, G. F.; Ershov, V. V.; Nikiforov, G. A.; Izv Akad Nauk, Ser Khim (IASKEA) 1996 (2), 426–429. TOKUNAGA, Y.; Ihara, M.; Fukumoto, K.; Heterocycles (HTCYAM) 1996, 43 (8), 1771–1775. AHMED, G. A.; J Indian Chem Soc (JICSAH) 1995, 72 (3) 181–183. LU, T. J.; Yang, J. F.; Sheu, L. J.; J Org Chem (JOCEAH) 1995, 60 (23) 7701–7705. EASTON, C. J.; Hughes, C. M. M.; Tiekink, E. R. T.; Savage, G. P.; Simpson, G. W.; Tetrahedron Lett (TELEAY) 1995, 36 (4) 629–632. WALLACE, R. H.; Liu, J.; Tetrahedron Lett (TELEAY) 1994, 35 (41) 7493–7496. BALDOLI, C.; Gioffreda, F.; Zecchi, G.; J Heterocycl Chem (JHTCAD) 1994, 31 (1), 251–253. WEIDNER WELLS, M. A.; Fraga, S. A.; Demers, J. P.; Tetrahedron Lett (TELEAY) 1994, 35 (35), 6473–6476. HANSEN, J. F.; Georgiou, P. J.; J Heterocycl Chem (JHTCAD) 1994, 31 (6), 1487–1491. ANKHIWALA, M. D.; Hathi, M. V.; J Indian Chem Soc (JICSAH) 1994 71 (9) 587–589. KAMIMURA, A.; Hori, K.; Tetrahedron (TETRAB) 1994, 50 (27) 7969–7980. ABBADY, M. A.; Hebbachy, R.; Indian J Chem, Sect B (IJSBDB) 1993, 32 (11), 1119–1124. MORIYA, O.; Takenaka, H.; lyoda, M.; Urata, Y.; Endo, T.; J Chem Soc, Perkin Trans 1 (JCPRB4) 1994 (4), 413–417. TANAKA, S.; Kohmoto, S.; Yamamoto, M.; Yamada, K.; Nippon Kagaku Kaishi (NKAKB8) 1992 (4), 420–422. NAGARAJAN, A.; Pillay, M. K.; Indian J Chem, Sect B (IJSBDB) 1993, 32 (4), 471–474. STOYANOVICH, F. M.; Bulgakova, V. N.; Krayushkin, M. M.; Lzv Akad Nauk SSSR, Ser Khim (IASKA6) 1991 (11), 2606–2611. BALDOLI, C.; Del Buttero, P.; Manorana, S.; Zecchi, G.; Moret, M.; Tetrahedron Lett (TELEAY) 1993, 34 (15), 2529–2532. MIZUNO, K.; Ichinose, N.; Tamai, T.; Otsuji, Y.; J Org Chem (JOCEAH) 1992, 57 (17), 4669–4675. HUANG, Z. T.; Wang, M. X.; Synth Commun (SYNCAV) 1991, 21, 1167–1176. MOHAMED, T. A.; Kandeel, M. M.; Awad, I. M. A.; Youssef, M. S. K.; Collect Czech Chem Commun (CCCCAK) 1991, 56 (12), 2999–3005. MORIYA, O.; Urata, Y.; Endo, T.; J Chem Soc. Chem Commun (JCCCAT) 1991 (13), 884–885. HUANG, Z. T.; Wang, M. X.; Synth Commun (SYNCAV) 1991, 21, 1167–1176. MORIYA. O.; Takenaka, H.; Urata, Y.; Endo, T.; J Chem Soc, Chem Commun (JCCCAT) 1991 (23), 1671–1672. SOUFIAOUI, M.; Syassi, B.; Daou, B.; Baba, N.; Tetrahedron Lett (TELEAY) 1991, 32 (30), 3699–3700. SAGINOVA, L. G.; Kukhareva, I. L.; Lebedev, A. T.; Shabarov, YU, S.; Zh Org Khim (ZORKAE) 1991, 27 (9) 1852–1860. KANEMASA, S.; Nishiuchi, M.; WADA, E.; Tetrahedron Lett (TELEAY) 1992, 33 (10), 1357–1360. MAMAEVA, O. O.; Krayushkin, M. M.; Stoyanovich, F. M.; Izv Akad Nauk SSSR, Ser Khim (IASKAG) 1990 (4), 913–916. BRTOKHOVETSKII, D. B.; Belenkii, L. I.; Krayushkin, M. M.; Izv Akad Nauk SSSR, Ser Khim (IASKAG) 1990 (7), 1692–1693. ITO, S.; Sato, M.; Bull Chem Soc Jpn (BCSJA8) 1990, 63 (9), 2739–2741. MORIYA, O.; Urata, Y.; Endo, T.; J Chem Soc, Chem Commun (JCCCAT) 1991 (1), 17–18. ALMTORP, G. T.; Bachmann, T. L.; Torssell, K. B. G.; Acta Chem Scand (ACHSE7) 1991, 45 (2), 212–215. KHAN, M. S. Y.; Khan, M. H.; Kumar, M.; Javed, K.; J Indian Chem Soc (JICSAH) 1990, 67 (8), 689–691. KHALIL, Z. H.; Yanni, A. S.; Abdel-Hafez, A. A.; Khalaf, A. A.; J Indian Chem Soc (JICSAH) 1990, 67 (10), 821–823. SHIMIZU, T.; Hayashi, Y.; Furukawa, N.; Teramura, K.; Bull Chem Soc Jpn (BCSJA8) 1991, 64 (1), 318–320. FADDA, A. A.; Indian J Chem, Sect B (IJSBDB) 1991, 30 (8), 749–753. RAMA RAO, K.; Bhanumathi, N.; Srinivasan, T. N.; Sattur, P. B.; Tetrahedron Lett (TELEAY) 1990, 31, 899. ICHINOSE, N.; Mizuno, K.; Yoshida, K.; Otsuji, Y.; Chem Lett (CMLTAG) 1988, 723. SINISTERRA, J. V.; Marinas, J. M.; Bull Soc Chim Belg (BSCBAG) 1987, 96 (4), 293. BALABAN, A. T.; Zugravescu, I.; Avramovici, S.; Silhan, W.; Monatsh Chem (MOCMB7) 1970, 101, 704. LITINAS, K. E.; Nicolaides, D. N.; Varelia, E. A.; J Heterocycl Chem (JHTCAD) 1990, 27, 769. ICHINOSE, N.; Mizuno, K.; Tamai, T.; Otsuji, Y.; Chem Lett (CMLTAG) 1988, 233. THOSEN, I.; Torsseli, K. B. G.; Acta Chem Scand, Ser B (ACBOCV) 1988, 42, 303. ROCHE; Synthesis (SYNTBF) 1984 (12), 1083. CURRAN, D. P.; J Am Chem Soc (JACSAT) 1983, 105 (18), 5826. JAGER, V.; et al.; Bull Soc Chim Beig (BSCBAG) 1983, 92, 1039. RAO, C. J.; Reddy, K. M.; Murthy, A. K.; Indian J Chem, Sect B (IJSBDB) 1981, 20, 282. EIKASABY, M. A.; Salem, M. A. I.; Indian J Chem (IJOCAP) 1950, 19, 571. CHINCHOLKAR, M. M.; Jamoda, V. S.; Indian J Chem (IJOCAP) 1979, 17 610. SHABAROV, Y. S.; Saginova, L. G.; Gazzaeva, R. A.; J Org Chem USSR (Engl Transl) (JOCYA9) 1982, 18, 2319. SHIMIZU, T.; Hayashi, Y.; Yamada, K.; Nishlo, T.; Teramura, K.; Bull Chem Soc Jpn (BCSJA8) 1981, 54, 217. WITZCAK, Z.; Heterocycles (HTCYAM) 1980, 14, 1319. DEMINA, L. A.; et al.; Zh Org Khim (ZORKAE) 1979, 15, 735. CHEM ABSTRA (CHABA8), 91 (74512). ARCHIBALD, A. T.; Nielsen, T. G.; Tetrahedron Lett (TELEAY) 1968, 3375. KOHLER, E. P.; Barrett, G. R.; J Am Chem Soc (JACSAT) 1924, 46, 2105. DEMINA, L. A.; Khismutdinov, G. K.; Tkachev, S. V.; Fainzilberg, A. A.; J Org Chem USSR (Engl Transl) (JOCYA9) 1979, 15, 654. BAAVA, L. N.; Demina, L. A.; Trusova, T. V.; Furin, G. G.; Khisamutdinov, G. K.; J Org Chem USSR (Engl Transl) (JOCYA9) 1979, 15, 2179. CARAMELLA, P.; Cellerino, G.; Houk, K. N.; Albini, F. M.; Santiago, C.; J Org Chem (JOCEAH) 1978, 43, 3007. CARAMELLA, P.; Cellerino, G.; Houk, K.; Albini, F. M.; Santiago, C.; J Org Chem (JOCEAH) 1978, 43, 3006. SAUTER, F.; Buyuk, G.; Monatsh Chem (MOCMB7) 1974, 105, 254. ELKASABY, M. A.; Salem, M. A. I.; Indian J Chm (IJOCAP) 1980, 19, 571. BAEVA, L. N.; Demina, L. A.; Trusova, T. V.; Furin, G. G.; Khisamutdinov, G. K.; J Org Chem USSR (Engl Transl) (JOCYA9) 1979, 15, 2179. MAKSOUD, A. A.; Hosnig, G.; Hassan, O.; Shafik, S.; Rev Roum Chim (RRCHAX) 1978, 23, 1541. FUKUNAGA, K.; Synthesis (SYNTBF) 1978, 55. FARAGHER, R.; Gilchrist, T. L.; J Chem Soc, Perkin Trans I (JCPRB4) 1977, 1196. BIANCHI, G.; De Micheli, C.; Gandolfi, R.; J Chem Soc, Perkin Trans I (JCPRB4) 1976, 1518. LO VECCHIO, G.; Atti Accad Peloritana Periocolanti, CI Sci Fis, Mat Nat (AAPFAO) 1972, 52, 207. JURD, L.; Chem Ind (London) (CHINAG) 1970, 2, 624. BELTRAME, P. L.; Cattania, M. G.; Redaelli, V.; Zecchi, G.; J Chem Soc, Perkin Trans 2 (JCPKBH) 1977, 706. PARK, C. A.; Beam, C. F.; Kaiser, E. M.; Hauser, C. R.; et al.; J Heterocyol Chem (JHTCAD) 1976, 13, 449. LO VECCHIO, G.; Atti Accad Peloritana Pericolanti, CI Sci Fis, Mat Nat (AAPFAO) 1972, 52, 217. BORKHADE, K. T.; Marathey, M. G.; Indian J Chem (IJOCAP) 1970, 8, 796. WAKEFIELD, B. J.; Wright, D. J.; J Chem Soc C (JSOOAX) 1970, 1165. UNTERHALT, B.; Pham Zentralhalle (PHZEBE) 1968, 107, 356. NIELSEN, A. T.; Archibald, T. G.; Tetrahedron Lett (TELEAY) 1968, 3375. KIRTZ, D. W.; Shechter, H.; J Chem Soc, Chem Commun (JCCCAT) 1965, 689. JOSHI, K. C.; Jauhar, A. K.; J Indian Chem Soc (JICSAH) 1965, 42, 733. NIELSEN, A. T.; Archibald, T. G.; J Org Chem (JOCEAH) 1969, 34, 984. BATTAGLIA, A.; Dondoni, A.; Rio Sci (RISCAZ) 1968, 38, 201. MONIORTE, F.; Lo Vecchio, G.; Atti Accad Peloritana Periocolanti, Cl Sci Fis, Mat Nat (AAPFAO) 1966, 49, 169. ARBASINO, M.; Finzi, P. V.; Rio Sci (RISCAZ) 1966, 36, 1339. ROTH, H. J.; Schwartz, M.; Arch Pharm Ber Dtsch Pharm Ges (APBDAJ) 1961, 294, 769. ROTH, H. J.; Schwarz, M.; Arch Pharm Ber Dtsch Pharm Ges (APBDAJ) 1961, 294, 761. GRUNANGER, P.; Gandini, C.; Quilico, A.; Rend -1st Lomb Accad Sci Lett, A: Sci Mat, Fis, Chim Geol (RLMAAK) 1959, 93, 467. RUPE, H.; Schneider, F.; Chem Ber (CHBEAM) 1895, 28, 957. BARLUENGA, J.; Aznar, F.; Palomero, M. A.; Chem Eur J (CEUJED) 2001, 7 (24), 5318–5324. ASCHWANDEN, P.; Frantz, D. E.; Carreira, E. M.; Org Lett (ORLEF7) 2000, 2 (15), 2331–2333. BALASUNDARAM, B.; Veluchamy, T. P.; Velmurugan, D.; Perumal, P. T.; Indian J Chem, Sect B (IJSBDB) 1995, 34 (5), 367–371. CHAN, K. S.; Yeung, M. L.; Chan, W.; Wang, R.-J.; Mak, T. C. W.; J Org Chem (JOCEAH) 1995, 60 (6), 1741–1747. CHIACCHIO, U.; Casuscelli, F.; Liguori, A.; Rescifina, A.; Romeo, G.; Sindona, G.; Uccella, N.; Heterocycles (HTCYAM) 1993, 36 (3), 585–600. CHAN, K. S.; J Chem Soc, Perkin Trans I (JCPRB4) 1991 (10), 2602–2603. LIGUORI, A.; Ottana, R.; Romeo, G.; Sindona, G.; Uccelia, N.; Heterocycles (HTCYAM) 1988, 27, 1365. STAMM, H.; Staudie, H.; Arch Pharm (Weinheim, Ger) (ARPMAS) 1976, 309, 1014. TASZ, M. K.; Plenat, F.; Christau, H.-J.; Skowronski, R.; Phosphorus, Sulfur Silicon Relat Elem (PSSLEC) 1991, 57, 143–146. ALBEROIA, A.; Gonzalez, A. M.; Laguna, M. A.; Pulido, F. J.; Synthesis (SYNTBF) 1982, 1067. JACOB K. C.; Jadhar, G. V.; Vakharia, M. N.; Pesticides (PSTDAN) 1972, 6, 94. CLERICI, F.; Gelmi, M. L.; Pini, E.; Valle, M.; Tetrahedron [TETRAB] 2001, 57 (25), 5455–5459. JURD, L.; Chem Ind (London) [CHINAG] 1970, 2, 624. JURD, L.; Tetrahedron [TETRAB] 1975, 31, 2884.

Further guidance for synthesizing pyrazoles may be found in J. Elguero in *Comprehensive Heterocyclic Chemistry II*, A. R. Katritzky, C. W. Reees, E. F. V. Scriven., Eds.; Pergamon Press, Oxford, 1996; Vol. 3, p.1.

Figure 8A:
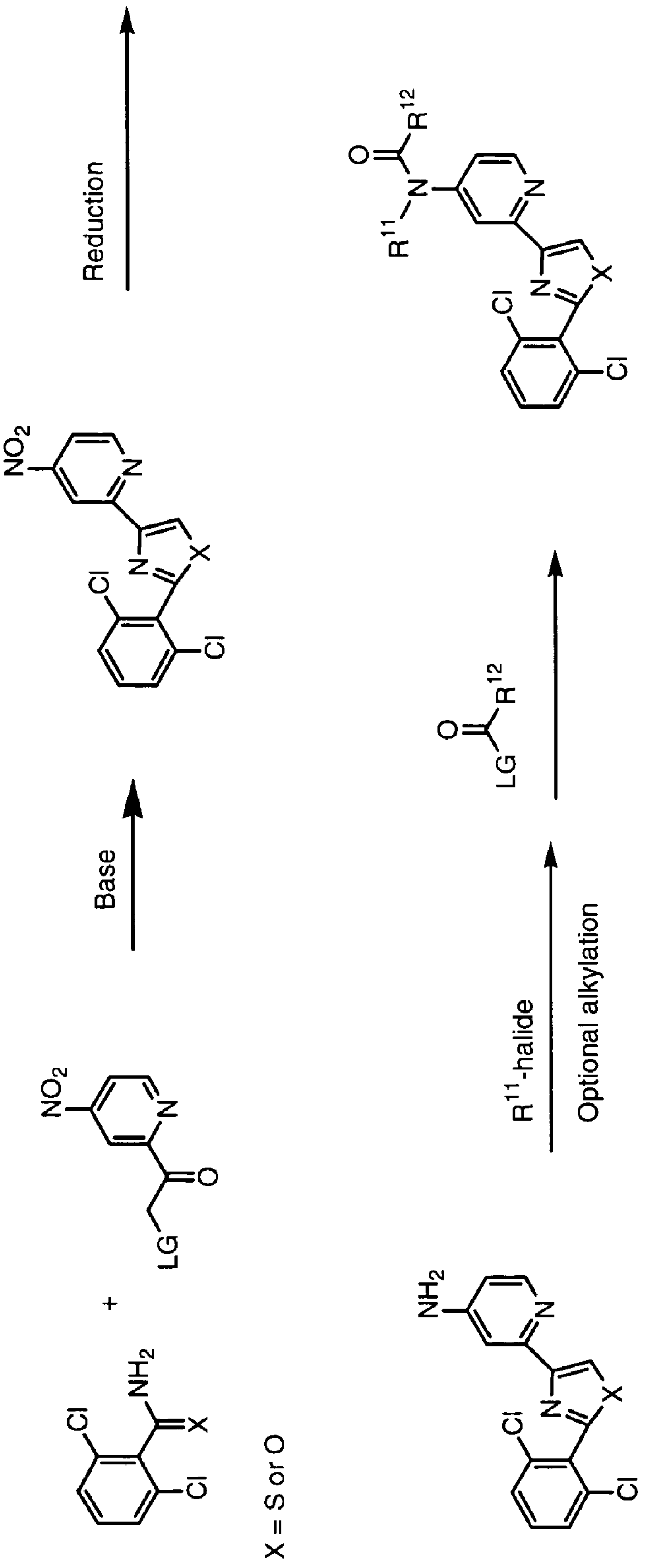
Figure 8B:
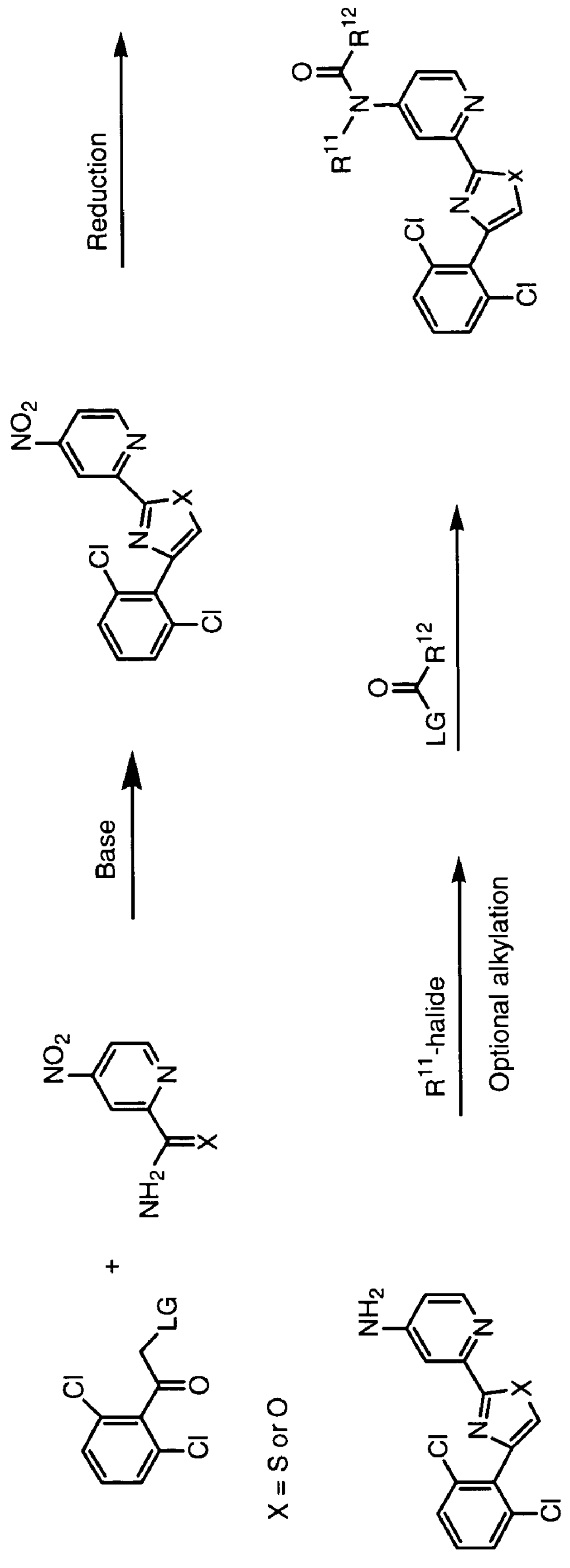

Guidance for synthesizing compounds as described in FIGS. 8A and 8B may be found in LHOTAK, P.; Kurfuerst, A.; Collect Czech Chem Commun [CCCCAK] 1993, 58 (11), 2720–2728. BRAIN, C. T.; Paul, J. M.; Synlett [SYNLES] 1999, (10), 1642–1644. VARMA, R. S.; Kumar, D.; J Heterocycl Chem [JHTCAD] 1998, 35 (6), 1533–1534. FEDYUNYAEVA, I. A.; Yushko, E. G.; Bondarenko, V. E.; Khim Geterotsikl Soedin [KGSSAQ] 1996 (3), 333–337. DOROSHENKO, A. O.; Patsenker, L. D.; Baumer, V. N.; Chepeleva, L. V.; Vankevich, A. V.; Shilo, O. P.; Yannolenko, S. N.; Shershukov, V. M.; Mitina, V. G.; Ponomarev, O. A.; Zh Obshch Khim [ZOKHA4] 1994, 64 (4), 646–652. FEDYUNYAEVA, I. A.; Shershukov, V. M.; Khim Geterotsikl Soedin [KGSSAQ] 1993 (2), 234–237. KLEIN, R. F. X.; Horak, V.; Baker, G. A. S.; Collect Czech Chem Commun [CCCCAK] 1993, 58 (7), 1631–1635. KERR, V. N.; Hayes, F. N.; Ott, D. G.; Lier, R.; Hansbury, E., J Org Chem (JOCEAH] 1959, 24, 1864. NISHIO, T.; Ori, M.; Helv Chim Acta [HCACAV] 2001, 84 (8), 2347–2354. LHOTAK, P.; Kurfuerst, A.; Collect Czech Chem Commun [CCCCAK] 1993, 58 (11), 2720–2728. SIEGREST, A. E.; Helv Chim Acta [HCACAV] 1967, 50, 906; and GABRIEL, S.; Chem Ber [CHBEAM] 1910, 43, 134.

Figure 9A:
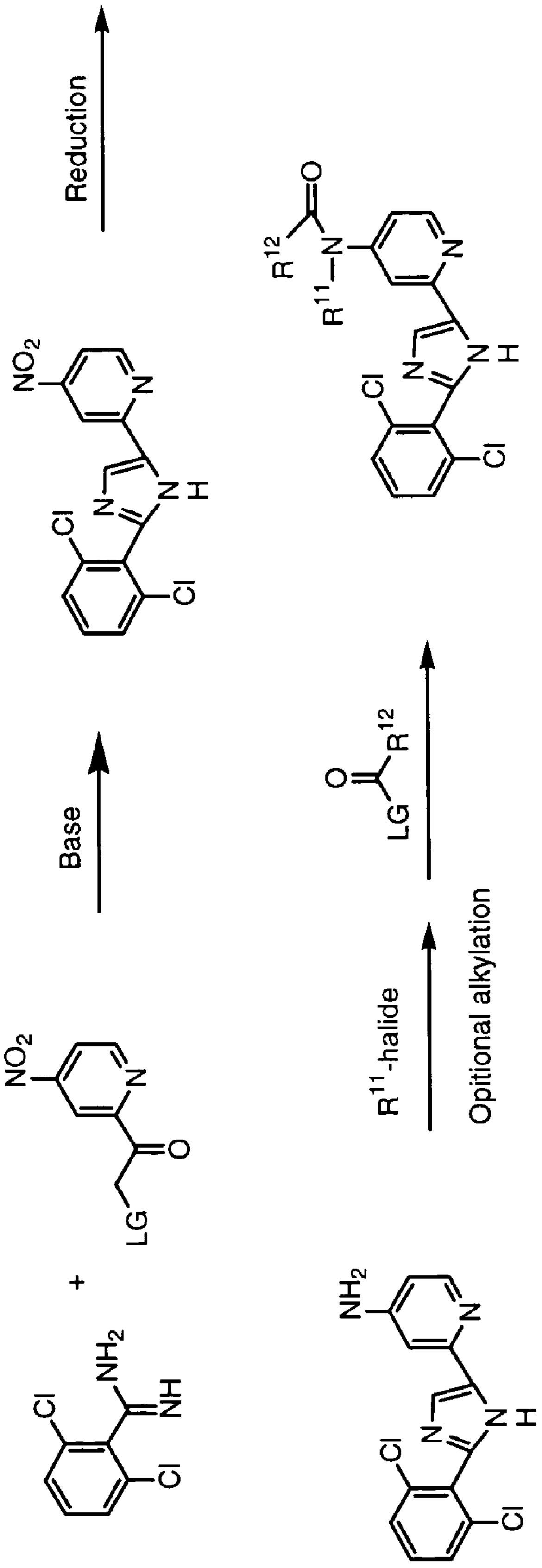
Figure 9B:
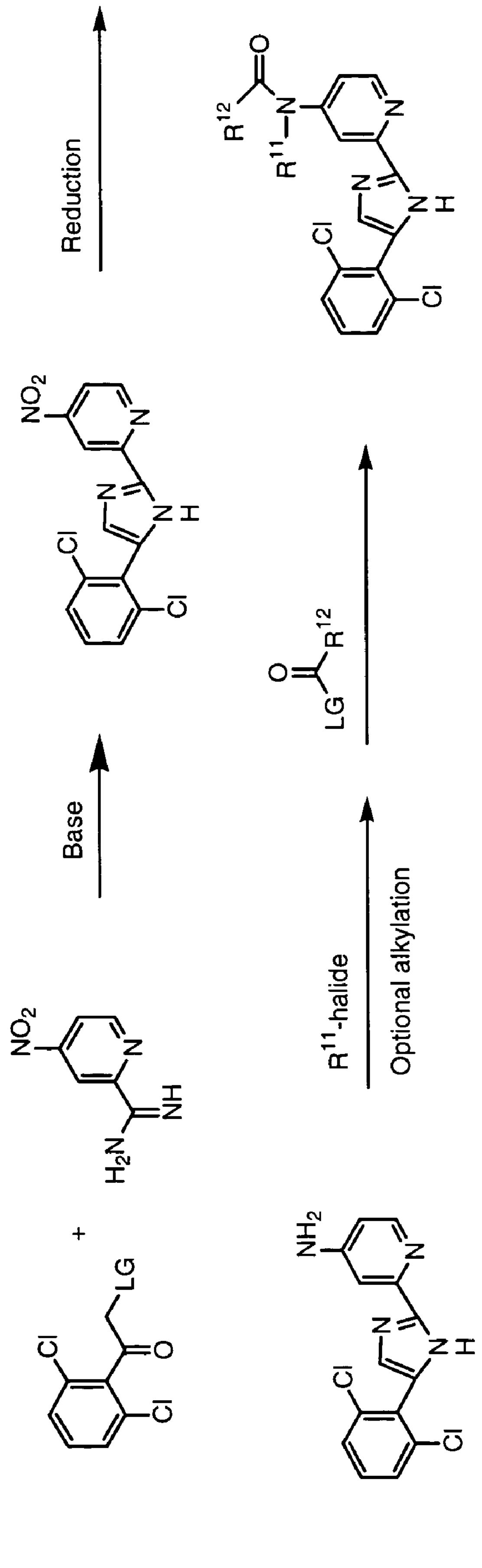

Guidance for synthesizing compounds as described in FIGS. 9A and 9B may be found in ZHANG, P.-F.; Chen, Z.-C.; Synthesis (SYNTBF) 2001, (14), 2075–2077. BUTLER, R. N.; Cloonan, M. O.; McMahon, J. M.; Burke, L. A.; J Chem Soc, Perkin Trans 1 (JCPRB4) 1999, (12), 1709–1712. NAKAWISHI, S.; Otsuji, Y.; Nantaku, J.; Chem Lett (CMLTAG) 1983, 341. POCAR, D.; Stradi, R.; Tetrahedron Lett (TELEAY) 1976, 1839. POPILIN, O. N.; Tishchenko, V. G.; Khim Geterotsikl Soedin (KGSSAQ) 1972, 1264; and KUNCKELL, F.; Chem Ber (CHBEAM) 1901, 34, 637.

Figure 10A:
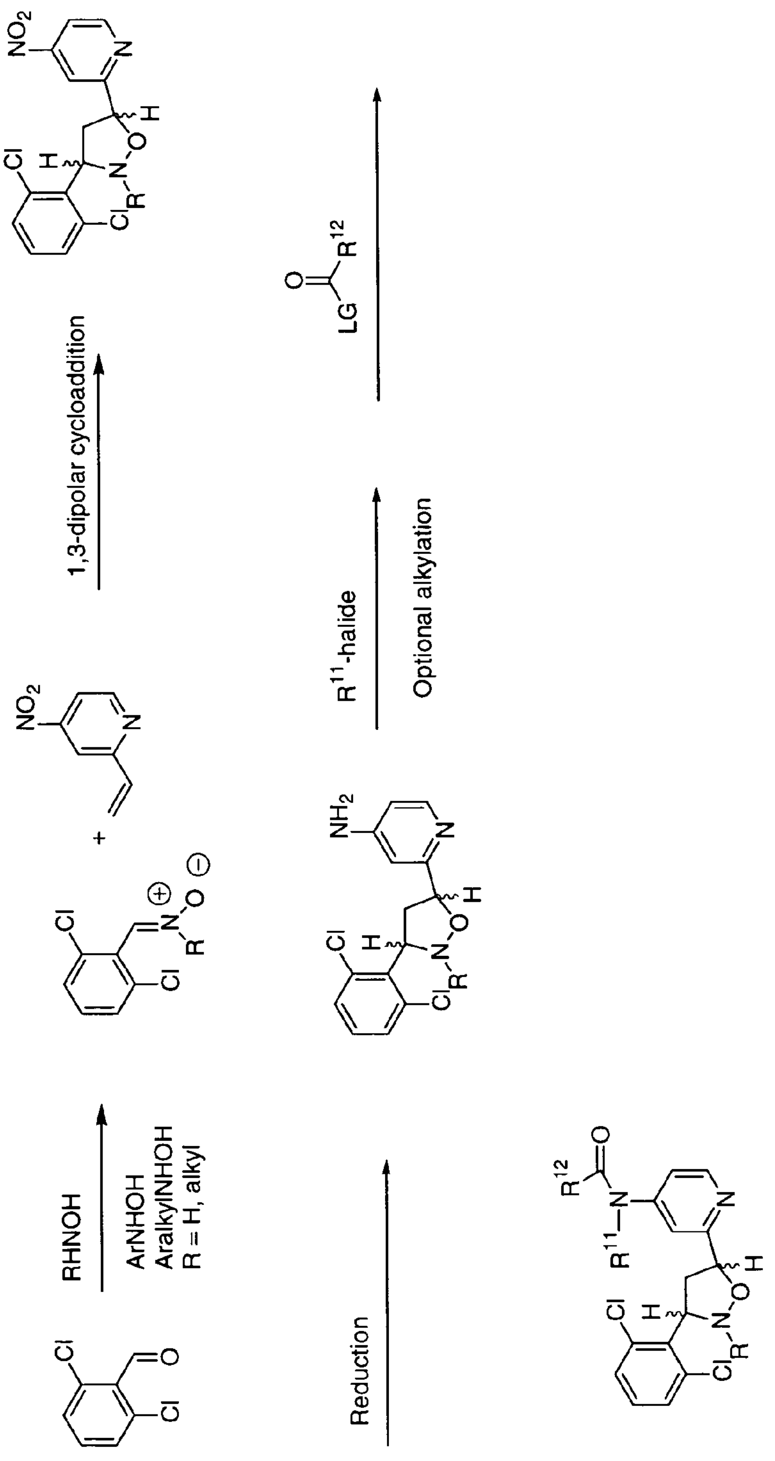
Figure 10B:
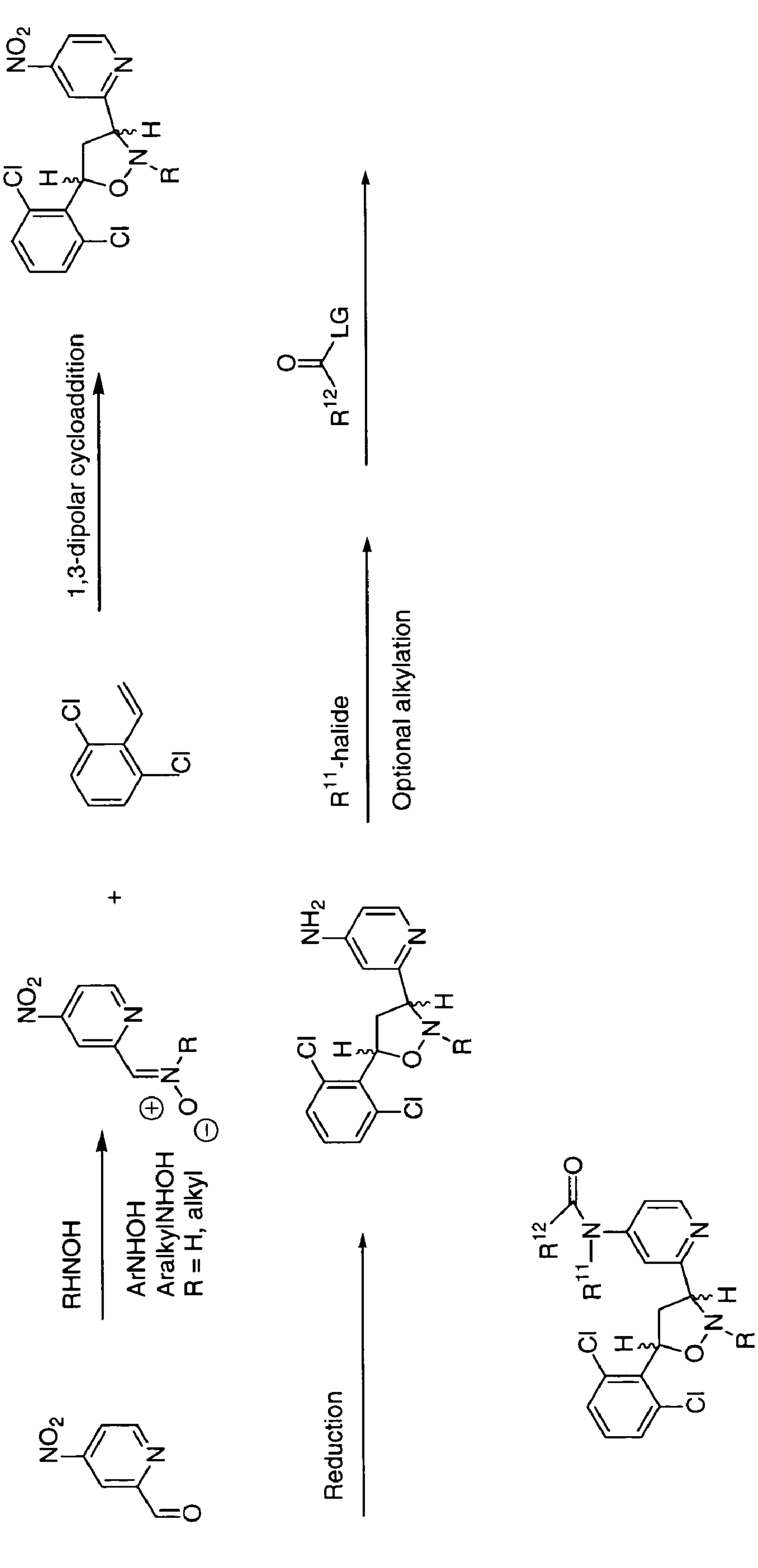

Guidance for synthesizing compounds as described in FIGS. 10A and 10B may be found in VARLAMOV, A. V.; Turchin, K. F.; Chernyshev, A. I.; Zubkov, F. I.; Borisova, T. N.; Chem Heterocycl Compd (N Y) [CHCCAL] 2000, 36 (5), 621–622. CASUSCELLI, F.; Chiacchio, U.; Rescifina, A.; Romeo, R.; Romeo, G.; Tommasini, S.; Uccella, N.; Tetrahedron (TETRAB) 1995, 51 (10), 2979–2990. CHIACCHIO, U.; Casuscelli, F.; Corsaro, A.; Rescifina, A.; Romeo, G.; Uccella, N.; Tetrahedron (TETRAB) 1994, 50 (22), 6671–6680. MUKAI, C.; Kim, I. J.; Cho, W. J.; Kido, M.; Hanaoka, M.; J Chem Soc, Perkin Trans 1 (JCPRB4) 1993 (20), 2495–2503. MINAMI, T.; Isonaka, T.; Okada, Y.; Ichikawa, J.; J Org Chem (JOCEAH) 1993, 58 (25), 7009–7015. TANAKA, K.; Mori, T; Mitsuhashi, K.; Bull Chem Soc Jpn (BCSJA8) 1993, 66 (1), 263–268. HUISGEN, R.; et al.; Tetrahedron Lett (TELEAY) 1960, 12, 5. CHEM BER (CHBEAM) 1968, 101, 2043. CHEM BER (CHBEAM) 1968, 101, 2568. CHEM BER (CHBEAM) 1969, 102, 117. SASAKI, T.; Bull Soc Chim Fr (BSCFAS) 1968, 41, 2960; and SASAKI, T.; Bull Chem Soc Jpn (BCSJA8) 1968, 41, 2964.

Figure 11A:
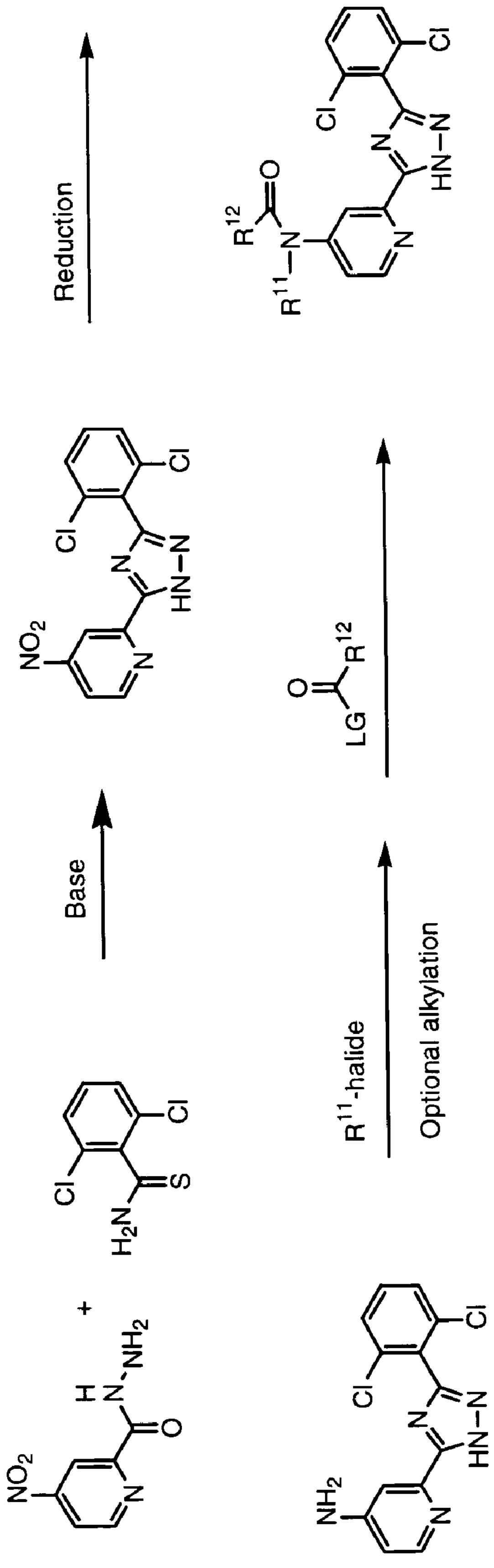
Figure 11B:
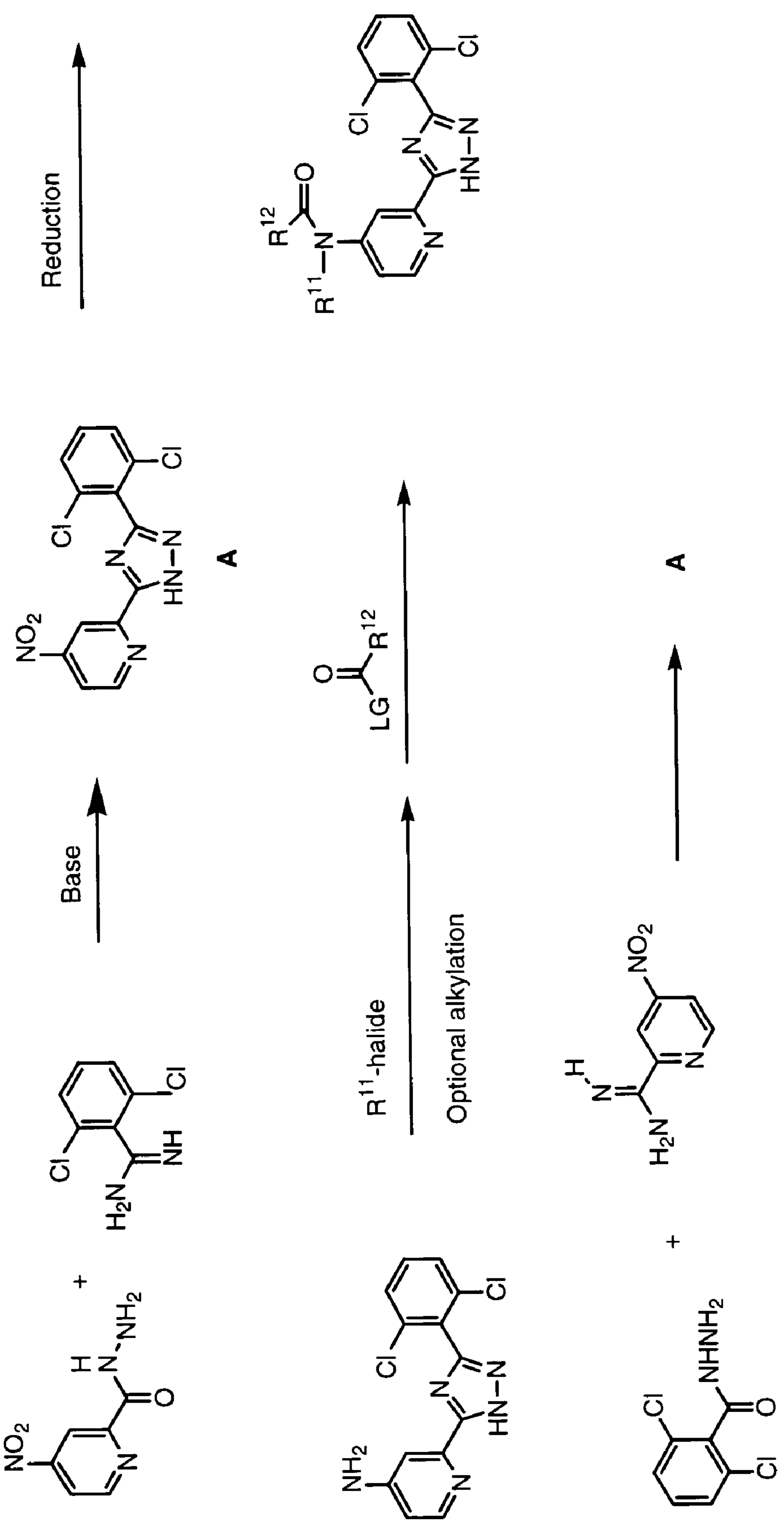

Guidance for synthesizing compounds as described in FIGS. 11A and 11B may be found in KATRIZKY, A. R.; Qi, M.; Feng, D.; Zhang, G.; Griffith, M. C.; Watson, K.; Org Lett (ORLEF7) 1999, 1 (8), 1189–1191. FRANCIS, J. E.; Cash, W. D.; Barbaz, B. S.; Bernard, P. S.; Lovell, R. A.; Mazzenga, G. C.; Friedmann, R. C.; Hyun, J. L.; Braunwalder, A. F.; Loo, P. S.; Bennett, D. A.; J Med Chem (JMCMAR) 1991, 34 (1), 281–290. POTTS, K. T.; J Chem Soc (JCSOA9) 1954, 3461. EINHORN, A.; Justus Liebigs Ann Chem (JLACBF) 1905, 343, 207. SHIBA, S. A.; El-Khamry, A. A.; Shaban, M. E.; Atia, K. S.; Pharmazie (PHARAT) 1997, 52 (3), 189–194; and MOLINA, P.; Tarranga, A.; Espinosa, A.; Lidon, M. J.; Synthesis (SYNTBF) 1987 (2), 128.

Figure 12A:
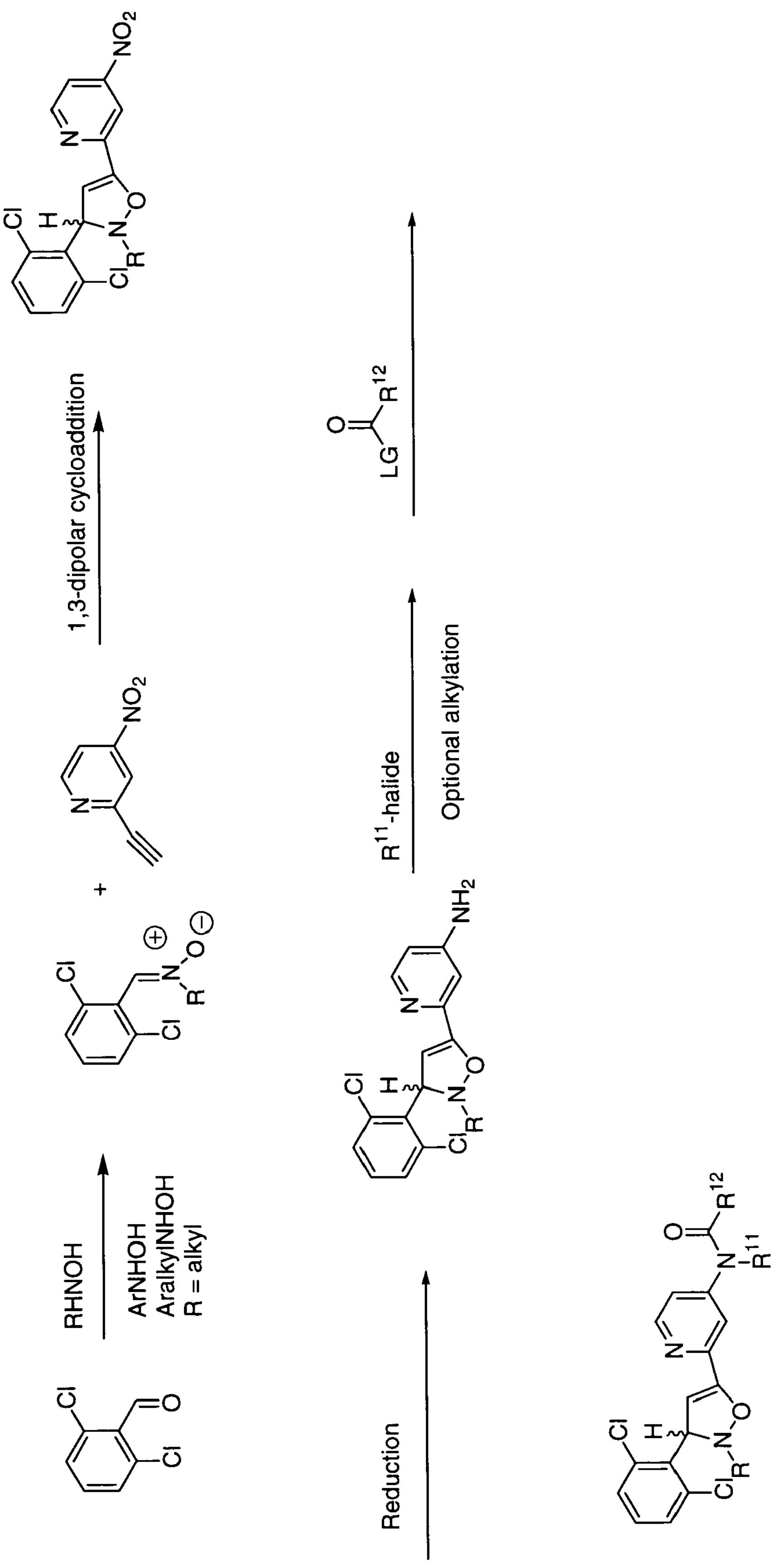
Figure 12B:
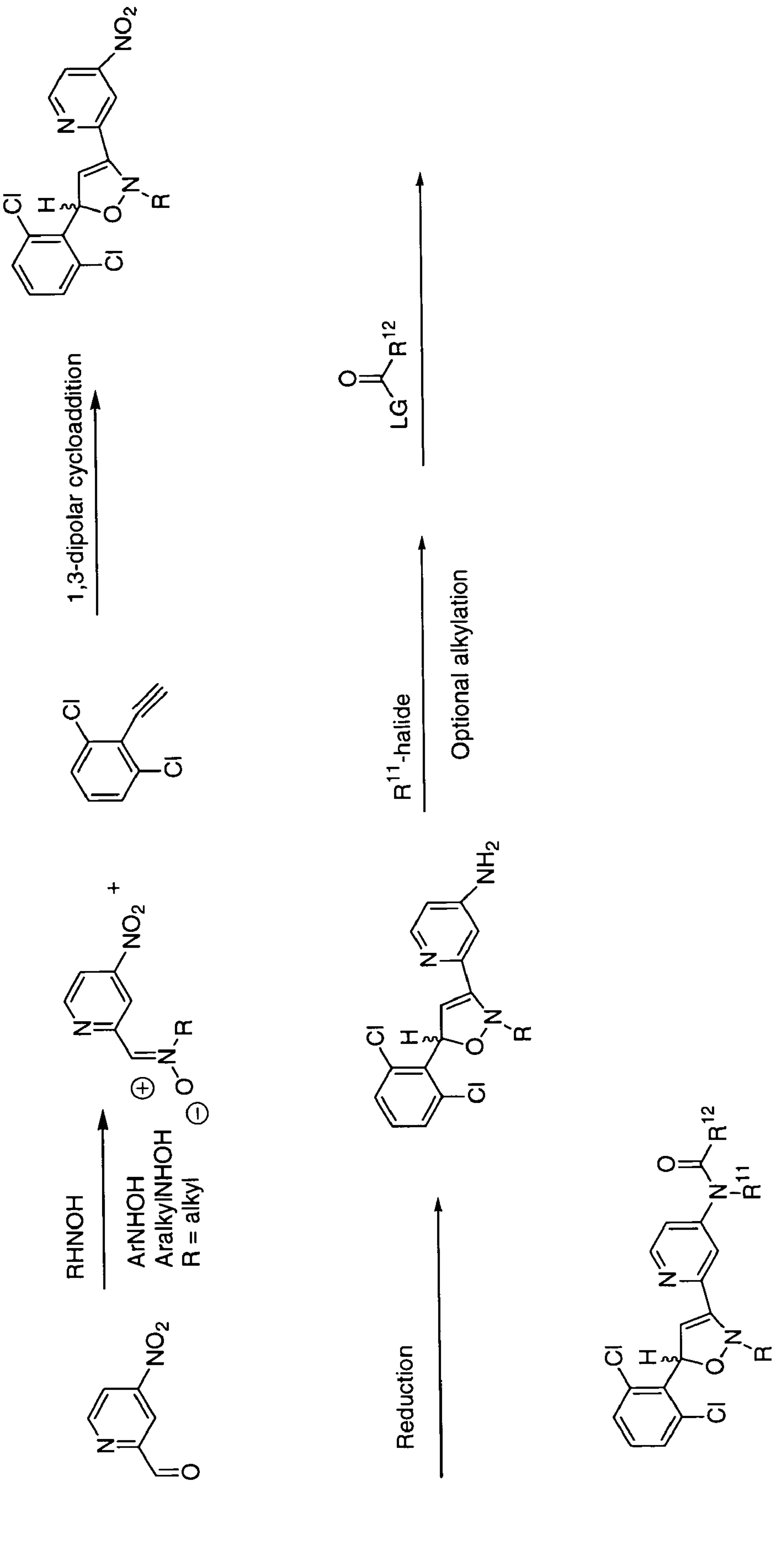
Figure 12C:
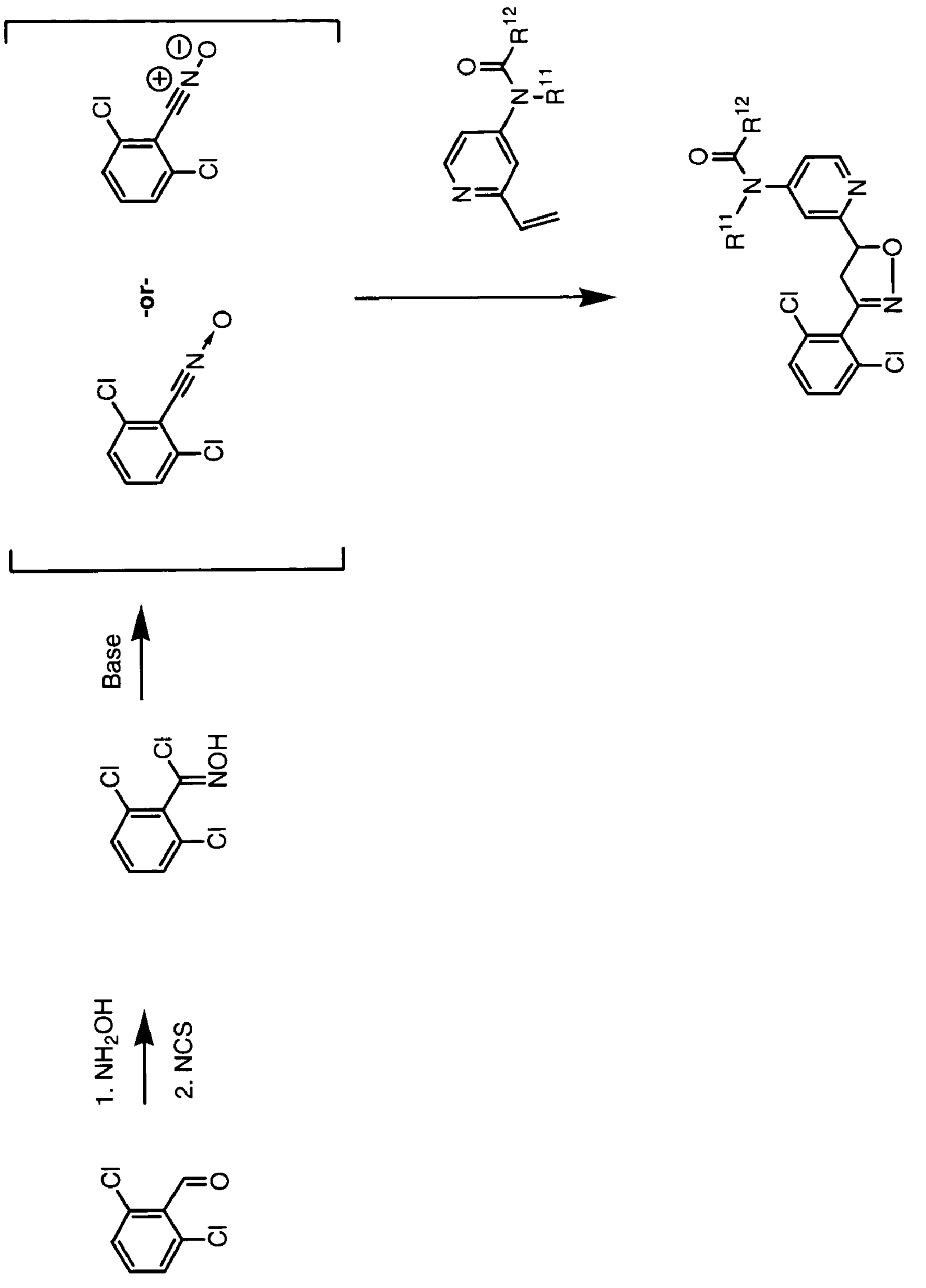
Figure 12D:
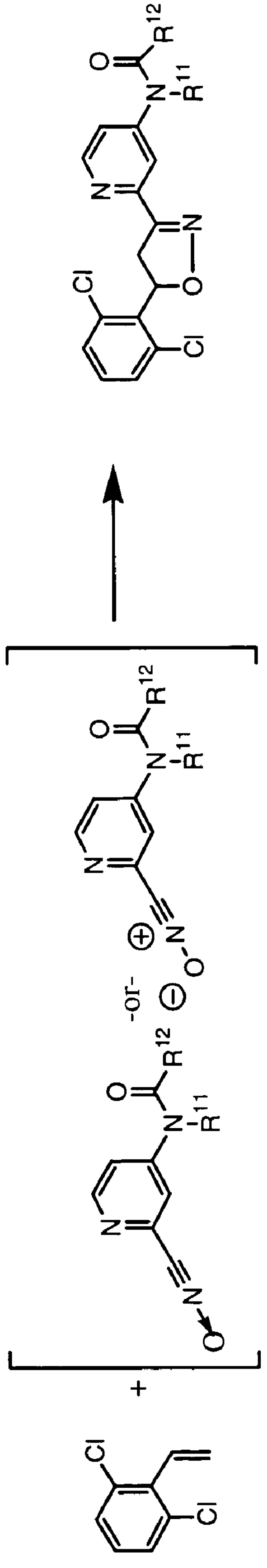
Figure 12E:
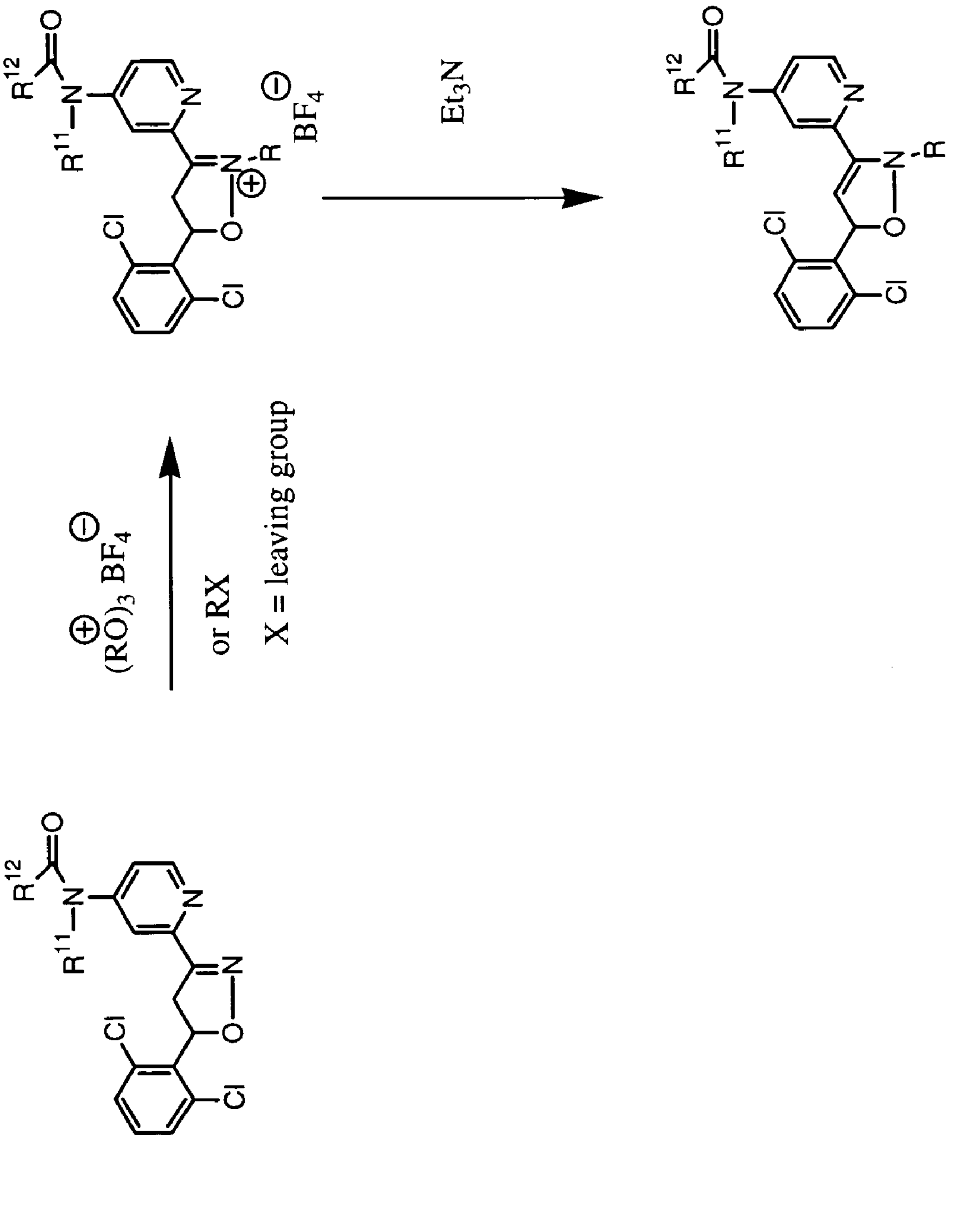
Figure 13:
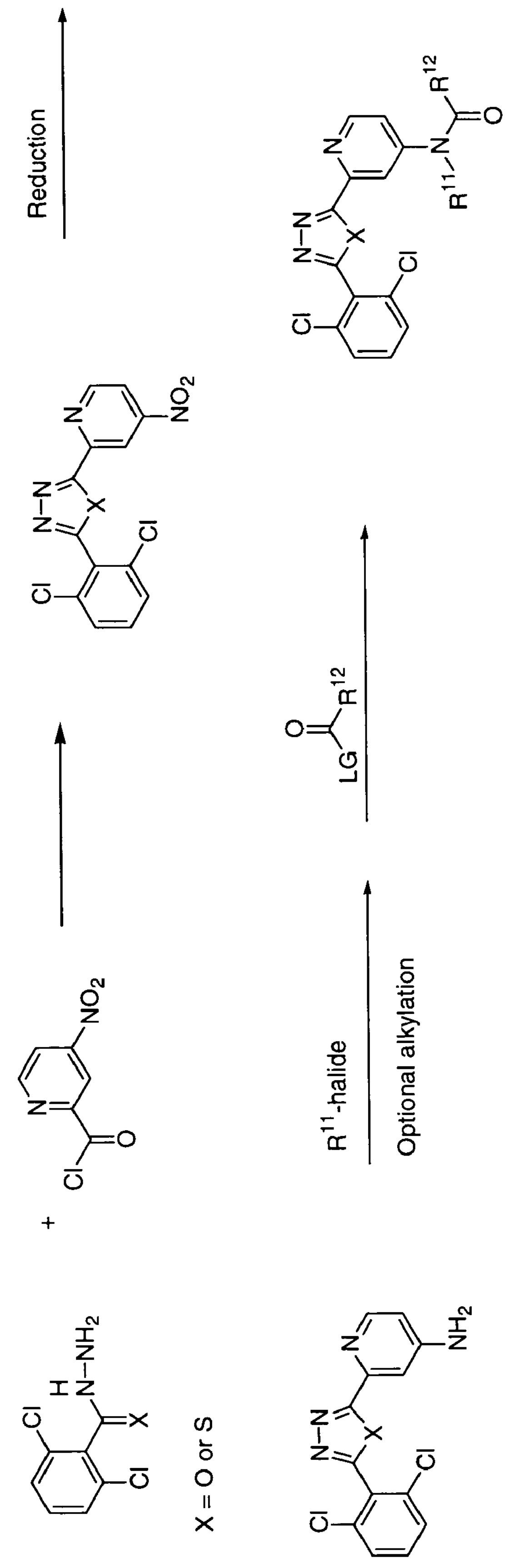
Figure 14:
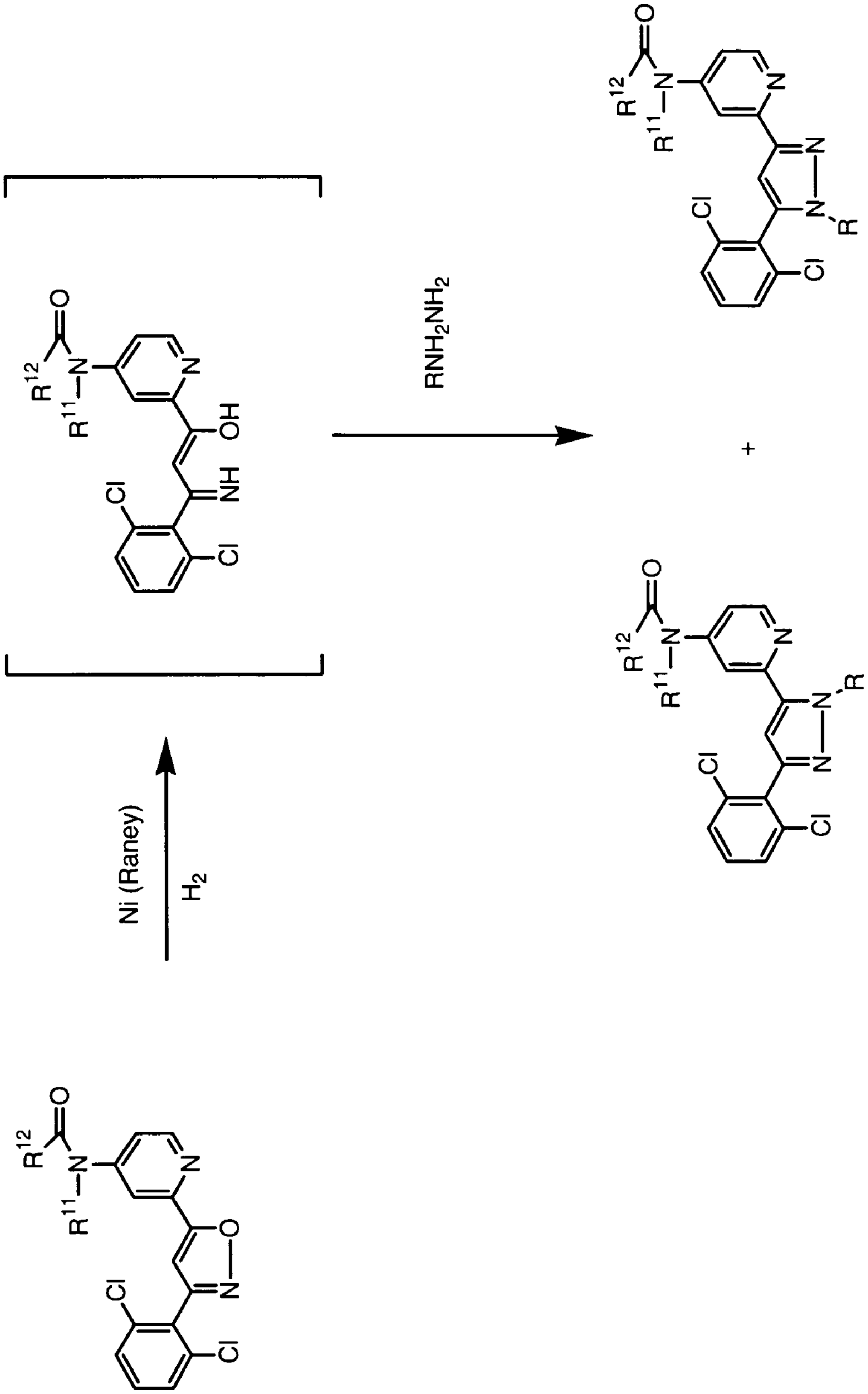

Guidance for synthesizing compounds as described in FIGS. 12A and 12B may be found in ASCHWANDEN, P.; Frantz, D. E.; Carreira, E. M.; Org Lett (ORLEF7) 2000, 2 (15), 2331–2333. BALASUNDARAM, B.; Veluchamy, T. P.; Velmurugan, D.; Perumal, P. T.; Indian J Chem, Sect B (IJSBDB) 1995, 34 (5), 367–371. CHAN, K. S.; Yeung, M. L.; Chan, W.; Wang, R.-J.; Mak, T. C. W.; J Org Chem (JOCEAH) 1995, 60 (6), 1741–1747. ALBEROLA, A.; Gonzalez, A. M.; Laguna, M. A.; Pulido, F. J.; Synthesis (SYNTBF) 1982, 1067; and JACOB, K. C.; Jadhar, G. V.; Vakharia, M. N.; Pesticides (PSTDAN) 1972, 6, 94.

The following compounds are representative examples of the invention. The compounds identified below were prepared by methods outlined throughout the specification.

Melting Point Methods

Melting points were obtained on an Electrothermal IA9100 series digital melting point apparatus. All Melting points are uncorrected.

Elemental Analysis

Elemental analysis was performed by Desert Analytics, Tucson, Ariz.

NMR Methods

NMR spectra were obtained on a 300 MHz Varian Mercury system.

LC-MS Methods

General

LC-MS was performed on a Waters Micromass ZQ instrument with electrospray ionization. The HPLC component was a Waters Model 2690 Separation module coupled to a Waters Model 996 photodiode array detector.

Method W

This method utilized a 2.1×250 mm 5 μM C-18 Altima reversed phase column (Alltech) with a flow rate of 0.25 mL/min and a gradient of 5–85% acetonitrile with water containing 0.1% trifluoroacetic acid over 36 min. The gradient then ramps to 100% acetonitrile over 0.5 min and continues at 100% acetonitrile for 3.5 min.

Method X

This method utilized a 2.1×250 mm 5 μM C-18 Altima reversed phase column (Alltech) with a flow rate of 0.25 mL/min and a gradient of 5–85% acetonitrile with water containing 0.1% trifluoroacetic acid over 15 min. The gradient then ramps to 100% acetonitrile over 0.5 min and continues at 100% acetonitrile for 25 min.

Method Y

This method utilized a 2.1×150 mm Agilent Zorbax 5 μM C-18 reversed phase column with a flow rate of 0.3 mL/min and a gradient of 10–100% acetonitrile with water containing 0.1% trifluoroacetic acid over 16 min, then continuing for 2 min with 100% acetonitrile.

Method Z

This method utilized a 2.1×5 mm Agilent Zorbax 5 μM C-18 reversed phase column with a flow rate of 0.5 mL/min and a gradient of 5–100% acetonitrile with water containing 0.1% trifluoroacetic acid over 8 min, then continuing for 2 min with 100% acetonitrile.

Compound 1. (R909850) 2,2-Dichloro-N-[2-[3-(2-chloro-6-fluorophenyl)-5-isoxazolyl]-(4-pyridyl)]Acetamide MW=401 confirmed by LC-MS, $t_r$=32.63 min (Method W) $MH^+$=399–403

Compound 3. (R909794) 2,2-Dichloro-N-[2-[3-(2-fluoro-6-trifluoromethylphenyl)-5-isoxazolyl]-(4-pyridyl)]Acetamide MW=434 confirmed by LC-MS, $t_r$=34.01 min (Method W) $MH^+$=432–436

Compound 5. (R911427) 2,2-Dichloro-N-[2-[3-(2-fluoro-6-methoxyphenyl)-5-isoxazolyl]-(4-pyridyl)]Acetamide MW=396 confirmed by LC-MS, $t_r$=31.28 min (Method W) $MH^+$=394–398

Compound 7. (R911418) 2,2-Dichloro-N-[5-[3-(2,6-dichlorophenyl)-5-isoxazolyl]-(3-pyridyl)]Acetamide MW=417 confirmed by LC-MS, $t_r$=33.10 min (Method W) $MH^+$=415–419

Compound 9. (R909921) 2,2-Dichloro-N-[2-[3-(2,6-dichlorophenyl)-5-isoxazolyl]-(4-pyridyl)]Acetamide MW=417 confirmed by LC-MS, $t_r$=34.25 min (Method W) $MH^+$=415–419

M.P.=187–188° C.

Compound 11. (R909833) 2,2-Dichloro-N-[3-[3-[(2,6-dichloro)-4-pyridyl]-5-isoxazolyl]phenyl]Acetamide MW=417 confirmed by LC-MS, $t_r$=34.13 min (Method W) $MH^+$=415–419

Compound 13. (R909845) 2,2-Dichloro-N-[5-[3-(2-chloro-6-fluorophenyl)-5-isoxazolyl]-(3-pyridyl)]Acetamide MW=401 confirmed by LC-MS, $t_r$=32.55 min (Method W) $MH^+$=399–403

Compound 17. (R911424) 2,2-Dichloro-N-[5-[3-(2-fluoro-6-methoxyphenyl)-5-isoxazolyl]-(3-pyridyl)]Acetamide MW=396 confirmed by LC-MS, $t_r$=30.47 min (Method W) $MH^+$=394–398

Compound 19. (R909851) 2,2-Dichloro-N-[2-[3-(2,6-dimethylphenyl)-5-isoxazolyl]-(4-pyridyl)]Acetamide MW=376 confirmed by LC-MS, $t_r$=34.63 min (Method W) $MH^+$=374–378

Compound 21. (R909846) 2,2-Dichloro-N-[5-[3-(2,6-dimethylphenyl)-5-isoxazolyl]-(3-pyridyl)]Acetamide MW=376 confirmed by LC-MS, $t_r$=29.69 min (Method W) $MH^+$=374–378

Compound 27. (R911422) 2,2-Dichloro-N-[5-[3-(2,6-difluorophenyl)-5-isoxazolyl]-(3-pyridyl)]Acetamide MW=384 confirmed by LC-MS, $t_r$=31.64 min (Method W) $MH^+$=382–386

Compound 29. (R911423) 2,2-Dichloro-N-[5-[3-(2,3-dichlorophenyl)-5-isoxazolyl]-(3-pyridyl)]Acetamide MW=417 confirmed by LC-MS, $t_r$=34.99 min (Method W) $MH^+$=415–419

Compound 31. (R909864) 2,2-Dichloro-N-[2-[3-(2-morpholino-6-trifluoromethylphenyl)-5-isoxazolyl]-(4-pyridyl)]Acetamide MW=501 confirmed by LC-MS, $t_r$=6.97 min (Method Z) $MH^+$=499–503

Compound 33.(R904855) 2,2-Dichloro-N-[3-[3-(3-methyl-2-pyridyl)-5-isoxazolyl]phenyl]Acetamide MW=362 confirmed by LC-MS, $t_r$=30.89 min (Method W) $MH^+$=360–364

Compound 35. (R904800) 2,2-Dichloro-N-[6-[3-(2,6-dichlorophenyl)-5-isoxazolyl]-(2-pyridyl)]Acetamide MW=417 confirmed by LC-MS, $t_r$=20.74 min (Method X) $MH^+$=415–419

Compound 37. (R909793) 2,2-Dichloro-N-[5-[3-(2-fluoro-6-trifluoromethylphenyl)-5-isoxazolyl]-(3-pyridyl)] Acetamide MW=434 confirmed by LC-MS, $t_r$=32.79 min (Method W) $MH^+$=432–436

Compound 43. (R909873) 2,2-Dichloro-N-[2-[3-(2,6-dichlorophenyl)-5-isoxazolyl]-[4-(1-oxypyridyl)]Acetamide MW=433 confirmed by LC-MS, $t^r$=6.44 min (Method Z) $MH^+$=431–435

Compound 45. (R909878) 2,2-Dichloro-N-[3-[3-[(3-ethoxycarbonyl)-2-pyridyl]-5-isoxazolyl]phenyl]Acetamide MW=420 confirmed by LC-MS, $t^r$=6.65 min (Method Z) $MH^+$=418–422

Compound 47. (R909884) 2,2-Dichloro-N-[2-[3-(2-fluoro-6-morpholinosulfamoylphenyl)-5-isoxazolyl]-(4-pyridyl)]Acetamide MW=515 confirmed by LC-MS, $t_r$=6.32 min (Method Z) $MH^+$=513–517

Compound 49. (R905952) 2,2-Dichloro-N-[2-[3-(2-methoxy-6-trifluoromethylphenyl)-5-isoxazolyl]-(4-pyridyl)]Acetamide MW=446 confirmed by LC-MS, $t_r$=14.41 min (Method Y) $MH^+$=444–448

Compound 51. (R909909) 2,2-Dichloro-N-[2-[3-(2,6-dichlorophenyl)-5-isoxazolyl]-(4-pyridyl)]-N-methyl Acetamide MW=431 confirmed by LC-MS, $t^r$=14.99 min (Method Y) $MH^+$=429–433

Compound 53. (R905954) 2,2-Dichloro-N-[2-[3-[2-chloro-6-[4-(N-2-pyridyl)piperazino]phenyl])-5-isoxazolyl]-(4-pyridyl)]Acetamide MW=544 confirmed by LC-MS, $t_r$=11.81 min (Method Y) $MH^+$=542–546

Compound 57. (R905948) 2,2-Dichloro-N-[5-[3-(2-methoxy-6-trifluoromethylphenyl)-5-isoxazolyl]-(3-pyridyl)]Acetamide MW=446 confirmed by LC-MS, $t_r$=13.45 min (Method Y) $MH^+$=444–448

Compound 61. (R905961) 2,2-Dichloro-N-[5-[3-[2-chloro-6-[4-(N-acetyl)piperazino]phenyl])-5-isoxazolyl]-(3-pyridyl)]Acetamide MW=509 confirmed by LC-MS, $t_r$=12.11 min (Method Y) $MH^+$=507–511

Compound 63. (R905962) 2,2-Dichloro-N-[5-[3-[2-chloro-6-[4-(N-ethyl)piperazino]phenyl])-5-isoxazolyl]-(3-pyridyl)]Acetamide MW=495 confirmed by LC-MS, $t_r$=9.48 min (Method Y) $MH^+$=493–497

Compound 65. (R904857) 2,2-Dichloro-N-[5-[3-(2,6-dichlorophenyl)-5-isoxazolyl]-(2-pyridyl)]Acetamide MW=417 confirmed by LC-MS, $t_r$=35.19 min (Method W) $MH^+$=415–419

Compound 67. (R905451) 2,2-Dichloro-N-[5-[3-(2-trifluoromethylphenyl)-5-isoxazolyl]-(3-pyridyl)]Acetamide MW=416 confirmed by LC-MS, $t_r$=13.81 min (Method Y) $MH^+$=414–418

Compound 69. (R905949) 2,2-Dichloro-N-[5-[3-[2-chloro-6-[4-(N-2-pyridyl)piperazino]phenyl])-5-isoxazolyl]-(3-pyridyl)]Acetamide MW=544 confirmed by LC-MS, $t_r$=11.29 min (Method Y) $MH^+$=542–546

Compound 71. (R905965) 2,2-Dichloro-N-[5-[3-[2-chloro-6-[4-(N-tert-butoxycarbonyl) piperazino]phenyl])-5-isoxazolyl]-(3-pyridyl)]Acetamide MW=567 confirmed by LC-MS, $t_r$=15.91 min (Method Y) $MH^+$=565–569

Compound 73. (R905966) 2,2-Dichloro-N-[5-[3-(2-chloro-6-piperazinophenyl)-5-isoxazolyl]-(3-pyridyl)]Acetamide MW=467 confirmed by LC-MS, $t_r$=9.51 min (Method Y) $MH^+$=465–469

Compound 75. (R905967) 2,2-Dichloro-N-[5-[3-(2-chloro-6-tert-butyldimethylsilyloxyphenyl)-5-isoxazolyl]-(3-pyridyl)]Acetamide MW=513 confirmed by LC-MS, $t_r$=17.49 min (Method Y) $MH^+$=511–515

Compound 77. (R905968) 2,2-Dichloro-N-[5-[3-(2-chloro-6-hydroxyphenyl)-5-isoxazolyl]-(3-pyridyl)]Acetamide MW=399 confirmed by LC-MS, $t_r$=12.51 min (Method Y) $MH^+$=397–401

Compound 79. (R905969) 2,2-Dichloro-N-[5-[3-(2-chloro-6-N-ethylcarbamoyloxyphenyl)-5-isoxazolyl]-(3-pyridyl)]Acetamide MW=470 confirmed by LC-MS, $t_r$=12.85 min (Method Y) $MH^+$=468–472

Compound 81. (R905970) 2,2-Dichloro-N-[5-[3-[2-chloro-6-[4-(N-ethylcarboxamido) piperazino]phenyl])-5-isoxazolyl]-(3-pyridyl)]Acetamide MW=538 confirmed by LC-MS, $t_r$=12.77 min (Method Y) $MH^+$=536–540

Compound 83. (R905971) 2,2-Dichloro-N-[2-[3-(2-chloro-6-tert-butyldimethylsilyloxyphenyl)-5-isoxazolyl]-(4-pyridyl)]Acetamide MW=513 confirmed by LC-MS, $t_r$=17.96 min (Method Y) $MH^+$=511–515

Compound 85. (R905973) 2,2-Dichloro-N-[2-[3-(2-chloro-6-N-propylcarbamoyloxyphenyl)-5-isoxazolyl]-(4-pyridyl)]Acetamide MW=484 confirmed by LC-MS, $t_r$=13.36 min (Method Y) $MH^+$=482–486

Compound 87. (R905982) 2,2-Dichloro-N-[2-[3-(2-chloro-6-methoxymethoxyphenyl)-5-isoxazolyl]-(4-pyridyl)]Acetamide MW=443 confirmed by LC-MS, $t_r$=14.65 min (Method Y) $MH^+$=441–445

Compound 89. (R905983) 2,2-Dichloro-N-[2-[3-(2-chloro-6-hydroxyphenyl)-5-isoxazolyl]-(4-pyridyl)]Acetamide MW=399 confirmed by LC-MS, $t_r$=13.53 min (Method Y) $MH^+$=397–401

Compound 91. (R905984) 2,2-Dichloro-N-[3-[3-[(4-chloro-2-dimethylamino)-3-pyridyl]-5-isoxazolyl]phenyl] Acetamide MW=426 confirmed by LC-MS, $t_r$=13.33 min (Method Y) $MH^+$=424–428

Compound 93. (R905985) 2,2-Dichloro-N-[3-[3-[(2,4-dichloro)-3-pyridyl]-5-isoxazolyl]phenyl]Acetamide MW=417 confirmed by LC-MS, $t_r$=15.37 min (Method Y) $MH^+$=415–419

Compound 95. (R905987) 2,2-Dichloro-N-[3-[3-[(2-chloro-4-morpholino)-3-pyridyl]-5-isoxazolyl]phenyl]Acetamide MW=468 confirmed by LC-MS, $t_r$=13.73 min (Method Y) $MH^+$=466–470

Compound 97. (R909874) 2,2-Dichloro-N-[3-[3-[(6-bromo)-2-pyridyl]-5-isoxazolyl]-(4-pyridyl)]Acetamide MW=427 confirmed by LC-MS, $t_r$=36.03 min (Method W) $MH^+$=425–429

(R904871) 2,2-Dichloro-N-[2-[3-(2,6-dichlorophenyl)-5-isoxazolyl]-(4-pyridyl)]Acetamide Hydrochloride Salt

MW=453

M.P.=240–241° C.

Elemental Analysis: $C_{16}H_{10}Cl_5N_2O_2$ requires: C, 42.37; H, 2.22; Cl, 39.09; N, 9.27; found: C, 42.51; H, 2.18; Cl, 39.06; N, 9.05

(R909919) 2,2-Dichloro-N-[2-[3-(2,6-dichlorophenyl)-5-isoxazolyl]-(4-pyridyl)]Acetamide Toluenesulfonate Salt

MW=589

M.P.=246–247° C.

Elemental Analysis: $C_{23}H_{17}C_{14}N_3O_5S$ requires: C, 46.88; H, 2.91; N, 7.13; S, 5.44; found: C, 47.05; H, 3.06; N, 7.00; S, 5.30

(R909920) 2,2-Dichloro-N-[2-[3-(2,6-dichlorophenyl)-5-isoxazolyl]-(4-pyridyl)]Acetamide Ethanesulfonate Salt

MW=527

M.P.=210–211° C.

Elemental Analysis: $C_{18}H_{15}Cl_4N_3O_5S$ requires: C, 41.01; H, 2.87; N, 7.97; S, 6.08; found: C, 41.00; H, 2.77; N, 7.72; S, 5.80

(R909923) 2,2-Dichloro-N-[2-[3-(2,6-dichlorophenyl)-5-isoxazolyl]-(4-pyridyl)]Acetamide mono-Nitrate Salt

MW=480

M.P.=175–176° C.

Elemental Analysis: $C_{16}H_{10}C4N_4O_5$ requires: C, 40.03; H, 2.10; N, 11.67; found: C, 40.33; H, 1.94; N, 11.25

The following are additional experimentals useful in the syntheses of certain of the compounds of the invention.

Figure 15:
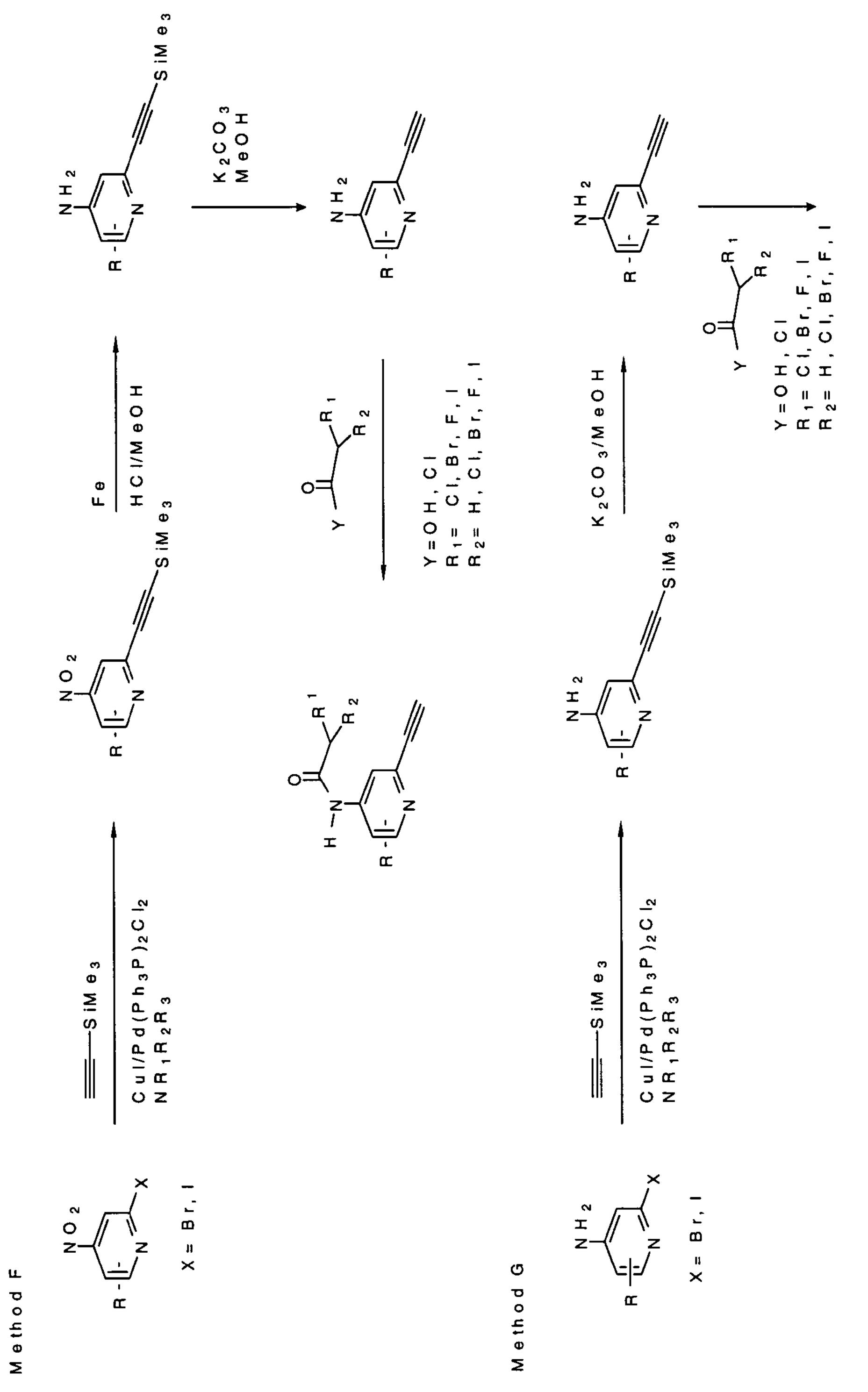
Figure 16:
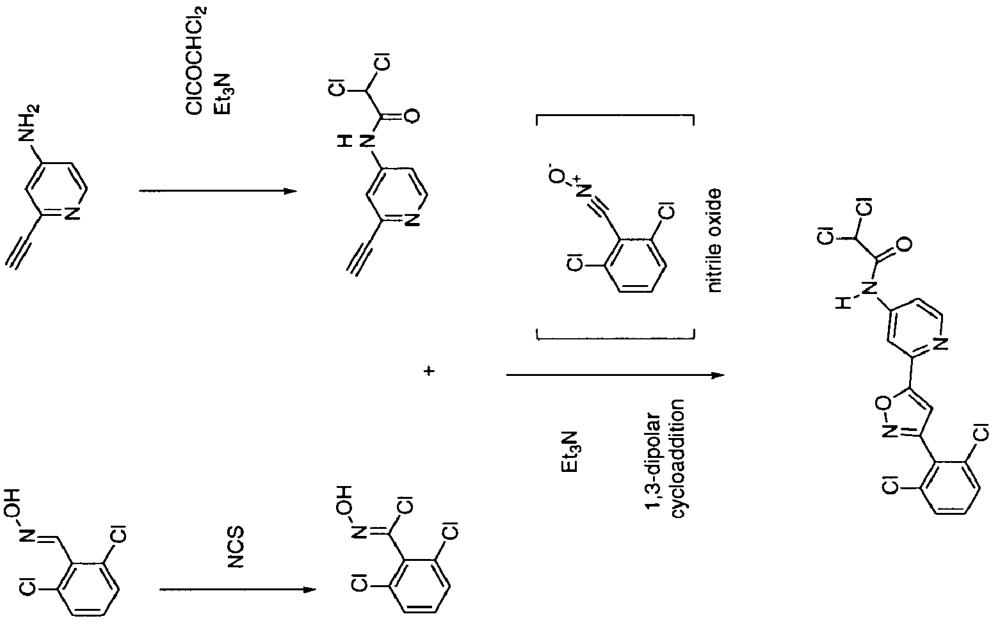

Method F (See FIG. 15)

Step 1. Acetylenic Cross-Coupling Reactions

The appropriately substituted o-bromonitrobenzene or substituted o-iodonitrobenzene was dissolved in a suitable solvent such as p-dioxane or THF and then treated with at least five molar equivalents of a suitable amine base, which could be triethylamine, diethylamine or diisopropylethylamine. Alternatively, the amine base alone could be used as the solvent. A stream of argon gas was then bubbled through the solution for several minutes, followed by the addition of dichlorobis(triphenylphosphine) palladium (II) (3–4 mole percent), CuI (6–8 mole percent) and finally trimethylsilylacetylene (1.2–1.5 molar equivalents). The reaction mixture was then heated at 50–80° C. until the reaction was complete, as monitored by TLC or LC-MS. When the more reactive substituted o-iodonitrobenzenes were used, the acetylenic cross-coupling reaction could be performed at room temperature. If the reaction appeared sluggish, additional trimethylsilylacetylene was added. This general procedure is known in the literature as the Sonogashira coupling (K. Sonogashira et.al., Tetrahedron Lett., 1975, 4467). The reaction mixture was then diluted with ethyl acetate and this solution was washed several times with brine. Alternatively, the crude reaction mixture was filtered over a pad of Celite, then diluted with ethyl acetate and washed with brine. The organic layer so obtained was dried over anhydrous sodium sulfate, filtered and concentrated to dryness under reduced pressure. The residue was purified by column chromatography on silica gel, eluting with mixtures of ethyl acetate and hexanes to give the desired substituted o-(trimethylsilylethynyl) nitrobenzenes.

Step 2. Reduction of the Nitro Group to Amines

The substituted o-(trimethylsilylethynyl) nitrobenzene prepared in Step 1 was dissolved in a mixture of 10–15 volume percent of concentrated hydrochloric acid in methanol. Then, iron powder (Aldrich Chemical Co.) (5–10 molar equivalents) was added and the mixture was heated at 70–80° C. for 3–4h. This reaction can be highly exothermic when performed on a large scale. After cooling to room temperature, the reaction mixture was filtered over Celite and the filtrate was concentrated under reduced pressure. The residue was dissolved in ethyl acetate and then carefully washed with either aqueous sodium hydroxide or aqueous sodium bicarbonate solution. The aqueous layer was discarded and the organic layer was washed with brine, dried over anhydrous sodium sulfate, filtered and concentrated to dryness under reduced pressure. If necessary the crude product could be purified by column chromatography on silica gel, eluting with mixtures of hexanes and ethyl acetate to give the desired substituted o-(trimethylsilylethynyl) anilines.

Step 3. Removal of the Trimethylsilyl Group from the Acetylenes

The substituted o-(trimethylsilylethynyl) aniline prepared in Step 2 was dissolved in methanol containing 2–5% water. If the solubility of the aniline in methanol was poor, an appropriate amount of tetrahydrofuran (THF) was used as a co-solvent. Then anhydrous potassium carbonate (1 molar equivalent) was added and the mixture was stirred at room temperature for 1–24h until the reaction was complete by TLC analysis. The reaction mixture was concentrated under reduced pressure and the residue was dissolved in ethyl acetate and washed with brine. The organic layer was dried over anhydrous sodium sulfate, filtered and concentrated under reduced pressure. The substituted o-aminophenylacetylenes could be purified by column chromatography on silica gel, eluting with hexanes and ethyl acetate, if necessary.

Step 4. Introduction of the Haloacetamide or Dihaloacetamide Side Chains

The substituted o-aminophenylacetylene prepared in Step 3 was dissolved in dichloromethane. Triethylamine (1.3 molar equivalents) was added and the solution was cooled in an ice-bath under nitrogen. Then a solution of haloacetyl chloride or dihaloacetyl chloride (1.0 molar equivalents) in dichloromethane was added dropwise. After the addition was complete, the reaction was allowed to stir 0.5–1 h at 0° C. and then allowed to warm to room temperature. After a total of 1–4 h reaction time the reaction mixture was diluted with water. The organic layer was separated and further washed with saturated aqueous sodium bicarbonate solution and brine. The organic layer was dried over anhydrous sodium sulfate, filtered and concentrated under reduced pressure to give the substituted 2-halo- or 2,2-dihalo-N-(2-ethynylphenyl) acetamide. Alternatively, the substituted o-aminophenylacetylene starting material was dissolved in dichloromethane and treated successively with 1-(3-dimethylaminopropyl)-3-ethylcarbodiimide hydrochloride (1 molar equivalent), the halo- or dihaloacetic acid (1 molar equivalent) and finally triethylamine (1 molar equivalent). The reaction mixture was then stirred at room temperature until the substituted o-aminophenylacetylene starting material was consumed as determined by TLC analysis. The mixture was washed with water and the organic layer was dried over anhydrous sodium sulfate, filtered and concentrated to dryness under reduced pressure to give either the substituted 2-halo- or 2,2-dihalo-N-(2-ethynylphenyl) acetamides.

Method G (See FIG. 15)

An appropriately substituted o-iodoaniline or o-bromoaniline starting material was coupled with trimethylsilylacetylene as described in Step 1 of Method F. The resulting substituted o-(trimethylsilylethynyl) aniline was then deprotected using the procedure described in Step 3 of Method F to give the substituted o-aminophenylacetylene which was then converted to the desired 2-halo- or 2,2-dihalo-N-(2-ethynylphenyl) acetamide as described in Step 4 of Method F.

General Procedures for the Preparation of 2-Halo- or 2,2-Dihalo-N-(4-ethynylphenyl) Acetamides.

Figure 17:
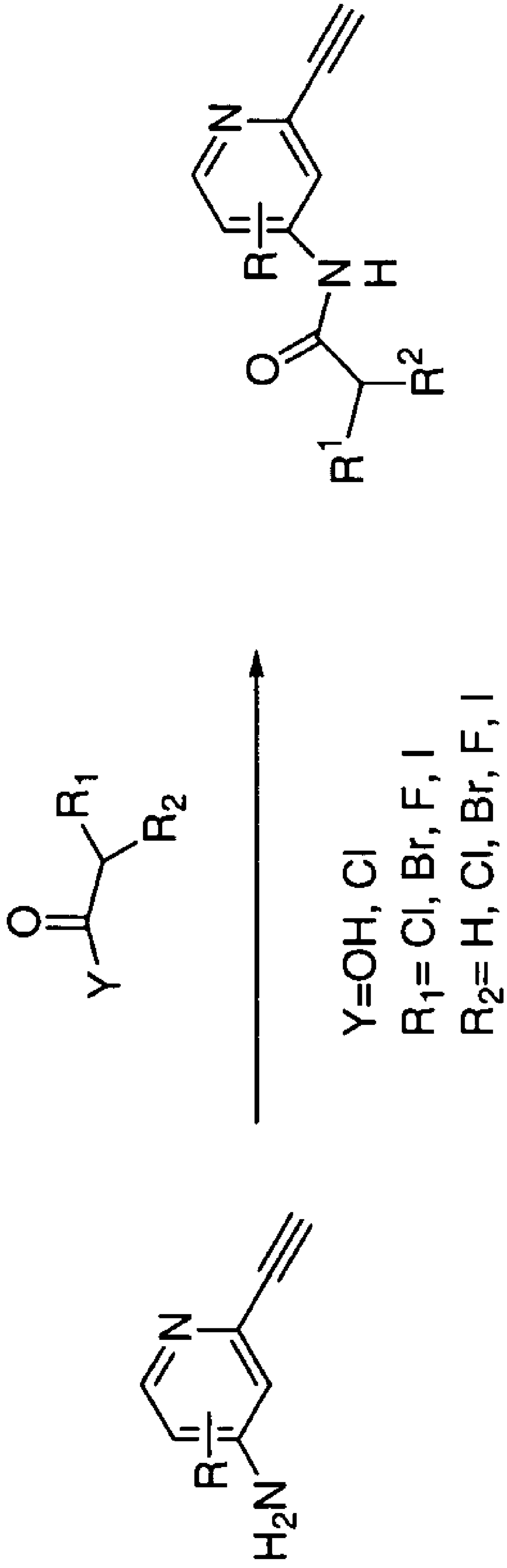
Figure 18:
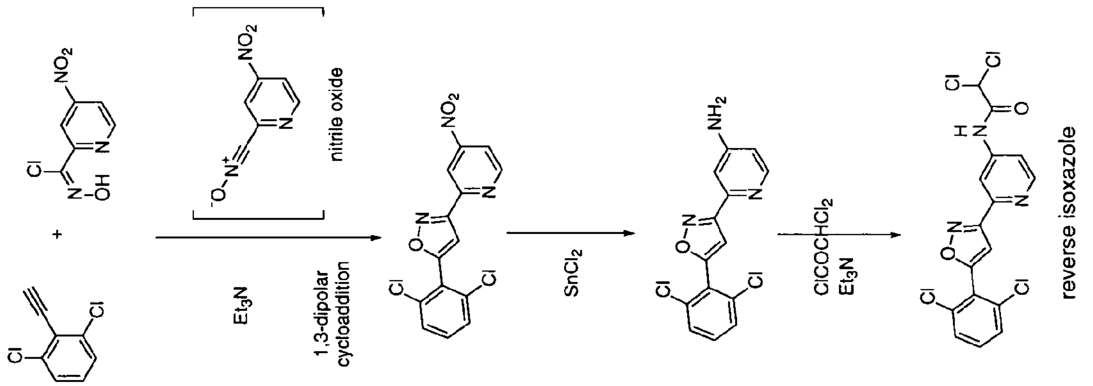
Figure 19:
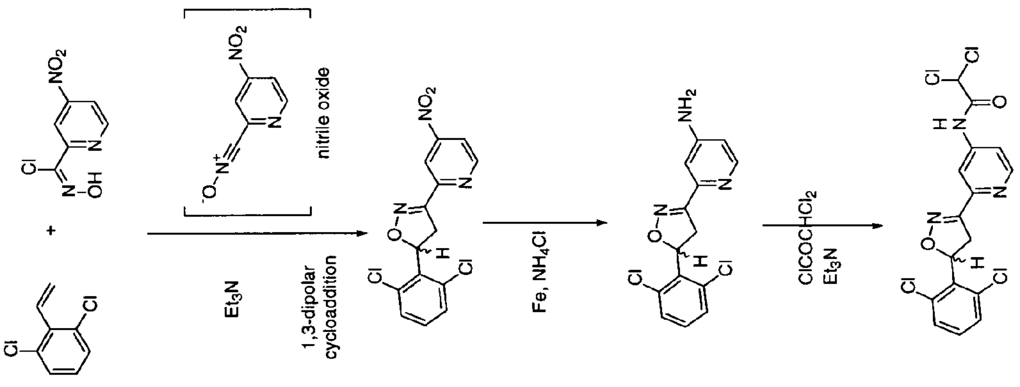
Figure 20:
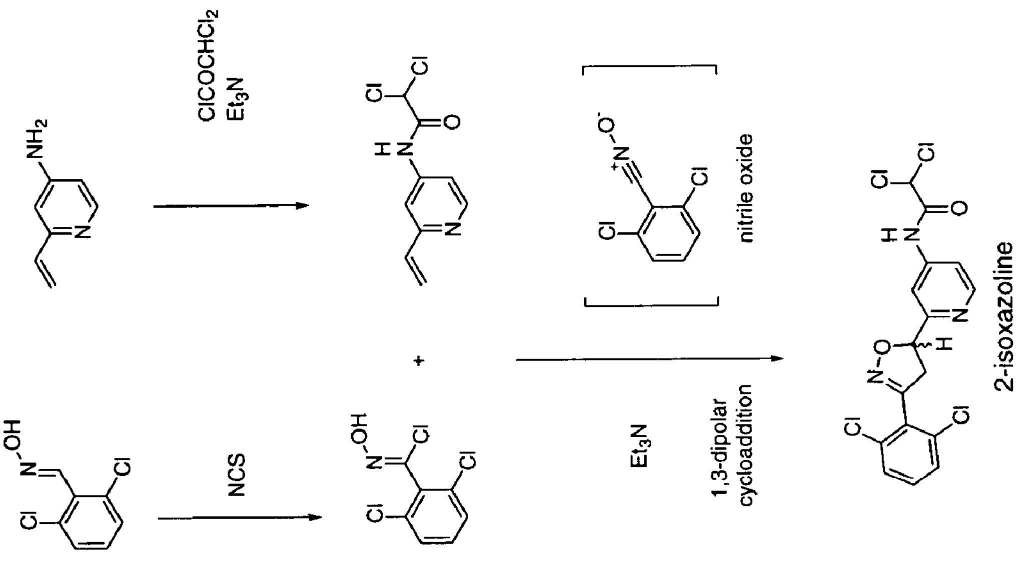
Figure 21:
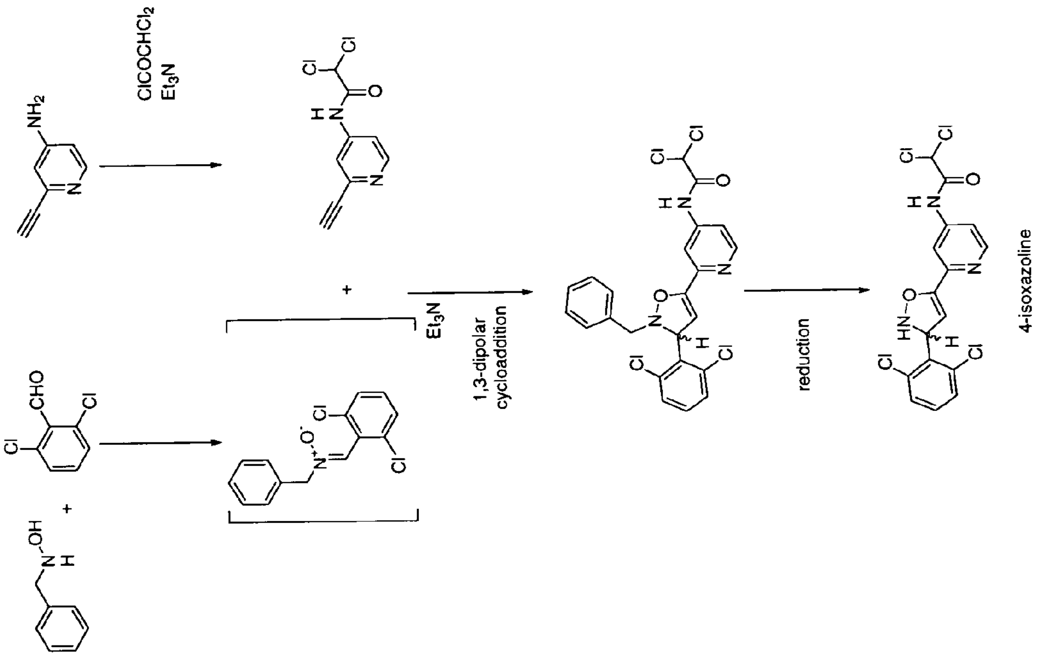
Figure 22:
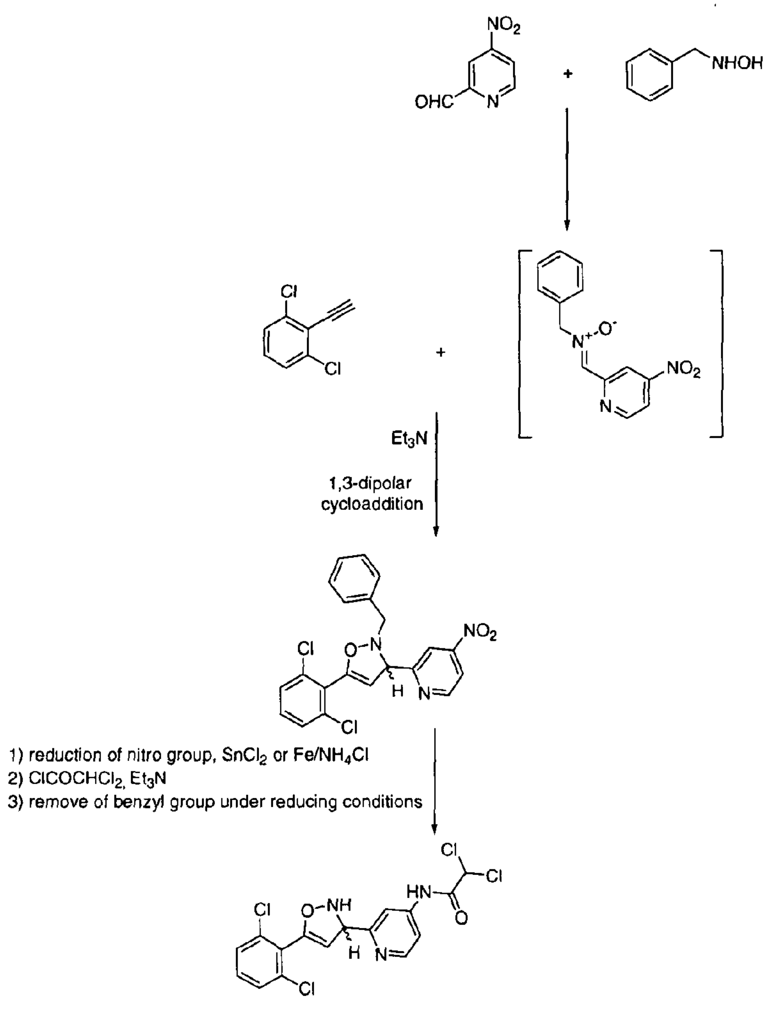
Figure 23:
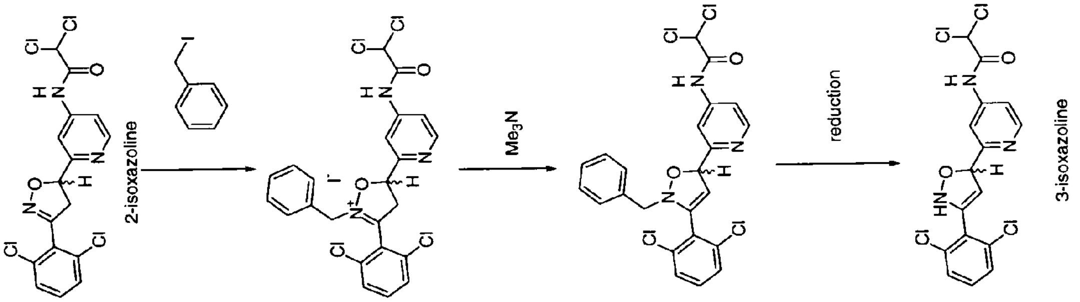
Figure 24:
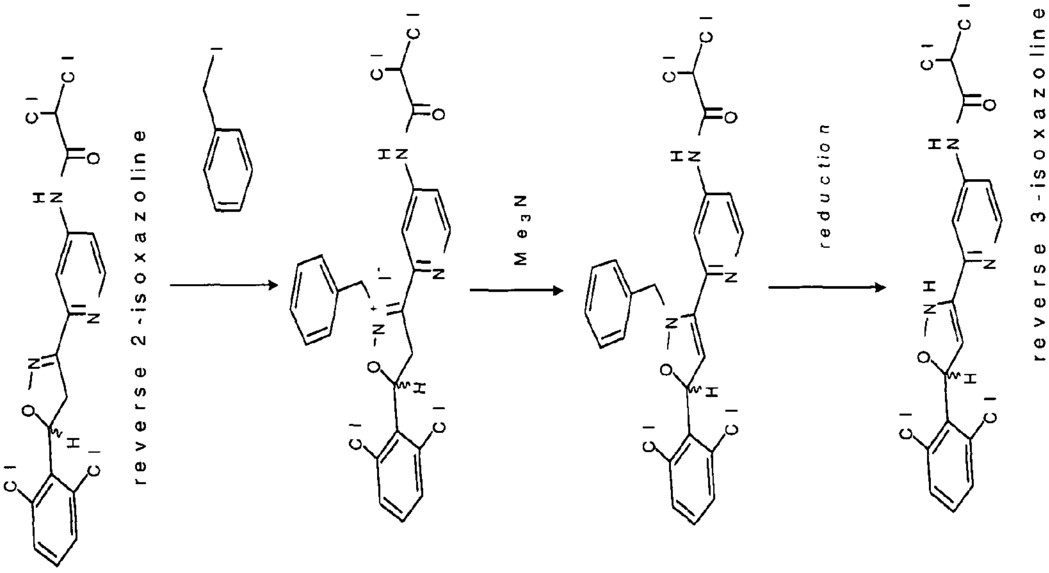
Figure 25:
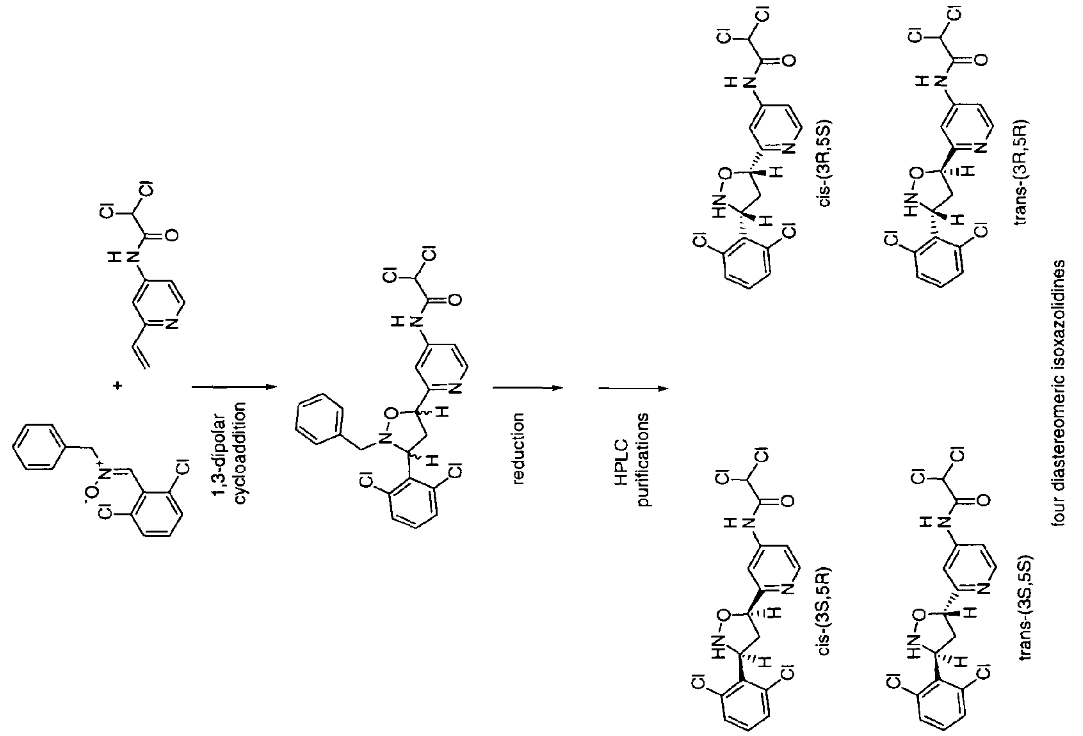
Figure 26:
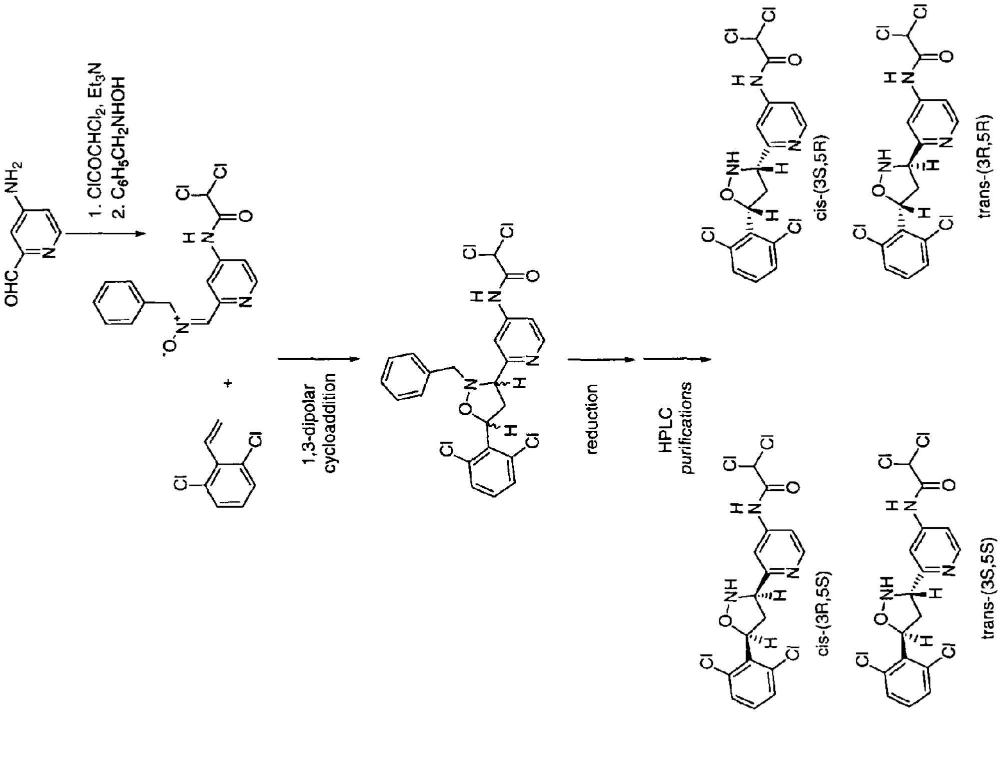
Figure 27:
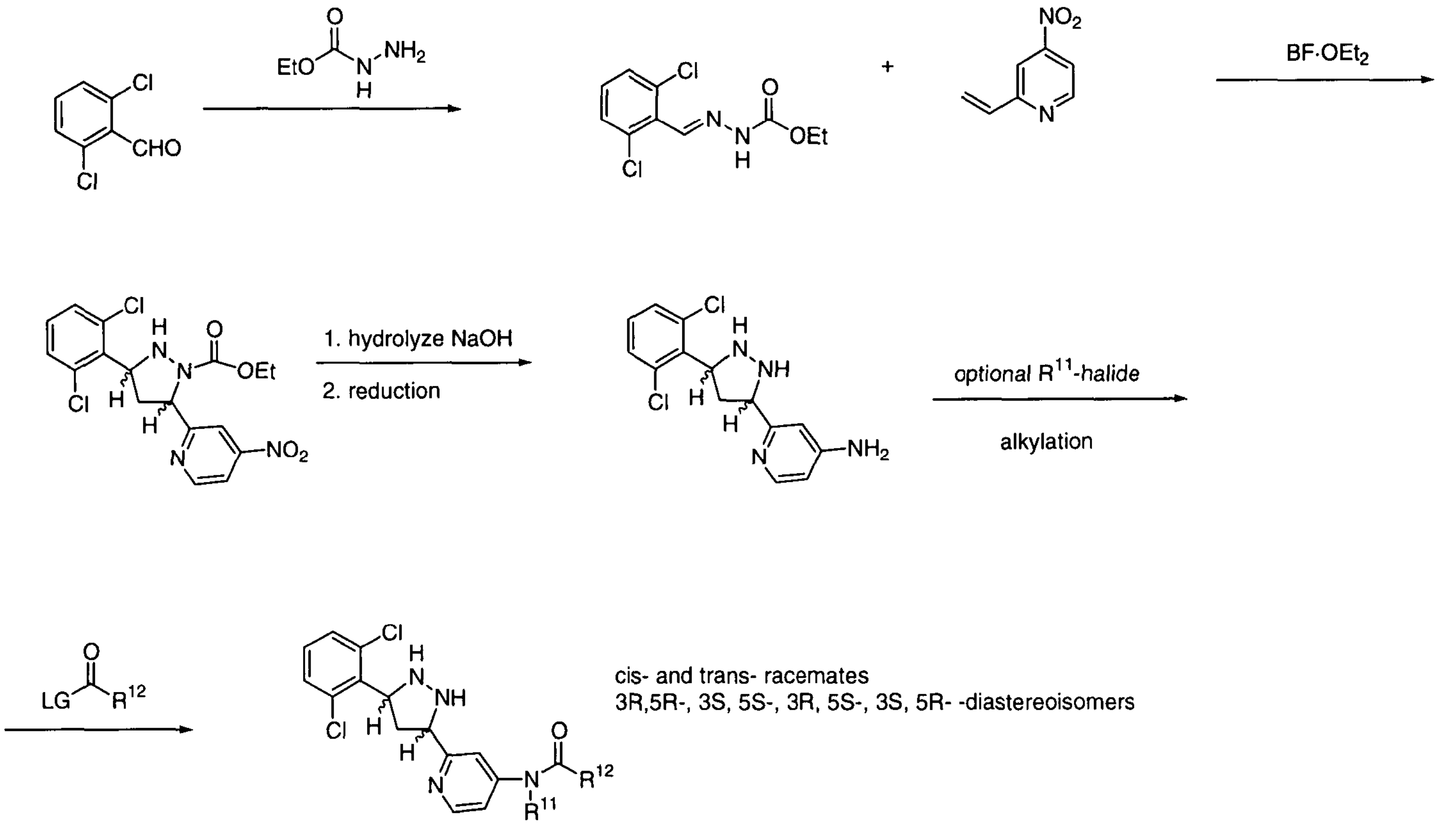
Figure 28:
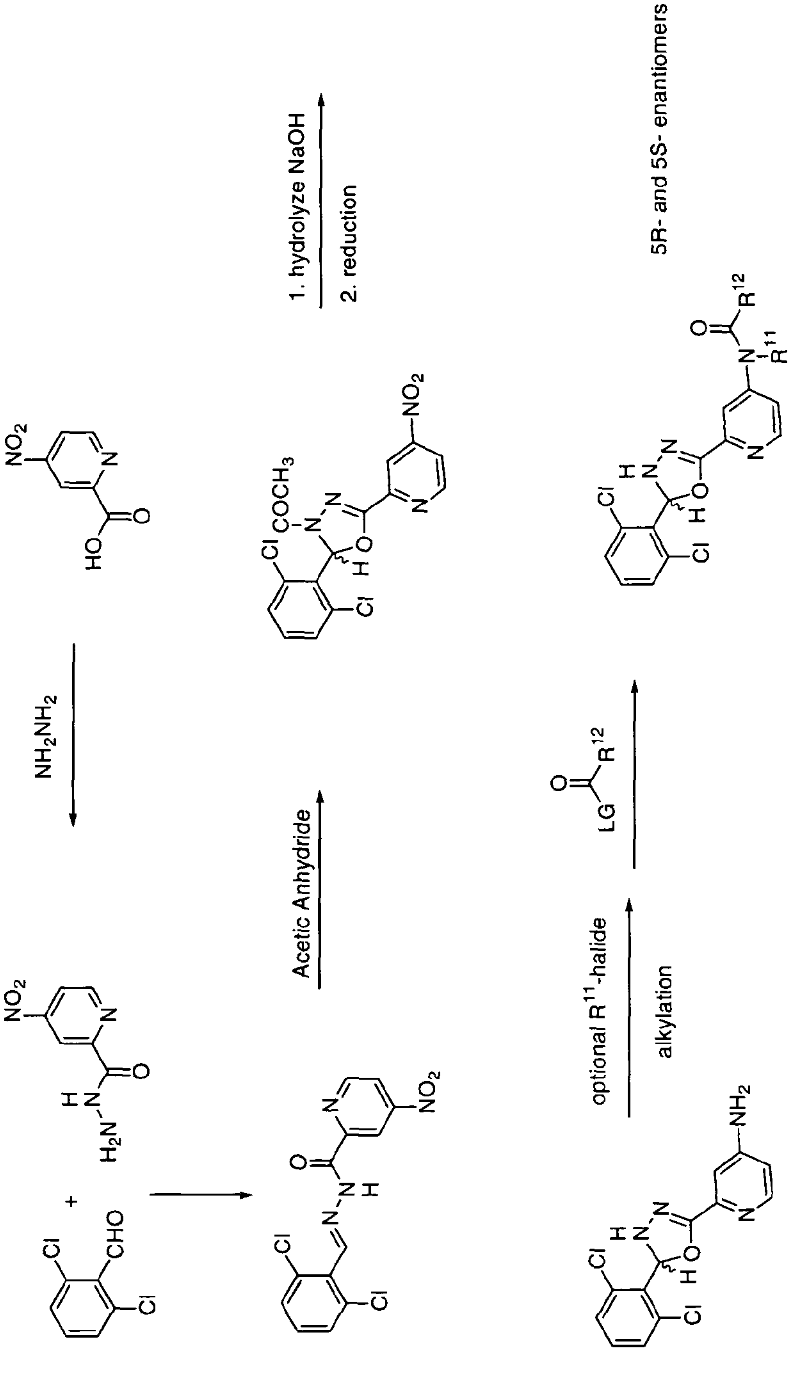
Figure 29:
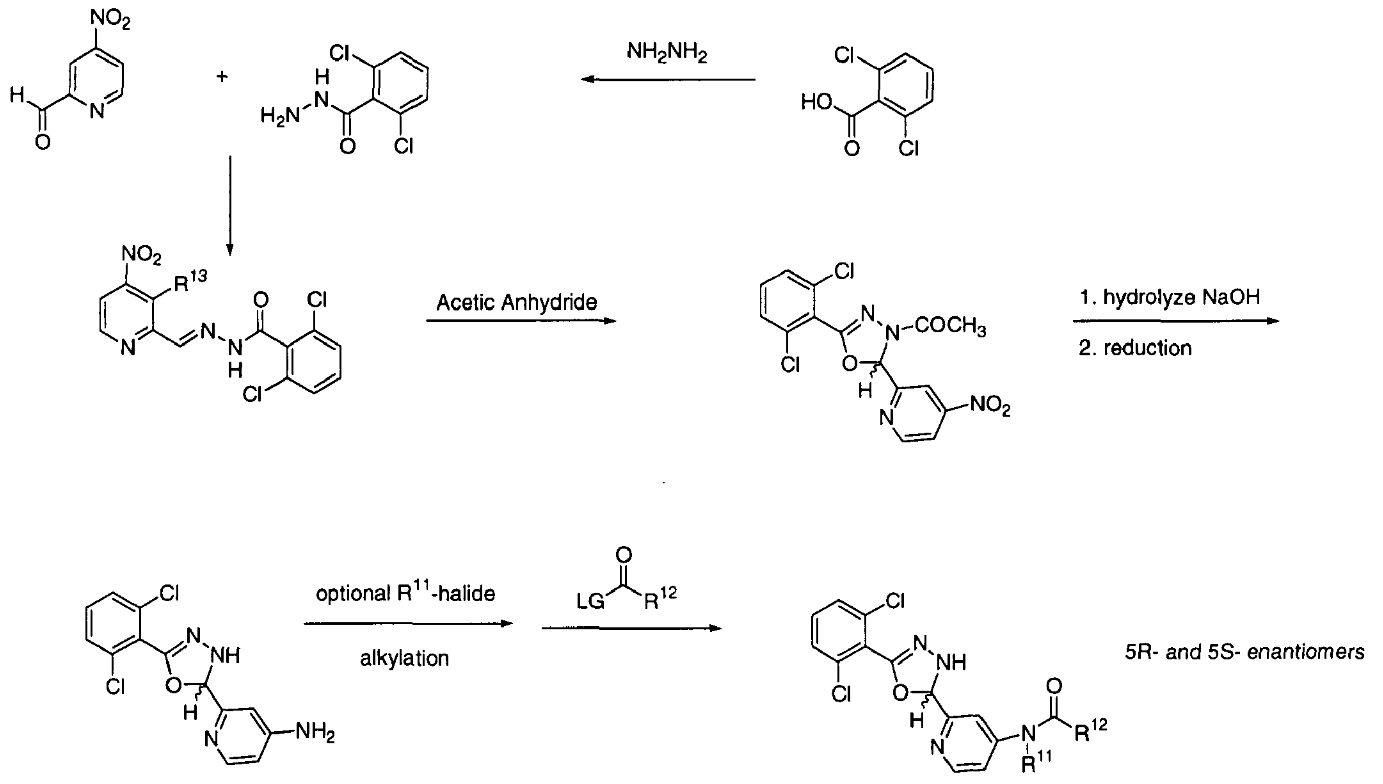
Figure 30:
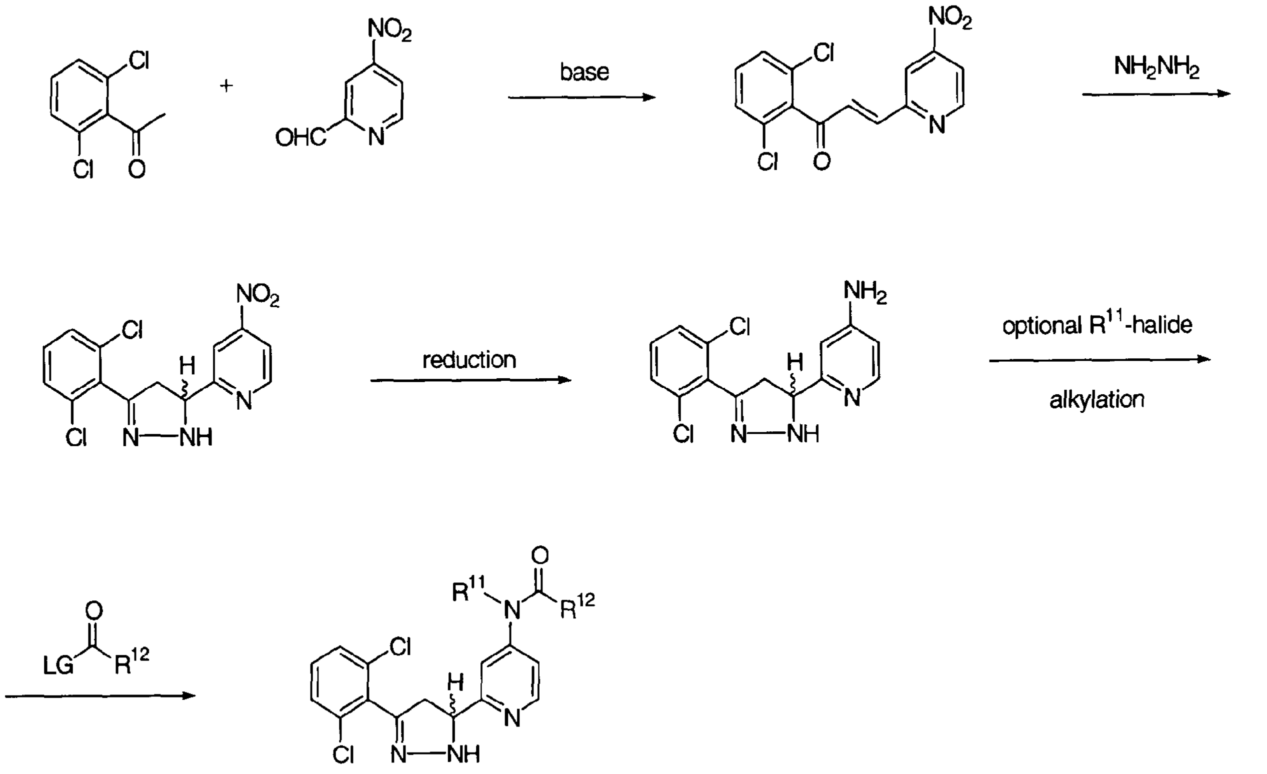
Figure 31:
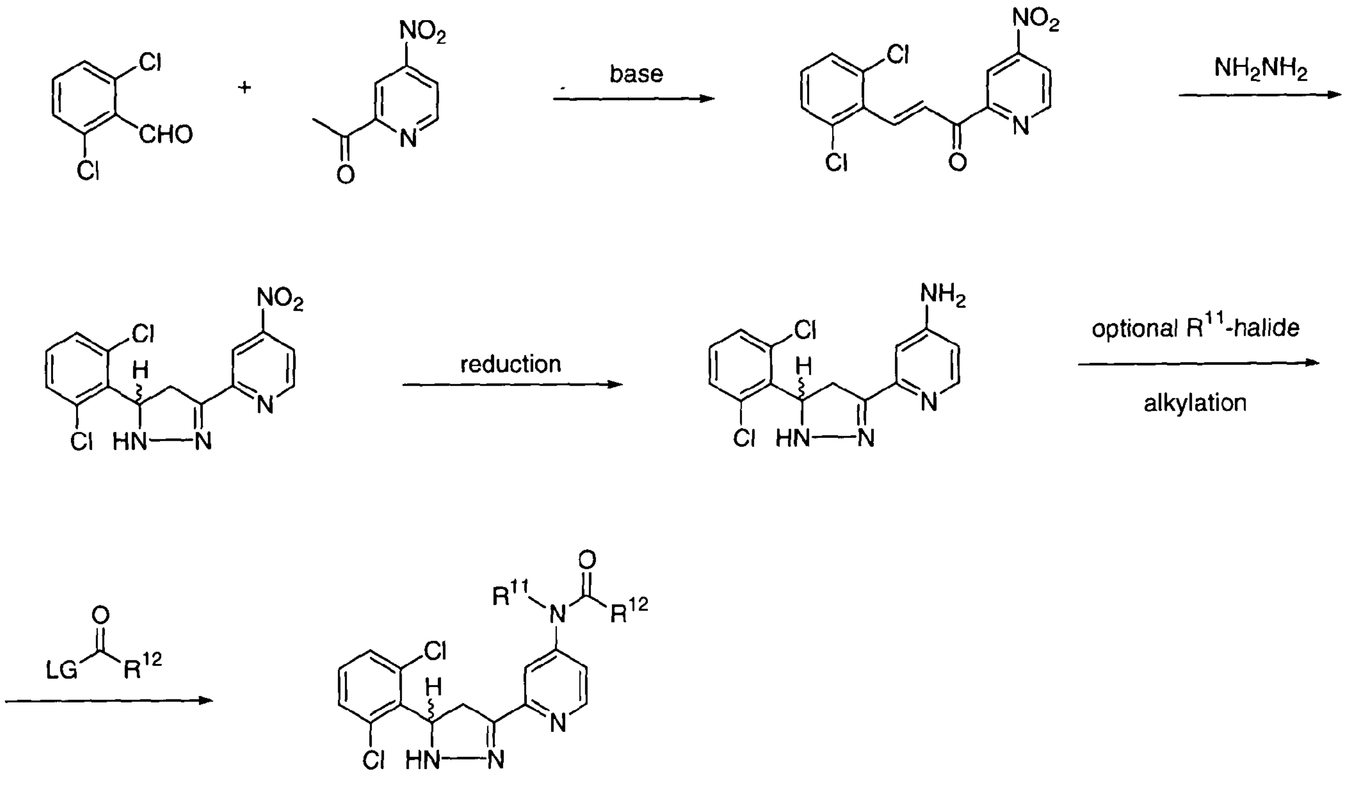
Figure 32:
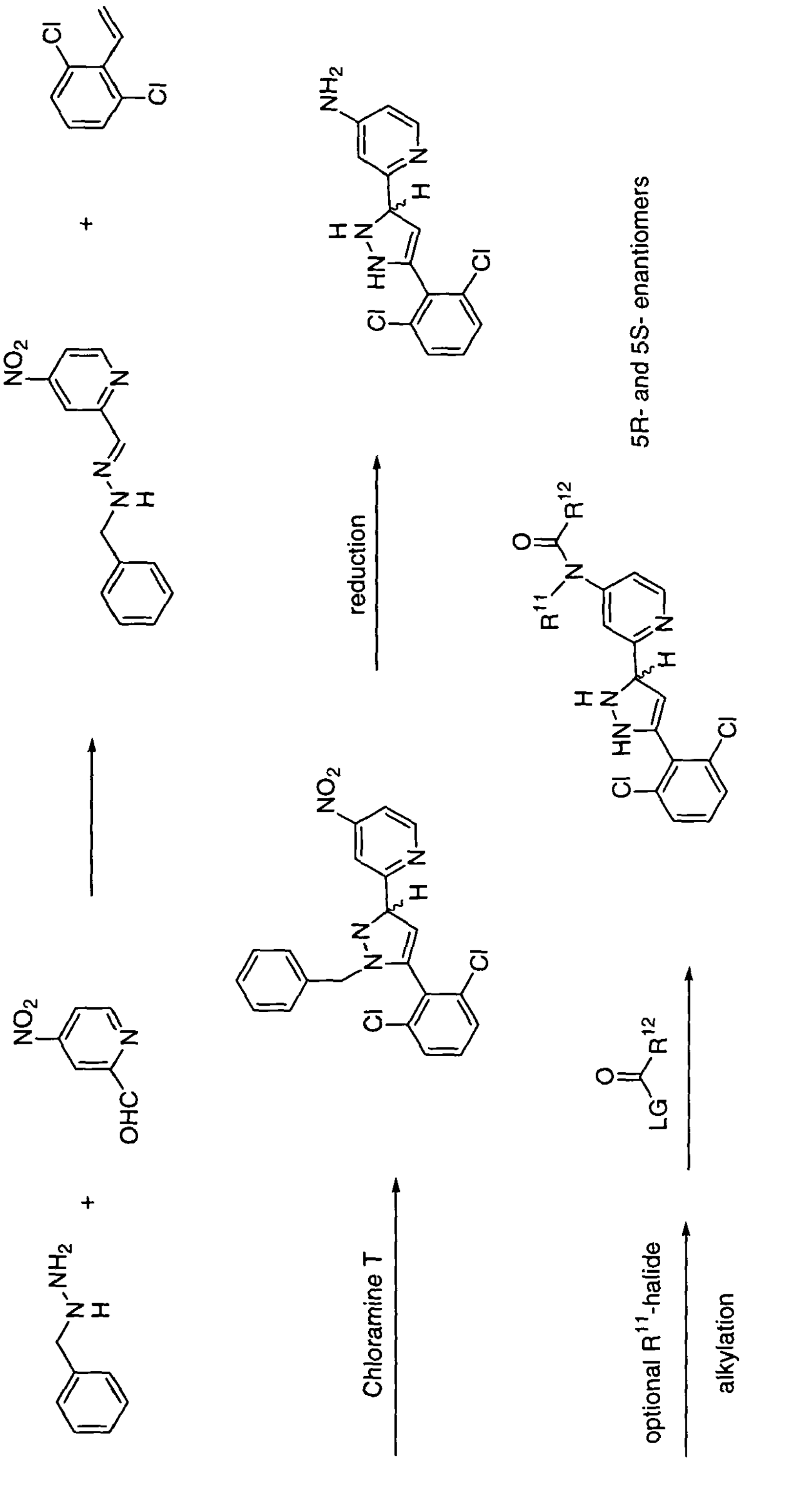
Figure 33:
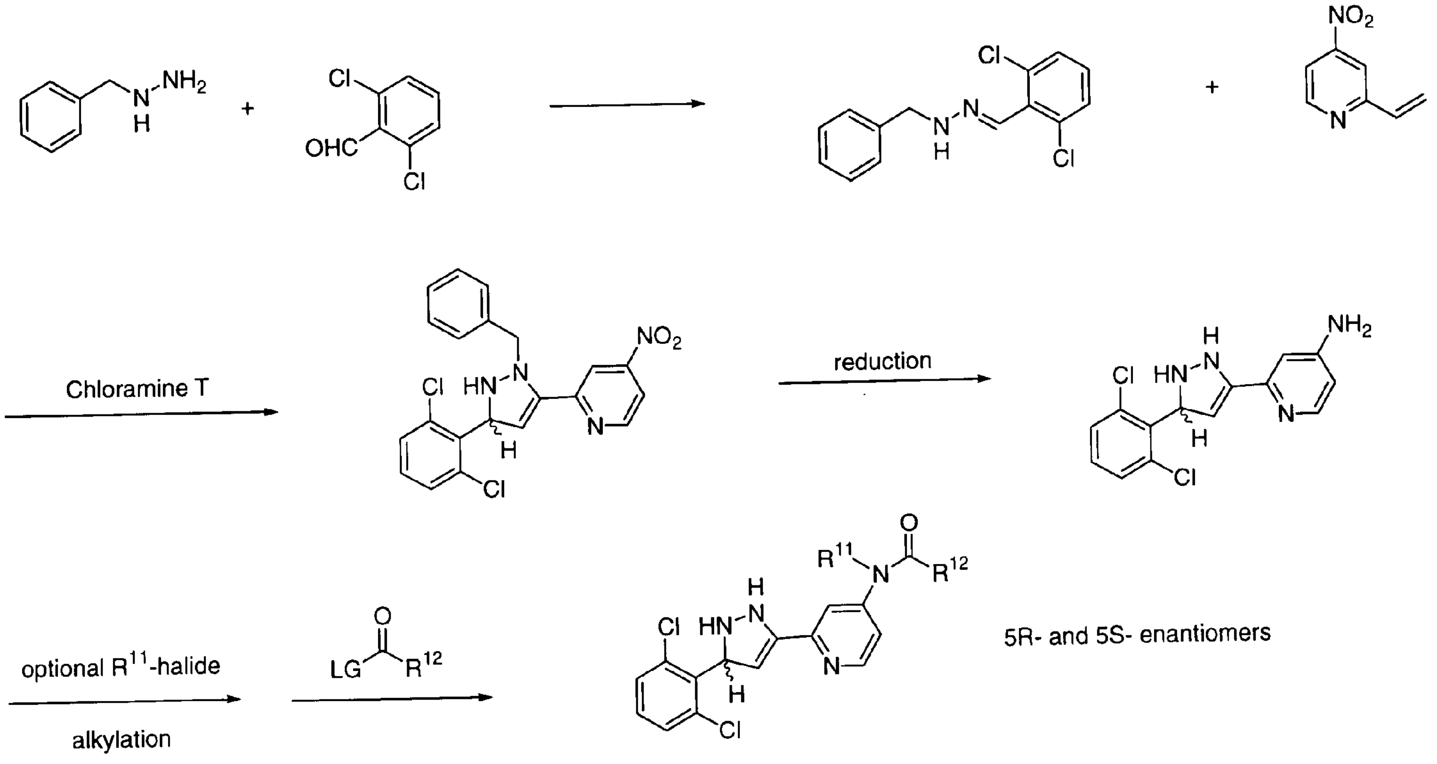
Figure 34:
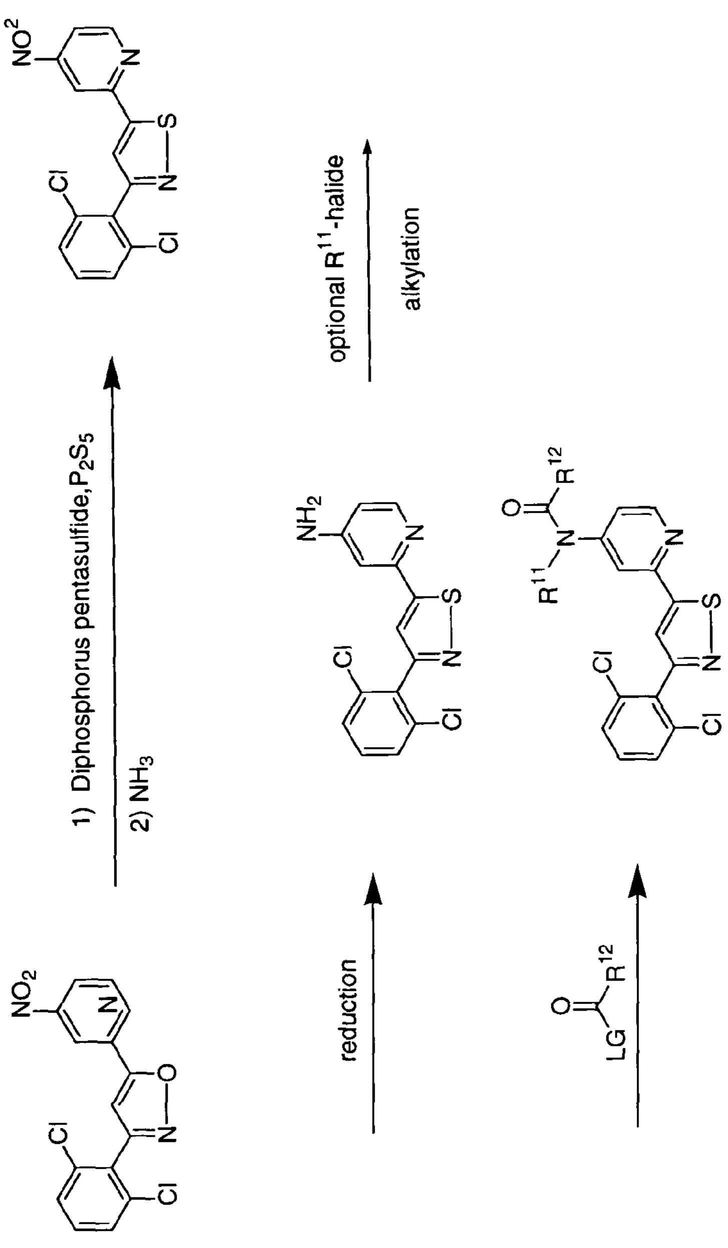
Figure 35:
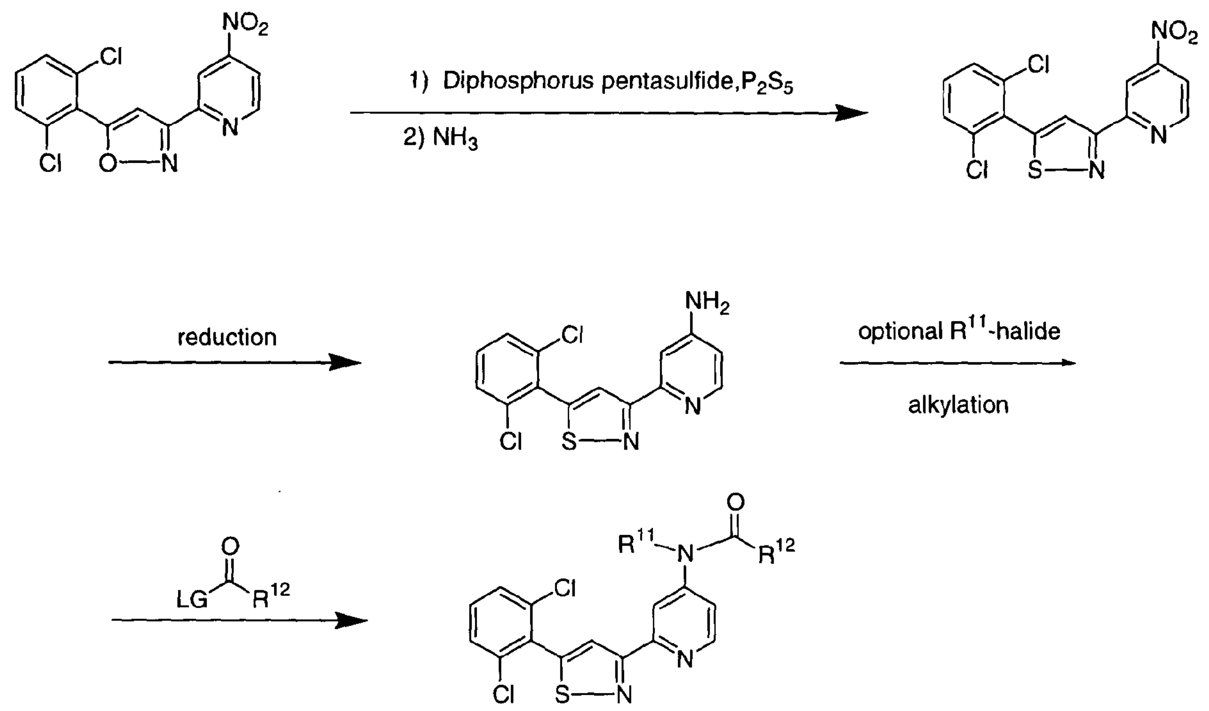
Figure 36:
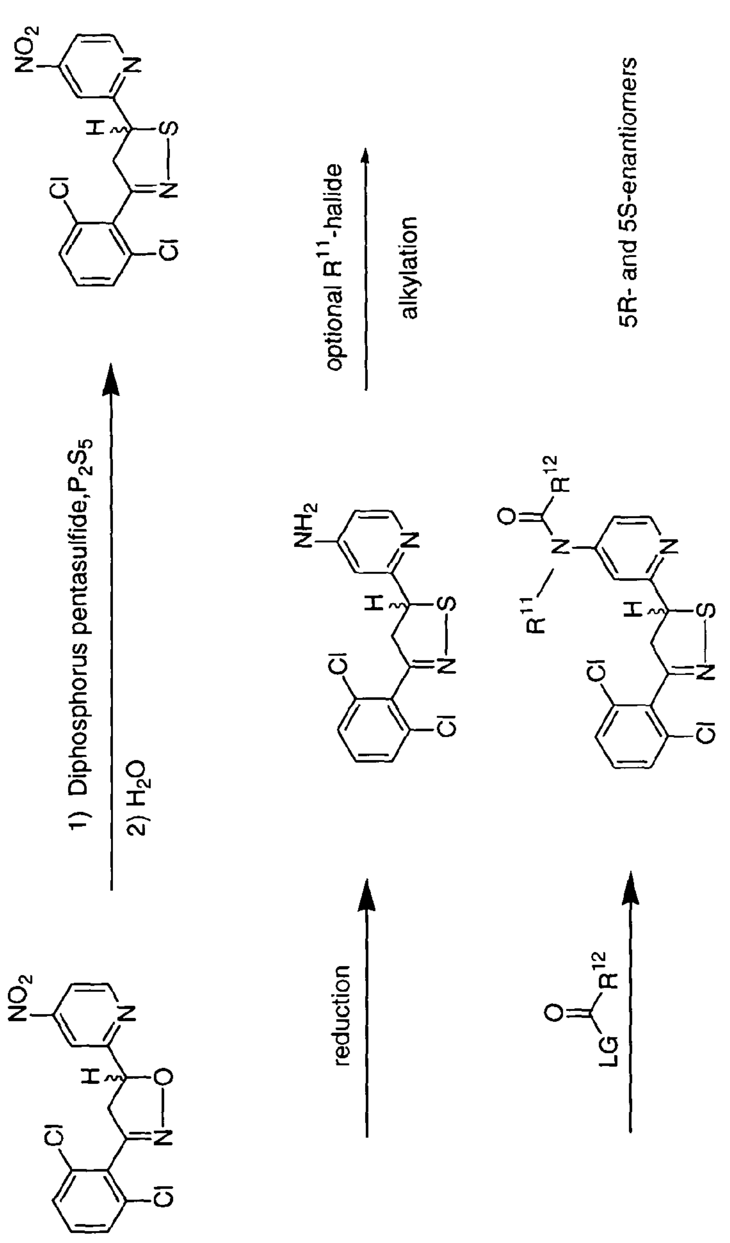
Figure 37:
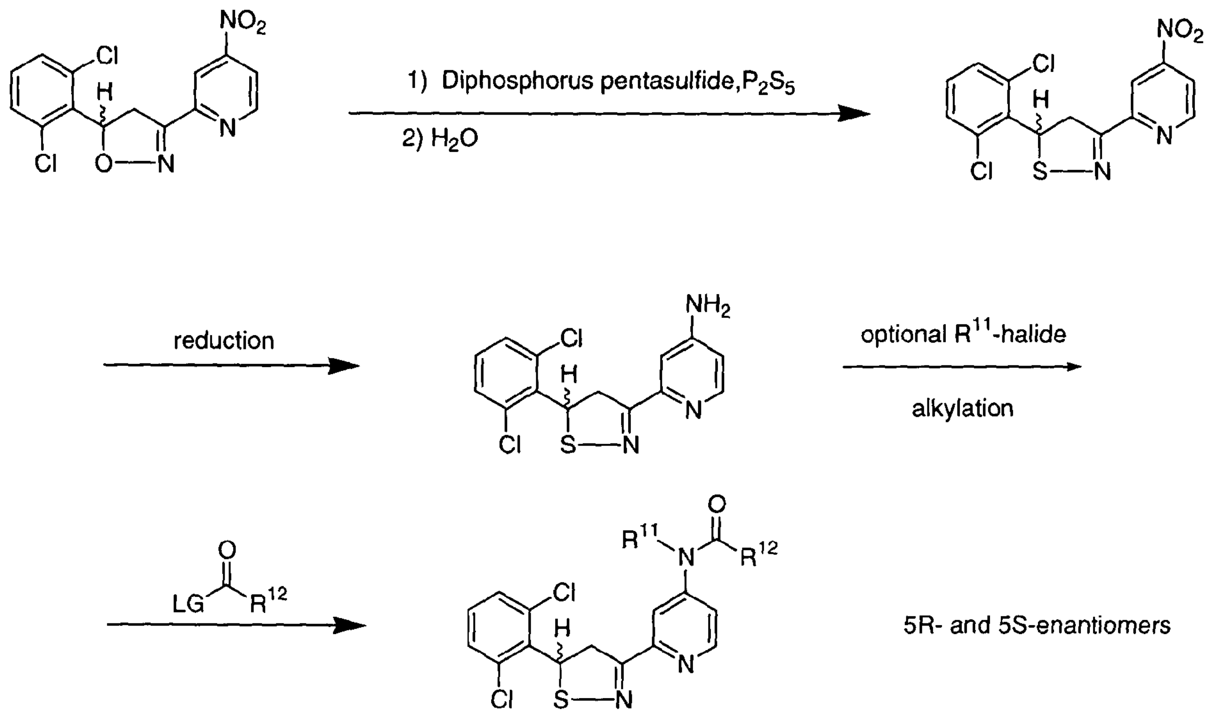
Figure 38:
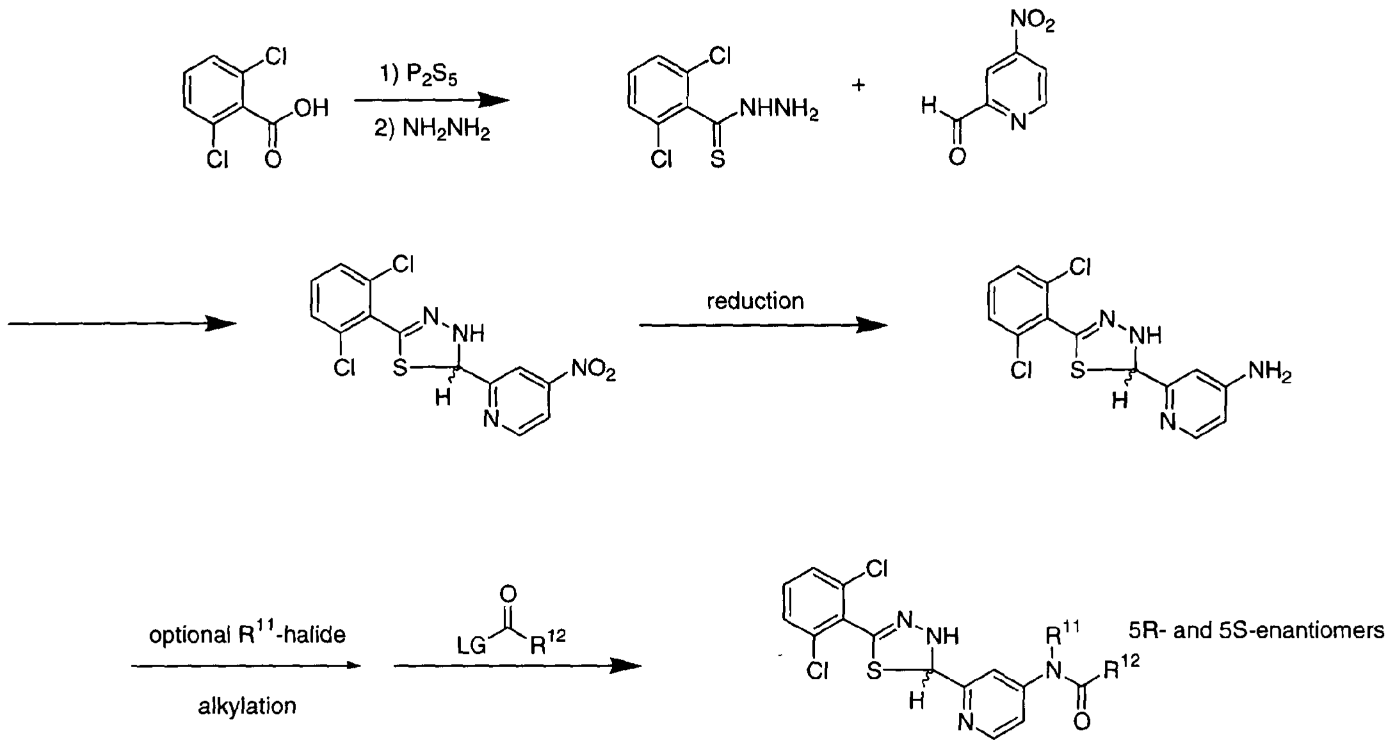
Figure 39:
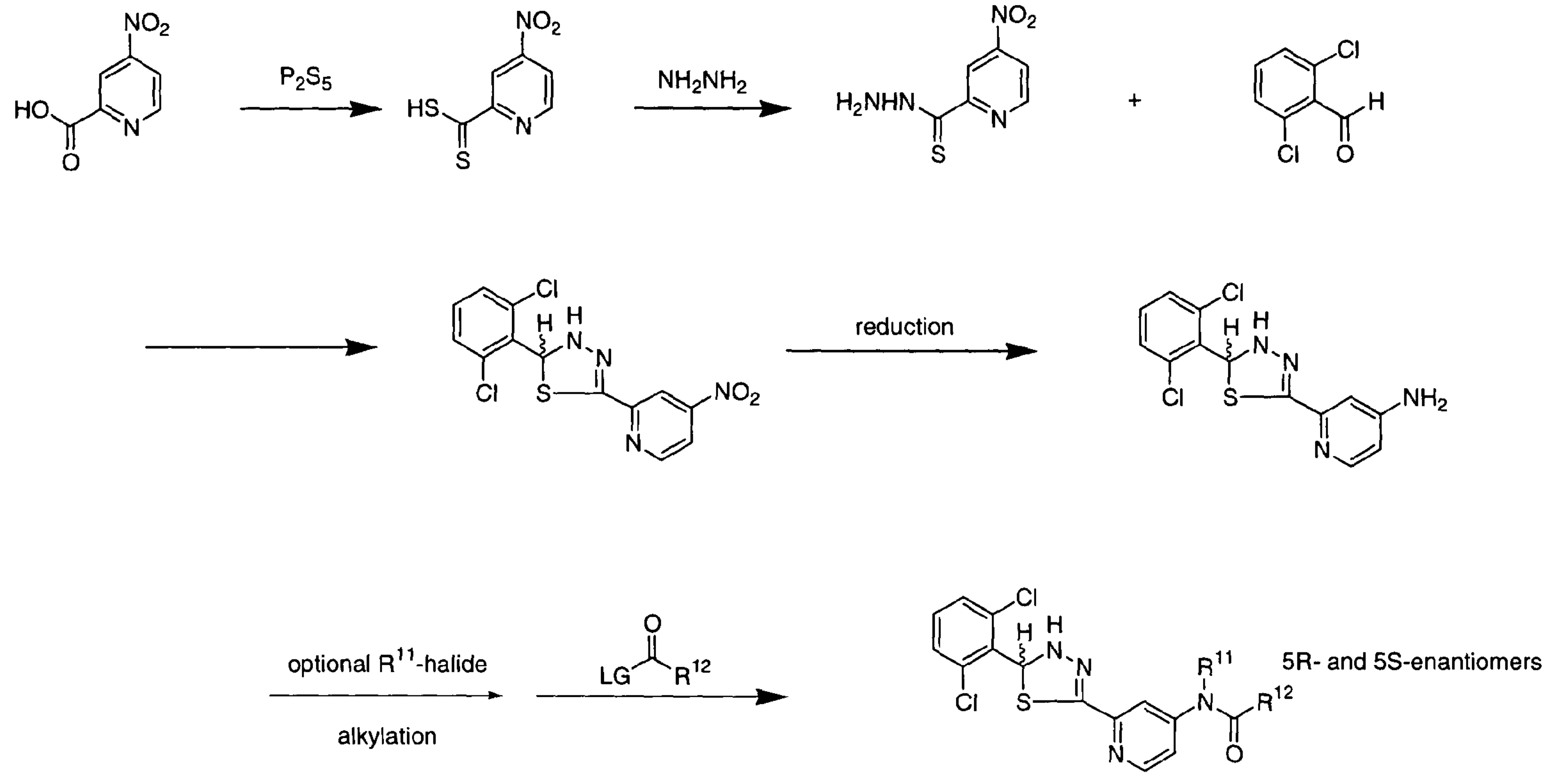
Figure 40:
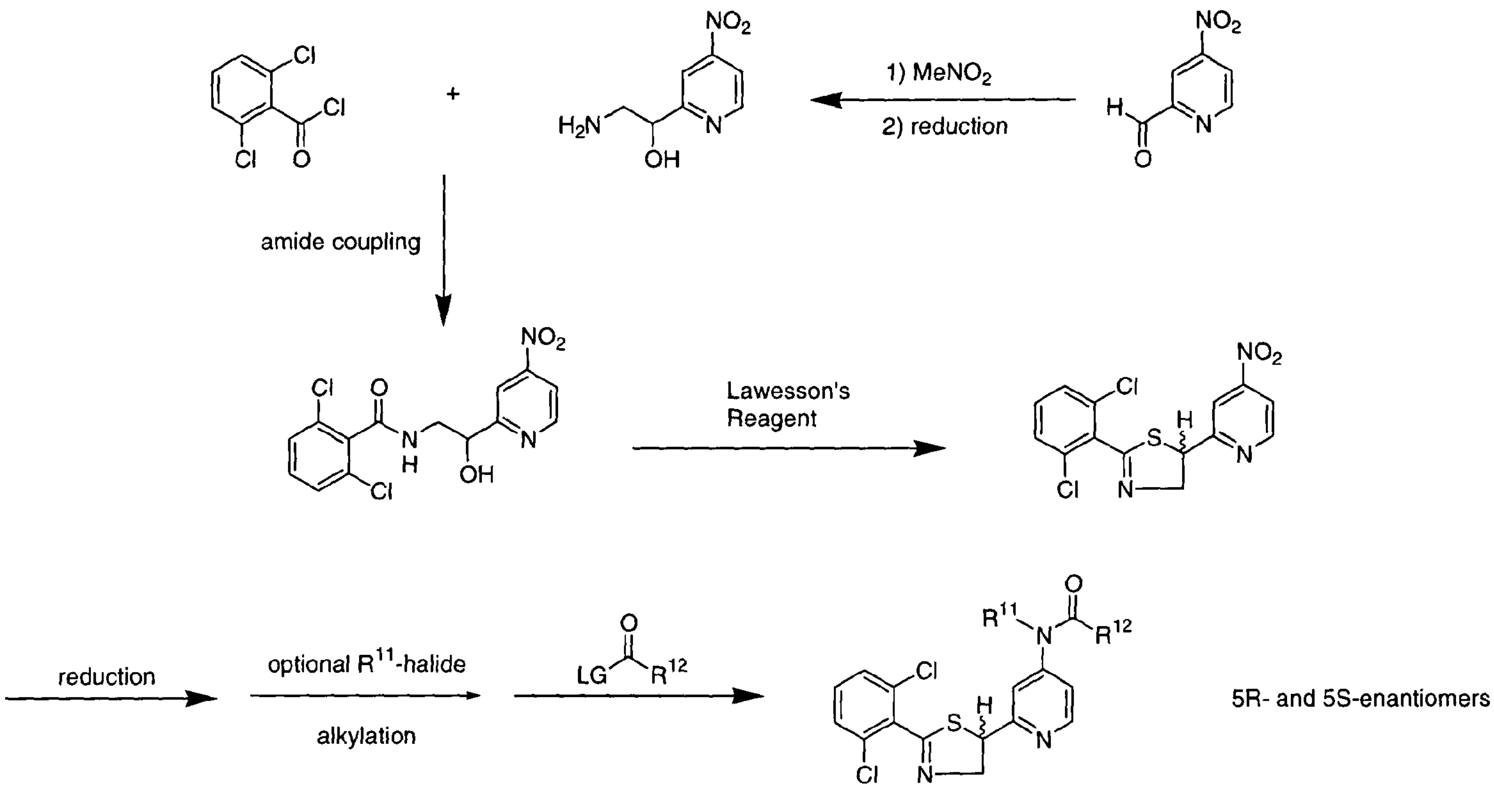
Figure 41:
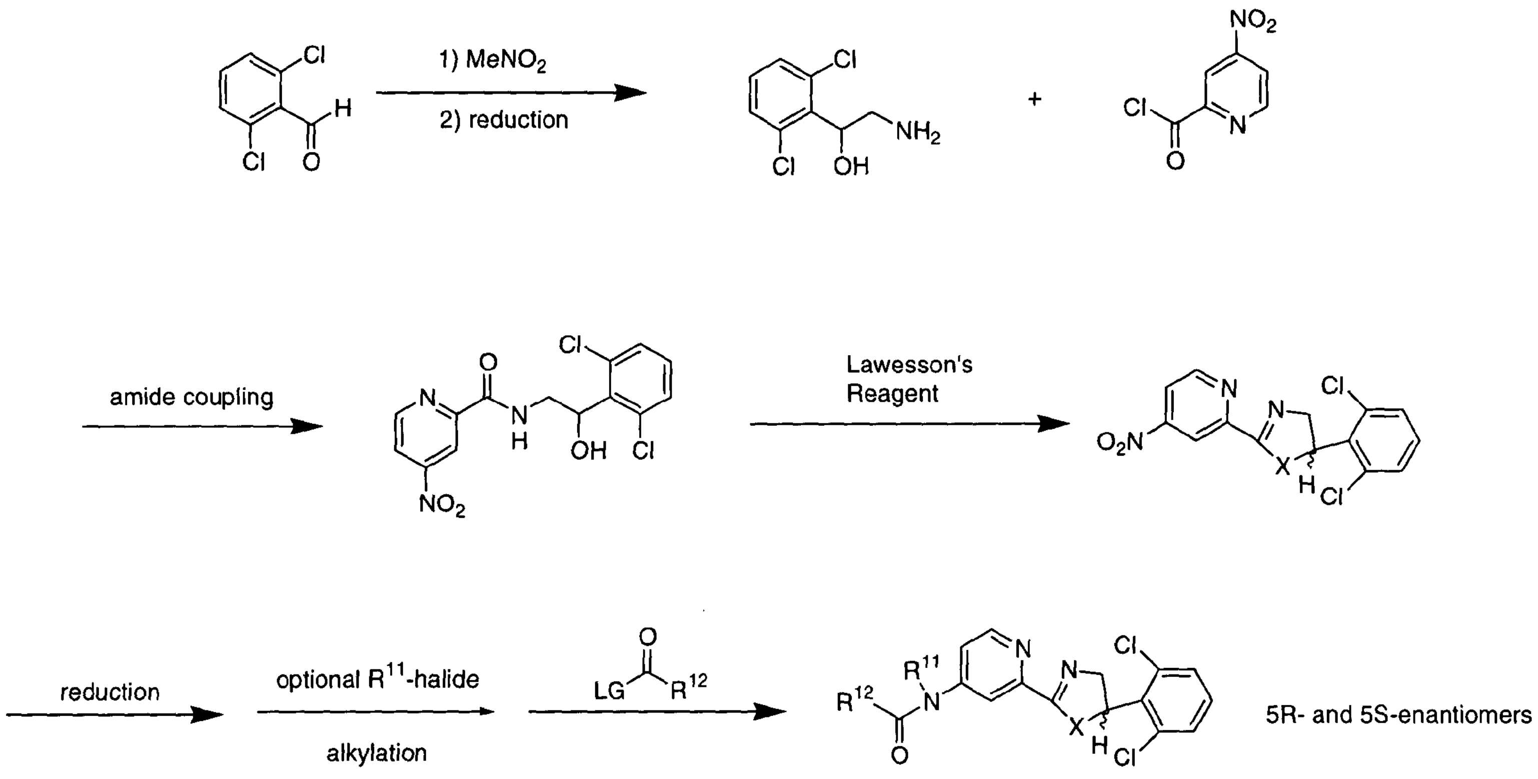
Figure 42:
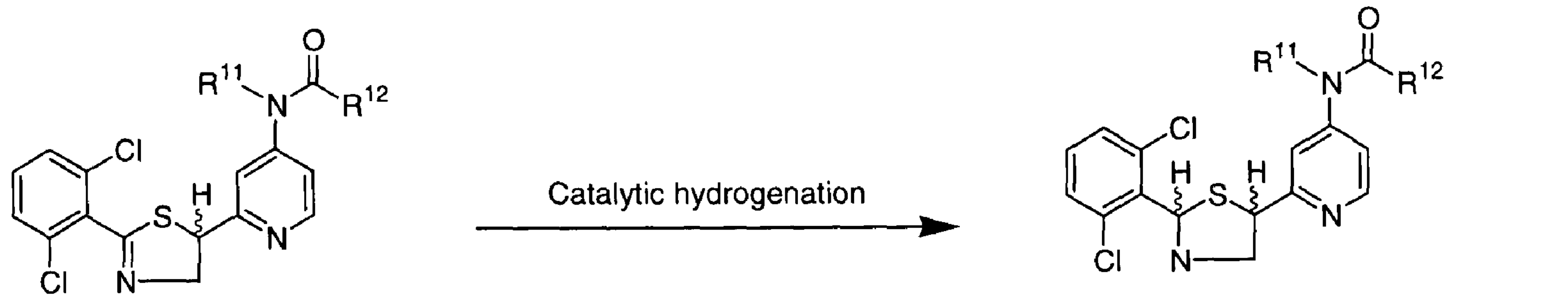
Figure 43:
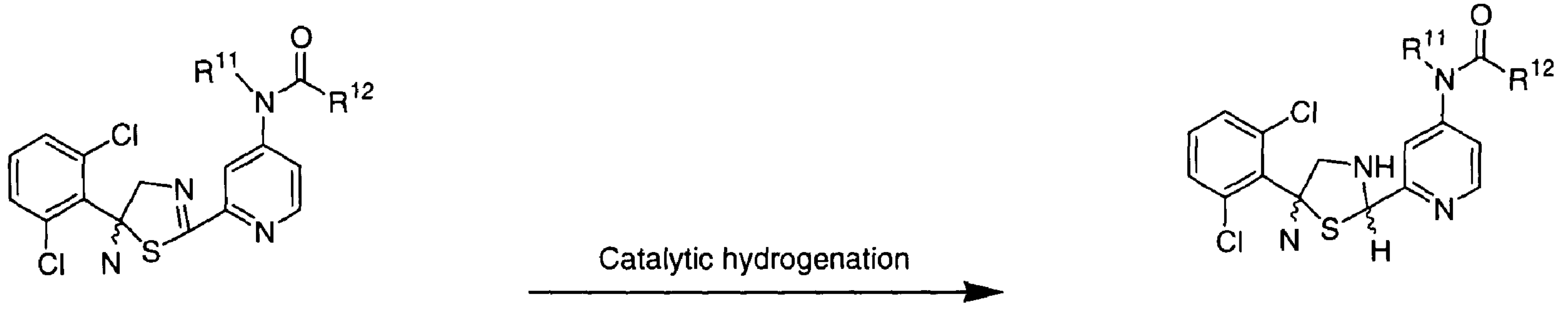
Figure 44:
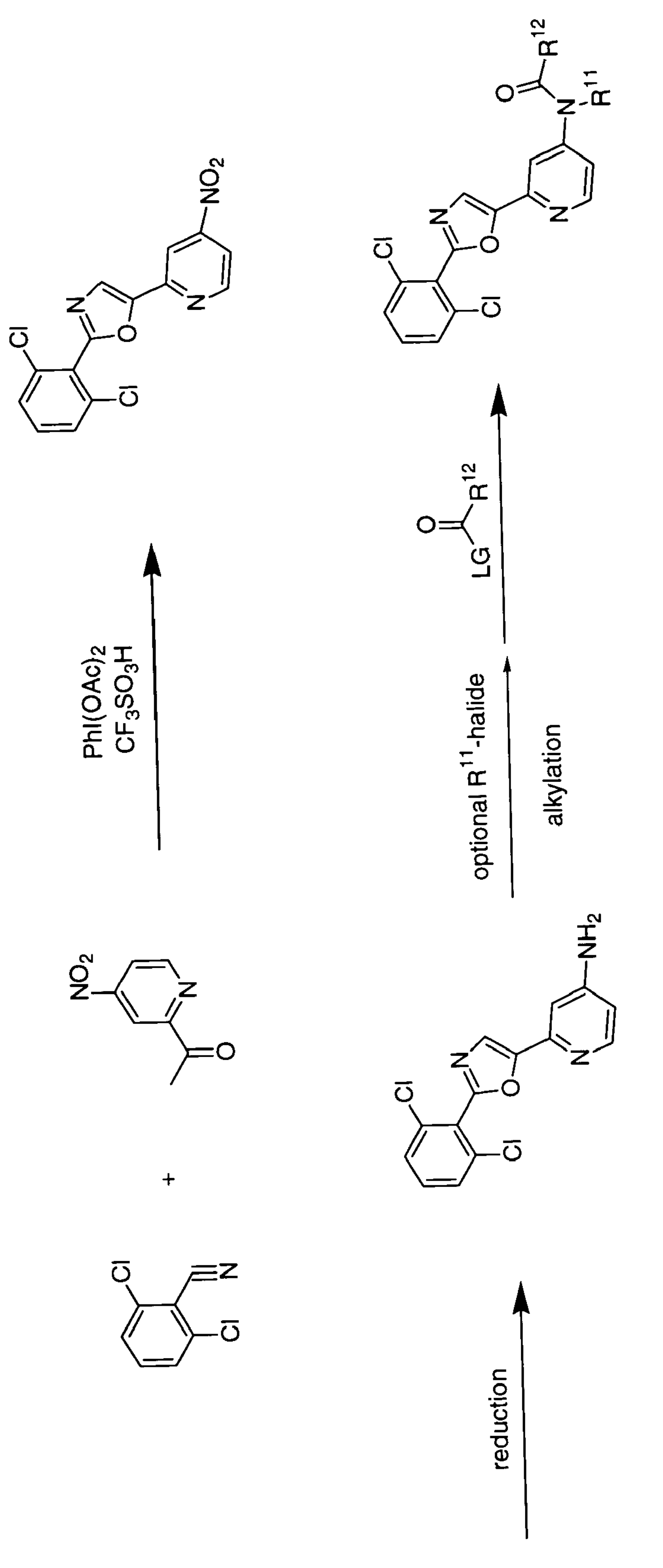
Figure 45:
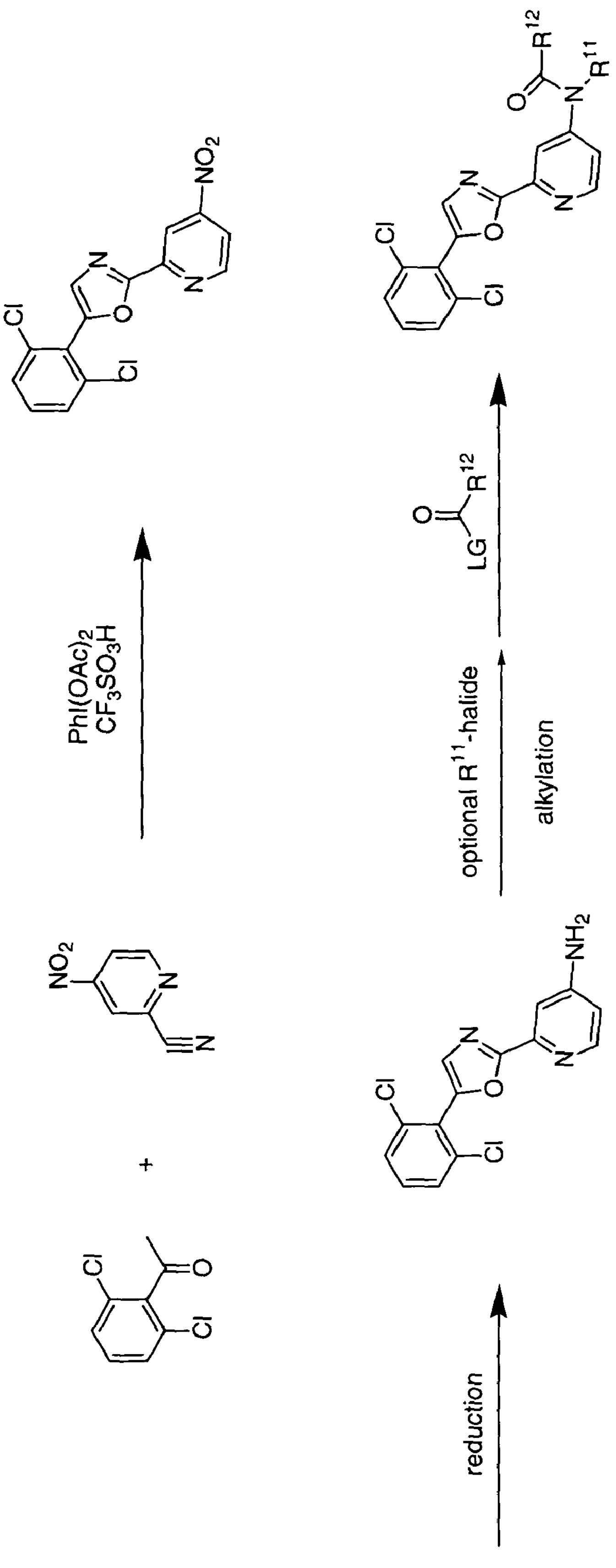
Figure 46:
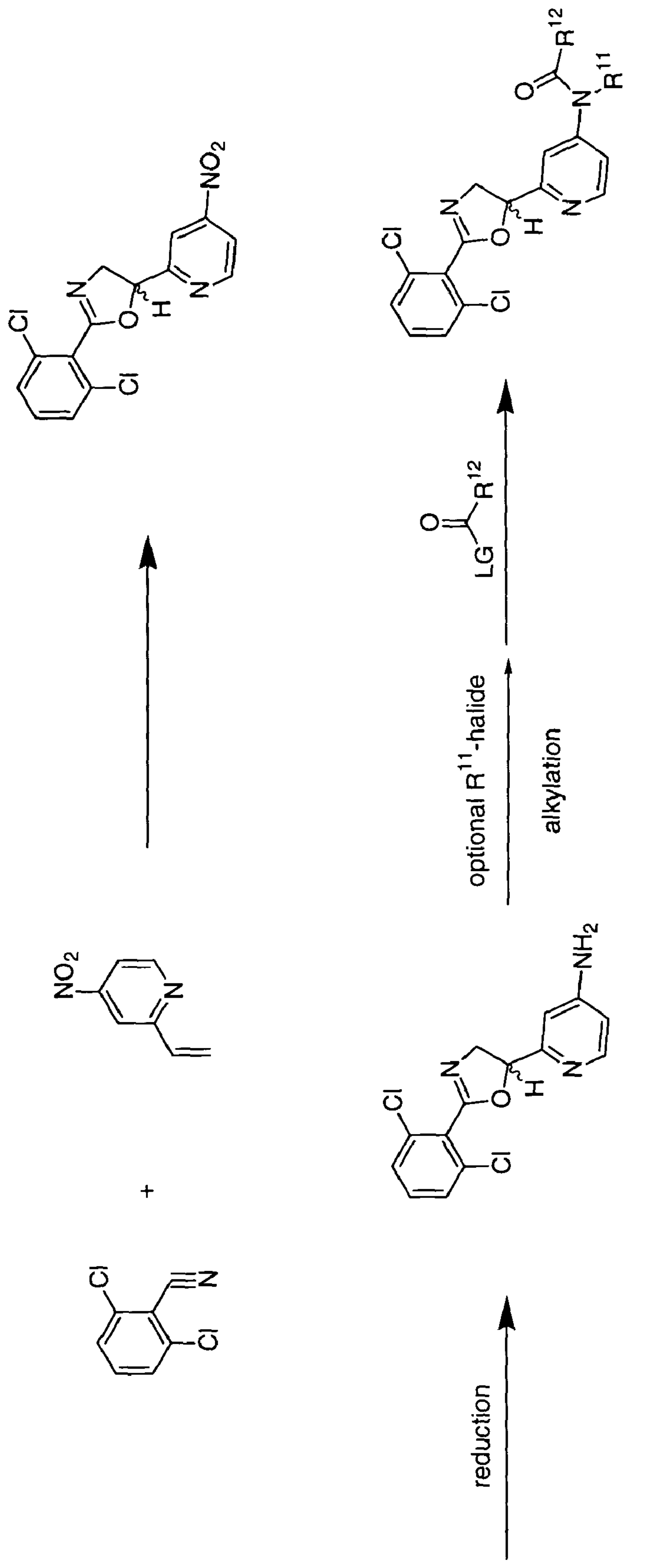
Figure 47:
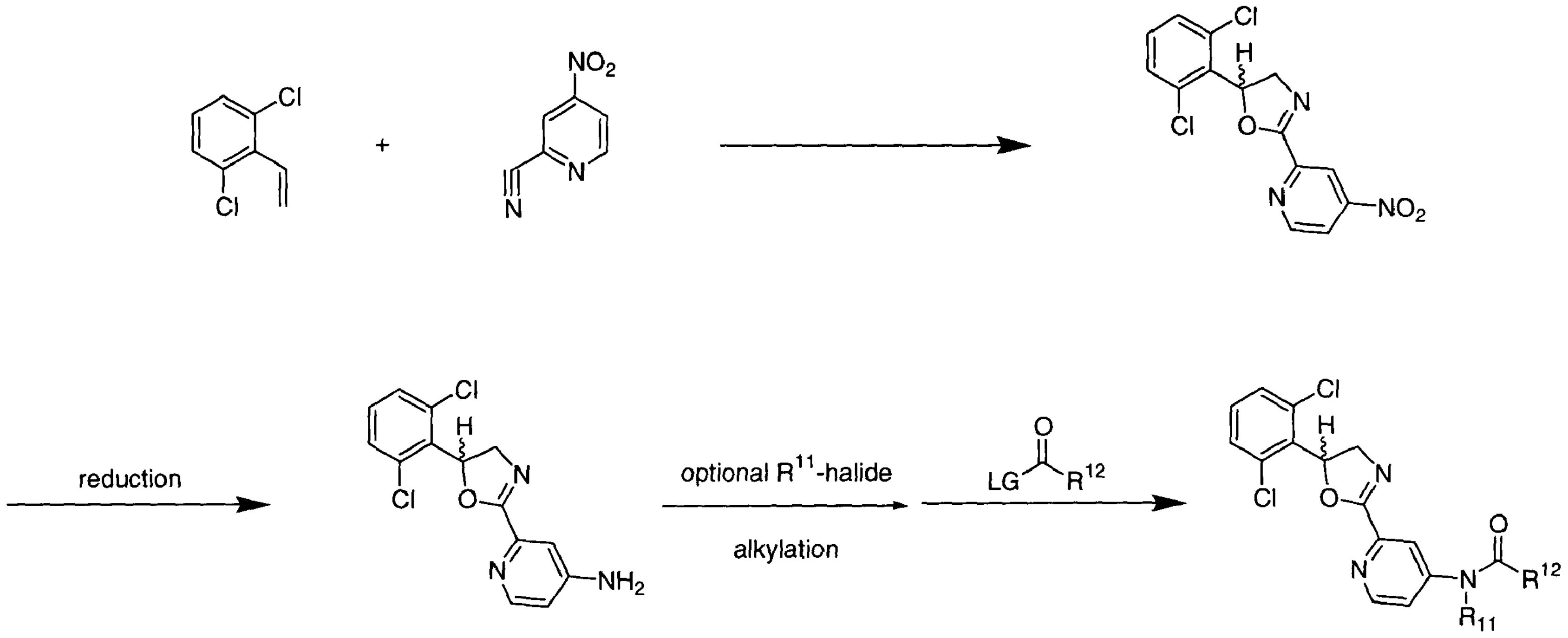
Figure 48:
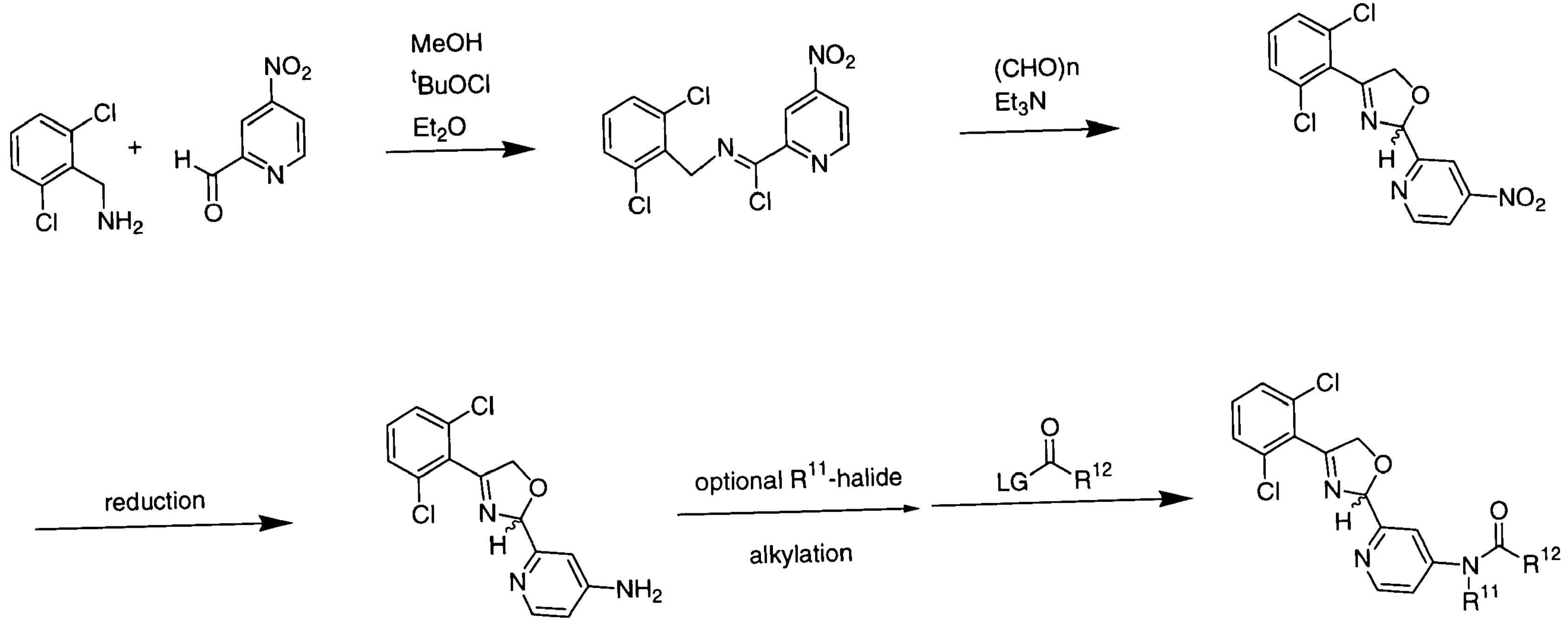
Figure 49:
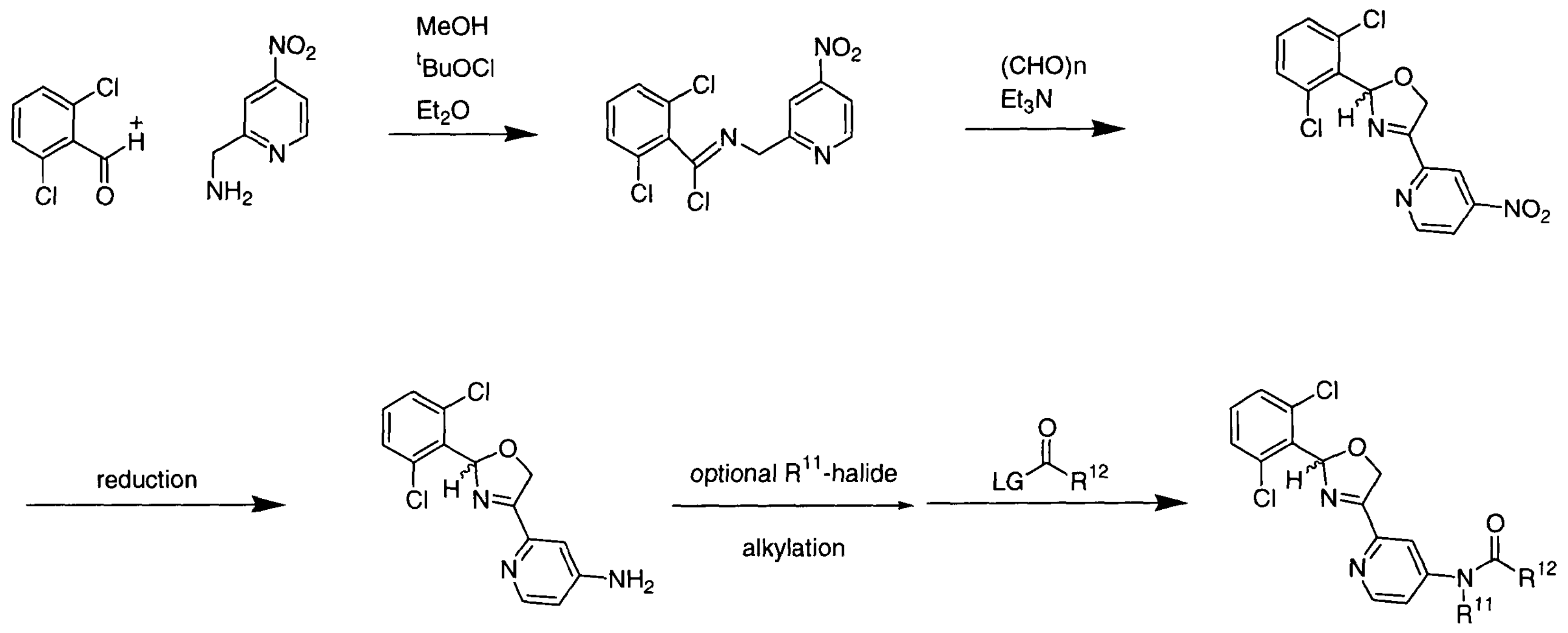
Figure 50:
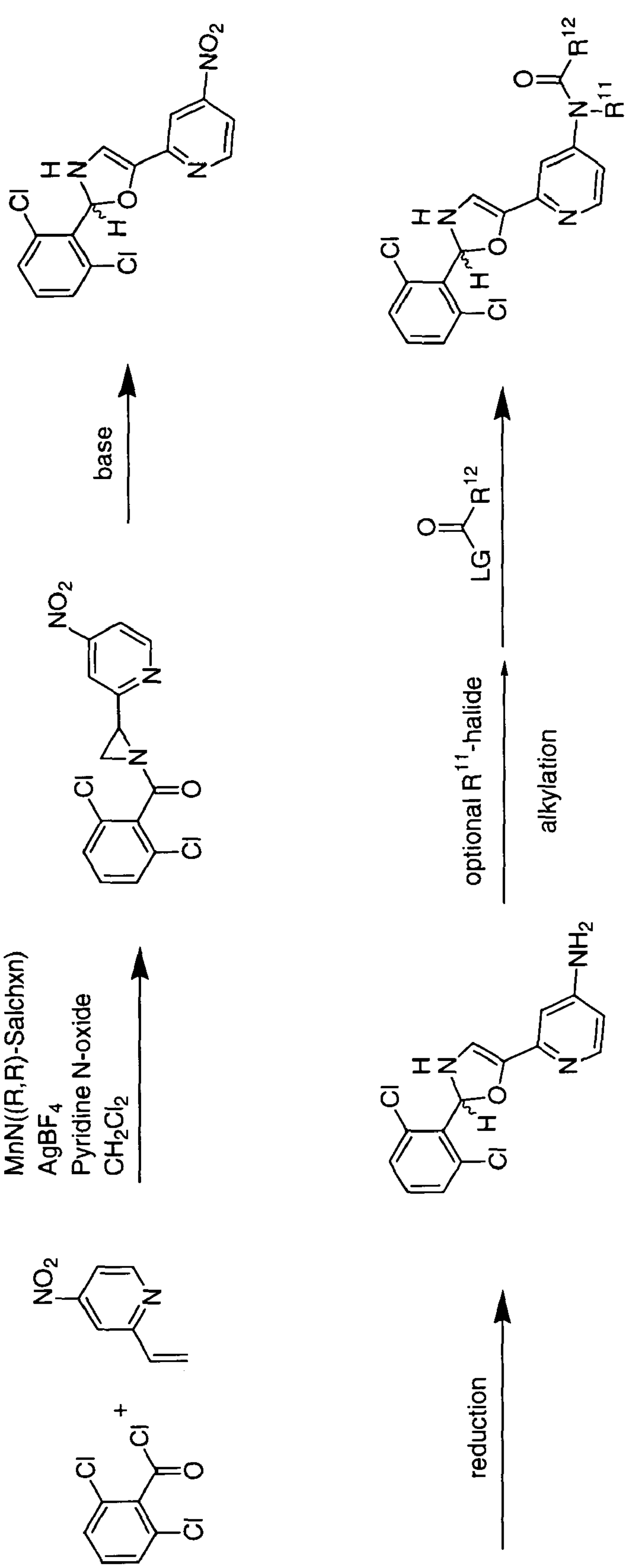
Figure 51:
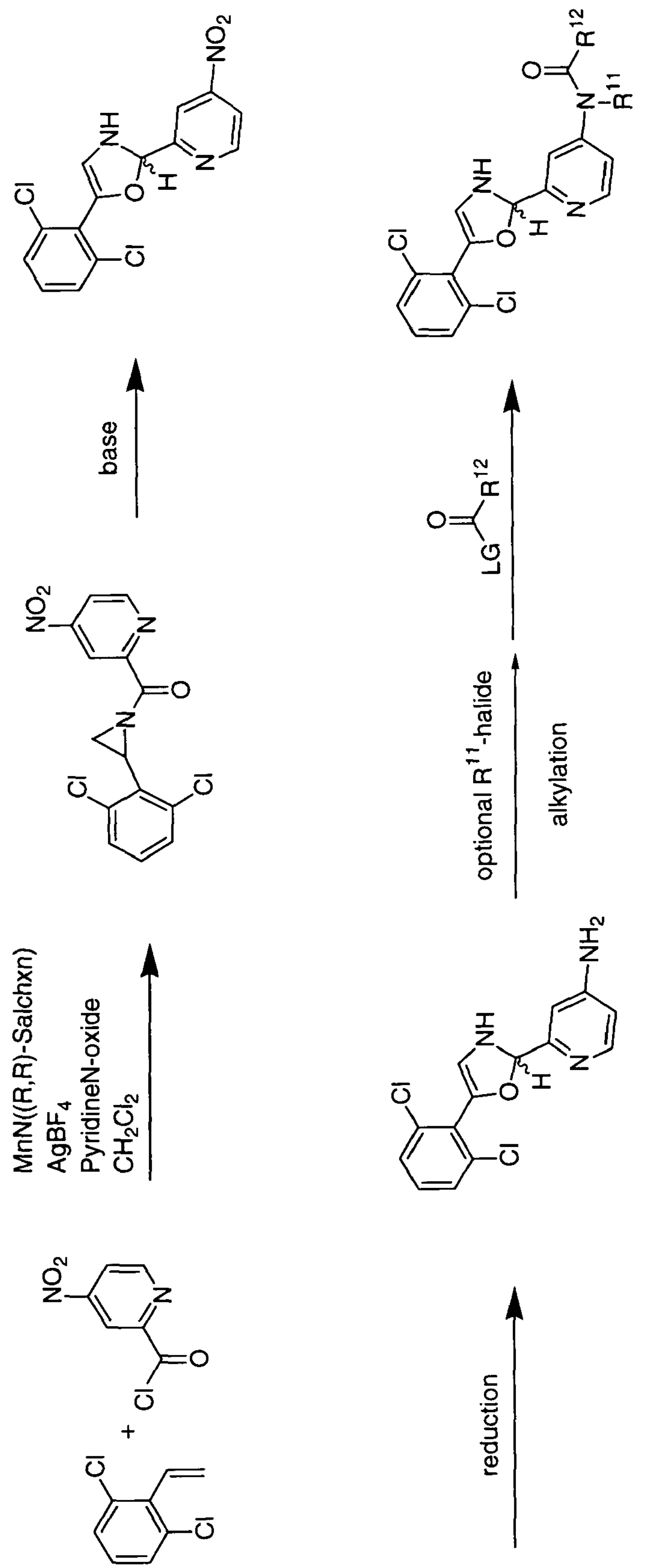
Figure 52:
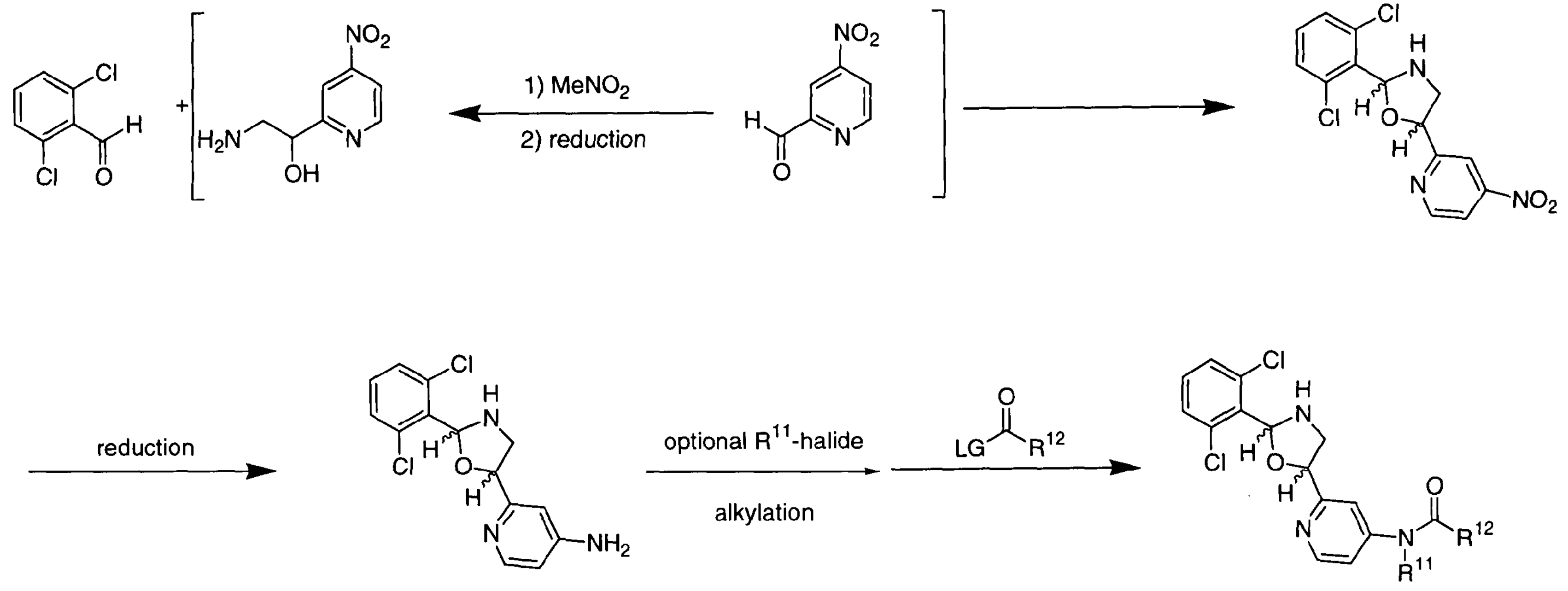
Figure 53:
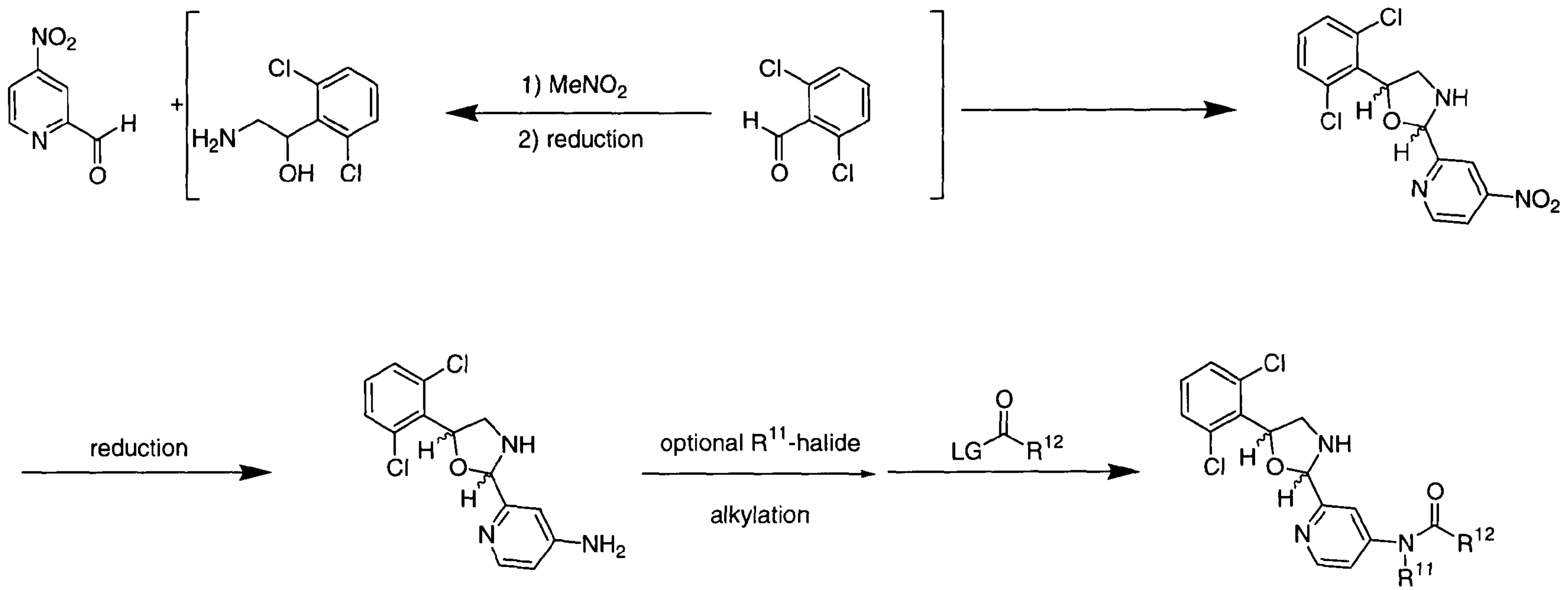
Figure 54:
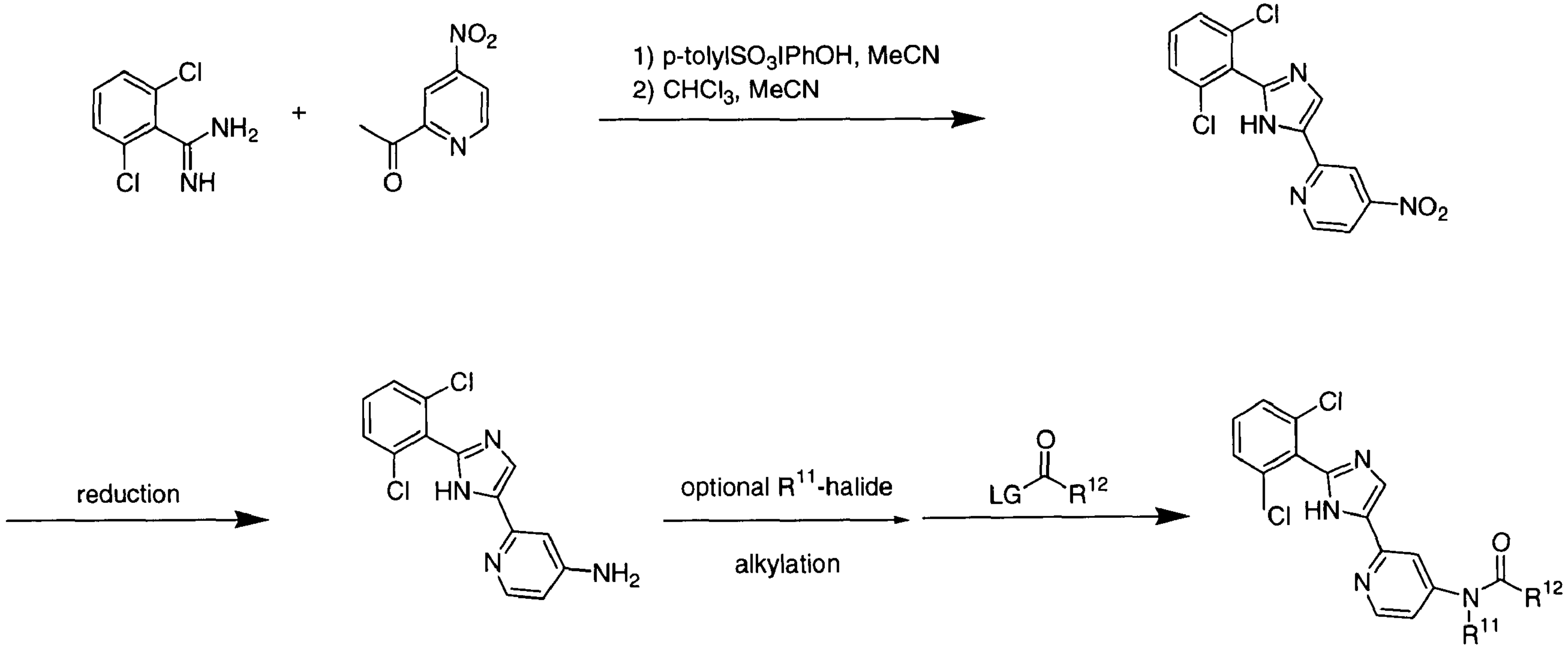
Figure 55:
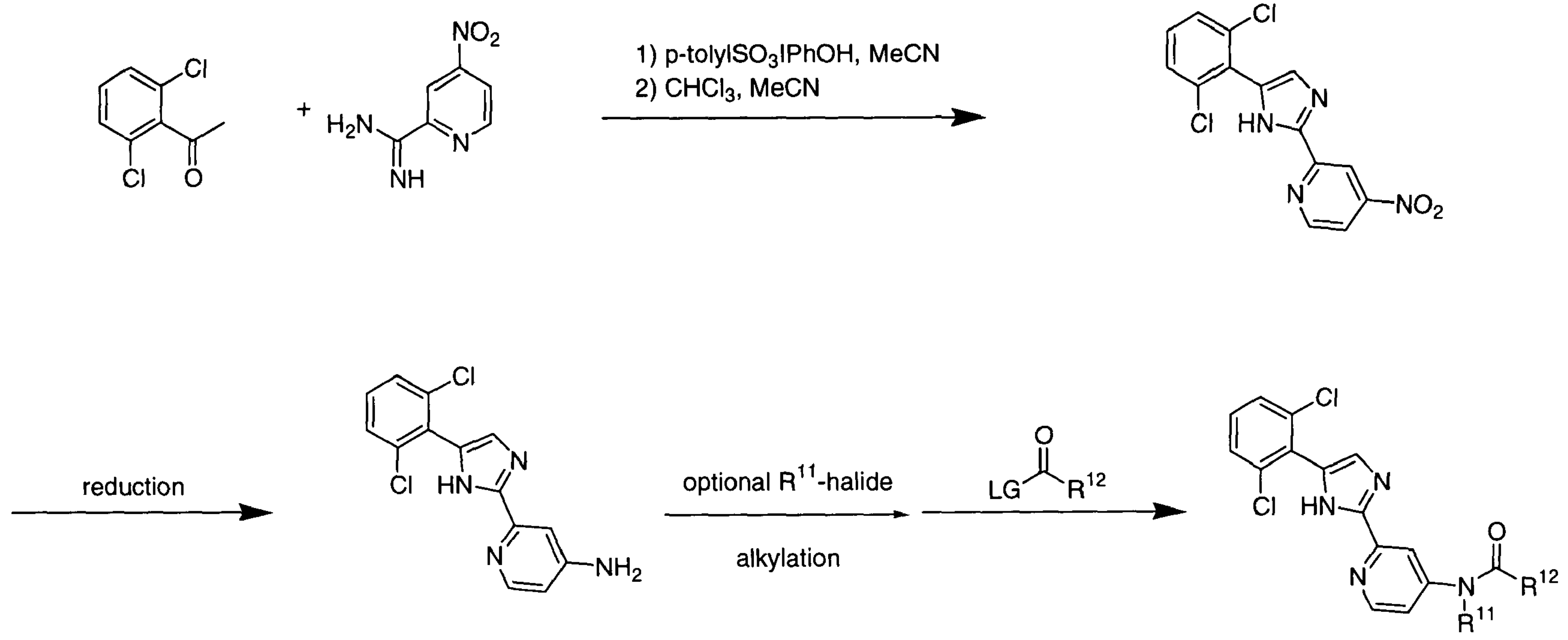
Figure 56:
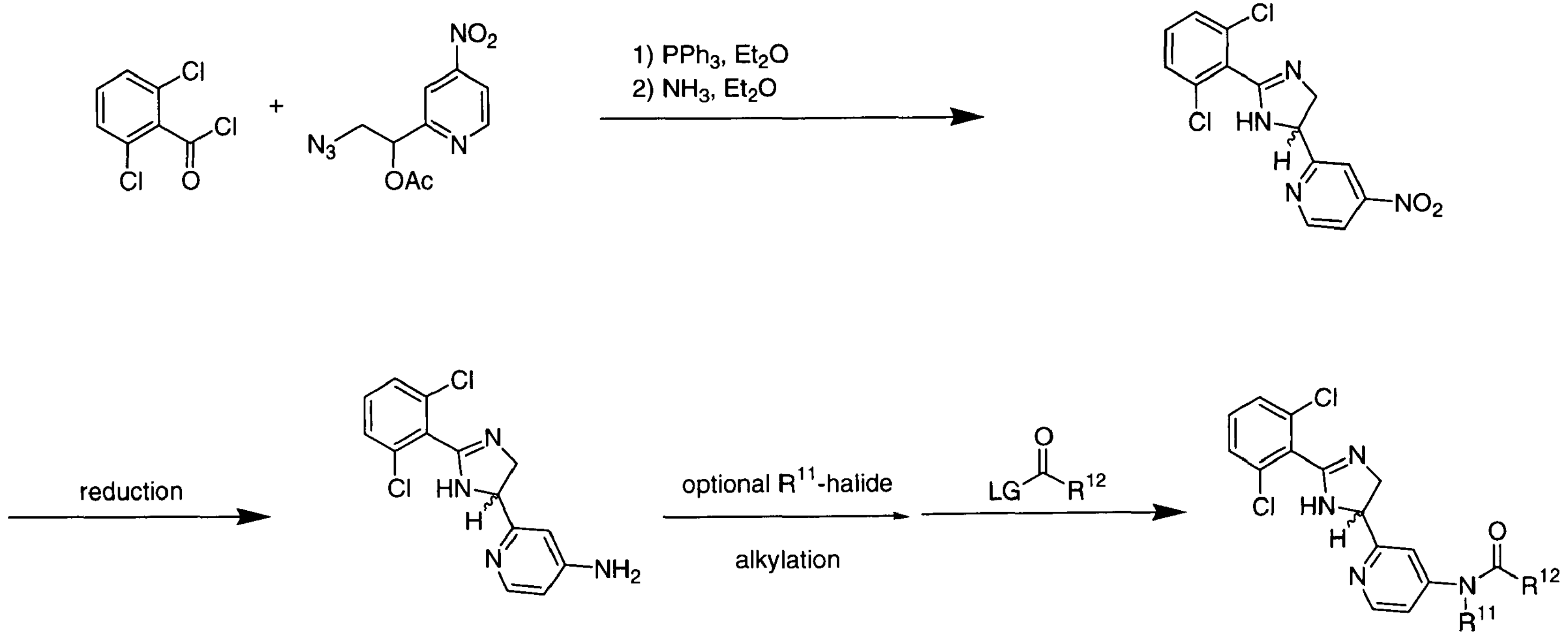
Figure 57:
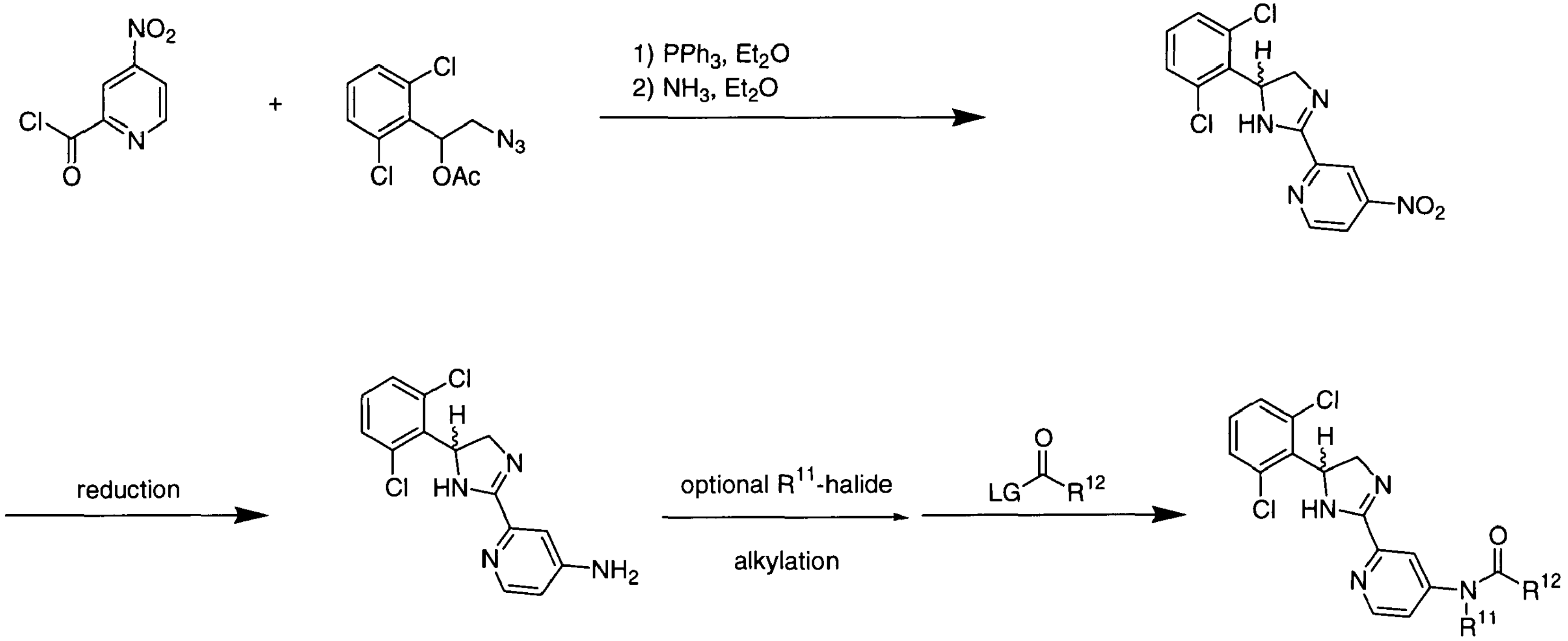
Figure 58:
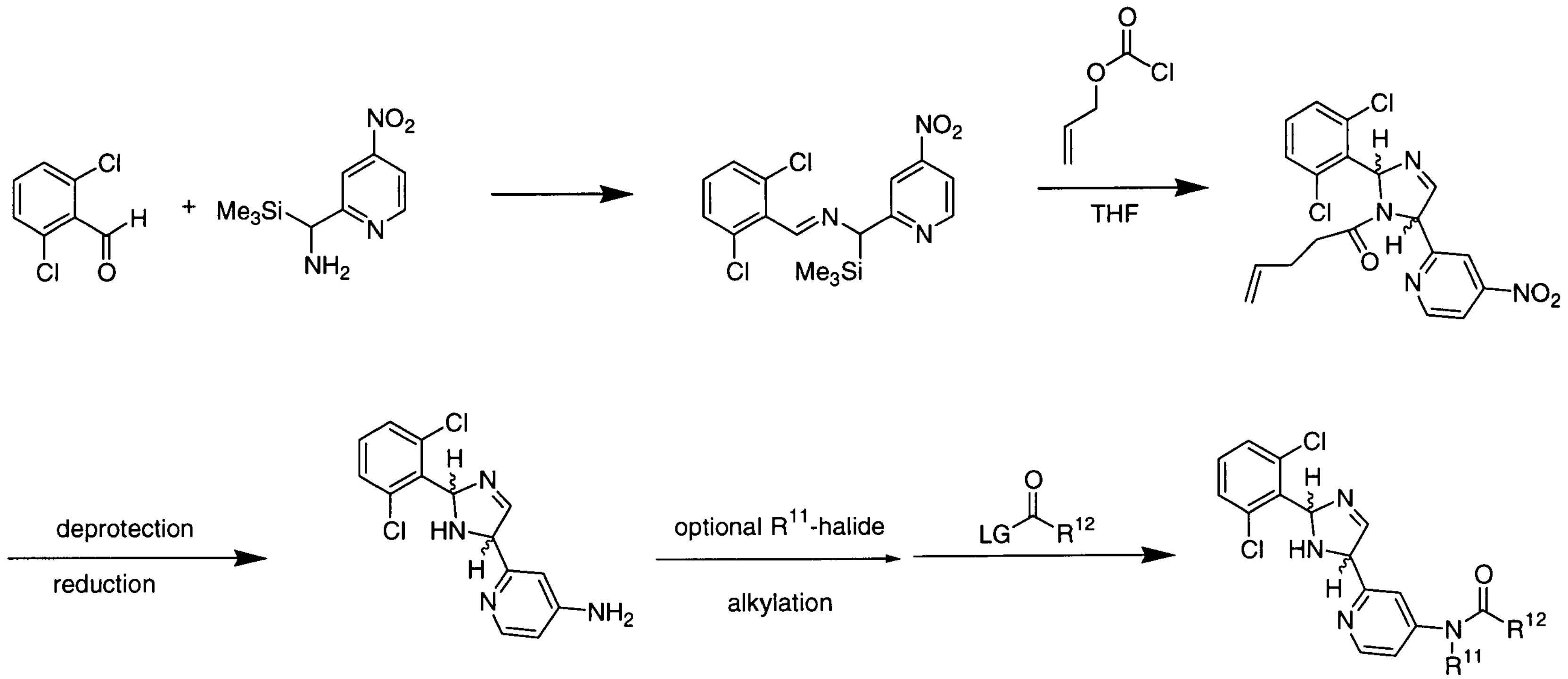
Figure 59:
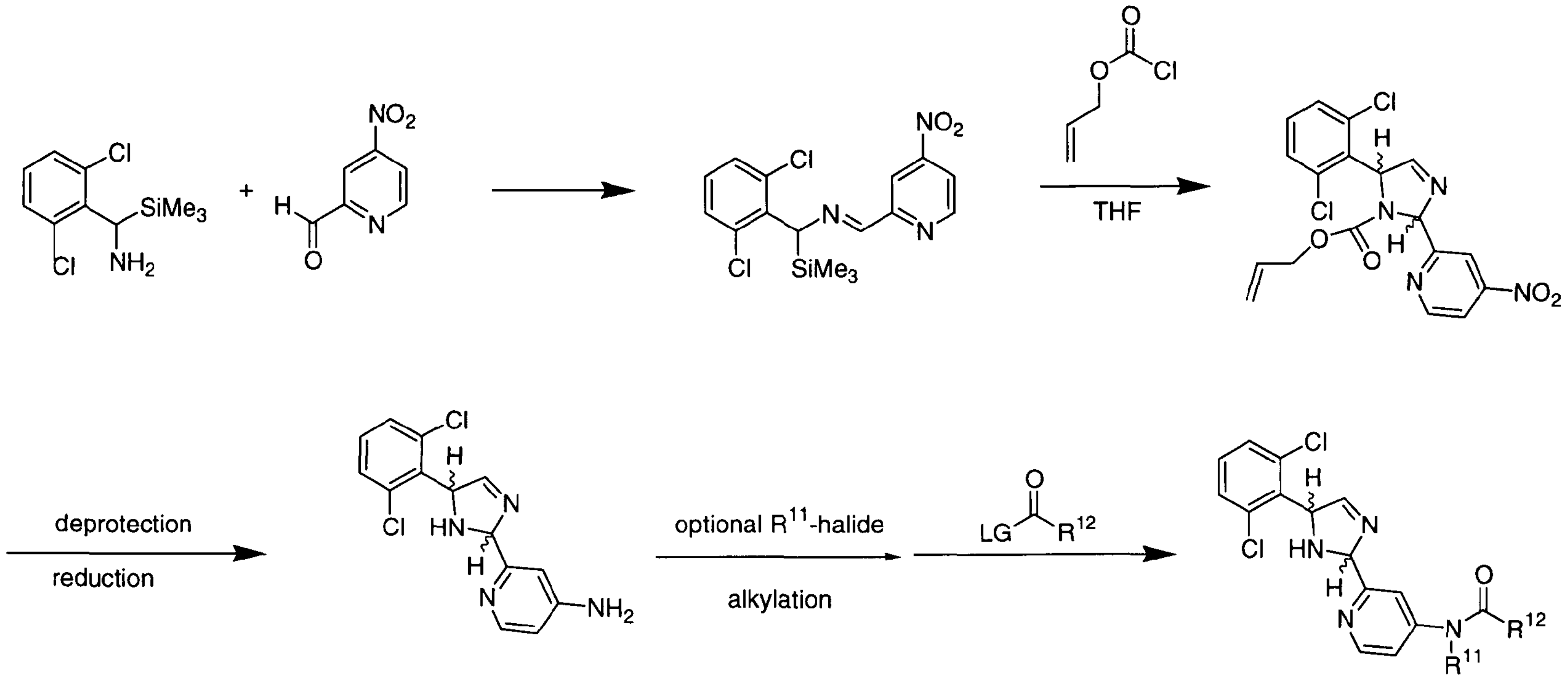
Figure 60:
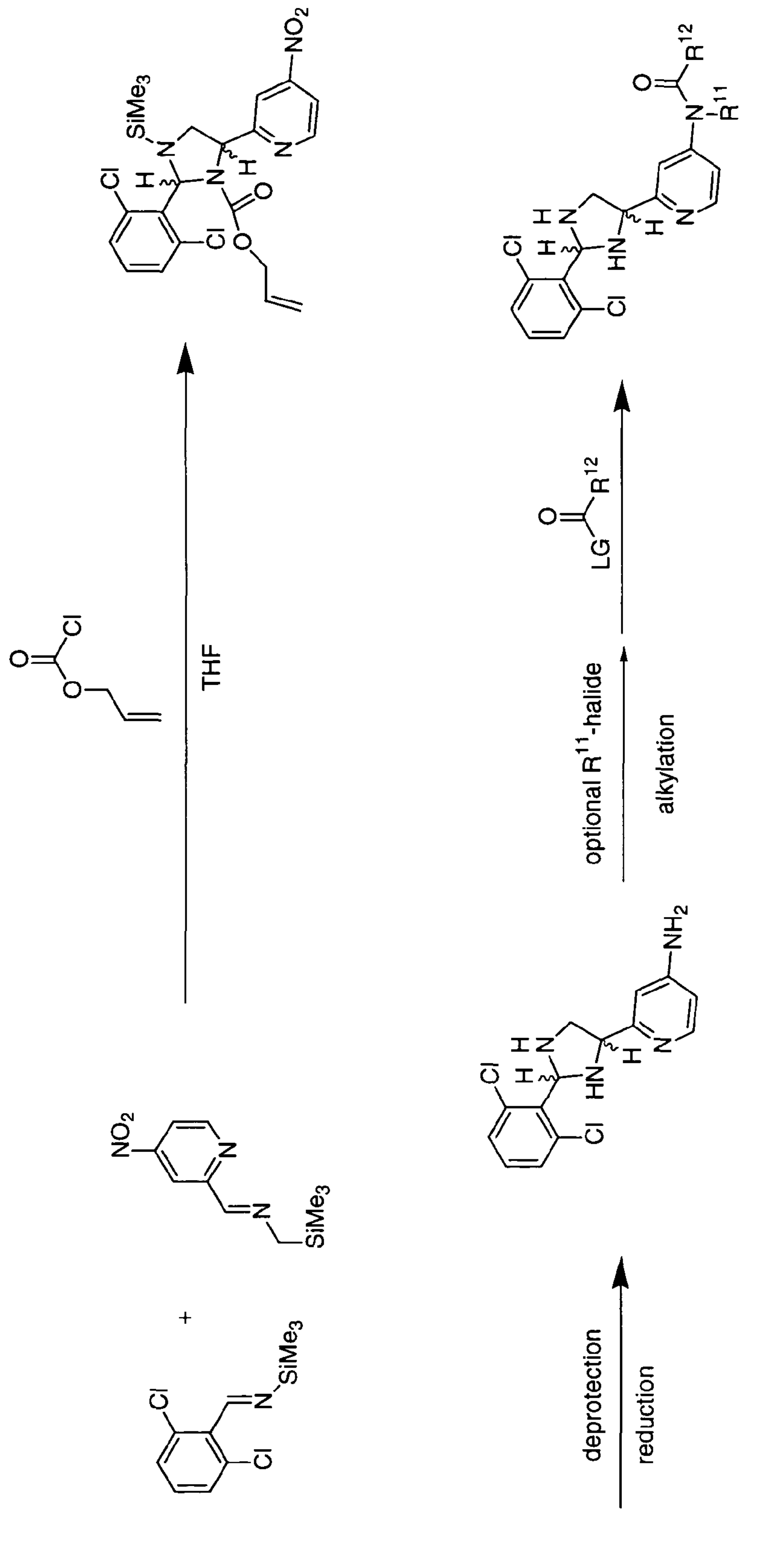
Figure 61:
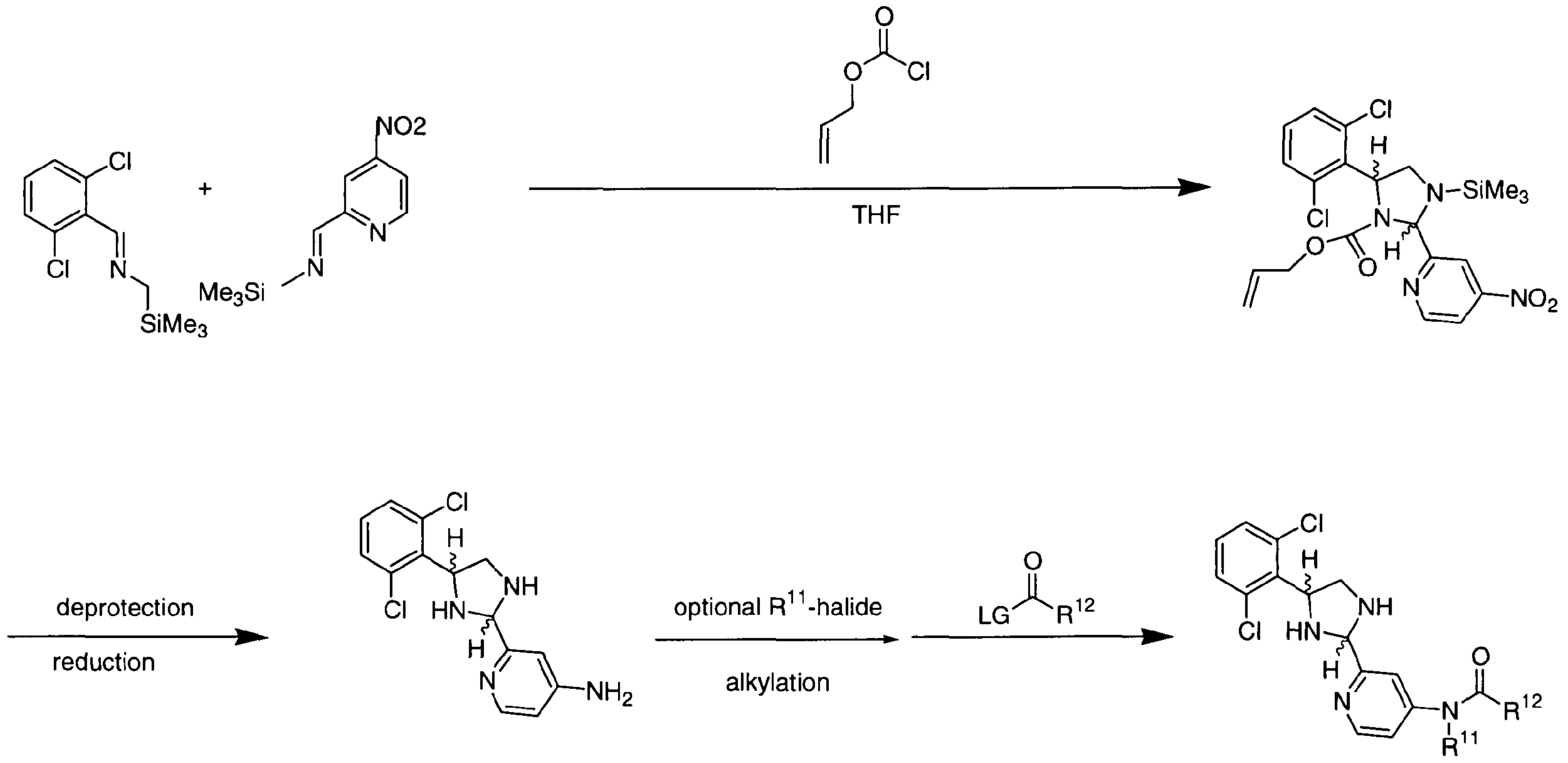
Figure 62:
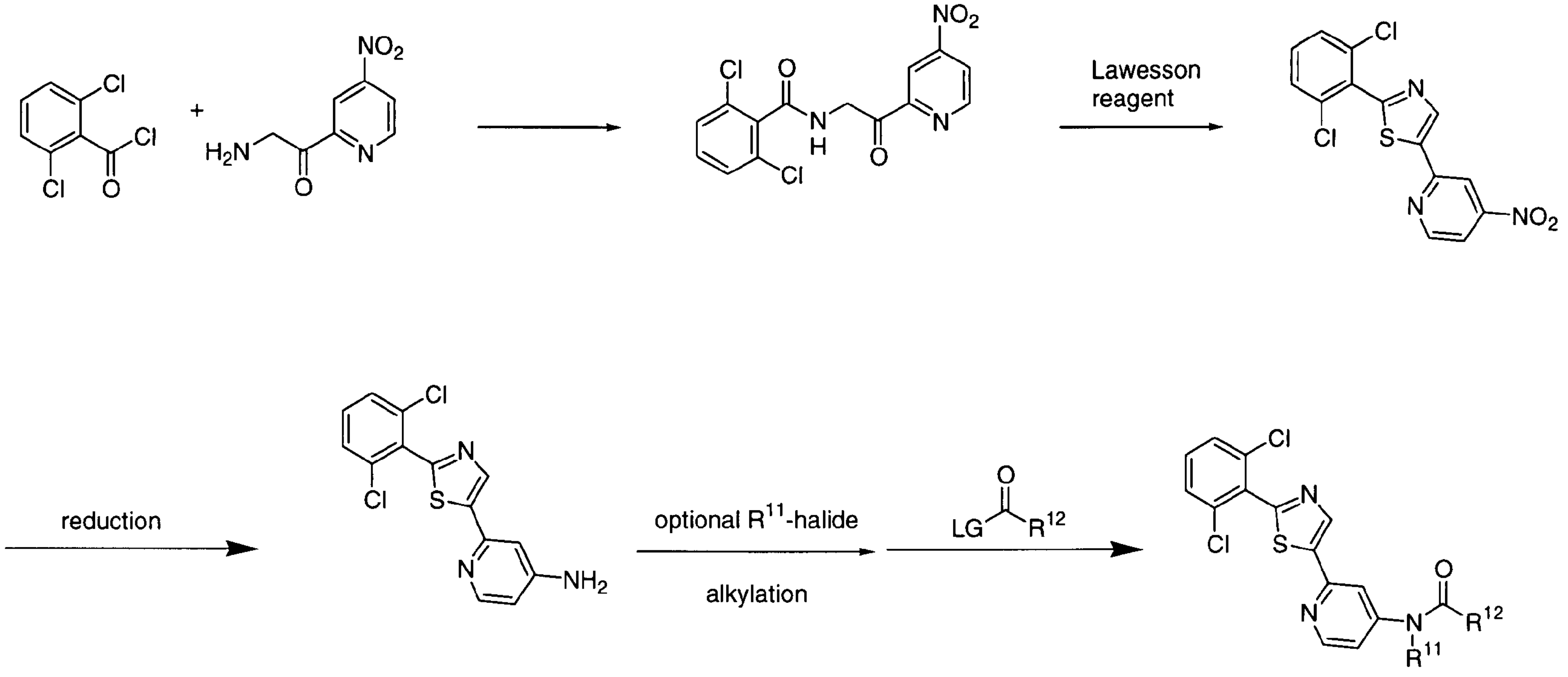

Method H (See FIG. 17)

Introduction of the haloacetamide or dihaloacetamide side chains

The p-aminophenylacetylene, purchased from Aldrich Chemical Co was dissolved in dichloromethane. Triethylamine (1.3 molar equivalents) was added and the solution was cooled in an ice-bath under nitrogen. Then a solution of haloacetyl chloride or dihaloacetyl chloride (1.0 molar equivalents) in dichloromethane was added dropwise. After the addition was complete, the reaction was allowed to stir 0.5–1 h at 0° C. and then allowed to warm to room temperature. After a total of 1–4 h reaction time the reaction mixture was diluted with water. The organic layer was separated and further washed with saturated aqueous sodium bicarbonate solution and brine. The organic layer was dried over anhydrous sodium sulfate, filtered and concentrated under reduced pressure to give the substituted 2-halo- or 2,2-dihalo-N-(4-ethynylphenyl) acetamide. Alternatively, the substituted p-aminophenylacetylene starting material was dissolved in dichloromethane and treated successively with 1-(3-dimethylaminopropyl)-3-ethylcarbodiimide hydrochloride (1 molar equivalent), the halo- or dihaloacetic acid (1 molar equivalent) and finally triethylamine (1 molar equivalent). The reaction mixture was then stirred at room temperature until the substituted p-aminophenylacetylene starting material was consumed as determined by TLC analysis. The mixture was washed with water and the organic layer was dried over anhydrous sodium sulfate, filtered and concentrated to dryness under reduced pressure to give either the substituted 2-halo- or 2,2-dihalo-N-(4-ethynylphenyl) acetamides.

All publications, patents and patent applications cited in this specification are herein incorporated by reference as if each individual publication, patent or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

What is claimed is:

1. A compound according to structural formula (I) or (II):

(I)

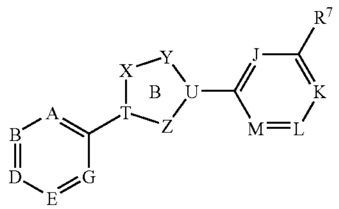

(II)

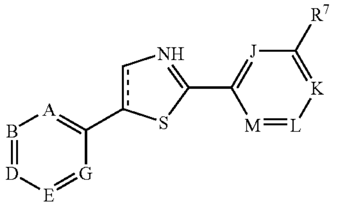

or a pharmaceutically acceptable salt, hydrate, solvate or N-oxide thereof, wherein:

the B ring is an aromatic or nonaromatic ring that includes from one to four heteroatoms, wherein X, Y, and Z are each, independently of one another selected from C, CH, N, $NR^{16}$, $NR^{18}$, S or O, provided that X and Y are not both O;

U and T are each, independently of one another, selected from C, or CH;

A is N or —$CR^2$—;

B is N or —$CR^3$—;

D is N or —$CR^4$—;

E is N or —$CR^5$—;

G is N or —$CR^6$—;

J is N or —$CR^8$—;

K is N or —$CR^8$—;

L is N or —$CR^9$—;

M is N or —$CR^{10}$—;

$R^2$ and $R^6$ are each, independently of one another, selected from the group consisting of hydrogen, halo, $C_1$–$C_{15}$ alkyl, substituted $C_1$–$C_{15}$ alkyl, alkylthio, substituted $C_1$–$C_{15}$ alkylthio, alkoxy, substituted alkoxy, alkoxycarbonyl, substituted alkoxycarbonyl, $C_1$–$C_{15}$ arylalkyloxycarbonyl, substituted aryl-$C_1$–$C_{15}$ arylalkyloxycarbonyl, aryloxycarbonyl, substituted aryloxycarbonyl, cycloheteroalkyl, substituted cycloheteroalkyl, carbamoyl, substituted carbamoyl, halo-$C_1$–$C_{15}$ alkyl, sulfamoyl, substituted sulfamoyl and silyl ethers, provided that one of $R^2$ and $R^6$ is other than hydrogen;

$R^3$ and $R^5$ are each, independently of one another, selected from the group consisting of hydrogen, halo, $C_1$–$C_{15}$ alkyl, substituted $C_1$–$C_{15}$ alkyl, $C_1$–$C_{15}$ alkylthio, substituted $C_1$–$C_{15}$ alkylthio, alkoxy, substituted alkoxy, alkoxycarbonyl, substituted alkoxycarbonyl, aryl-$C_1$–$C_{15}$ arylalkyloxycarbonyl, substituted aryl-$C_1$–$C_{15}$ alkyloxycarbonyl, aryloxycarbonyl, substituted aryloxycarbonyl, cycloheteroalkyl, substituted cycloheteroalkyl, carbamoyl, substituted carbamoyl, halo-$C_1$–$C_{15}$ alkyl, sulfamoyl and substituted sulfamoyl;

$R^4$ is selected from the group consisting of hydrogen, halo, $C_1$–$C_{15}$ alkyl, substituted $C_1$–$C_{15}$ alkyl, $C_1$–$C_{15}$ alkylthio, substituted $C_1$–$C_{15}$ alkylthio, carbamoyl, substituted carbamoyl, alkoxy, substituted alkoxy, alkoxycarbonyl, substituted alkoxycarbonyl, aryl-$C_1$–$C_{15}$ alkyloxycarbonyl, substituted aryl-$C_1$–$C_{15}$ alkyloxycarbonyl, aryloxycarbonyl, substituted aryloxycarbonyl, di-$C_1$–$C_{15}$ alkylamino, substituted di-$C_1$–$C_{15}$ alkylamino, halo-$C_1$–$C_{15}$ alkyl, sulfamoyl and substituted sulfamoyl;

$R^7$ is —$NR^{11}C(O)R^{12}$;

$R^8$, $R^9$, $R^{10}$ and $R^{14}$ are each, independently of one another, hydrogen, halo or fluoro;

$R^{11}$ is hydrogen, or $C_1$–$C_{15}$ alkyl; and $R^{12}$ is selected from the group consisting of substituted $C_1$–$C_{15}$ alkyl, halo-$C_1$–$C_{15}$ alkyl, cycloheteroalkyl and substituted cycloheteroalkyl;

$R^{16}$ and $R^{18}$ are each, independently of one another, selected from the group consisting of hydrogen, lower alkyl, substituted lower alkyl, lower heteroalkyl, substituted lower heteroalkyl, cycloalkyl, substituted cycloalkyl, cycloheteroalkyl, substituted cycloheteroalkyl, lower haloalkyl, lower alkylthio, substituted lower alkylthio, lower alkoxy, substituted lower alkoxy, methoxy, substituted methoxy, lower heteroalkoxy, substituted lower heteroalkoxy, cycloalkoxy, substituted cycloalkoxy, cycloheteroalkoxy, substituted cycloheteroalkoxy, lower haloalkoxy, monohalomethoxy, dihalomethoxy, trihalomethoxy, trifluoromethoxy, lower di- or monoalkylamino, substituted lower di- or monoalkylamino, aryl, substituted aryl, aryloxy, substituted aryloxy, phenoxy, substituted phenoxy, aryl-$C_1$–$C_{15}$ alkyl, substituted aryl-$C_1$–$C_{15}$ alkyl, aryl-$C_1$–$C_{15}$ alkyloxy, substituted aryl-$C_1$–$C_{15}$ alkyloxy, benzyl, benzyloxy, heteroaryl, substituted heteroaryl, heteroaryloxy, substituted heteroaryloxy, heteroaryl-$C_1$–$C_{15}$ alkyl, substituted heteroaryl-$C_1$–$C_{15}$ alkyl, heteroaryl-$C_1$–$C_{15}$ alkyloxy, substituted heteroaryl-$C_1$–$C_{15}$ alkyloxy, carboxyl, lower alkoxycarbonyl, substituted lower alkoxycarbonyl, aryloxycarbonyl, substituted aryloxycarbonyl, aryl-$C_1$–$C_{15}$ alkyloxycarbonyl, substituted aryl-$C_1$–$C_{15}$ alkyloxycarbonyl, carbamate, substituted carbamate, carbamoyl, substituted carbamoyl, sulfamoyl, substituted sulfamoyl and a group of the formula -L-$R^{17}$, where "L" is a linker and $R^{17}$ is cycloalkyl, substituted cycloalkyl, cycloheteroalkyl or substituted cycloheteroalkyl with the provisos that:

(i) at least one of A, B, D, E, G, J, K, L or M is N;

(ii) no more than one of A, B, D, E or G is N; and (iii) no more than one of J, K, L or M is N.

2. The compound of claim 1 in which one of A, B, D, E or G is N and one of J, K, L or M is N.

3. The compound of claim 1 in which one of A, B, D, E or G is N and none of J, K, L or M is N.

4. The compound of claim 1 in which none of A, B, D, E or G is N and one of J, K, L or M is N.

5. The compound of claim 1 in which the B-ring is an oxazole or hydro isomer thereof.

6. The compound of claim 1 in which the B ring is a thiazole or a hydro isomer thereof.

7. The compound of claim 1 in which the B ring is an imidazoleor a hydro isomer thereof.

8. The compound of claim 1 in which the B ring is a triazole or a hydro isomer thereof.

9. The compound of claim 1 in which the B ring is an oxadiazole or a hydro isomer thereof.

10. The compound of claim 1 in which the B ring is an isoxazole or a hydro isomer thereof.

11. The compound of claim 1 in which the B ring is a pyrazole or a hydro isomer thereof.

12. The compound of claim 1 in which the B ring is a thiadiazole or a hydro isomer thereof.

13. The compound of any one of claims 1–12 in which $R^7$ is $—NR^{11}C(O)R^{12}$, wherein $R^{11}$ is hydrogen or methyl and $R^{12}$ is $—CHCl_2$.

14. The compound of claim 13 in which X is N, Y is O and Z is —CH—.

15. The compound of claim 1 in which A is $—CR^2—$, G is $—CR^6—$, $R^7$ is $—NR^{11}C(O)R^{12}$, where $R^{11}$ is hydrogen or methyl and $R^{12}$ is $—CHCl_2$.

16. The compound of claim 15 in which B is $—CR^3—$, D is N, E is $—CR^5—$, J is $—CR^{14}—$, K is $—CR^8—$, L is $—CR^9—$, M is $—CR^{10}—$, and $R^3$, $R^5$, $R^9$, $R^{10}$ and $R^{14}$ are each hydrogen.

17. The compound of claim 16 in which $R^8$ is fluorine.

18. The compound of claim 15 in which B is $—CR^3—$, D is $—CR^4—$, E is $—CR^5—$, J is $—CR^{14}—$, K is $—CR^8—$, L is $—CR^9—$, M is N and $R^3$, $R^4$, $R^5$, $R^8$, $R^9$ and $R^{14}$ are each hydrogen.

19. The compound of claim 15 in which B is $—CR^3—$, D is $—CR^4—$, E is $—CR^5—$, J is $—CR^{14}—$, K is $—CR^8—$, L is N, M is $—CR^{10}—$ and $R^3$, $R^4$, $R^5$, $R^8$, $R^{10}$ and $R^{14}$ are each hydrogen.

20. The compound of any one of claims 15–19 in which $R^2$ and $R^6$ are each, independently of one another, selected from the group consisting of chloro, fluoro, methyl, triflouromethyl, thiomethyl, methoxy, i-propoxy, N-morpholino and N-morpholinosulfamoyl.

21. The compound of any one of claims 15–19 in which $R^2$ and $R^6$ are each, independently of one another, selected from the group consisting of chloro, fluoro, methyl, triflouromethyl, methoxy or i-propoxy.

22. The compound of any one of claims 15–19 in which $R^2$ and $R^6$ are each the same or different halo.

23. The compound of any one of claims 15–19 in which X is N, Y is O and Z is —CH—.

24. The compound of claim 1 in which A is $—CR^2—$, G is $—CR^6—$ and $R^7$ is $—NR^{11}C(O)R^{12}$, where $R^{11}$ is hydrogen or methyl and $R^{12}$ is $—CH_2I$.

25. The compound of claim 24 in which $R^2$ and $R^6$ are each, independently of one another, selected from the group consisting of chloro, fluoro, methyl, triflouromethyl, thiomethyl, methoxy, i-propoxy, N-morpholino and N-morpholinosulfamoyl.

26. The compound of claim 24 in which $R^2$ and $R^6$ are each, independently of one another, selected from the group consisting of chloro, fluoro, methyl, triflouromethyl, methoxy and i-propoxy.

27. The compound of claim 24 in which $R^2$ and $R^6$ are each the same or different halo.

28. The compound of claim 24 in which X is N, Y is O and Z is —CH—.

29. The compound of claim 1 in which A is $—CR^2—$, B is $—CR^3—$, $R^7$ is $—NR^{11}C(O)R^{12}$, where $R^{11}$ is hydrogen or methyl and $R^{12}$ is $—CHCl_2$.

30. The compound of claim 29 in which D is $—CR^4—$, G is $—CR^6—$, E is $—CR^5—$, J is $—CR^{14}—$, K is $—CR^8—$, L is $—CR^9—$, M is N and $R^4$, $R^5$, $R^6$, $R^8$, $R^9$ and $R^{14}$ are each hydrogen.

31. The compound of claim 29 in which D is $—CR^4—$, G is $—CR^6—$, E is $—CR^5—$, J is $—CR^4—$, K is $—CR^8—$, L is N, M is $—CR^{10}—$ and $R^4$, $R^5$, $R^6$, $R^8$, $R^{10}$ and $R^{14}$ are each hydrogen.

32. The compound of any one of claims 29–31 in which $R^2$ is chloro, fluoro, methyl, triflouromethyl, thiomethyl, methoxy, i-propoxy, N-morpholino or N-morpholinosulfamoyl and $R^3$ is chloro, fluoro, methyl, triflouromethyl or methoxy.

33. The compound of any one of claims 29–31 in which $R^2$ is chloro, fluoro, methyl, triflouromethyl or methoxy and $R^3$ is chloro, fluoro or triflouromethyl.

34. The compound of any one of claims 29–31 in which $R^2$ and $R^3$ are each the same or different halo.

35. The compound of any one of claims 29–31 in which X is N, Y is O and Z is —CH—.

36. The compound of claim 1 in which A is $—CR^2—$, G is $—CR^6—$ and $R^2$ and $R^6$ are each identical, provided that R and $R^6$ are not hydrogen.

37. The compound of claim 1 in which A is $—CR^2—$, B is $—CR^3—$ and $R^2$ and $R^3$ are each identical, provided that R and $R^3$ are not hydrogen.

38. The compound of claim 1 in which B is $—CR^3—$, E is $—CR^5—$ and $R^3$ and $R^5$ are each identical, provided that $R^3$ and $R^5$ are not hydrogen.

39. The compound of claim 1 in which B is $—CR^3—$, D is $—CR^4—$, E is $—CR^5—$, J is $—CR^{14}—$, K is $—CR^8—$ and $R^3$, $R^4$, $R^5$, $R^8$ and $R^{14}$ are each hydrogen.

40. The compound of claim 1 in which -D is $—CR^4—$, E is $—CR^5—$, G is $CR^6$, J is $—CR^{14}—$, K is $—CR^8—$ and $R^4$, $R^5$, $R^6$, R and $R^{14}$ are each hydrogen.

41. The compound of claim 1 which has the structural formula (Ia), (Ib), (Ic), (Id) or (Ie):

(Ia)

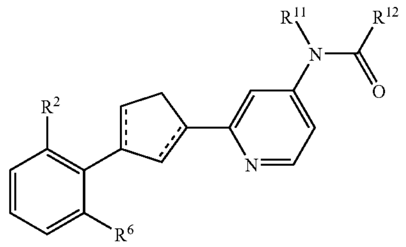

(Ib)

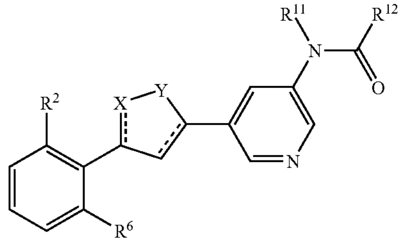

-continued (Ic)

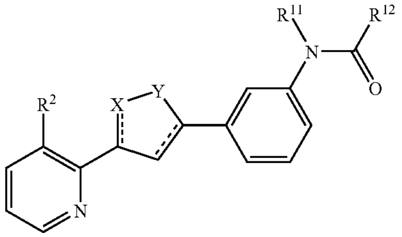

(Id)

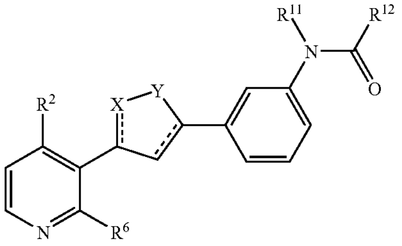

(Ie)

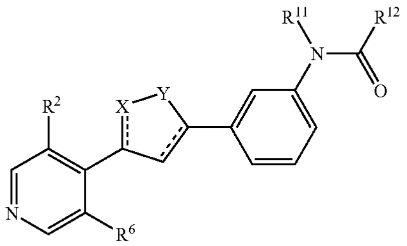

or a pharmaceutically acceptable salt, hydrate or solvate thereof, wherein X, Y, $R^2$, $R^6$, $R^{11}$ and $R^{12}$ are as previously defined for claim 1 and - - - represents a single or double bond.

42. The compound of claim 41 in which $R^{11}$ is hydrogen, $R^{12}$ is dichloromethyl and $R^2$ and $R^6$ are each, independently of one another, selected from the group consisting of fluoro, chloro, trifluoromethyl and methoxy.

43. The compound of claim 1 which has the structural formula (If):

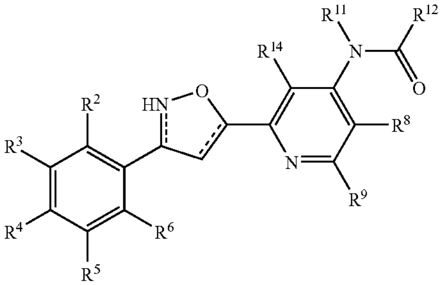

or pharmaceutically acceptable salt, hydrate or solvate thereof, wherein $R^2$, $R^3$, $R^4$, $R^5$, $R^6$, $R^8$, $R^9$, $R^{11}$, $R^{12}$ and $R^{14}$ are as previously defined for claim 1 and subject to the same provisos and - - - represents a single or double bond.

44. A compound which inhibits HCV replication and/or proliferation as measured in an in vitro assay, the compound selected from the group consisting of.

1

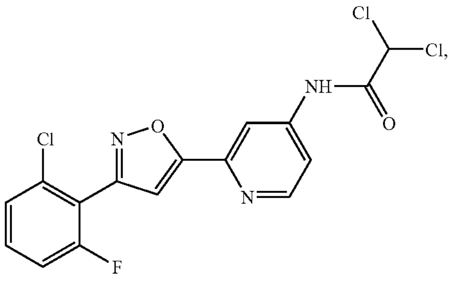

3

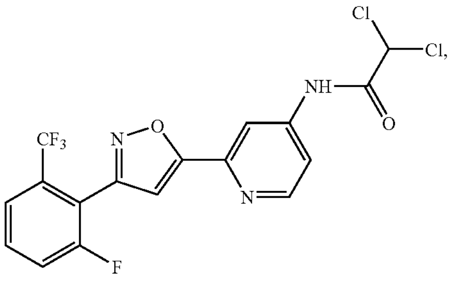

5

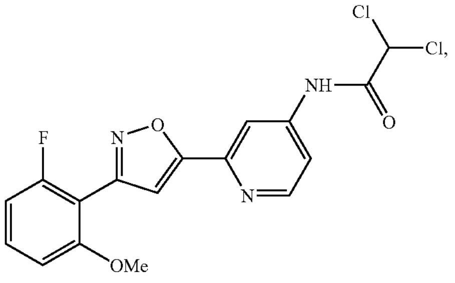

7

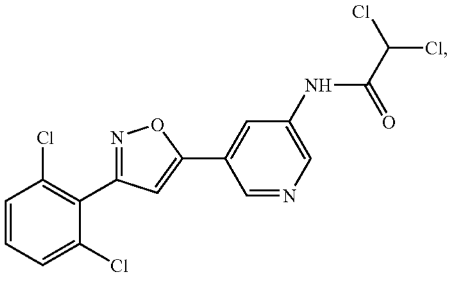

-continued
9
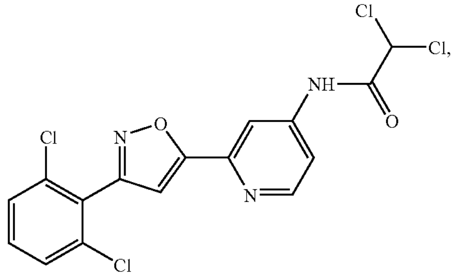
11
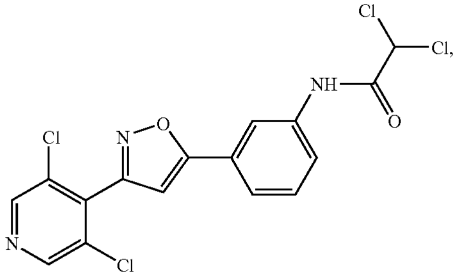
13
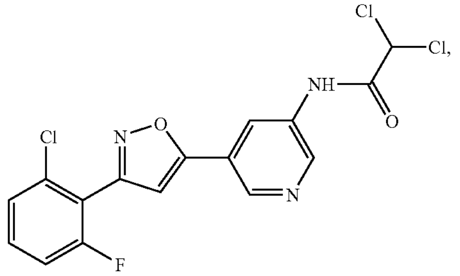
17
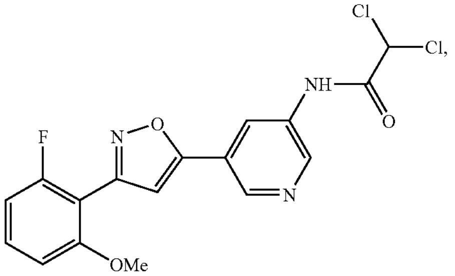
19
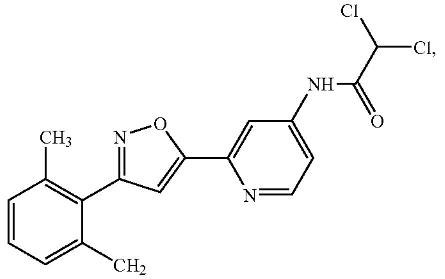
21
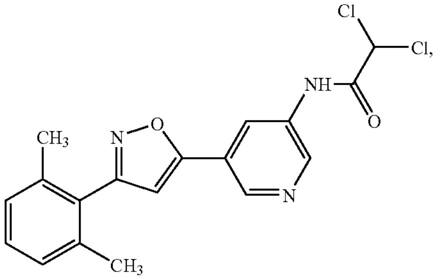
27
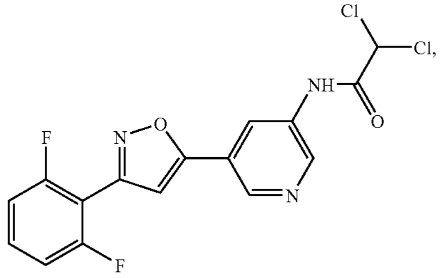
29
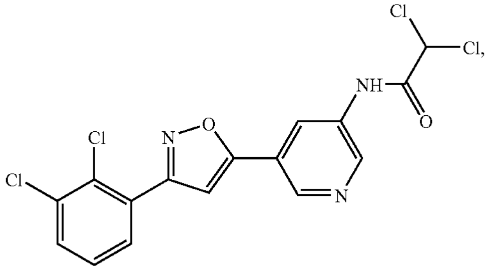
31
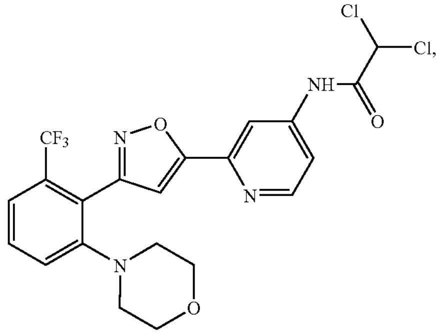
33
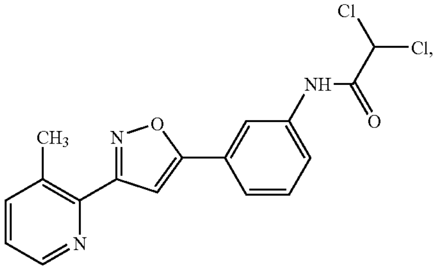

-continued
35
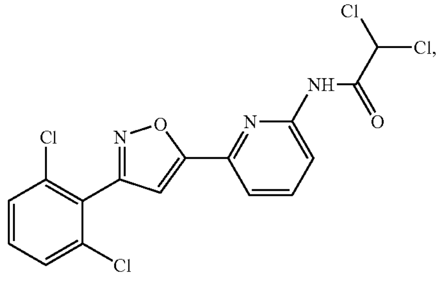
37
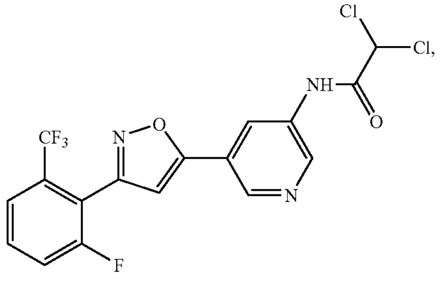
39
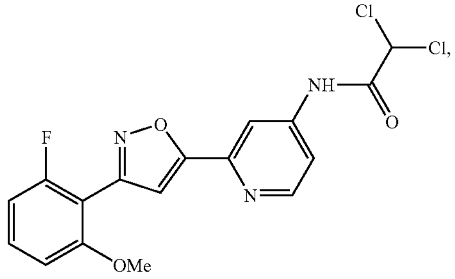
43
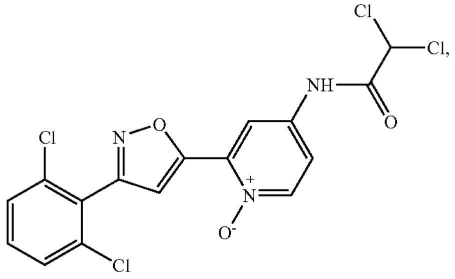
45
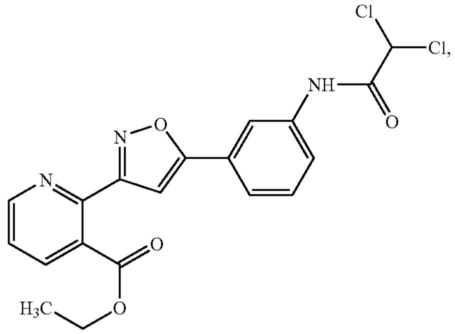
47
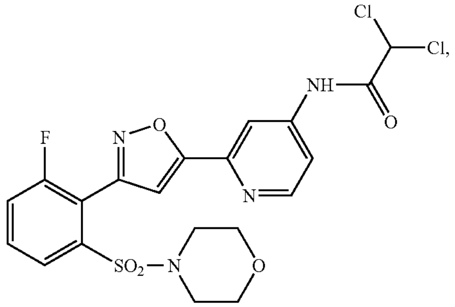
49
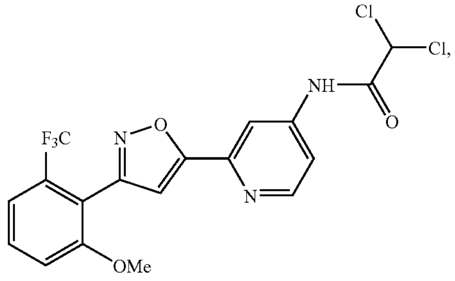
51
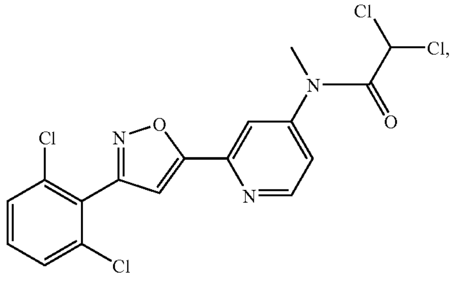
53
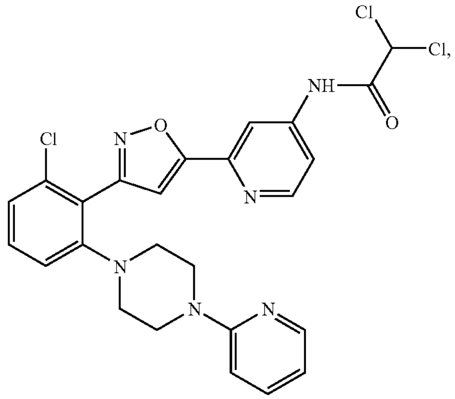
57
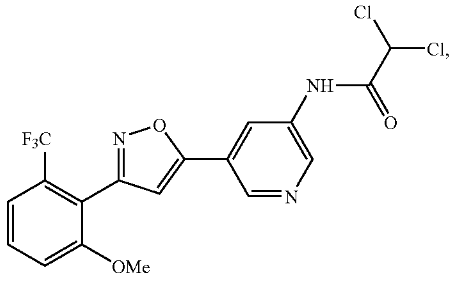

-continued

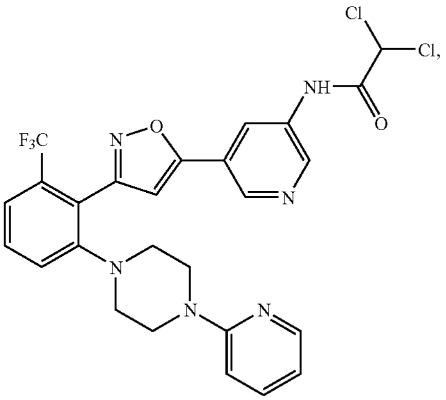

and

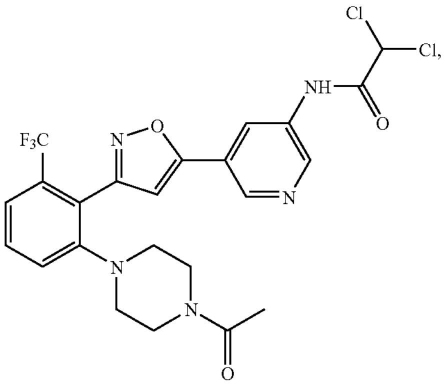

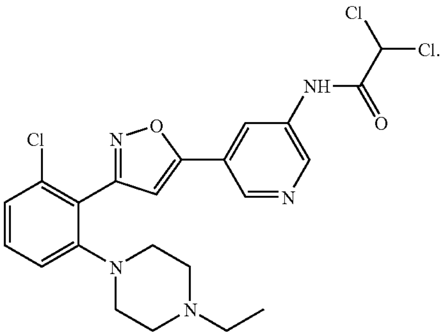

45. A method of inhibiting replication or proliferation of a hepatitis C ("HC") virion, comprising the step of contacting a HC virion with an amount of a compound of any one of claims 1–12 effective to inhibit replication of the HC virion.

46. The method of claim 45 which is practiced in vitro.

47. The method of claim 45 which is practiced in vivo.

48. A method of inhibiting an HCV infection, comprising the steps of administering to a subject an effective amount of a compound of any one of claims 1–12 effective to treat or prevent an HCV infection.

49. The method of claim 48, wherein the subject is a human.

50. The method of claim 48, wherein the compound is administered in an amount of 0.1 mg/kg to 200 mg/kg.

51. The method of claim 48, wherein the compound is administered in an amount of 10 mg/kg to 100 mg/kg.

52. The method of claim 48, wherein the compound is administered orally.

53. The method of claim 48, wherein the compound is administered by injection.

54. The method of claim 48, wherein the compound is selected from the group of compounds depicted in FIG. 1 and which inhibits HCV replication and/or proliferation with an $IC_{50}$ of about 10 μM or less, as measured in an in vitro assay.

55. The method of claim 48 which is practiced therapeutically in a subject having an HCV infection.

56. The method of claim 48 which is practiced prophylactically in a subject at risk of developing an HCV infection.

57. A composition comprising a compound of any one of claims 1–12 and a pharmaceutically acceptable vehicle.

* * * * *